United States Patent
Pauza et al.

(10) Patent No.: US 12,370,253 B2
(45) Date of Patent: Jul. 29, 2025

(54) PRE-IMMUNIZATION AND IMMUNOTHERAPY

(71) Applicant: American Gene Technologies International Inc., Rockville, MD (US)

(72) Inventors: Charles David Pauza, Rockville, MD (US); Haishan Li, Rockville, MD (US); Tyler Lahusen, Rockville, MD (US); Jeffrey A. Galvin, Rockville, MD (US)

(73) Assignee: American Gene Technologies International Inc., Rockville, MD (US)

( * ) Notice: Subject to any disclaimer, the term of this patent is extended or adjusted under 35 U.S.C. 154(b) by 0 days.

(21) Appl. No.: 18/227,796

(22) Filed: Jul. 28, 2023

(65) Prior Publication Data
US 2024/0108714 A1    Apr. 4, 2024

Related U.S. Application Data

(63) Continuation of application No. 18/108,148, filed on Feb. 10, 2023, now abandoned, which is a continuation of application No. 17/175,278, filed on Feb. 12, 2021, now Pat. No. 11,612,649, which is a continuation of application No. 16/593,882, filed on Oct. 4, 2019, now Pat. No. 11,090,379, which is a continuation of application No. 16/218,010, filed on Dec. 12, 2018, now Pat. No. 10,494,647, which is a continuation of application No. 16/011,550, filed on Jun. 18, 2018, now Pat. No. 10,233,464, which is a continuation of application No. 15/668,223, filed on Aug. 3, 2017, now Pat. No. 10,036,038, which is a continuation of application No. PCT/US2017/013019, filed on Jan. 11, 2017.

(60) Provisional application No. 62/360,185, filed on Jul. 8, 2016, provisional application No. 62/385,864, filed on Sep. 9, 2016, provisional application No. 62/409,270, filed on Oct. 17, 2016.

(51) Int. Cl.
| | | |
|---|---|---|
| A61K 35/17 | (2025.01) | |
| A61K 31/7105 | (2006.01) | |
| A61K 35/14 | (2015.01) | |
| A61K 39/00 | (2006.01) | |
| A61K 39/12 | (2006.01) | |
| A61K 39/21 | (2006.01) | |
| A61K 39/39 | (2006.01) | |
| A61K 40/11 | (2025.01) | |
| A61K 40/46 | (2025.01) | |
| A61K 45/06 | (2006.01) | |
| A61P 31/18 | (2006.01) | |
| C07K 14/715 | (2006.01) | |
| C12N 5/078 | (2010.01) | |
| C12N 5/0783 | (2010.01) | |
| C12N 7/00 | (2006.01) | |
| C12N 15/11 | (2006.01) | |
| C12N 15/113 | (2010.01) | |
| C12N 15/86 | (2006.01) | |
| A61K 35/12 | (2015.01) | |

(52) U.S. Cl.
CPC .......... *A61K 39/21* (2013.01); *A61K 31/7105* (2013.01); *A61K 35/14* (2013.01); *A61K 39/12* (2013.01); *A61K 39/39* (2013.01); *A61K 40/11* (2025.01); *A61K 40/46* (2025.01); *A61K 45/06* (2013.01); *A61P 31/18* (2018.01); *C07K 14/7158* (2013.01); *C12N 5/0634* (2013.01); *C12N 5/0636* (2013.01); *C12N 7/00* (2013.01); *C12N 15/111* (2013.01); *C12N 15/1132* (2013.01); *C12N 15/1138* (2013.01); *C12N 15/86* (2013.01); *A61K 2035/124* (2013.01); *A61K 2039/545* (2013.01); *A61K 2039/55561* (2013.01); *A61K 2239/38* (2023.05); *C12N 2310/122* (2013.01); *C12N 2310/14* (2013.01); *C12N 2310/141* (2013.01); *C12N 2320/32* (2013.01); *C12N 2330/51* (2013.01); *C12N 2510/00* (2013.01); *C12N 2710/24143* (2013.01); *C12N 2740/15021* (2013.01); *C12N 2740/15034* (2013.01); *C12N 2740/15043* (2013.01); *C12N 2740/15052* (2013.01); *C12N 2740/16022* (2013.01); *C12N 2740/16034* (2013.01); *C12N 2740/16043* (2013.01)

(58) Field of Classification Search
CPC .............. C12N 5/0636; C12N 2510/00; C12N 5/0634; C12N 2740/16034; A61K 2239/38
See application file for complete search history.

(56) References Cited

U.S. PATENT DOCUMENTS

| | | |
|---|---|---|
| 5,668,255 A | 9/1997 | Murphy |
| 5,674,703 A | 10/1997 | Woo et al. |
| 6,156,514 A | 12/2000 | Acevedo et al. |
| 6,399,383 B1 | 6/2002 | Apt et al. |
| 6,635,472 B1 | 10/2003 | Lauermann |

(Continued)

FOREIGN PATENT DOCUMENTS

| | | |
|---|---|---|
| CN | 101160055 A | 4/2008 |
| CN | 101516365 A | 8/2009 |

(Continued)

OTHER PUBLICATIONS

Advisory Action for U.S. Appl. No. 13/333,882, mailed Nov. 16, 2018, 3 Pages.

(Continued)

*Primary Examiner* — Barry A Chestnut
(74) *Attorney, Agent, or Firm* — COOLEY LLP

(57) ABSTRACT

The present invention relates generally to immunization and immunotherapy for the treatment or prevention of HIV. In particular, the methods include in vivo and/or ex vivo enrichment of HIV-specific CD4+ T cells.

10 Claims, 40 Drawing Sheets
Specification includes a Sequence Listing.

(56) References Cited

U.S. PATENT DOCUMENTS

| | | |
|---|---|---|
| 7,371,542 B2 | 5/2008 | Ivanova et al. |
| 8,124,752 B2 | 2/2012 | Bumcrot et al. |
| 8,287,857 B2 | 10/2012 | Dudley et al. |
| 8,993,532 B2 | 3/2015 | Hannon et al. |
| 9,522,176 B2 | 12/2016 | DeRosa et al. |
| 9,527,904 B2 | 12/2016 | Balazs et al. |
| 9,834,790 B1 | 12/2017 | Pauza et al. |
| 9,834,791 B2 | 12/2017 | Zhang et al. |
| 9,914,938 B2 | 3/2018 | Pauza et al. |
| 10,023,880 B2 | 7/2018 | Pauza et al. |
| 10,036,038 B2 | 7/2018 | Pauza et al. |
| 10,036,040 B2 | 7/2018 | Pauza et al. |
| 10,137,144 B2 | 11/2018 | Pauza et al. |
| 10,208,295 B2 | 2/2019 | DeRosa et al. |
| 10,233,464 B2 | 3/2019 | Pauza et al. |
| 10,420,789 B2 | 9/2019 | Pauza et al. |
| 10,472,649 B2 | 11/2019 | Pauza et al. |
| 10,494,647 B2 | 12/2019 | Pauza et al. |
| 10,888,613 B2 | 1/2021 | Pauza et al. |
| 11,090,379 B2 | 8/2021 | Pauza et al. |
| 2002/0168345 A1 | 11/2002 | Dong |
| 2003/0013196 A1 | 1/2003 | Engelman et al. |
| 2003/0096787 A1 | 5/2003 | Perricaudet et al. |
| 2003/0119770 A1 | 6/2003 | Lai et al. |
| 2003/0138444 A1 | 7/2003 | Zavitz et al. |
| 2004/0142416 A1 | 7/2004 | Laipis et al. |
| 2004/0161412 A1 | 8/2004 | Penn et al. |
| 2004/0192629 A1 | 9/2004 | Xu et al. |
| 2004/0214158 A1 | 10/2004 | Sethi et al. |
| 2004/0248296 A1 | 12/2004 | Beresford et al. |
| 2004/0265306 A1 | 12/2004 | Arthos et al. |
| 2005/0019927 A1 | 1/2005 | Hildinger et al. |
| 2005/0138677 A1 | 6/2005 | Pfister et al. |
| 2006/0057553 A1 | 3/2006 | Aguilar-Cordova |
| 2006/0073576 A1 | 4/2006 | Barnett et al. |
| 2006/0183230 A1 | 8/2006 | Silla et al. |
| 2006/0246520 A1 | 11/2006 | Champagne et al. |
| 2007/0026521 A1 | 2/2007 | Colosi |
| 2007/0141679 A1 | 6/2007 | Sodroski et al. |
| 2007/0203333 A1 | 8/2007 | McSwiggen et al. |
| 2008/0003225 A1 | 1/2008 | Vie et al. |
| 2008/0003682 A1 | 1/2008 | Lois-Caballe et al. |
| 2008/0039413 A1 | 2/2008 | Morris et al. |
| 2008/0131940 A1 | 6/2008 | Chiu et al. |
| 2008/0153737 A1 | 6/2008 | Lieberman et al. |
| 2008/0199961 A1 | 8/2008 | Rasko et al. |
| 2008/0227736 A1 | 9/2008 | Chen et al. |
| 2008/0293142 A1 | 11/2008 | Liu et al. |
| 2009/0148936 A1 | 6/2009 | Stout et al. |
| 2009/0304688 A1 | 12/2009 | Fournie et al. |
| 2010/0017911 A1 | 1/2010 | Dawson et al. |
| 2010/0069372 A1 | 3/2010 | Kazantsev |
| 2010/0119511 A1 | 5/2010 | Wang et al. |
| 2010/0120155 A1 | 5/2010 | Brennan et al. |
| 2010/0286166 A1 | 11/2010 | Pey Rodríguez et al. |
| 2010/0316676 A1 | 12/2010 | Sanders et al. |
| 2011/0008417 A1 | 1/2011 | Peut et al. |
| 2011/0008803 A1 | 1/2011 | Stockwell |
| 2011/0177155 A1 | 7/2011 | Peer et al. |
| 2011/0207226 A1 | 8/2011 | Ni et al. |
| 2012/0027725 A1 | 2/2012 | Galvin et al. |
| 2012/0034197 A1 | 2/2012 | Young |
| 2012/0053223 A1 | 3/2012 | Benkirane et al. |
| 2012/0076763 A1 | 3/2012 | Anderson et al. |
| 2012/0114607 A1 | 5/2012 | Lai et al. |
| 2012/0201794 A1 | 8/2012 | Chen et al. |
| 2013/0078276 A1 | 3/2013 | Robinson et al. |
| 2013/0090371 A1 | 4/2013 | Lu |
| 2013/0122380 A1 | 5/2013 | Visco et al. |
| 2013/0142766 A1 | 6/2013 | Dodo et al. |
| 2013/0211380 A1 | 8/2013 | Cabrera Aquino et al. |
| 2014/0155468 A1 | 6/2014 | Gregory et al. |
| 2014/0162894 A1 | 6/2014 | Hatchwell et al. |
| 2014/0178340 A1 | 6/2014 | Robbins et al. |
| 2014/0234958 A1 | 8/2014 | Kasahara et al. |
| 2014/0248277 A1 | 9/2014 | Hoffman et al. |
| 2014/0336245 A1 | 11/2014 | Mingozzi et al. |
| 2014/0348794 A1 | 11/2014 | Chiorini et al. |
| 2015/0010578 A1 | 1/2015 | Balazs et al. |
| 2015/0018539 A1 | 1/2015 | Fellmann |
| 2015/0126580 A1 | 5/2015 | DePinho et al. |
| 2015/0132255 A1 | 5/2015 | Sorensen et al. |
| 2015/0176006 A1 | 6/2015 | Krause et al. |
| 2016/0060707 A1 | 3/2016 | Goldenberg et al. |
| 2016/0243169 A1 | 8/2016 | Chen et al. |
| 2016/0289681 A1 | 10/2016 | Rossi et al. |
| 2017/0015976 A1 | 1/2017 | Nelson |
| 2017/0028036 A1 | 2/2017 | Mingozzi et al. |
| 2017/0037369 A1 | 2/2017 | Ramsborg et al. |
| 2017/0240899 A1 | 8/2017 | Wu et al. |
| 2017/0335344 A1 | 11/2017 | Pauza et al. |
| 2018/0010147 A1 | 1/2018 | Pauza et al. |
| 2018/0142257 A1 | 5/2018 | Pauza et al. |
| 2018/0142258 A1 | 5/2018 | Pauza et al. |
| 2018/0161455 A1 | 6/2018 | Pauza et al. |
| 2018/0177866 A1 | 6/2018 | Pauza |
| 2018/0195046 A1 | 7/2018 | Deng et al. |
| 2018/0195050 A1 | 7/2018 | Szalay et al. |
| 2018/0256624 A1 | 9/2018 | Pauza et al. |
| 2018/0305716 A1 | 10/2018 | Pauza et al. |
| 2018/0355032 A1 | 12/2018 | Roberts et al. |
| 2019/0046633 A1 | 2/2019 | Pauza et al. |
| 2019/0062786 A1 | 2/2019 | Pauza et al. |
| 2019/0078096 A1 | 3/2019 | Lahusen et al. |
| 2019/0083523 A1 | 3/2019 | Pauza et al. |
| 2019/0218573 A1 | 7/2019 | Pauza et al. |
| 2019/0388456 A1 | 12/2019 | Pauza et al. |
| 2020/0063161 A1 | 2/2020 | Pauza et al. |
| 2020/0087682 A1 | 3/2020 | Lahusen et al. |
| 2020/0109417 A1 | 4/2020 | Pauza et al. |
| 2020/0155590 A1 | 5/2020 | Lai et al. |
| 2020/0181645 A1 | 6/2020 | Pauza et al. |
| 2020/0318081 A1 | 10/2020 | Lahusen et al. |
| 2021/0047644 A1 | 2/2021 | Lahusen et al. |
| 2021/0121561 A1 | 4/2021 | Pauza et al. |
| 2023/0241200 A1 | 8/2023 | Pauza |
| 2024/0115604 A1 | 4/2024 | Li et al. |

FOREIGN PATENT DOCUMENTS

| | | |
|---|---|---|
| CN | 101679466 A | 3/2010 |
| CN | 101805750 A | 8/2010 |
| CN | 103184224 A | 7/2013 |
| CN | 105112370 A | 12/2015 |
| CN | 108883100 A | 11/2018 |
| EP | 1647595 A1 | 4/2006 |
| EP | 3402483 A1 | 11/2018 |
| EP | 3413926 A1 | 12/2018 |
| EP | 3426777 A2 | 1/2019 |
| EP | 3468617 A1 | 4/2019 |
| EP | 3468618 A2 | 4/2019 |
| EP | 3481418 A1 | 5/2019 |
| EP | 3481435 A1 | 5/2019 |
| IN | 201947000153 | 2/2019 |
| JP | 2002506652 A | 3/2002 |
| JP | 2007527240 A | 9/2007 |
| JP | 2008518591 A | 6/2008 |
| JP | 2008538174 A | 10/2008 |
| JP | 2010520757 A | 6/2010 |
| JP | 2011036263 A | 2/2011 |
| JP | 2011517409 A | 6/2011 |
| JP | 2012508591 A | 4/2012 |
| JP | 2012533299 A | 12/2012 |
| JP | 2013507107 A | 3/2013 |
| JP | 2013530152 A | 7/2013 |
| JP | 2014511704 A | 5/2014 |
| JP | 2015518838 A | 7/2015 |
| JP | 2016502404 A | 1/2016 |
| JP | 2019509029 A | 4/2019 |
| WO | WO-9947691 A1 | 9/1999 |
| WO | WO-0220554 A2 | 3/2002 |
| WO | WO-03093436 A2 | 11/2003 |
| WO | WO-2004053137 A2 | 6/2004 |
| WO | WO-2004104185 A1 | 12/2004 |

(56) References Cited

FOREIGN PATENT DOCUMENTS

| | | |
|---|---|---|
| WO | WO-2005028634 A2 | 3/2005 |
| WO | WO-2005033282 A2 | 4/2005 |
| WO | WO-2005051927 A1 | 6/2005 |
| WO | WO-2006039721 A2 | 4/2006 |
| WO | WO-2006048215 A1 | 5/2006 |
| WO | WO-2007000668 A2 | 1/2007 |
| WO | WO-2007015122 A1 | 2/2007 |
| WO | WO-2007132292 A2 | 11/2007 |
| WO | WO-2007133674 A2 | 11/2007 |
| WO | WO-2008025025 A2 | 2/2008 |
| WO | WO-2008090185 A1 | 7/2008 |
| WO | WO-2008109837 A2 | 9/2008 |
| WO | WO-2009100928 A1 | 8/2009 |
| WO | WO-2009100955 A1 | 8/2009 |
| WO | WO-2009120947 A1 | 10/2009 |
| WO | WO-2009147445 A1 | 12/2009 |
| WO | WO-2010051521 A1 | 5/2010 |
| WO | WO-2010117974 A2 | 10/2010 |
| WO | WO-2010127166 A2 | 11/2010 |
| WO | WO-2011008348 A2 | 1/2011 |
| WO | WO-2011042180 A1 | 4/2011 |
| WO | WO-2011071476 A2 | 6/2011 |
| WO | WO-2011119942 A1 | 9/2011 |
| WO | WO-2012048303 A2 | 4/2012 |
| WO | WO-2012061075 A2 | 5/2012 |
| WO | WO-2012140127 A2 | 10/2012 |
| WO | WO-2012145624 A2 | 10/2012 |
| WO | WO-2013096455 A1 | 6/2013 |
| WO | WO-2014016817 A2 | 1/2014 |
| WO | WO-2014117050 A2 | 7/2014 |
| WO | WO-2014187881 A1 | 11/2014 |
| WO | WO2015012924 | 1/2015 |
| WO | WO-2015017755 A1 | 2/2015 |
| WO | WO-2015042308 A2 | 3/2015 |
| WO | WO-2015061491 A1 | 4/2015 |
| WO | WO-2015078999 A1 | 6/2015 |
| WO | WO-2015086854 A1 | 6/2015 |
| WO | WO-2015164759 A2 | 10/2015 |
| WO | WO-2016046234 A2 | 3/2016 |
| WO | WO-2016054654 A1 | 4/2016 |
| WO | WO-2016061232 A2 | 4/2016 |
| WO | WO-2016069518 A2 | 5/2016 |
| WO | WO-2016069716 A1 | 5/2016 |
| WO | WO-2016186708 A1 | 11/2016 |
| WO | WO-2016189159 A1 | 12/2016 |
| WO | WO-2016200997 A1 | 12/2016 |
| WO | WO-2017007994 A1 | 1/2017 |
| WO | WO2017053556 | 3/2017 |
| WO | WO-2017068077 A1 | 4/2017 |
| WO | WO-2017100551 A1 | 6/2017 |
| WO | WO-2017123918 A1 | 7/2017 |
| WO | WO-2017139065 A1 | 8/2017 |
| WO | WO-2017156311 A2 | 9/2017 |
| WO | WO-2017173453 A1 | 10/2017 |
| WO | WO-2017213697 A1 | 12/2017 |
| WO | WO-2017214327 A2 | 12/2017 |
| WO | WO-2018009246 A1 | 1/2018 |
| WO | WO-2018009847 A1 | 1/2018 |
| WO | WO-2018017882 A1 | 1/2018 |
| WO | WO-2018025923 A1 | 2/2018 |
| WO | WO-2018126112 A1 | 7/2018 |
| WO | WO-2018129540 A1 | 7/2018 |
| WO | WO-2018148443 A1 | 8/2018 |
| WO | WO-2018187231 A1 | 10/2018 |
| WO | WO-2018232359 A1 | 12/2018 |
| WO | WO-2019070674 A2 | 4/2019 |
| WO | WO-2020011247 A1 | 1/2020 |
| WO | WO-2020097049 A1 | 5/2020 |
| WO | WO-2020243717 A1 | 12/2020 |

OTHER PUBLICATIONS

Advisory Action for U.S. Appl. No. 15/736,284, mailed Jul. 23, 2019, 3 Pages.

Akinsheye I., et al., "Fetal Hemoglobin in Sickle Cell Anemia," Blood, Jul. 7, 2011, vol. 118, No. 1, pp. 19-27.

Anderson J., et al., "Safety and Efficacy of a Lentiviral Vector Containing Three Anti-HIV Genes—CCR5 Ribozyme, Tat-rev siRNA, and TAR Decoy-in SCID-hu Mouse-Derived T Cells," Molecular Therapy, 2007, vol. 15, pp. 1182-1188.

Anderson J., et al., "HIV-1 Resistance Conferred by siRNA Cosuppression of CXCR4 and CCR5 Coreceptors by a Bispecific Lentiviral Vector," AIDS Research and Therapy, 2005, vol. 2, No. 1, 13 Pages.

Anderson J.S., et al., "Specific Transduction of HIV-Susceptible Cells forCCR5 Knockdown and Resistance to HIV Infection: A Novel Method for Targeted Gene Therapy and Intracellular Immuniczation," Journal of acquired immune deficiency syndromes, Oct. 1, 2009, vol. 52, No. 2, pp. 152-161.

Anderson J.S., et al., "Preintegration HIV-1 Inhibition by a Combination Lentiviral Vector Containing a Chimeric TRIM5a Protein, a CCR5 shRNA, and TAR Decoy," Molecular Therapy, Dec. 2009, vol. 17, No. 12, pp. 2103-2114.

Benyamine A., et al., "BTN3A Molecules Considerably Improve Vγ9Vδ2T Cells-based Immunotherapy in Acute Myeloid Leukemia," Oncolmmunology, Oct. 2, 2016, vol. 5, No. 10, 10 Pages, (E1146843) *the whole document*.

Bergvall M., et al. "The E1 Proteins," Virology, 2013, vol. 445, pp. 35-56.

Blau N., et al., "Phenylketonuria," The Lancet, Oct. 23, 2010, vol. 376(9750), pp. 1417-1427.

Blick G., et al., "Cyclophosphamide Enhances SB-728-T Engraftment to Levels Associated with HIV-RNA Control," CROI Conference on Retroviruses and Opportunistic Infections, Mar. 3-6, 2014, 3 Pages.

Bourguigon P., et al., "Processing Of Blood Samples Influences PBMC Viability And Outcome Of Cell-mediated Immune Responses In Antiretroviral Therapy-naïve HIV-1-infected Patients," Journal of Immunological Methods, Dec. 1, 2014, vol. 414, pp. 1-10.

Brites C., et al., "Infection by HTLV-1 Is Associated with High Levels of Proinflammatory Cytokines in HIV-HCV-Coinfected Patients," Journal of Acquired Immune Deficiency Syndromes, Feb. 1, 2018, vol. 77, No. 2, pp. 230-234.

Briz V., et al., "Validation of Generation 4 Phosphorus-Containing Polycationic Dendrimer for Gene Delivery Against HIV-1," Current Medical Chemistry, 2012, vol. 19, No. 29, pp. 5044-5051.

Cannon J.R., et al., "Pseudotype-Dependent Lentiviral Transduction of Astrocytes or Neurons in the Rat Substantia Nigra," Experimental Neurology, Mar. 2011, vol. 228, No. 1, pp. 41-52, DOI:10.1016/J.expneurol.2010.10.016.

Capietto A-H., et al., "Stimulated Yδ T Cells Increase the in Vivo Efficacy of Trastuzumab in HER-2+ Breast Cancer," Journal of Immunology, 2011, vol. 187(2), pp. 1031-1038.

Chandler R.J., et al., "Vector Design Influences Hepatic Genotoxicity After Adeno-Associated Virus Gene Therapy," Journal of Clinical Investigation, Feb. 2015, vol. 125, No. 2, pp. 870-880.

Charron C.E., et al., "Dominant-Negative Interference in the Pahenu2 Mouse Model of PKU: Effectiveness of Vectors Expressing Either Modified Forms of Phenylalanine Hydroxylase (PAH) or Ribozymes Plus a Hardened PAH mRNA," Molecular Therapy, 2005, vol. 11, pp. S163- S164.

Charron C.E., "Gene Therapy for Phenylketonuria: Dominant-Negative Interference in a Recessive Disease," Dissertation, University of Florida, 2005, 89 pages, [Retrieved on Jul. 26, 2018] Retrieved from URL: http://etd.fcla.edu/UF/UFE0011392/charron_c.pdf.

Chavez L., et al., "HIV Latency Is Established Directly and Early in Both Resting and Activated Primary CD4 T Cells," PLoS Pathogens, Jun. 11, 2015, vol. 11, No. 6, e1004955, 21 Pages.

Chen Z., et al., "CD16+ Gammadelta T Cells Mediate Antibody Dependent Cellular Cytotoxicity: Potential Mechanism In The Pathogenesis Of Multiple Sclerosis," Clinical Immunology, 2008, vol. 128(2), pp. 219-227.

Chiang C-M., et al., "Viral E1 and E2 Proteins Support Replication Of Homologous And Heterologous Papillomaviral Origins," Proceedings of the National Academy of Sciences of the United States of America, Jul. 1, 1992, vol. 89, pp. 5799-5803.

(56) References Cited

OTHER PUBLICATIONS

Choi J-G., et al., "Multiplexing Seven miRNA-Based shRNAs to Suppress HIV Replication," Molecular Therapy : The Journal of the American Society of Gene Therapy, Feb. 2015, vol. 23, No. 02, pp. 310-320, DOI: 10.1038/mt.2014.205, ISSN 1525-0016, XP055432740.
Christophersen E.B., et al., "A Technique of Transumbilical Portal Vein Catheterization in Adults," The Archives of Surgery, 1967, vol. 95(6), pp. 960-963, (Abstract Only).
Condiotti R., et al., "Prolonged Liver-Specific Transgene Expression by a NonPrimate Lentiviral Vector," Biochemical and Biophysical Research Communications, Jul. 30, 2004, vol. 320, No. 3, pp. 998-1006.
Corrected Notice of Allowance for U.S. Appl. No. 16/687,525, mailed Mar. 3, 2021,2 Pages.
Couzi L., et al., "Antibody-Dependent Anti-Cytomegalovirus Activity of Human Gammadelta T Cells Expressing CD16 (FcgammaRIIIa)," Blood, 2012, vol. 119(6), pp. 1418-1427.
Craenenbroeck K.V., et al., "Episomal Vectors for Gene Expression in Mammalian Cells," European Journal Biochemistry, Jul. 14, 2000, vol. 267, pp. 5665-5678.
Cronin J., et al., "Altering The Tropism Of Lentiviral Vectors Through Pseudotyping," Current Gene Therapy, Aug. 2005, vol. 5, No. 4, pp. 387-398.
Curriu M., et al., "Viremic HIV Infected Individuals with High CD4 T Cells and Functional Envelope Proteins Show Anti-gp41 Antibodies with Unique Specificity and Function," PLoS ONE, Feb. 2012, vol. 7, No. 2, e30330, 11 Pages.
Davis-Gardner M.E., et al., "eCD4-Ig promotes ADCC activity of sera from HIV-1-infected patients", Department of Immunology and Microbiology, The Scripps Research Institute, PLOS Pathogen, Dec. 18, 2017, 19 Pages, Retrieved from URL: https://doi.org/10.1371/journal.ppat.1006786.
Dickler H.B., et al., "Lymphocyte Binding of Aggregated IgG and Surface Ig Staining in Chronic Lymphocytic Leukaemia," Clinical and Experimental Immunology, 1973, vol. 14, No. 01, pp. 97-106.
Dieli F., et al., "Targeting Human γδ T Cells with Zoledronate and Interleukin-2 for Immunotherapy of Hormone-Refractory Prostate Cancer," Europe PMC Funders Group, Cancer Research, Aug. 1, 2007, vol. 67, No. 15, pp. 7450-7457.
Ding Z., et al., "Administration-Route and Gender-Independent Longterm Therapeutic Correction of Phenylketonuria (PKU) in a Mouse Model by Recombinant Adeno-Associated Virus 8 Pseudotyped Vector-Mediated Gene Transfer," Gene Therapy, Dec. 1, 2005, vol. 13, pp. 587-593.
Ding Z., et al., "Liver-Directed, AAV-and Lentivirus-Mediated Gene Therapy in the Phenylketonuria Mouse Model Pah-enu2," Molecular Therapy, May 2005, vol. 11, Supplement. 1, p. S348, XP055751452.
Donsante A., et al., "AAV Vector Integration Sites in Mouse Hepatocellular Carcinoma," Science, Jul. 27, 2007, vol. 317, No. 5837, p. 477.
Douek D.C., et al., "HIV Preferentially Infects HIV-Specific CD4+ T Cells," Nature, May 2, 2002, vol. 417, No. 6884, pp. 95-98.
Eguchi K., et al., "Primary Sjogren's Syndrome with Antibodies to HTLV-I: Clinical and Laboratory Features," Annals of the Rheumatic Diseases, 1992, vol. 51, No. 6, pp. 769-776.
Eisensmith R.C., et al., "Multiple Origins for Phenylketonuria in Europe," American Journal of Human Genetics, 1992, vol. 51, No. 6, pp. 1355-1365.
Examination Report No. 1 for Australian Patent Application No. 2018205388 dated Mar. 3, 2023, 5 Pages.
Extended European Search Report for European Application No. 16904834.5, mailed Dec. 19, 2019, 8 Pages.
Extended European Search Report for European Application No. 17750547.6, mailed Sep. 6, 2019, 6 Pages.
Extended European Search Report for European Application No. 17764128.9, mailed Aug. 12, 2019, 8 Pages.
Extended European Search Report for European Application No. 17810976.5, mailed Dec. 19, 2019, 8 Pages.
Extended European Search Report for European Application No. 17824652.6, mailed Feb. 6, 2020, 8 Pages.
Extended European Search Report for European Application No. 17825011.4, mailed Feb. 6, 2020, 8 Pages.
Extended European Search Report for European Application No. 17831904.2, mailed Mar. 11, 2020, 9 Pages.
Extended European Search Report for European Application No. 18736295.9, mailed Aug. 20, 2020, 12 Pages.
Extended European Search Report for European Application No. 18781288.8, mailed Dec. 8, 2020,11 Pages.
Extended European Search Report for European Application No. 18817253.0, mailed Feb. 10, 2021,8 Pages.
Extended European Search Report for European Application No. 19777212.2, mailed Nov. 2, 2021, 8 Pages.
Extended European Search Report for European Application No. 16808223.8, mailed Dec. 13, 2018, 9 Pages.
Extended European Search Report for European Application No. 16822021.8, mailed Dec. 11, 2018, 8 Pages.
Extended European Search Report for European Application No. 17739028.3, mailed Jun. 6, 2019, 8 Pages.
Final Office Action for U.S. Appl. No. 13/333,882, mailed Aug. 27, 2018, 11 Pages.
Final Office Action for U.S. Appl. No. 15/580,661, mailed Jun. 2, 2020, 16 Pages.
Final Office Action for U.S. Appl. No. 15/736,284, mailed May 2, 2019, 22 Pages.
Final Office Action for U.S. Appl. No. 15/736,284, mailed May 27, 2021, 23 Pages.
Final Office Action for U.S. Appl. No. 16/076,655, mailed Jul. 27, 2020, 17 Pages.
Final Office Action for U.S. Appl. No. 16/132,247, mailed Jul. 1, 2019, 7 Pages.
Final Office Action for U.S. Appl. No. 16/182,443, mailed May 2, 2019, 07 Pages.
Final Office Action for U.S. Appl. No. 16/312,056, mailed Feb. 26, 2021,22 Pages.
Final Office Action for U.S. Appl. No. 17/089,468, mailed Nov. 1, 2022, 19 pages.
Final Office Action for U.S. Appl. No. 16/312,056, dated Jan. 31, 2023, 36 pages.
Final Office Action in Japanese Application No. 2018-541270, mailed Dec. 23, 2021, 19 Pages, (with English translation).
First Office Action in the CN Application No. 201780017712.6, mailed May 8, 2020, 10 Pages.
Fisher D.B., et al., "The Inhibition of Phenylalanine and Tyrosine Hydroxylases by High Oxygen Levels," Journal of Neurochemistry, May 1972, vol. 19, No. 5, pp. 1359-1365, (Abstract Only).
Fisher J.P.H., et al., "Effective Combination Treatment of GD2-Expressing Neuroblastoma and Ewing's Sarcoma Using Anti-GD2 ch14.18/CHO Antibody with Vγ9Vδ2+ γT Cells," Oncolmmunology, 2016, vol. 5, Issue No. 1, e1025194, 32 Pages.
Franchini G., et al., "Genetic Relatedness of the Human Immunodeficiency Viruses Type 1 And 2 (Hiv-1, Hiv-2) and the Simian Immunodeficiency Virus," Annals of the New York Academy of Sciences, 1989, vol. 554, No. 1, pp. 81-87.
Fusetti F., et al., "Structure of Tetrameric Human Phenylalanine Hydroxylase and Its Implications for Phenylketonuria," Journal of Biological Chemistry, Jul. 3, 1998, vol. 273, No. 27, pp. 16962-16967, DOI: 10.1074/jbc.273.27.16962, XP055559179.
Futsch N., et al., "HTLV-1, the Other Pathogenic Yet Neglected Human Retrovirus: From Transmission to Therapeutic Treatment," Viruses, 2018, vol. 10, No. 01,25 Pages, DOI:10.3390/Y10010001.
GenBank Accession No. JG619773, "MNESC1NG-T3-001_L15_Feb. 6, 2009_054 MNESC1NG Cell Culture from Mahonia Nervosa Berberis Nervosa cDNA, mRNA Sequence," Feb. 13, 2014, 1 Page, Entire document, [Retrieved on Dec. 5, 2017], Retrieved from URL: https://www.ncbi.nlm.nih.gov/nucest/JG619773.
GenBank: "(long Control Region) [Human Papillomavirus, Type 16, Genomic, 860 nt]" GenBank Accession No. S60559, May 7, 1993, entire DNA sequence, pp. 1, [Located online Nov. 21, 2017] Retrieved from URL: https://ncbi.nlm.nih.gov/nuccore/S60559.

(56) References Cited

OTHER PUBLICATIONS

Gertner-Dardenne J., et al., "Bromohydrin Pyrophosphate Enhances Antibody-Dependent Cell-Mediated Cytotoxicity Induced by Therapeutic Antibodies," Blood, 2009, vol. 113(20), pp. 4875-4884.
Gessain A., et al., "Antibodies to Human T-Lymphotropic Virus Type-I in Patients with Tropical Spastic Paraparesis," The Lancet, Aug. 24, 1985, vol. 02, No. 8452, pp. 407-410.
Gessain A., et al., "Epidemiological Aspects and World Distribution of HTLV-1 Infection," Frontiers in Microbiology, Nov. 2012, vol. 03, Article 388, 23 Pages.
Gober H-J., et al., "Human T Cell Receptor γδ Cells Recognize Endogenous Mevalonate Metabolites in Tumor Cells," Journal of Experimental Medicine, Jan. 20, 2003, vol. 197, No. 2, pp. 163-168.
Goepfert P.A., et al., "Specificity and 6-Month Durability Of Immune Responses Induced by DNA and Recombinant Modified Vaccinia Ankara Vaccines Expressing HIV-1 Virus-Like Particles," The Journal of Infectious Diseases, Jul. 1, 2014, vol. 210, pp. 99-110, XP055410056.
Goncalves D.U., et al., "Epidemiology, Treatment, and Prevention of Human T-Cell Leukemia Virus Type 1-Associated Diseases," Clinical Microbiology Reviews, Jul. 2010, vol. 23, No. 03, pp. 577-589.
Gorziglia M.I., et al., "Elimination of Both E1 and E2A from Adenovirus Vectors Further Improves Prospects for In Vivo Human gene Therapy," Journal of Virology, Jun. 1996, vol. 70, No. 6, pp. 4173-4178.
Grisch-Chan H.M., et al., "Low-Dose Gene Therapy for Murine PKU Using Episomal Naked DNA Vectors Expressing PAH from Its Endogenous Liver Promoter," Molecular Therapy Nucleic Acids, 2017, vol. 7, pp. 339-349.
Guldberg P., et al., "Aberrant Phenylalanine Metabolism in Phenylketonuria Heterozygotes," Journal of Inherited Metabolic Disease, 1998, vol. 21, No. 4, pp. 365-372.
Hafid A.Z., et al., "Phenylketonuria: A Review of Current and Future Treatments," Translational Pediatrics, 2015, vol. 4, No. 4 pp. 304-317.
Harly C., et al., "Key Implication of CD277/butyrophilin-3 (BTN3A) in Cellular Stress Sensing by a Major Human T-cell Subset," Blood, Sep. 13, 2012, vol. 120, No. 11, pp. 2269-2279, DOI:10.1182/blood-2012-05-430470, ISSN 00064971, XP055081172.
Hassan G., et al., "Isolation Of Umbilical Cord Mesenchymal Stem Cells Using Human Blood Derivative Accompanied With Explant Method," Stem Cell Investigation, 2019, pp. 1-8.
Huang Q., et al., "An Efficient Protocol to Generate Placental Chorionic Plate-derived Mesenchymal Stem Cells with Superior Proliferative and Immunomodulatory Properties," Stem Cell Research & Therapy, 2019, vol. 10(301), pp. 1-15.
International Preliminary Report on Patentability for International Application No. PCT/US2016/041456, mailed Jan. 18, 2018, 8 Pages.
International Preliminary Report on Patentability for International Application No. PCT/US2017/013019, mailed Jan. 17, 2019, 8 Pages.
International Preliminary Report on Patentability for International Application No. PCT/US2017/013024, mailed Aug. 23, 2018, 9 Pages.
International Preliminary Report on Patentability for International Application No. PCT/US2017/041168, mailed Jan. 17, 2019, 10 Pages.
International Preliminary Report on Patentability for International Application No. PCT/US2018/012998, mailed Jul. 18, 2019, 9 Pages.
International Preliminary Report on Patentability for International Application No. PCT/US2018/025733, mailed Oct. 17, 2019, 9 Pages.
International Preliminary Report on Patentability for International Application No. PCT/US2019/024410, mailed Oct. 8, 2020, 8 Pages.
International Search Report and Written Opinion for International Application No. PCT/US2019/024410, mailed Jul. 22, 2019, 10 Pages.
International Search Report and Written Opinion for International Application No. PCT/US2019/059828, mailed Feb. 14, 2020, 12 Pages.
International Search Report for International Application No. PCT/US2016/036519, mailed Nov. 7, 2016, 4 Pages.
International Search Report for International Application No. PCT/US2016/041456, mailed Oct. 19, 2016, 4 Pages.
International Search Report for International Application No. PCT/US2016/066185, mailed Jun. 9, 2017, 12 Pages.
International Search Report for International Application No. PCT/US2017/013019, mailed Jul. 17, 2017, 5 Pages.
International Search Report for International Application No. PCT/US2017/013024, mailed Jul. 14, 2017, 3 Pages.
International Search Report for International Application No. PCT/US2017/013399, mailed May 26, 2017, 4 Pages.
International Search Report for International Application No. PCT/US2017/021639, mailed Aug. 25, 2017, 5 Pages.
International Search Report for International Application No. PCT/US2017/036433, mailed Dec. 15, 2017, 5 Pages.
International Search Report for International Application No. PCT/US2017/041168, mailed Nov. 8, 2017, 4 Pages.
International Search Report for International Application No. PCT/US2017/043157, mailed Dec. 26, 2017, 7 Pages.
International Search Report for International Application No. PCT/US2018/012998, mailed May 29, 2018, 4 Pages.
International Search Report for International Application No. PCT/US2018/025733, mailed Sep. 24, 2018, 6 Pages.
International Search Report for International Application No. PCT/US2018/037924, mailed Nov. 9, 2018, 7 Pages.
International Search Report for International Application No. PCT/US2018/053919, mailed Apr. 12, 2019, 6 Pages.
Invitation to Pay Additional Fees and, Where Applicable, Protest Fee for International Application No. PCT/US2018/025733, mailed Jul. 17, 2018, 2 Pages.
Invitation to Pay Additional Fees and, where Applicable, Protest Fee for International Application No. PCT/US2018/037924, mailed Sep. 11, 2018, 3 Pages.
Invitation to Pay Additional Fees and, Where Applicable, Protest Fee for International Application No. PCT/US2018/053919, mailed Feb. 22, 2019, 3 Pages.
Jaalouk D.E., et al., "A Self-inactivating Retrovector Incorporating The IL-2 Promoter fOr Activation-Induced Transgene Expression Engineered T-cells," Virology, 2006, vol. 3, No. 97, 12 Pages.
Jakobsson J., et al., "Lentiviral Vectors for Use in the Central Nervous System," Molecular Therapy : The Journal of the American Society of Gene Therapy, Cell Press, US, Mar. 1, 2006, vol. 13, No. 3, pp. 484-493, DOI: 10.1016/J.YMTHE.2005.11.012, ISSN: 1525-0016, XP005326761.
Jiang X., et al., "A Novel EST-derived RNAi Screen Reveals a Critical Role For Farnesyl Diphosphate Synthase in Beta 2-adrenergic Receptor Internalization and Down-regulation," The FASEB Journal, Published Online on Jan. 27, 2012, vol. 26(5), pp. 1995-2007.
Kagdi H., et al., "Switching And Loss Of Cellular Cytokine Producing Capacity Characterize In Vivo Viral Infection And Malignant Transformation In Human T-lymphotropic Virus Type 1 Infection," PLoS Pathogens, Feb. 14, 2018, vol. 14, No. 2, 25 Pages, e1006861.
Kagdi H.H., et al., "Risk Stratification of Adult T-Cell Leukemia/Lymphoma Using Immunophenotyping," Cancer Medicine, 2017, vol. 06, No. 01, pp. 298-309.
Kam T-I., et al., "Poly (ADP-ribose) Derived Pathologic [alpha]—Synuclein Neurodegeneration in Parkinson's disease," Science, US, Nov. 2, 2018, vol. 362, No. 6414, eaat8407, 12 pages, ISSN: 00368075, DOI: 10.1126/science.aat8407, XP55672116.
Kaufman S., "A Model of Human Phenylalanine Metabolism in Normal Subjects and in Phenylketonuric Patients," Proceedings of the National Academy of Sciences, USA, Mar. 1999, vol. 96(6), pp. 3160-3164.

(56) References Cited

OTHER PUBLICATIONS

Kaufman S., et al., "Phenylalanine Hydroxylase Activity in Liver Biopsies from Hyperphenylalaninemia Heterozygotes: Deviation from Proportionality with Gene Dosage," Pediatric Research, 1975, vol. 9(8), pp. 632-634.
Kaur G., et al., "Antigen Stimulation Induces HIV Envelope gp120-specific CD4+ T Cells to Secret CCR5 Ligands and Suppress HIV Infection," Virology, Dec. 5, 2007, vol. 369, No. 1, pp. 214-225.
Kavanagh D.G., et al., "Expansion of HIV-specific CD4+ and CD8+ T Cells by Dendritic Cells Transfected with mRNA Encoding Cytoplasm- or lysosome-targeted Nef," Blood, American Society of Hematology, US, Mar. 2006, Oct. 25, 2005, vol. 107, No. 5, pp. 1963-1969, DOI: 10.1182/BLOOD-2005-04-1513, ISSN 0006-4971, XP008141565.
Kim H.Y., et al., "Farnesyl Diphosphate Synthase Is Important For The Maintenance Of Glioblastoma Stemness," Experimental & Molecular Medicine, Published Online on Oct. 17, 2018, vol. 50, No. 10, 12 pages, DOI: 10.1038/s12276-018-0166-2, XP055605154.
Krajinovic M., et al., "Sequencing Data On The Long Control Region Of Human Papillomavirus Type 16," Journal of General Virology, 1991, vol. 72, pp. 2573-2576.
Kretova O.V., et al., "Generation of Genetic Constructs that Simultaneously Express several shRNAs," Biotechniques, May 2012, vol. 52, 3 pages.
Lam S., et al., "T-cell Therapies for HIV," Immunotherapy, Future Medicine, London, Apr. 1, 2013, vol. 5, No. 4, pp. 407-414, DOI: 10.2217/IMT.13.23, ISSN 1750-7448, XP009182920.
Ledley F.D., et al., "Molecular Biology of Phenylalanine Hydroxylase and Phenylketonuria," Trends in Genetics, Elsevier Science Publishers, B.V. Amsterdam, NL, Nov. 1985, vol. 1, pp. 309-313, DOI: 10.1016/0168-9525(85)90121-0, ISSN 0168-9525, XP025943064.
Ledley F.D., et al., "Retroviral-Mediated Gene Transfer of Human Phenylalanine Hydroxylase Into NIH-3T3 and Hepatoma Cells," Proceedings of the National Academy of Sciences, National Academy of Sciences, Jan. 1986, vol. 83, No. 2, pp. 409-413, DOI: 10.1073/PNAS.83.2.409, ISSN 0027-8424, XP002583115.
Lee S-K., et al., "Lentiviral Delivery of Short Hairpin RNAs Protects CD4 Cells from Multiple Clades and Primary Isolates of HIV," Blood, Aug. 1, 2005, vol. 106, No. 3, pp. 818-826.
Lee Y., et al., "Poly (ADP-ribose) in the Pathogenesis of Parkinson's Disease," BMB Reports, Korean Society for Biochemistry and Molecular Biology, KR, Aug. 31, 2014, vol. 47, No. 8, pp. 424-432, DOI:10.5483/BMBRep.2014.47.8.119, ISSN: 1976-6696, XP055671927.
Li J., et al., "Reduced Expression of the Mevalonate Pathway Enzyme Farnesyl Pyrophosphate Synthase Unveils Recognition of Tumor Cells by V[gamma]9V[delta]2 T Cells," The Journal of Immunology, US, (Jun. 3, 2009), Jun. 2009, vol. 182, No. 12, pp. 8118-8124, doi: 10.4049/jimmunol.0900101, ISSN 0022-1767, XP055605150.
Li Z., et al., "Inhibition Of Farnesyl Pyrophosphate Synthase Prevents Angiotensin II-induced Cardiac Fibrosis In Vitro," Clinical & Experimental Immunology, 2014, vol. 176, pp. 429-437.
Lin Y., et al., "Up-Regulation of Bcl-2 is Required for the Progression of Prostate Cancer Cells from an Androgen-Dependent to an Androgen-Independent Growth Stage," Cell Research, Apr. 3, 2007, vol. 17, pp. 531-536.
Longo N., et al., "Single-Dose, Subcutaneous Recombinant Phenylalanine Ammonia Lyase Conjugated with Polyethylene Glycol in Adult Patients with Phenylketonuria: An Open-Label, Multicenter, Phase 1 Dose-Escalation Trial," The Lancet, Jul. 5, 2014, vol. 384(9937), pp. 37-44.
Lu R., et al., "Simian Virus 40-Based Replication of Catalytically Inactive Human Immunodeficiency Virus Type 1 Integrase Mutants in Nonpermissive T Cells and Monocyte-Derived Macrophages," Journal of Virology, Jan. 2004, pp. 658-668. DOI: 10.1128/JVI.78.2658-668.2004.
Lu X., et al., "Anti-sense-Mediated Inhibition of Human Immunodeficiency Virus (HIV) Replication by Use of an HIV Type 1-Based Vector Results in Severely Attenuated Mutants Incapable of Developing Resistance," Journal of Virology, Jul. 2004, vol. 79, No. 13, pp. 7079-7088.
MacNamara A., et al., "HLA Class I Binding of HBZ Determines Outcome in HTLV-1 Infection," PLoS Pathog, Sep. 2010, vol. 06, No. 09:e1001117, pp. 1-12.
Manel N., et al., "The Ubiquitous Glucose Transporter GLUT-1 is a Receptor for HTLV," Cell, Nov. 14, 2003, vol. 115, No. 04, pp. 449-459.
Martinez M.P., et al., "Comparative Virology of HTLV-1 and HTLV-2," Retrovirology, Aug. 7, 2019, vol. 16, Article. 21, No. 1,12 Pages.
Mason R.D., et al., "Inactivated Simian Immunodeficiency Virus-Pulsed Autologous Fresh Blood Cells as an Immunotherapy Strategy," Journal of Virology, Feb. 2009, vol. 83, No. 3, pp. 1501-1510.
McBride A.A, "The Papillomavirus E2 Proteins," Virology, Oct. 2013, vol. 445, No. 1-2, pp. 57-79.
Miettinen T.P., et al., "Mevalonate Pathway Regulates Cell Size Homeostasis and Proteostasis Through Autophagy," Cell Reports, Dec. 22, 2015, vol. 13(11), pp. 2610-2620.
Miltenyi Biotec, "CD4+ T Cell Isolation Kit human," MACS, 2015, Retrieved on Mar. 6, 2023, Retrieved from Internet URL: http://www.ulab360.com/files/prod/manuals/201606/30/598263001.pdf, 3 pages.
Mochizuki M et al., "HTLV-I Uveitis: A Distinct Clinical Entity Caused by HTLV-1," Japanese Journal of Cancer Research, Mar. 1992, vol. 83, No. 3, pp. 236-239.
Mochizuki S., et al., "Long-Term Correction of Hyperphenylalaninemia by AAV-Mediated Gene Transfer Leads to Behavioral Recovery in Phenylketonuria Mice," Gene Therapy, 2004, vol. 11 (13), pp. 1081-1086.
Moser B., et al., "γ T Cells: Novel Initiators of Adaptive Immunity," Immunological Reviews, Feb. 2, 2007, vol. 215, pp. 89-102.
Mosley A.J., et al., "Cell-Mediated Immune Response to Human T-Lymphotropic Virus Type I," Viral Immunology, 2005, vol. 18, No. 2, pp. 293-305.
Munoz N.M., et al., "Ex Vivo Expansion and Lentiviral Transduction of Macaca Nemestrina CD4 + T Cells," Journal of Medical Primatology, Dec. 2009, vol. 38, No. 6, pp. 438-443.
Nada M.H., et al., "Enhancing Adoptive Cancer Immunotherapy with Vγ2Vδ2 T Cells Through Pulse Zoledronate Stimulation," Journal for Immunotherapy of Cancer, Feb. 21, 2017, vol. 5, No. 1, pp. 1-23, DOI: 10.1186/S40425-017-0209-6, XP021242440.
Nagai M., et al., "Human T-Cell Lymphotropic Virus Type I and Neurological Diseases," Journal of NeuroVirology, Apr. 2003, vol. 9, No. 2, pp. 228-235.
Nault J-C., et al., "Adeno-Associated Virus Type 2 as an Oncogenic Virus in Human Hepatocellular Carcinoma," Molecular & Cellular Oncology, 2016, vol. 3, No. 2, 4 Pages, e1095271.
NCBI: "Human Prothrombin Gene Liver-specific Enhancer," Nucleotide, Database Accession No. M65141.1,Apr. 27, 1993, 01 page, XP055613203, [Retrieved on Mar. 31, 2019] Retrieved from URL: https://www.ncbi.ntm.nih.goV/nuccore/M65141.1.
Nishioka K., et al., "Chronic Inflammatory Arthropathy Associated With HTLV-1," The Lancet, Feb. 25, 1989, vol. 1, No. 8635, 1 Page.
Non-Final Office Action for U.S. Appl. No. 13/333,882, mailed Apr. 18, 2019, 11 Pages.
Non-Final Office Action for U.S. Appl. No. 13/333,882, mailed Feb. 22, 2018, 08 Pages.
Non-Final Office Action for U.S. Appl. No. 15/580,661, mailed Jan. 13, 2020, 11 Pages.
Non-Final Office Action for U.S. Appl. No. 15/580,661, mailed Feb. 19, 2021, 27 Pages.
Non-Final Office Action for U.S. Appl. No. 15/736,284, mailed Oct. 19, 2018, 26 Pages.
Non-Final Office Action for U.S. Appl. No. 15/736,284, mailed Jun. 27, 2022, 34 Pages.
Non-Final Office Action for U.S. Appl. No. 15/736,284, mailed Oct. 29, 2020, 26 Pages.
Non-Final Office Action for U.S. Appl. No. 15/849,062, mailed Feb. 22, 2018, 05 Pages.
Non-Final Office Action for U.S. Appl. No. 15/850,937, mailed Feb. 22, 2018, 05 Pages.

(56) References Cited

OTHER PUBLICATIONS

Non-Final Office Action for U.S. Appl. No. 15/904,131, mailed Jun. 15, 2018, 07 Pages.
Non-Final Office Action for U.S. Appl. No. 16/008,991, mailed May 7, 2019, 07 Pages.
Non-Final Office Action for U.S. Appl. No. 16/011,550, mailed Sep. 17, 2018, 8 Pages.
Non-Final Office Action for U.S. Appl. No. 16/076,655, dated Feb. 21, 2020, 45 Pages.
Non-Final Office Action for U.S. Appl. No. 16/083,384, mailed Mar. 16, 2020, 9 Pages.
Non-Final Office Action for U.S. Appl. No. 16/132,247, mailed May 16, 2019, 06 Pages.
Non-Final Office Action for U.S. Appl. No. 16/182,443, mailed Dec. 31, 2018, 10 Pages.
Non-Final Office Action for U.S. Appl. No. 16/218,010, mailed May 24, 2019, 06 Pages.
Non-Final Office Action for U.S. Appl. No. 16/308,373, mailed Sep. 22, 2020, 32 Pages.
Non-Final Office Action for U.S. Appl. No. 16/312,056, mailed Jul. 6, 2020, 23 Pages.
Non-Final Office Action for U.S. Appl. No. 16/312,056, mailed Nov. 17, 2021, 26 Pages.
Non-Final Office Action for U.S. Appl. No. 16/318,345, mailed Nov. 18, 2020, 12 Pages.
Non-Final Office Action for U.S. Appl. No. 16/530,908, mailed Jun. 1, 2020, 6 Pages.
Non-Final Office Action for U.S. Appl. No. 16/563,738, mailed Mar. 12, 2021, 11 Pages.
Non-Final Office Action for U.S. Appl. No. 16/943,800, mailed Nov. 25, 2020, 08 Pages.
Notice of Allowance for Israeli Application No. 284348, mailed Oct. 23, 2022, 3 pages.
Notice of Allowance for U.S. Appl. No. 13/333,882, mailed Nov. 27, 2019, 3 Pages.
Notice of Allowance for U.S. Appl. No. 13/333,882, mailed Oct. 29, 2019, 8 Pages.
Notice of Allowance for U.S. Appl. No. 14/706,481, mailed Oct. 13, 2019, 05 Pages.
Notice of Allowance for U.S. Appl. No. 15/652,080, mailed Nov. 2, 2017, 05 Pages.
Notice of Allowance for U.S. Appl. No. 15/668,223, mailed Mar. 26, 2018, 07 Pages.
Notice of Allowance for U.S. Appl. No. 15/849,062, mailed Apr. 26, 2018, 05 Pages.
Notice of Allowance for U.S. Appl. No. 15/850,937, mailed Apr. 23, 2018, 05 Pages.
Notice of Allowance for U.S. Appl. No. 15/904,131, mailed Aug. 10, 2018, 05 Pages.
Notice of Allowance for U.S. Appl. No. 16/008,991, mailed Aug. 14, 2019, 5 Pages.
Notice of Allowance for U.S. Appl. No. 16/011,550, mailed Oct. 31, 2018, 5 Pages.
Notice of Allowance for U.S. Appl. No. 16/076,655 mailed Dec. 2, 2020, 3 Pages.
Notice of Allowance for U.S. Appl. No. 16/083,384, mailed May 18, 2020, 8 Pages.
Notice of Allowance for U.S. Appl. No. 16/132,247, mailed Jul. 19, 2019, 05 Pages.
Notice of Allowance for U.S. Appl. No. 16/182,443, mailed Jul. 3, 2019, 3 Pages.
Notice of Allowance for U.S. Appl. No. 16/182,443, mailed Jun. 18, 2019, 5 Pages.
Notice of Allowance for U.S. Appl. No. 16/218,010, mailed Sep. 25, 2019, 8 Pages.
Notice of Allowance for U.S. Appl. No. 16/530,908, mailed Jul. 10, 2020, 05 Pages.
Notice of Allowance for U.S. Appl. No. 16/593,882, dated Jan. 26, 2021, 8 Pages.
Notice of Allowance for U.S. Appl. No. 16/687,525, mailed Jan. 13, 2021, 8 Pages.
Notice of Allowance for U.S. Appl. No. 16/943,800, mailed Feb. 10, 2021, 7 Pages.
Notice of Allowance for U.S. Appl. No. 17/175,278, mailed Nov. 9, 2022, 16 pages.
Notice of Allowance in Japanese Application No. 2018-541270, mailed Aug. 31, 2022, 6 Pages (with English translation).
Notice of Allowance in Japanese Application No. 2019-500475, mailed Sep. 15, 2021, 6 Pages, (with English translation).
Notice of Final Rejection for Japanese Patent Application No. 2018-536892, dated Nov. 16, 2020, 8 Pages.
Notice of Final Rejection in Japanese Application No. 2019-500423, mailed Apr. 27, 2022, 9 Pages (with English translation).
Notice of Final Rejection in Japanese Application No. 2019-536901, mailed Jul. 28, 2022, 12 Pages.
Notice of Reasons for Refusal in Japanese Application No. 2019-536901, mailed Nov. 19, 2021, 16 Pages, (with English translation).
Notice of Reasons for Rejection for Japanese Patent Application No. 2018-547354, mailed Feb. 16, 2021, 22 Pages.
Notice of Reasons for Rejection in Application No. 2021-84813, mailed Jun. 23, 2022, 6 Pages.
Notice of Reasons for Rejection in Japanese Application No. 2019-500423, dated Jun. 2, 2021, 9 Pages.
Notice of Reasons for Rejection in Japanese Application No. 2019-500475, dated Mar. 4, 2021, 6 Pages.
Nowacki P., et al., "The PAH Mutation Analysis Consortium Database: Update 1996," Nucleic Acids Research, Jan. 1, 1997, vol. 25, No. 1, pp. 139-142, DOI: 10.1093/nar/25.1.139, XP055707752.
Nucleotide: "Human Papillomavirus Type 16 (HPV16), Complete Genome," GenBank: K02718.1, Publication [online], Mar. 18, 1994, 4 Pages, Retrieved from URL:https://www.ncbi.nlm.nih.gov/nucleotide/333031?report=genbank&log$=nucltop&blast_rank=22&RID=H3E1THFU014.
Nucleotide: "{Long Control Region} [Human Papillomavirus, type 16, Genomic, 660 nt]," Accession S60559, Publication (online), May 7, 1993 [Retrieved May 9, 2017], 1 Page, XP055455689, Retrieved from URL:https://www.ncbi. nlm.nih.gov/nucleotide/237343?report=genbank&log$=nucltop&blast_rank=I&RID=H3FCKA00014.
Office Action for Canadian Patent Application No. 3028982, mailed May 17, 2023, 7 pages.
Office Action for Chinese Application No. 202010396594.8, mailed Jan. 15, 2021, 12 Pages.
Office Action for Chinese Patent Application No. 201880016715, mailed Nov. 15, 2022, 13 pages.
Office Action for Chinese Patent Application No. 201880016715.2, mailed Dec. 24, 2022, 25 Pages.
Office Action for European Patent Application No. 18736295.9, mailed Dec. 20, 2022, 10 pages.
Office Action for European Patent Application No. 18736295.9, mailed Jan. 25, 2023, 10 pages.
Office Action for Indian Application No. 201947000153, mailed Oct. 28, 2022, 8 pages.
Office Action for Israel Patent Application No. 266188.3, mailed Nov. 21, 2022, 6 pages.
Office Action for Israel Patent Application No. 267794, mailed Nov. 21, 2022, 11 pages.
Office Action for Japanese Application No. 2017-564550, mailed Mar. 18, 2020, 12 Pages.
Office Action for Japanese Application No. 2017-567175, mailed Jun. 15, 2020, 7 Pages.
Office Action for Japanese Application No. 2018-536892, mailed Jun. 26, 2020, 07 Pages.
Office Action for Japanese Application No. 2018-563892 mailed Oct. 14, 2020, 11 Pages.
Office Action for Japanese Patent Application No. 2019-500475, mailed Jun. 12, 2020, 11 Pages.
Office Action for Japanese Patent Application No. 2019536901, mailed Mar. 3, 2023, 6 pages.
Office Action for Japanese Patent Application No. 2020551499, mailed Mar. 10, 2023, 10 pages.

(56) References Cited

OTHER PUBLICATIONS

Office Action for Japanese Patent Application No. 2021084813, mailed Feb. 10, 2023, 10 pages.
Office Action for Japanese Patent Application No. 2021174409, mailed May 2, 2023, 13 pages.
Office Action for Japanese Patent Application No. 2021174409, mailed Nov. 7, 2022, 4 pages.
Office Action for Japanese Patent Application No. 2022071538, mailed Apr. 4, 2023, 9 pages.
Office Action for Japanese Patent Application No. 2022133225, mailed Jun. 26, 2023, 10 Pages.
Office Action for Korean Patent Application No. 10-2019-7023287, mailed Apr. 21, 2023, 6 pages.
Office Action for U.S. Appl. No. 16/476,529, mailed Dec. 23, 2022, 65 pages.
Office Action in Brazil Application No. BR112019014082-4, mailed Jul. 26, 2022, 3 Pages.
Office Action in European Application No. 16822021, mailed Oct. 7, 2021, 4 Pages.
Office Action in European Application No. 17750547.6, mailed Apr. 29, 2022, 4 Pages.
Office Action in Israel Application No. 284348, mailed Jun. 12, 2022, 3 Pages.
Office Action in the EPO Application No. 16808223.8, mailed May 11, 2020, 5 Pages.
Office Action in the Japanese Application No. 2018-541270, mailed Jan. 8, 2021, 8 Pages.
Oh H-J., et al., "Reversal of Gene Expression Profile in the Phenylketonuria Mouse Model After Adeno-Associated Virus Vector-Mediated Gene Therapy," Molecular Genetics and Metabolism, 2005, vol. 86, Supplement. 1, pp. S124-S132.
Oh H-J., et al.. "Long-Term Enzymatic and Phenotypic Correction in the Phenylketonuria Mouse Model by Adeno-Associated Virus Vector-Mediated Gene Transfer," Pediatric Research, 2004, vol. 56, No. 2, pp. 278-284.
Oh T., et al., "Lentiviral Vector Design Using Alternative RNA Export Elements," Retrovirology, Jun. 5, 2007, vol. 4:38, pp. 1-10.
Olsen A.L. et al., "PARP Inhibitors and Parkinson's Disease," Clinical Implications of Basic Research, Jan. 31, 2019, pp. 492-494, XP55672111, [Retrieved on Feb. 27, 2020], Retrieved from URL:https://mfprac.com/web2019/07literature/literature/Neurology/ParkinsonPARPI_Olsen. pdf, *the whole document*.
Osame M., et al., "HTLV-I Associated Myelopathy, A New Clinical Entity," The Lancet, May 3, 1986, vol. 1, No. 8488, pp. 1031-1032.
Ostertag D., et al., "Brain Tumor Eradication and Prolonged Survival from Intratumoral Conversion of 5-Fluorocytosine to 5-fluorouracil Using a Nonlytic Retroviral Replicating Vector," Neoro-Oncology, Feb. 2012, vol. 14(2), pp. 145-159.
Pallikkuth S., et al., "Human Immunodeficiency Virus (HIV) Gag Anti-Specific T- Helperand Granule-Dependent CD8 T-Cell Activities in Exposed but Uninfected Heterosexual Partners of HIV Type 1-Infected Individuals in North India," Clinical and Vaccine Immunology, Sep. 2007, vol. 14, No. 9, pp. 1196-1202.
Pan D., et al., "Biodistribution and Toxicity Studies of VSVG-Pseudotyped Lentiviral Vector After Intravenous Administration in Mice with the Observation of in Vivo Transduction of Bone Marrow," Molecular Therapy, Jul. 2002, vol. 6, No. 1, pp. 19-29.
PCT Application No. PCT/CN2016/094828, filed Aug. 12, 2016, 85 Pages.
Poiesz B. J., et al., "Detection And Isolation Of Type C Retrovirus Particles From Fresh And Cultured Lymphocytes Of A Patient With Cutaneous T-cell Lymphoma," Proceedings of the National Academy of Sciences of the United States of America, Dec. 1980, vol. 77, No. 12, pp. 7415-7419.
Poiesz B.J., "T-cell Lines Established From Human T-lymphocytic Neoplasias By Direct Response To T-cell Growth Factor," Proceedings of the National Academy of Sciences of the United States of America, Nov. 1980, vol. 77, No. 11, pp. 6815-6819.
Poonia B., et al., "Gamma Delta T Cells From HIV+ Donors Can Be Expanded In Vitro By Zoledronate/Interleukin-2 To Become Cytotoxic Effectors For Antibody-dependent Cellular Cytotoxicity," Cytotherapy, 2012, vol. 14, No. 2, pp. 173-181.
Porichis F., et al., "HIV-specific CD4 T Cells and Immune Control of Viral Replication," Current Opinion in HIV and Aids, US, May 2011, vol. 6, No. 3, pp. 174-180, DOI: 10.1097/COH.0b013e3283454058, ISSN 1746-630X, XP055527164.
Quan J-J., et al., "Parp3 Interacts with FoxM1 to Confer Glioblastoma Cell Radio Resistance," Tumor Biology, Karger, BaseL CH, Published online on Jun. 4, 2015, vol. 36, No. 11, pp. 8617-8624, ISSN: 1010-4283, DOI: 10.1007/SI3277-015-3554-4, XP036217799.
Rana S., et al., "Role of CCR5 in Infection of Primary Macrophages and Lymphocytes by Macrophage-Tropic Strains of Human Immunodeficiency Virus: Resistance to Patient-Derived and Prototype Isolates Resulting from the delta ccr5 Mutation," Journal of Virology, Apr. 1997, vol. 71, No. 4, pp. 3219-3227.
Requirement for Restriction for U.S. Appl. No. 15/736,284, mailed Jul. 12, 2018, 9 Pages.
Restriction Requirement for U.S. Appl. No. 15/580,661, mailed Oct. 22, 2019, 14 Pages.
Restriction Requirement for U.S. Appl. No. 15/668,223, mailed Oct. 23, 2017, 06 Pages.
Restriction Requirement for U.S. Appl. No. 16/011,550, mailed Aug. 3, 2018, 06 Pages.
Restriction Requirement for U.S. Appl. No. 16/076,655, mailed Nov. 4, 2019, 8 Pages.
Restriction Requirement for U.S. Appl. No. 16/083,384, mailed Nov. 7, 2019, 8 Pages.
Restriction Requirement for U.S. Appl. No. 16/308,373, mailed Jun. 15, 2020, 16 Pages.
Restriction Requirement for U.S. Appl. No. 16/312,056, mailed Jan. 29, 2020, 7 Pages.
Restriction Requirement for U.S. Appl. No. 16/318,345, mailed Jun. 26, 2020, 9 Pages.
Restriction Requirement for U.S. Appl. No. 16/563,738, mailed Dec. 8, 2020,6 Pages.
Restriction Requirement for U.S. Appl. No. 16/593,882, mailed Nov. 19, 2020, 06 Pages.
Roc L., et al., "Rapid Subacute Myelopathy Following Kidney Transplantation From Htlv-1 Donors: Role Of Immunosuppresors And Failure Of Antiretrovirals," Therapeutic Advances in Infectious Disease, Jan.-Dec. 2019, vol. 6, 11 Pages.
Rose R.D., et al., "Safety, Immunogenicity and Efficacy of Peptide-Pulsed Cellular Immunotherapy in Macaques," Journal of Medical Primatology, 2008, vol. 37(2), pp. 69-78.
Schiller C.B., et al., "CD19-Specific Triplebody SPM-1 Engages NK and y T Cells for Rapid and Efficient Lysis of Malignant B-Lymphoid Cells," Oncotarget, 2016, vol. 7(50), pp. 83392-83408.
Schiller D.S., et al., "Parameters Influencing Measurement of the Gag Antigen-Specific T-Proliferative Response to HIV Type 1 Infection," AIDS Research and Human Retroviruses, US, 2000, vol. 16, No. 03, pp. 259-271, DOI: 10.1089/088922200309359, ISSN 0889-2229, XP055617438.
Seedorf et al., "Human Papillomavirus Type 16 DNA Sequence," Virology, Aug. 1985, vol. 145, pp. 181-185.
Shedlovsky A., et al., "Mouse Models of Human Phenylketonuria," Genetics, Aug. 1993, vol. 134, No. 4, pp. 1205-1210.
Smith P.L., et al., "Developments in HIV-1 Immunotherapy and Therapeutic Vaccination," F1000Prime Reports, Jun. 2, 2014, vol. 06, No. 43, 12 Pages.
Soker S., et al., "Neuropilin-1 is Expressed by Endothelial and Tumor Cells as an Isoform-Specific Receptor for Vascular Endothelial Growth Factor," Cell, Mar. 20, 1998, vol. 92, No. 06, pp. 735-745.
Spanevello et al., "Development of Lentiviral Vectors Simultaneously Expressing Multiple siRNAs Against CCR5, vif and tat/rev Genes for an HIV-1 Gene Therapy Approach," Molecular Therapy—Nucleic Acids, (Apr. 19, 2016), vol. 5, e312, ISSN 0004386246, pp. 1-12.
Spanevello F., et al., "Combinatorial RNA Interference as a Gene Therapy Strategy for HIV-1 Infection," Retrovirology, 2013, vol. 10 (Supp 1): p. 85, 2 pages.
Spartevello F., et al., "Development of Lentiviral Vectors Simultaneously Expressing Multiple siRNAs Against CCR5, vif and tat/rev

(56) References Cited

OTHER PUBLICATIONS

Genes for an HIV-1 Gene Therapy Approach," Molecular TherapyNucleic Acids, Apr. 19, 2016, vol. 5, pp. 1-12.
Stunkel W., et al., "The Chromatin Structure of the Long Control Region of Human Papillomavirus Type 16 Represses Viral Oncoprotein Expression," Journal of Virology, Mar. 1999, vol. 73, No. 3, pp. 1918-1930.
Sverdrup FM., et al., "Development of Human Papillomavirus Plasmids Capable of Episomal Replication in Human Cell Lines," Gene Therapy, Mar. 26, 1999, pp. 1317-1321, Retrieved from URL: http://www.stockton-pressco.uk/gt.
Tebas P., et al., "Antiviral Effects Of Autologous CD4 T Cells Genetically Modified With A Conditionally Replicating Lentiviral Vector Expressing Long Antisense To HIV," Pre published on Dec. 20, 2012, Blood, Feb. 28, 2013, vol. 121, No. 9, pp. 1524-1533, XP055345565.
Tebas P., et al., "Gene Editing of CCR5 in Autologous CD4 T Cells of Persons Infected with HIV," The New England Journal of Medicine, Mar. 6, 2014, vol. 370, No. 10, pp. 901-910, DOI:10.1056/NEJMoa1300662, ISSN 0028-4793, XP055172314.
Thompson K., et al., "Alkylamines Cause Vγ9Vδ2 T-cell Activation and Proliferation by Inhibiting the Mevalonate Pathway," Blood, Jan. 15, 2006, vol. 107, No. 2, pp. 651-654.
Tokuyama H., et al., "Vγ9Vδ2 T Cell Cytotoxicity Against Tumor Cells is Enhanced by Monoclonal Antibody Drugs—Rituximab and Trastuzumab," International Journal of Cancer, 2008, vol. 122 (11), pp. 2526-2534.
Tolmachov O.E., et al., "Designing Lentiviral Gene Vectors," Viral Gene Therapy, Jul. 20, 2011, Chapter. 13, 23 Pages, ISBN: 978-953-307-539-6, Retrieved from URL: http://www.intechopen.com/books/viral-gene-therapy/designing-lentiviral-gene-vectors.
Tracey A., "Human DNA Sequence from Clone RP1-288M22 on Chromosome 6q 12-13, Complete Sequence," National Center for Biotechnology, GenBank Entry, Jan. 24, 2013, pp. 1-34, Retrieved from URL:https://www.ncbi.nlm.nih.gov/nucleotide/AL035467.23?report=genbank&log$=nucltop& blast_rank=1&RID=UUD4GX2DO14.
Twitty C.G., et al., "Retroviral Replicating Vectors Deliver Cytosine Deaminase Leading to Targeted 5-Fluorouracil-Mediated Cytotoxicity in Multiple Human Cancer Types," Human Gene Therapy Methods, Feb. 1, 2016, vol. 27, No. 1, pp. 17-31.
Uchiyama T., et al., "Adult T-Cell Leukemia: Clinical and Hematologic Features of 16 Cases," Blood, Sep. 1977, vol. 50, No. 03, pp. 481-492.
Vargas J., Jr., et al., "Novel Integrase-defective Lentiviral Episomal Vectors For Gene Transfer", Human Gene Therapy, Liebert, US, Apr. 2004, vol. 15, No. 4, pp. 361-372, DOI: 10.1089/104303404322959515, ISSN 1043-0342, XP001205920.
Vargas Jr J., et al., "Conditionally Replicating Lentiviral-Hybrid Episomal Vectors for Suicide Gene Therapy," Antiviral Research, Elsevier BV, NL, Dec. 1, 2008, Jul. 21, 2008, vol. 80, No. 3, pp. 288-294, DOI: 10.1016/J.ANTIVIRAL.2008.06.015, ISSN 0166-3542, XP025684743.
Venturini S., et al., "Characterization of Human Immunodeficiency Virus Type 1 (HIV-1) Gag- and Gag Peptide-Specific CD4+ T-Cell Clones from an HIIV-1-Seronegative Donor following In Vitro Immunization," Journal of Virology, Jul. 2002, vol. 76, No. 14, pp. 6987-6999.
Wang H., et al., "Butyrophilin 3A1 Plays An Essential Role In Prenyl Pyrophosphate Stimulation Of Human Vγ2Vδ2 T cell," The Journal of Immunology, 2013, vol. 191, No. 3, pp. 1029-1042, DOI:10.4049/jimmunol.1300658, ISSN 0004789817, XP055557660.
Wang H., et al., "Indirect Stimulation of Human Vγ2Vδ2 T Cells through Alterations in Isoprenoid Metabolism," Journal of Immunology, 2011, vol. 187, pp. 5099-5113.
Wang H-B., et al., "HIV Vaccine Research: The Challenge and the Way Forward," Journal of Immunology Research, 2015, vol. 2015, Article. 503978, 5 pages.
Wang Y., et al., "Intravenous Delivery of SIRNA Targeting CD47 Effectively Inhibits Melanoma TumorGrmYth and Lung Metastasis," Molecular Therapy, Oct. 2013, vol. 21, No. 10, pp. 1919-1929.
Wendelburg B.J., et al., "An Enhanced EBNA1 Variant With Reduced IR3 Domain for Long-term Episomal Maintenance and Transgene Expression of Orip-based Plasmids in Human Cells," Gene Therapy, Nature Publishing Group, GB, Oct. 6, 1998, vol. 5, pp. 1389-1399, DOI: 10.1038/SJ.GT.3300736, ISSN: 0969-7128, XP002931315.
Westerhout E.M., et al., "A Conditionally Replicating HIV-based Vector That Stably Expresses an Antiviral shRNA Against HIV-1 Replication," Molecular Therapy, The Journal of the American Society of Gene Therapy, Academic Press, Nature Publishing Group, US, May 11, 2006, vol. 14, No. 2, pp. 268-275, DOI: 10.1016/J.YMTHE.2006.03.018, ISSN 1525-0016, XP005524738.
Wolstein O., et al., "Preclinical Safety and Efficacy of an Anti-HIV-1 Lentiviral Vector Containing a Short Hairpin RNA to CCR5 and the C46 Fusion Inhibitor," Molecular Therapy—Methods & Clinical Development, 2014, vol. 1, No. 11, 15 Pages.
Written Opinion for International Application No. PCT/US2016/036519, mailed Nov. 7, 2016, 6 Pages.
Written Opinion for International Application No. PCT/US2016/041456, mailed Oct. 19, 2016, 6 Pages.
Written Opinion for International Application No. PCT/US2016/066185, mailed Jun. 9, 2017, 12 Pages.
Written Opinion for International Application No. PCT/US2017/013019, mailed Jul. 17, 2017, 5 Pages.
Written Opinion for International Application No. PCT/US2017/013024, mailed Jul. 14, 2017, 7 Pages.
Written Opinion for International Application No. PCT/US2017/013399, mailed May 26, 2017, 8 Pages.
Written Opinion for International Application No. PCT/US2017/021639, mailed Aug. 25, 2017, 7 Pages.
Written Opinion for International Application No. PCT/US2017/036433, mailed Dec. 15, 2017, 10 Pages.
Written Opinion for International Application No. PCT/US2017/041168, mailed Nov. 8, 2017, 8 Pages.
Written Opinion for International Application No. PCT/US2017/043157, mailed Dec. 26, 2017, 10 Pages.
Written Opinion for International Application No. PCT/US2018/012998, mailed May 29, 2018, 07 Pages.
Written Opinion for International Application No. PCT/US2018/025733, mailed Sep. 24, 2018, 07 Pages.
Written Opinion for International Application No. PCT/US2018/037924, mailed Nov. 9, 2018, 11 Pages.
Written Opinion for International Application No. PCT/US2018/053919, mailed Apr. 12, 2019, 8 Pages.
Yagi H., et al., "Complete Restoration of Phenylalanine Oxidation in Phenylketonuria Mouse by a Self-Complementary Adena-Associated Virus Vector," Journal of Gene Medicine, 2011, vol. 13(2), pp. 114-122.
Yamano Y., et al., "Clinical Pathophysiology of Human T-Lymphotropic Virus-Type 1-Associated Myelopathy/Tropical Spastic Paraparesis," Frontiers in Microbiology, Nov. 9, 2012, vol. 3, Article. 389, pp. 1-10.
Yang H.L., et al., "Construction of PARP-1 gene Silencing Cell Lines by Lentiviral-Mediated RNA Interference Technology," School of Public Health, Guangdong Medical College, 2006, 1 Page. (Abstract).
Yang J., et al., "Lentiviral-Mediated Silencing of Famelsyl Pyrophosphate Synthase through RNA Interference in Mice," Biomed Research International, 2015, vol. 2015, Article ID. 914026, 07 pages.
Yano S., et al., "Evaluation of Tetrahydrobiopterin Therapy with Large Neutral Amino Acid Supplementation in Phenylketonuria: Effects on Potential Peripheral Biomarkers, Melatonin and Dopamine, for Brain Monoamine Neurotransmitters," PLoS One, Aug. 11, 2016, vol. 11(8), e0160892, 14 pages.
Ye Y., et al., "Knockdown of Farnesylpyrophosphate Synthase Prevents Angiotensin II-Medicated Cardiac Hypertrophy," The International Journal of Biochemistry & Cell Biology, 2010, vol. 42, pp. 2056-2064.

(56) References Cited

OTHER PUBLICATIONS

Yokota T., "Gene Therapy of Virus Replication with RNAi," Virus, 2005, vol. 55, No. 1, pp. 1-8.

Yoo L., et al., "PARP-1 Regulates the Expression of Caspase-11," Biochemical and Biophysical Research Communications, Apr. 22, 2011, vol. 408, No. 3, pp. 489-493, DOI: 10.1016/ J. BBRC.20 11.04.070, ISSN: 0006-291X, XP028209824.

Zhang Z., et al., "Uracils at Nucleotide Position 9-11 are Required for the Rapid Turnover of miR-29 Family," Nucleic Acids Research, 2011, vol. 39, No. 10, pp. 4387-4398.

Zufferey R., et al., "Self-Inactivating Lentivirus Vector for Safe and Efficient In Vivo Gene Delivery," Journal of Virology, Dec. 1998, vol. 72(12), pp. 9873-9880.

CN; Office Action issued in Application No. 201880016715.2 on Sep. 21, 2023.

KR; Office Action issued in Application No. 10-2023-7020872 on Sep. 26, 2023.

US; Office Action issued in U.S. Appl. No. 16/476,529 on Sep. 29, 2023.

KR; Office Action issued in Application No. 10-2019-7023287 on Oct. 11, 2023.

Hill et al., "Functional and Evolutionary Significance of Human MicroRNA Seed Region Mutations," PLoS ONE 9(12), e115241, pp. 1-13, Dec. 2014.

JP; Office Action issued in Application No. 2022-071538 on Dec. 21, 2023.

CA; Office Action issued in Application No. 3048634 on Jan. 11, 2024.

CN; Office Action issued in Application No. 201880016715.2 on Jan. 23, 2024.

JP; Office Action issued in Application No. 2021-174409 on Jan. 17, 2024.

Prebensen et al., "Regulation of Gag- and Env-Specific CD8* T Cell Responses in ART-Naïve HIV-Infected Patients: Potential Implications for Individualized Immunotherapy," PloS ONE 9(12), e115241, pp. 1-13, Dec. 2014.

Lam et al., "Broadly-Specific Cytotoxic T Cells Targeting Multiple HIV Antigens Are Expanded From HIV+ Patients: Implications for Immunotherapy," Molecular Therapy, vol. 23, No. 2, pp. 387-295, Feb. 2015.

US; Office Action issued in U.S. Appl. No. 17/042,043 on Dec. 6, 2023.

JP; Office Action issued in Application No. 2021-84813 on Oct. 31, 2023.

JP; Office Action issued in Application No. 2020-551499 on Nov. 22, 2023.

JP; Office Action issued in Application No. 2022-189475 on Oct. 10, 2023.

Kuhlmann et al. "Long-Term Persistence of Anti-HIV Broadly Neutralizing Antibody-Secreting Hematopoietic Cells in Humanized Mice," Molecular Therapy, vol. 27, No. 1, pp. 164-177, Jan. 1, 2019.

Yongjiao et al., "Expression of HIV-1 Broadly Neutralizing Antibodies Mediated By Recombinant Adeno-Associated Virus 8 In Vitro and In Vivo," Molecular Immunology, vol. 80, pp. 68-77, 2016.

Falkenhagen et al., "Control of HIV Infection In Vivo Using Gene Therapy with a Secreted Entry Inhibitor," Molecular Therapy-Nucleic Acids, vol. 9, pp. 132-144, Dec. 1, 2017.

EP; Office Action issued in Application No. 17750547.6 on Feb. 23, 2024.

IN; Office Action issued in Application No. 201947031955 on Feb. 23, 2024.

AU; Office Action issued in Application No. 2018205388 on Mar. 1, 2024.

KR; Decision for Grant issued in Application No. 10-2019-7023287 on Feb. 28, 2024.

JP; Office Action issued in Application No. 2022-133225 on Feb. 29, 2024.

AU; Office Action issued in Application No. 2018205388 on Feb. 26, 2024.

Elongation Factor-1 alpha (EF1-alpha) promoter (SEQ ID NO: 105)

*CCGGTGCCTAGAGAAGGTGGCGCGGGGTAAACTGGGAAAGTGATGTCGTGTACTGGCTCCGCCTT*
*TTTCCCGAGGGTGGGGGAGAACCGTATATAAGTGCAGTAGTCGCCGTGAACGTTCTTTTTCGCAA*
*CGGGTTTGCCGCCAGAACACAGGTAAGTGCCGTGTGTGGTTCCCGCGGGCCTGGCCTCTTTACGG*
*GTTATGGCCCTTGCGTGCCTTGAATTACTTCCACGCCCTGGCTGCAGTACGTGATTCTTGATCC*
*CGAGCTTCGGGTTGGAAGTGGGTGGAGAGTTCGAGGCCTTGCGCTTAAGGAGCCCCTTCGCCTC*
*GTGCTTGAGTTGAGGCCTGGCCTGGGCGCTGGGCCGCCGCGTGCAATCTGGTGGCACCTTCGC*
*GCCTGTCTCGCTGCTTTCGATAAGTCTCTAGCCATTTAAAATTTTTGATGACCTGCTGCGACGCT*
*TTTTTCTGGCAAGATAGTCTTGTAAATGCGGGCCAAGATCTGCACACTGGTATTTCGGTTTTTG*
*GGGCCGCGGGCGGCGACGGGCCCGTGCGTCCAGCGCACATGTTCGGCGAGGCGGGGCCTGCGA*
*GCGCGGCCACCGAGAATCGGACGGGGGTAGTCTCAAGCTGGCCGGCCTGCTCTGGTGCCTGGCCT*
*CGCGCCGCCGTGTATCGCCCCGCCCTGGGCGGCAAGGCTGGCCCGGTCGGCACCAGTTGCGTGAG*
*CGGAAAGATGGCCGCTTCCCGGCCCTGCTGCAGGGAGCTCAAAATGGAGGACGCGGCGCTCGGGA*
*GAGCGGGCGGGTGAGTCACCCACACAAGGAAAAGGGCCTTTCCGTCCTCAGCCGTCGCTTCATG*
*TGACTCCACGGAGTACCGGGCGCCGTCCAGGCACCTCGATTAGTTCTCGAGCTTTTGGAGTACGT*
*CGTCTTTAGGTTGGGGGAGGGGTTTTATGCGATGGAGTTTCCCCACACTGAGTGGGTGGAGACT*
*GAAGTTAGGCCAGCTTGGCACTTGATGTAATTCTCCTTGGAATTTGCCCTTTTTGAGTTTGGATC*
*TTGGTTCATTCTCAAGCCTCAGACAGTGGTTCAAAGTTTTTTCTTCCATTTCAGGTGTCGTGAT*
*GTACA* miR30 CCR5 (SEQ ID NO: 1)
<u>AGGTATATTGCTGTTGACAGTGAGCGACTGTAAACTGAGCTTGCTCTACTGTGAAGCCACAGATG</u>
<u>GGTAGAGCAAGCACAGTTTACCGCTGCCTACTGCCTCGGACTTCAAGGGGCTT</u> miR21 Vif (SEQ ID NO: 106)
CCCGGG<u>CATCTCCATGGCTGTACCACCTTGTCGGGGATGTGTACTTCTGAACTTGTGTTGAATC</u>
<u>TCATGGAGTTCAGAAGAACACATCCGCACTGACATTTTGGTATCTTTCATCTGACCA</u> miR185 Tat (SEQ ID NO: 107; SEQ ID NO: 108 (underlined portion))
GCTAGC<u>GGGCCTGGCTCGAGCAGGGGGCGAGGGATTCCGCTTCTTCCTGCCATAGCGTGGTCCCC</u>
<u>TCCCCTATGGCAGGCAGAAGCGGCACCTTCCCTCCCAATGACCGCGTCTTCGTC</u>

FIG. 6

Vector 1
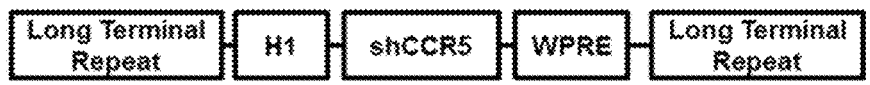
Vector 2
Vector 3
Vector 4
Vector 5
Vector 6
Vector 7
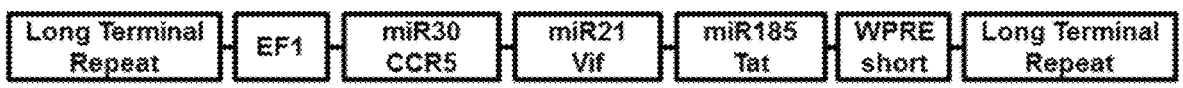
Vector 8
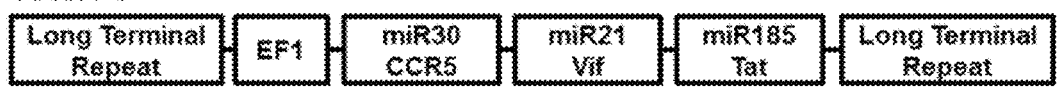
Vector 9
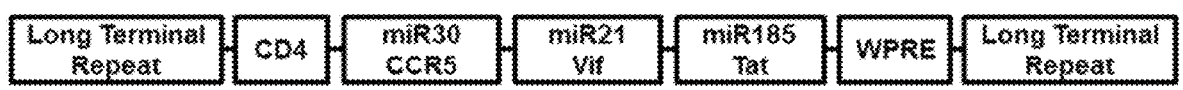
FIG. 7

SEQUENCE LISTING

```
Sequence total quantity: 108
SEQ ID NO: 1            moltype = DNA  length = 118
FEATURE                 Location/Qualifiers
misc_feature            1..118
                        note = miR30 CCR5
source                  1..118
                        mol_type = other DNA
                        organism = synthetic construct
```

```
SEQUENCE: 1
aggtatattg ctgttgacag tgagcgactg taaactgagc ttgctctact gtgaagccac   60
agatgggtag agcaagcaca gtttaccgct gcctactgcc tcggacttca aggggctt    118

SEQ ID NO: 2              moltype = DNA   length = 116
FEATURE                   Location/Qualifiers
misc_feature              1..116
                          note = miR21 Vif
source                    1..116
                          mol_type = other DNA
                          organism = synthetic construct
SEQUENCE: 2
catctccatg gctgtaccac cttgtcgggg gatgtgtact tctgaacttg tgttgaatct   60
catggagttc agaagaacac atccgcactg acattttggt atctttcatc tgacca      116

SEQ ID NO: 3              moltype = DNA   length = 114
FEATURE                   Location/Qualifiers
misc_feature              1..114
                          note = miR185 Tat
source                    1..114
                          mol_type = other DNA
                          organism = synthetic construct
SEQUENCE: 3
gggcctggct cgagcagggg gcgaggggatt ccgcttcttc ctgccatagc gtggtcccct   60
cccctatggc aggcagaagc ggcaccttcc ctcccaatga ccgcgtcttc gtcg        114

SEQ ID NO: 4              moltype = DNA   length = 1104
FEATURE                   Location/Qualifiers
misc_feature              1..1104
                          note = Elongation Factor-1 alpha (EF1-alpha) promoter
source                    1..1104
                          mol_type = other DNA
                          organism = synthetic construct
SEQUENCE: 4
ccggtgccta gagaaggtgg cgcggggtaa actgggaaag tgatgtcgtg tactggctcc   60
gcctttttcc cgagggtggg ggagaaccgt atataagtgc agtagtcgcc gtgaacgttc  120
tttttcgcaa cgggtttgcc gccagaacac aggtaagtgc cgtgtgtggt tcccgcgggc  180
ctggcctctt tacgggttat ggcccttgcg tgccttgaat tacttccacg ccctggctg   240
cagtacgtga ttcttgatcc cgagcttcgg gttggaagtg ggtgggagag ttcgaggcct  300
tgcgcttaag gagccccttc gcctcgtgct tgagttgagg cctggcctgg gcgctgggcc  360
cgccgcgtgc gaatctggtg gcaccttcgc gcctgtctcg ctgctttcga taagtctcta  420
gccatttaaa attttttgatg acctgctgcg acgctttttt tctggcaaga tagtcttgta  480
aatgcgggcc aagatctgca cactggtatt tcggttttg gggccgcggg cggcgacggg   540
gcccgtgcgt cccagcgcac atgttcggcc aggcggggcc tgcgagcgcg gccaccgaga  600
atcgacgggg ggtagtctca agctggccgg cctgctctgg tgcctggcct cgcgccgccg  660
tgtatcgccc cgccctgggc ggcaaggctg gcccggtcgg caccagttgc gtgagcgaa   720
agatgccgc ttcccggccc tgctgcaggg agctcaaaat ggaggacggg cgctcggga   780
gagcgggcgg gtgagtcacc cacacaaagg aaaagggcct ttccgtcctc agccgtcgct  840
tcatgtgact ccacggagta ccgggcgccg tccaggcacc tcgattagtt ctcgagcttt  900
tggagtacgt cgtcttttagg ttggggggag gggttttatg cgatggagtt tccccacact  960
gagtgggtgg agactgaagt taggccagct tggcacttga tgtaattctc cttgaatttt  1020
gcccttttttg agtttggatc ttggttcatt ctcaagcctc agacagtggt tcaaagtttt  1080
tttcttccat ttcaggtgtc gtga                                         1104

SEQ ID NO: 5              moltype = DNA   length = 18
FEATURE                   Location/Qualifiers
misc_feature              1..18
                          note = CCR5 target sequence
source                    1..18
                          mol_type = other DNA
                          organism = synthetic construct
SEQUENCE: 5
gagcaagctc agtttaca                                                 18

SEQ ID NO: 6              moltype = DNA   length = 21
FEATURE                   Location/Qualifiers
misc_feature              1..21
                          note = Vif target sequence
source                    1..21
                          mol_type = other DNA
                          organism = synthetic construct
SEQUENCE: 6
gggatgtgta cttctgaact t                                             21

SEQ ID NO: 7              moltype = DNA   length = 20
FEATURE                   Location/Qualifiers
misc_feature              1..20
                          note = Tat target sequence
```

```
source                  1..20
                        mol_type = other DNA
                        organism = synthetic construct
SEQUENCE: 7
tccgcttctt cctgccatag                                                    20

SEQ ID NO: 8            moltype = DNA  length = 126
FEATURE                 Location/Qualifiers
misc_feature            1..126
                        note = TAR decoy sequence
source                  1..126
                        mol_type = other DNA
                        organism = synthetic construct
SEQUENCE: 8
cttgcaatga tgtcgtaatt tgcgtcttac ctcgttctcg acagcgacca gatctgagcc        60
tgggagctct ctggctgtca gtaagctggt acagaaggtt gacgaaaatt cttactgagc       120
aagaaa                                                                  126

SEQ ID NO: 9            moltype = DNA  length = 21
FEATURE                 Location/Qualifiers
misc_feature            1..21
                        note = Rev/Tat target sequence
source                  1..21
                        mol_type = other DNA
                        organism = synthetic construct
SEQUENCE: 9
gcggagacag cgacgaagag c                                                  21

SEQ ID NO: 10           moltype = DNA  length = 56
FEATURE                 Location/Qualifiers
misc_feature            1..56
                        note = Rev/Tat shRNA sequence
source                  1..56
                        mol_type = other DNA
                        organism = synthetic construct
SEQUENCE: 10
gcggagacag cgacgaagag cttcaagaga gctcttcgtc gctgtctccg ctttttt          56

SEQ ID NO: 11           moltype = DNA  length = 19
FEATURE                 Location/Qualifiers
misc_feature            1..19
                        note = Gag target sequence
source                  1..19
                        mol_type = other DNA
                        organism = synthetic construct
SEQUENCE: 11
gaagaaatga tgacagcat                                                     19

SEQ ID NO: 12           moltype = DNA  length = 52
FEATURE                 Location/Qualifiers
misc_feature            1..52
                        note = Gag shRNA sequence
source                  1..52
                        mol_type = other DNA
                        organism = synthetic construct
SEQUENCE: 12
gaagaaatga tgacagcatt tcaagagaat gctgtcatca tttcttcttt tt               52

SEQ ID NO: 13           moltype = DNA  length = 18
FEATURE                 Location/Qualifiers
misc_feature            1..18
                        note = Pol target sequence
source                  1..18
                        mol_type = other DNA
                        organism = synthetic construct
SEQUENCE: 13
caggagcaga tgatacag                                                      18

SEQ ID NO: 14           moltype = DNA  length = 47
FEATURE                 Location/Qualifiers
misc_feature            1..47
                        note = Pol shRNA sequence
source                  1..47
                        mol_type = other DNA
                        organism = synthetic construct
SEQUENCE: 14
caggagatga tacagttcaa gagactgtat catctgctcc tgttttt                     47

SEQ ID NO: 15           moltype = DNA  length = 19
```

```
FEATURE              Location/Qualifiers
misc_feature         1..19
                     note = CCR5 target sequence #1
source               1..19
                     mol_type = other DNA
                     organism = synthetic construct
SEQUENCE: 15
gtgtcaagtc caatctatg                                                    19

SEQ ID NO: 16        moltype = DNA  length = 52
FEATURE              Location/Qualifiers
misc_feature         1..52
                     note = CCR5 shRNA sequence #1
source               1..52
                     mol_type = other DNA
                     organism = synthetic construct
SEQUENCE: 16
gtgtcaagtc caatctatgt tcaagagaca tagattggac ttgacacttt tt               52

SEQ ID NO: 17        moltype = DNA  length = 19
FEATURE              Location/Qualifiers
misc_feature         1..19
                     note = CCR5 target sequence #2
source               1..19
                     mol_type = other DNA
                     organism = synthetic construct
SEQUENCE: 17
gagcatgact gacatctac                                                    19

SEQ ID NO: 18        moltype = DNA  length = 52
FEATURE              Location/Qualifiers
misc_feature         1..52
                     note = CCR5 shRNA sequence #2
source               1..52
                     mol_type = other DNA
                     organism = synthetic construct
SEQUENCE: 18
gagcatgact gacatctact tcaagagagt agatgtcagt catgctcttt tt               52

SEQ ID NO: 19        moltype = DNA  length = 19
FEATURE              Location/Qualifiers
misc_feature         1..19
                     note = CCR5 target sequence #3
source               1..19
                     mol_type = other DNA
                     organism = synthetic construct
SEQUENCE: 19
gtagctctaa caggttgga                                                    19

SEQ ID NO: 20        moltype = DNA  length = 52
FEATURE              Location/Qualifiers
misc_feature         1..52
                     note = CCR5 shRNA sequence #3
source               1..52
                     mol_type = other DNA
                     organism = synthetic construct
SEQUENCE: 20
gtagctctaa caggttggat tcaagagatc caacctgtta gagctacttt tt               52

SEQ ID NO: 21        moltype = DNA  length = 19
FEATURE              Location/Qualifiers
misc_feature         1..19
                     note = CCR5 target sequence #4
source               1..19
                     mol_type = other DNA
                     organism = synthetic construct
SEQUENCE: 21
gttcagaaac tacctctta                                                    19

SEQ ID NO: 22        moltype = DNA  length = 52
FEATURE              Location/Qualifiers
misc_feature         1..52
                     note = CCR5 shRNA sequence #4
source               1..52
                     mol_type = other DNA
                     organism = synthetic construct
SEQUENCE: 22
gttcagaaac tacctcttat tcaagagata agaggtagtt tctgaacttt tt               52
```

| | | |
|---|---|---|
| SEQ ID NO: 23<br>FEATURE<br>misc_feature<br><br>source | moltype = DNA   length = 20<br>Location/Qualifiers<br>1..20<br>note = CCR5 target sequence #5<br>1..20<br>mol_type = other DNA<br>organism = synthetic construct | |

SEQUENCE: 23
gagcaagctc agtttacacc                                              20

| | | |
|---|---|---|
| SEQ ID NO: 24<br>FEATURE<br>misc_feature<br><br>source | moltype = DNA   length = 54<br>Location/Qualifiers<br>1..54<br>note = CCR5 shRNA sequence #5<br>1..54<br>mol_type = other DNA<br>organism = synthetic construct | |

SEQUENCE: 24
gagcaagctc agtttacacc ttcaagagag gtgtaaactg agcttgctct tttt         54

| | | |
|---|---|---|
| SEQ ID NO: 25<br>FEATURE<br>misc_feature<br><br>source | moltype = DNA   length = 141<br>Location/Qualifiers<br>1..141<br>note = CCR5 gene, sequence 1<br>1..141<br>mol_type = other DNA<br>organism = synthetic construct | |

SEQUENCE: 25
atggattatc aagtgtcaag tccaatctat gacatcaatt attatacatc ggagccctgc   60
caaaaaatca atgtgaagca aatcgcagcc cgcctcctgc ctccgctcta ctcactggtg  120
ttcatctttg gttttgtggg c                                            141

| | | |
|---|---|---|
| SEQ ID NO: 26<br>FEATURE<br>misc_feature<br><br>source | moltype = DNA   length = 633<br>Location/Qualifiers<br>1..633<br>note = CCR5 gene, sequence 2<br>1..633<br>mol_type = other DNA<br>organism = synthetic construct | |

SEQUENCE: 26
aacatgctgg tcatcctcat cctgataaac tgcaaaaggc tgaagagcat gactgacatc   60
tacctgctca acctggccat ctctgacctg tttttccttc ttactgtccc cttctgggct  120
cactatgctg ccgcccagtg ggactttgga aatacaatgt gtcaactctt gacagggctc  180
tattttatag gcttcttctc tggaatcttc ttcatcatcc tcctgacaat cgataggtac  240
ctggctgtcg tccatgctgt gtttgcttta aaagccagga cggtcacctt ggggtggtg   300
acaagtgtga tcacttgggt ggtggctgtg tttgcgtctc tcccaggaat catctttacc  360
agatctcaaa aagaaggtct tcattacacc tgcagctctc attttccata cagtcagtat  420
caattctgga agaatttcca gacattaaag atagtcatct ggggctggt cctgccgctg  480
cttgtcatgg tcatctgcta ctcgggaatc ctaaaaactc tgcttcggtg tcgaaatgag  540
aagaagaggc acagggctgt gaggcttatc ttcaccatca tgattgttta ttttctcttc  600
tgggctccct acaacattgt ccttctcctg aac                               633

| | | |
|---|---|---|
| SEQ ID NO: 27<br>FEATURE<br>misc_feature<br><br>source | moltype = DNA   length = 70<br>Location/Qualifiers<br>1..70<br>note = CCR5 gene, sequence 3<br>1..70<br>mol_type = other DNA<br>organism = synthetic construct | |

SEQUENCE: 27
accttccagg aattctttgg cctgaataat tgcagtagct ctaacaggtt ggaccaagct   60
atgcaggtga                                                         70

| | | |
|---|---|---|
| SEQ ID NO: 28<br>FEATURE<br>misc_feature<br><br>source | moltype = DNA   length = 140<br>Location/Qualifiers<br>1..140<br>note = CCR5 gene, sequence 4<br>1..140<br>mol_type = other DNA<br>organism = synthetic construct | |

SEQUENCE: 28
cagagactct tgggatgacg cactgctgca tcaaccccat catctatgcc tttgtcgggg   60
agaagttcag aaactacctc ttagtcttct tccaaaagca cattgccaaa cgcttctgca  120
aatgctgttc tattttccag                                              140

| | | |
|---|---|---|
| SEQ ID NO: 29<br>FEATURE<br>misc_feature | moltype = DNA   length = 75<br>Location/Qualifiers<br>1..75<br>note = CCR5 gene, sequence 5 | |

```
source                    1..75
                          mol_type = other DNA
                          organism = synthetic construct
SEQUENCE: 29
caagaggctc ccgagcgagc aagctcagtt tacacccgat ccactgggga gcaggaaata    60
tctgtgggct tgtga                                                    75

SEQ ID NO: 30             moltype = DNA  length = 541
FEATURE                   Location/Qualifiers
misc_feature              1..541
                          note = CD4 promoter sequence
source                    1..541
                          mol_type = other DNA
                          organism = synthetic construct
SEQUENCE: 30
tgttggggtt caaatttgag ccccagctgt tagccctctg caaagaaaaa aaaaaaaaaa    60
aaagaacaaa gggcctagat ttcccttctg agccccaccc taagatgaag cctcttcttt   120
caagggagtg gggttggggt ggaggcggat cctgtcagct ttgctctctc tgtgtggctg   180
agtttctcca aagggtaaca ggtgtcagct ggctgagcgt aggctgaacc ctgagacatg   240
ctacctctgt cttctcatgg ctggaggcag cctttgtaag tcacagaaag tagctgaggg   300
gctctggaaa aaagacagcc agggtggagg tagattggtc tttgactcct gatttaagcc   360
tgattctgct taactttttc ccttgacttt ggcattttca ctttgacatg ttccctgaga   420
gcctgggggg tggggaaccc agctccagct ggtgacgttg ggggccggcc caggcctagg   480
gtgtggagga gccttgccat cgggcttcct gtctctcttc atttaagcac gactctgcag   540
a                                                                  541

SEQ ID NO: 31             moltype = DNA  length = 359
FEATURE                   Location/Qualifiers
misc_feature              1..359
                          note = miR30-CCR5/miR21-Vif/miR185 Tat microRNA cluster
                            sequence
source                    1..359
                          mol_type = other DNA
                          organism = synthetic construct
SEQUENCE: 31
aggtatattg ctgttgacag tgagcgactg taaactgagc ttgctctact gtgaagccac    60
agatgggtag agcaagcaca gtttaccgct gcctactgcc tcggacttca aggggcttcc   120
cgggcatctc catggctgta ccaccttgtc gggggatgtg tacttctgaa cttgtgttga   180
atctcatgga gttcagaaga acacatccgc actgacattt tggtatcttt catctgacca   240
gctagcgggc ctggctcgag caggggggcga gggattccgc ttcttcctgc catagctgtg   300
tccctcccc tatggcaggc agaagcggca ccttccctcc caatgaccgc gtcttcgtc    359

SEQ ID NO: 32             moltype = DNA  length = 590
FEATURE                   Location/Qualifiers
misc_feature              1..590
                          note = Long WPRE sequence
source                    1..590
                          mol_type = other DNA
                          organism = synthetic construct
SEQUENCE: 32
aatcaacctc tgattacaaa atttgtgaaa gattgactgg tattcttaac tatgttgctc    60
cttttacgct atgtggatac gctgcttaa tgcctttgta tcatgctatt gcttcccgta   120
tggctttcat tttctcctcc ttgtataaat cctggttgct gtctctttat gaggagttgt   180
ggcccgttgt caggcaacgt ggcgtggtgt gcactgtgtt tgctgacgca accccactg    240
gttgggcat tgccaccacc tgtcagctcc tttccgggac tttcgctttc ccctccccta   300
ttgccacggc ggaactcatc gccgcctgcc ttgcccgctg ctggacaggg gctcggctgt   360
tgggcactga caattccgtg gtgttgtcgg ggaaatcatc gtcctttcct ggctgctcg    420
cctgtgttgc cacctggatt ctgcgcggga cgtccttctg ctacgtccct tcggccctca   480
atccagcgga ccttccttcc gcggcctgc tgccggctct gcggcctctt ccgcgtcttc   540
gccttcgccc tcagacgagt cggatctccc tttgggccgc ctccccgcct               590

SEQ ID NO: 33             moltype = DNA  length = 1469
FEATURE                   Location/Qualifiers
misc_feature              1..1469
                          note = Elongation Factor-1 alpha (EF1-alpha) promoter -
                            miR30CCR5 - miR21Vif - miR185 Tat
source                    1..1469
                          mol_type = other DNA
                          organism = synthetic construct
SEQUENCE: 33
ccggtgccta gagaaggtgg cgcggggtaa actgggaaag tgatgtcgtg tactggctcc    60
gcctttttcc cgagggtggg ggagaaccgt atataagtgc agtagtcgcc gtgaacgttc   120
ttttttcgcaa cgggtttgcc gccagaacac aggtaagtgc cgtgtgtggt tcccgcgggc   180
ctggcctctt tacgggttat ggcccttgcg tgccttgaat tacttccacg cccctggctg   240
cagtacgtga ttcttgatcc cgagcttcgg gttggaagtg ggtgggagag ttcgaggcct   300
tgcgcttaag gagccccttc gcctcgtgct tgagttgagg cctggcctgg gcgctgggc    360
cgccgcgtgc gaatctggtg gcaccttcgc gcctgtctcg ctgctttcga taagtctcta   420
gccatttaaa attttgatg acctgctgcg acgcttttt tctggcaaga tagtcttgta   480
aatgcgggcc aagatctgca cactggtatt tcggtttttg gggccgcggg cggcgacggg   540
```

```
gcccgtgcgt cccagcgcac atgttcggcg aggcggggcc tgcgagcgcg gccaccgaga    600
atcggacggg ggtagtctca agctggccgg cctgctctgg tgcctggcct cgcgccgccg    660
tgtatcgccc cgccctgggc ggcaaggctg gcccggtcgg caccagttgc gtgagcggaa    720
agatggccgc ttcccggccc tgctgcaggg agctcaaaat ggaggacgcg gcgctcggga    780
gagcgggcgg gtgagtcacc cacacaaagg aaaagggcct ttccgtcctc agccgtcgct    840
tcatgtgact ccacggagta ccgggcgccg tccaggcacc tcgattagtt ctcgagcttt    900
tggagtacgc gtctcttagg ttggggggag gggttttatg cgatgagtt tccccacact     960
gagtgggtga agactgaagt taggccagct tggcacttga tgtaattctc cttggaattt   1020
gcccttttg agtttggatc ttggttcatt ctcaagcctc agacagtggt tcaaagtttt    1080
tttcttccat ttcaggtgtc gtgatgtaca aggtatattg ctgttgacag tgagcgactg   1140
taaactgagc ttgctctact gtgaagccac agatgggtag agcaagcaca gtttaccgct   1200
gcctactgcc tcggacttca aggggcttcc cgggcatctc catggctgta ccaccttgtc   1260
gggggatgtg tacttctgaa cttgtgttga atctcatgga gttcagaaga acacatccgc   1320
actgacattt tggtatcttt catctgacca gctagcgggc ctggctcgag caggggggcga  1380
gggattccgc ttcttcctgc catagcgtgg tcccctcccc tatggcaggc agaagcggca   1440
ccttccctcc caatgaccgc gtcttcgtc                                     1469

SEQ ID NO: 34          moltype = DNA   length = 228
FEATURE                Location/Qualifiers
misc_feature           1..228
                       note = Rous Sarcoma virus (RSV) promoter
source                 1..228
                       mol_type = other DNA
                       organism = synthetic construct
SEQUENCE: 34
gtagtcttat gcaatactct tgtagtcttg caacatggta acgatgagtt agcaacatgc    60
cttacaagga gagaaaaagc accgtgcatg ccgattggtg gaagtaaggt ggtacgatcg   120
tgccttatta ggaaggcaac agacgggtct gacatggatt ggacgaacca ctgaattgcc   180
gcattgcaga gatattgtat ttaagtgcct agctcgatac aataaacg                228

SEQ ID NO: 35          moltype = DNA   length = 180
FEATURE                Location/Qualifiers
misc_feature           1..180
                       note = 5' Long terminal repeat (LTR)
source                 1..180
                       mol_type = other DNA
                       organism = synthetic construct
SEQUENCE: 35
ggtctctctg gttagaccag atctgagcct gggagctctc tggctaacta gggaacccac    60
tgcttaagcc tcaataaagc ttgccttgag tgcttcaagt agtgtgtgcc cgtctgttgt   120
gtgactctgg taactagaga tccctcagac ccttttagtc agtgtggaaa atctctagca   180

SEQ ID NO: 36          moltype = DNA   length = 41
FEATURE                Location/Qualifiers
misc_feature           1..41
                       note = Psi Packaging signal
source                 1..41
                       mol_type = other DNA
                       organism = synthetic construct
SEQUENCE: 36
tacgccaaaa attttgacta gcggaggcta gaaggagaga g                        41

SEQ ID NO: 37          moltype = DNA   length = 233
FEATURE                Location/Qualifiers
misc_feature           1..233
                       note = Rev response element (RRE)
source                 1..233
                       mol_type = other DNA
                       organism = synthetic construct
SEQUENCE: 37
aggagctttg ttccttgggt tcttgggagc agcaggaagc actatgggcg cagcctcaat    60
gacgctgacg gtacaggcca gacaattatt gtctggtata gtgcagcagc agaacaattt   120
gctgagggct attgaggcgc aacagcatct gttgcaactc acagtctggg gcatcaagca   180
gctccaggca agaatcctgg ctgtggaaag atacctaaag gatcaacagc tcc           233

SEQ ID NO: 38          moltype = DNA   length = 118
FEATURE                Location/Qualifiers
misc_feature           1..118
                       note = Central polypurine tract (cPPT)
source                 1..118
                       mol_type = other DNA
                       organism = synthetic construct
SEQUENCE: 38
ttttaaaaga aaaggggggga ttggggggta cagtgcaggg gaaagaatag tagacataat   60
agcaacagac atacaaacta aagaattaca aaaacaaatt acaaaattca aaattttta    118

SEQ ID NO: 39          moltype = DNA   length = 250
FEATURE                Location/Qualifiers
```

| | | |
|---|---|---|
| misc_feature | 1..250 | |
| | note = 3' delta LTR | |
| source | 1..250 | |
| | mol_type = other DNA | |
| | organism = synthetic construct | |

SEQUENCE: 39

```
tggaagggct aattcactcc caacgaagat aagatctgct ttttgcttgt actgggtctc    60
tctggttaga ccagatctga gcctgggagc tctctggcta actagggaac ccactgctta   120
agcctcaata aagcttgcct tgagtgcttc aagtagtgtg tgcccgtctg ttgtgtgact   180
ctggtaacta gagatccctc agaccctttt agtcagtgtg aaaatctct agcagtagta    240
gttcatgtca                                                          250
```

| | | |
|---|---|---|
| SEQ ID NO: 40 | moltype = DNA   length = 352 | |
| FEATURE | Location/Qualifiers | |
| misc_feature | 1..352 | |
| | note = Helper/Rev - CMV early (CAG) enhancer - EnhanceTranscription | |
| source | 1..352 | |
| | mol_type = other DNA | |
| | organism = synthetic construct | |

SEQUENCE: 40

```
tagttattaa tagtaatcaa ttacggggtc attagttcat agcccatata tggagttccg    60
cgttacataa cttacggtaa atggcccgcc tggctgaccg cccaacgacc cccgcccatt   120
gacgtcaata atgacgtatg ttcccatagt aacgccaata gggactttcc attgacgtca   180
atgggtggac tatttacggt aaactgccca cttggcagta catcaagtgt atcatatgcc   240
aagtacgccc cctattgacg tcaatgacgg taaatggccc gcctggcatt atgcccagta   300
catgacctta tgggactttc ctacttggca gtacatctac gtattagtca tc           352
```

| | | |
|---|---|---|
| SEQ ID NO: 41 | moltype = DNA   length = 290 | |
| FEATURE | Location/Qualifiers | |
| misc_feature | 1..290 | |
| | note = Helper/Rev - Chicken beta actin (CAG) promoter - Transcription | |
| source | 1..290 | |
| | mol_type = other DNA | |
| | organism = synthetic construct | |

SEQUENCE: 41

```
gctattacca tgggtcgagg tgagccccac gttctgcttc actctcccca tctcccccc    60
ctccccaccc ccaattttgt atttatttat tttttaatta ttttgtgcag cgatgggggc   120
ggggggggggg ggggcgcgcg ccaggcgggg cggggcgggg cgaggggcgg ggcggggcga   180
ggcggagagg tgcggcggca gccaatcaga gcggcgcgct ccgaaagttt ccttttatgg   240
cgaggcggcg gcgcggcgg ccctataaaa agcgaagcgc gcggcgggcg                290
```

| | | |
|---|---|---|
| SEQ ID NO: 42 | moltype = DNA   length = 960 | |
| FEATURE | Location/Qualifiers | |
| misc_feature | 1..960 | |
| | note = Helper/Rev - Chicken beta actin intron - Enhance gene expression | |
| source | 1..960 | |
| | mol_type = other DNA | |
| | organism = synthetic construct | |

SEQUENCE: 42

```
ggagtcgctg cgttgccttc gccccgtgcc ccgctccgcg ccgcctcgcg ccgcccgccc    60
cggctctgac tgaccgcgtt actcccacag gtgagcgggc gggacggccc ttctcctccg   120
ggctgtaatt agcgcttggt ttaatgacgg ctcgtttctt ttctgtggct gcgtgaaagc   180
cttaaagggc tccggagggc cctttgtgc ggggggagc ggctcgggg gtgcgtgcgt     240
gtgtgtgtgc gtggggagcg ccgcgtgcgg ccgcgctgc ccggcggctg tgagcgctgc    300
gggcgcggcg cggggctttg tgcgctccgc gtgtgcgcga ggggagcgcg gccggggcg    360
gtgccccgcg gtgcgggggg gctgcgaggg gaacaaaggc tgcgtgcggg gtgtgtgcgt   420
ggggggtga gcaggggtg tgggcgcggc ggtcggggctg taacccccc ctgcacccc     480
ctccccgagt tgctgagcac ggcccggctt cgggtgcggg gctccgtgcg gggcgtggcg   540
cgggctcgc cgtgccgggc gggggtgc ggcaggtgg ggtgccgggc ggggcggggc      600
cgcctcgggc cggggagggc tcggggagg ggcgcggcgg ccccgagcg ccggcggctg     660
tcgaggcgcg gcgagccgca gccattgcct tttatggtaa tcgtgcgaga gggcgcaggg   720
acttcctttg tcccaaatct ggcggagccg aaatctggga ggcgccgcg cacccctctc    780
agcgggcgcg gcgaagcgg tgcggcgccg gcaggaagga atgggcgg gagggccttc    840
gtgcgtcgcc gcgccgccgt ccccttctcc atctccagcc tcggggctgc cgcaggggga   900
cggctgcctt cgggggggac ggggcagggc ggggttcgg ttctggcgtg tgaccggcgg    960
```

| | | |
|---|---|---|
| SEQ ID NO: 43 | moltype = DNA   length = 1503 | |
| FEATURE | Location/Qualifiers | |
| misc_feature | 1..1503 | |
| | note = Helper/Rev - HIV Gag - Viral capsid | |
| source | 1..1503 | |
| | mol_type = other DNA | |
| | organism = synthetic construct | |

SEQUENCE: 43

```
atgggtgcga gagcgtcagt attaagcggg ggagaattag atcgatggga aaaaattcgg    60
ttaaggccag ggggaaagaa aaaatataaa ttaaaacata tagtatgggc aagcagggag   120
```

```
ctagaacgat tcgcagttaa tcctggcctg ttagaaacat cagaaggctg tagacaaata    180
ctgggacagc tacaaccatc ccttcagaca ggatcagaag aacttagatc attatataat    240
acagtagcaa ccctctattg tgtgcatcaa aggatagaga taaaagacac caaggaagct    300
ttagacaaga tagaggaaga gcaaaacaaa agtaagaaaa aagcacagca agcagcagct    360
gacacaggac acagcaatca ggtcagccaa aattacccta tagtgcagaa catccagggg    420
caaatggtac atcaggccat atcacctaga actttaaatg catgggtaaa agtagtagaa    480
gagaaggctt tcagcccaga agtgataccc atgttttcag cattatcaga aggagccacc    540
ccacaagatt taaacaccat gctaaacaca gtggggggac atcaagcagc catgcaaatg    600
ttaaaagaga ccatcaatga ggaagctgca gaatgggata gagtgcatcc agtgcatgca    660
gggcctattg caccaggcca gatgagagaa ccaaggggaa gtgacatagc aggaactact    720
agtacccttc aggaacaaat aggatggatg acacataatc cacctatccc agtaggagaa    780
atctataaaa gatggataat cctgggatta aataaaatag taagaatgta tagccctacc    840
agcattctgg acataagaca aggaccaaag gaaccctttta gagactatgt agaccgattc    900
tataaaactc taagagccga gcaagcttca caagaggtaa aaaattggat gacagaaacc    960
ttgttggtcc aaaatgcgaa cccagattgt aagactattt taaaagcatt gggaccagga   1020
gcgacactag aagaaatgat gacagcatgt caggagtggg ggacccggc cataaagca    1080
agagttttgg ctgaagcaat gagccaagta acaaatccag ctaccataat gatacagaaa   1140
ggcaattttta ggaaccaaag aaagactgtt aagtgtttca attgtggcaa agaagggcac   1200
atagccaaaa attgcagggc ccctaggaaa aagggctgtt ggaaatgtgg aaaggaagga   1260
caccaaatga aagattgtac tgagagacag gctaattttt tagggaagat ctggccttcc   1320
cacaagggaa ggccagggaa ttttcttcag agcagaccag agccaacagc cccaccagaa   1380
gagagcttca ggtttgggga agacaacaa actccctctc agaagcagga gccgatagac   1440
aaggaactgt atccttttagc ttccctcaga tcactctttg gcagcgaccc ctcgtcacaa   1500
taa                                                                  1503

SEQ ID NO: 44          moltype = DNA   length = 1872
FEATURE                Location/Qualifiers
misc_feature           1..1872
                       note = Helper/Rev - HIV Pol - Protease and reverse
                        transcriptase
source                 1..1872
                       mol_type = other DNA
                       organism = synthetic construct
SEQUENCE: 44
atgaatttgc caggaagatg gaaaccaaaa atgatagggg gaattggagg ttttatcaaa     60
gtaggacagt atgatcagat actcatagaa atctgcggac ataaagctat aggtacagta    120
ttagtaggac ctacacctgt caacataatt ggaagaaatc tgttgactca gattggctgc    180
actttaaatt ttcccattag tcctattgag actgtaccag taaaattaaa gccaggaatg    240
gatggcccaa aagttaaaca atggccattg acagaagaaa aaataaaagc attagtagaa    300
atttgtacag aaatggaaaa ggaaggaaaa atttcaaaaa ttgggcctga aaatccatac    360
aatactccag tatttgccat aaagaaaaaa gacagtacta atggagaaaa attagtagat    420
ttcagagaac ttaataagag aactcaagat ttctgggaag ttcaattagg aataccacat    480
cctgcagggt taaaacagaa aaaatcagta acagtactgg atgtgggga tgcatatttt    540
tcagttccct tagataaaga cttcaggaag tatactgcat ttaccatacc tagtataaac    600
aatgagacac cagggattag atatcagtac aatgtgcttc cacagggatg gaaaggatca    660
ccagcaatat tccagtgtag catgacaaaa atcttagagc cttttagaaa acaaaatcca    720
gacatagtca tctatcaata catggatgat ttgtatgtag gatctgactt agaaataggg    780
cagcatagaa caaaaataga ggaactgaga caacatctgt tgaggtgggg atttaccaca    840
ccagacaaaa aacatcagaa agaacctcca ttcctttgga tgggttatga actccatcct    900
gataaatgga cagtacagcc tatagtgctg ccagaaaagg acagctggac tgtcaatgac    960
atacagaaat tagtgggaaa attgaattgg gcaagtcaga tttatgcagg gattaaagta   1020
aggcaattat gtaaacttct taggggaacc aaagcactaa cagaagtagt accactaaca   1080
gaagaagcag agctagaact ggcagaaaac agggagattc taaaagaacc ggtacatgga   1140
gtgtattatg acccatcaaa agacttaata gcagaaatac agaagcaggg gcaaggccaa   1200
tggacatatc aaatttatca agagccattt aaaaatctga aaacaggaaa atatgcaaga   1260
atgaagggtg cccacactaa tgatgtaaaa caattaacag aggcagtaca aaaaatagcc   1320
acagaaagca tagtaatatg gggaaagact cctaaattta aattacccat acaaaaggaa   1380
acatgggaag catggtggac agagtattgg caagccacct ggattcctga gtgggagttt   1440
gtcaataccc ctcccttagt gaagttatgg taccagttag agaaagaacc cataatagga   1500
gcagaaactt tctatgtaga tggggcagcc aataggaaa ctaaattagg aaaagcagga   1560
tatgtaactg acagaggaag acaaaaagtt gtccccctaa cggacacaac aaatcagaag   1620
actgagttac aagcaattca tctagctttg caggattcgg gattagaagt aaacatagta   1680
acagactcac aatatgcatt gggaatcatt caagcacaac cagataagag tgaatcagag   1740
ttagtcagtc aaataataga gcagttaata aaaaaggaaa agtctacctg gcatgggta   1800
ccagcacaca aaggaattgg aggaaatgaa caagtagatg ggttggtcag tgctggaatc   1860
aggaaagtac ta                                                        1872

SEQ ID NO: 45          moltype = DNA   length = 867
FEATURE                Location/Qualifiers
misc_feature           1..867
                       note = Helper Rev - HIV Integrase - Integration of viral RNA
source                 1..867
                       mol_type = other DNA
                       organism = synthetic construct
SEQUENCE: 45
tttttagatg gaatagataa ggcccaagaa gaacatgaga aatatcacag taattggaga     60
gcaatggcta tgattttaa cctaccacct gtagtagcaa agaaaatagt agccagctgt    120
gataaatgtc agctaaaagg ggaagccatg catggacaag tagactgtag cccaggaata    180
tggcagctag attgtacaca tttagaagga aaagttatct tggtagcagt tcatgtagcc    240
```

```
agtggatata tagaagcaga agtaattcca gcagagacag ggcaagaaac agcatacttc    300
ctcttaaaat tagcaggaag atggccagta aaaacagtac atacagacaa tggcagcaat    360
ttcaccagta ctacagttaa ggccgcctgt tggtgggcgg ggatcaagca ggaatttggc    420
attccctaca atccccaaag tcaaggagta atagaatcta tgaataaaga attaaagaaa    480
attataggac aggtaagaga tcaggctgaa catcttaaga cagcagtaca aatggcagta    540
ttcatccaca attttaaaag aaaggggggg attggggggt acagtgcagg ggaaagaata    600
gtagacataa tagcaacaga catacaaact aaagaattac aaaaacaaat tacaaaaatt    660
caaaattttc gggtttatta caggacagc agagatccag tttggaaagg accagcaaag    720
ctcctctgga aaggtgaagg ggcagtagta atacaagata atagtgacat aaaagtagtg    780
ccaagaagaa aagcaaagat catcagggat tatgaaaaac agatggcagg tgatgattgt    840
gtggcaagta gacaggatga ggattaa                                        867

SEQ ID NO: 46           moltype = DNA  length = 234
FEATURE                 Location/Qualifiers
misc_feature            1..234
                        note = Helper/Rev - HIV RRE- Binds Rev element
source                  1..234
                        mol_type = other DNA
                        organism = synthetic construct
SEQUENCE: 46
aggagctttg ttccttgggt tcttgggagc agcaggaagc actatgggcg cagcgtcaat    60
gacgctgacg gtacaggcca gacaattatt gtctggtata gtgcagcagc agaacaattt    120
gctgagggct attgaggcgc aacagcatct gttgcaactc acagtctggg gcatcaagca    180
gctccaggca agaatcctgg ctgtggaaag ataccctaaag gatcaacagc tcct          234

SEQ ID NO: 47           moltype = DNA  length = 351
FEATURE                 Location/Qualifiers
misc_feature            1..351
                        note = Helper/Rev - HIV Rev - Nuclear export and stabilize
                          viral mRNA
source                  1..351
                        mol_type = other DNA
                        organism = synthetic construct
SEQUENCE: 47
atggcaggaa gaagcggaga cagcgacgaa gaactcctca aggcagtcag actcatcaag    60
tttctctatc aaagcaaccc acctcccaat cccgagggga cccgacaggc ccgaaggaat    120
agaagaagaa ggtggagaga gagacagaga cagatccatt cgattagtga acggatcctt    180
agcacttatc tgggacgatc tgcggagcct gtgcctcttc agctaccacc gcttgagaga    240
cttactcttg attgtaacga ggattgtgga acttctggga cgcaggggt gggaagccct    300
caaatattgg tggaatctcc tacaatattg gagtcaggag ctaaagaata g             351

SEQ ID NO: 48           moltype = DNA  length = 448
FEATURE                 Location/Qualifiers
misc_feature            1..448
                        note = Helper/Rev - Rabbit beta globin poly A - RNA
                          stability
source                  1..448
                        mol_type = other DNA
                        organism = synthetic construct
SEQUENCE: 48
agatcttttt ccctctgcca aaaattatgg ggacatcatg aagccccttg agcatctgac    60
ttctggctaa taaaggaaat ttattttcat tgcaatagtg tgttggaatt ttttgtgtct    120
ctcactcgga aggacatatg ggagggcaaa tcatttaaaa catcgaatg agtatttggt    180
ttagagtttg gcaacatatg ccatatgctg gctgccatga acaaaggtgg ctataaagag    240
gtcatcagta tatgaaacag ccccctgctg tccattcctt attccataga aaagccttga    300
cttgaggtta gatttttttt atatttttgtt tgtgttatt ttttttctta acatccctaa    360
aattttcctt acatgttttta ctagccagat ttttcctcct ctcctgacta ctcccagtca    420
tagctgtccc tcttctctta tgaagatc                                        448

SEQ ID NO: 49           moltype = DNA  length = 352
FEATURE                 Location/Qualifiers
misc_feature            1..352
                        note = Helper - CMV early (CAG) enhancer -
                          Enhancetranscription
source                  1..352
                        mol_type = other DNA
                        organism = synthetic construct
SEQUENCE: 49
tagttattaa tagtaatcaa ttacggggtc attagttcat agcccatata tggagttccg    60
cgttacataa cttacggtaa atggcccgcc tggctgaccg cccaacgacc cccgcccatt    120
gacgtcaata atgacgtatg ttcccatagt aacgccaata gggactttcc attgacgtca    180
atgggtggac tatttacggt aaactgccca cttggcagta catcaagtgt atcatatgcc    240
aagtacgccc cctattgacg tcaatgacgg taaatggccc gcctggcatt atgcccagta    300
catgacctta tgggactttc ctacttggca gtacatctac gtattagtca tc             352

SEQ ID NO: 50           moltype = DNA  length = 290
FEATURE                 Location/Qualifiers
```

| | |
|---|---|
| misc_feature | 1..290<br>note = Helper - Chicken beta actin (CAG) promoter - Transcription |
| source | 1..290<br>mol_type = other DNA<br>organism = synthetic construct |

SEQUENCE: 50

```
gctattacca tgggtcgagg tgagccccac gttctgcttc actctcccca tctcccccc     60
ctccccaccc ccaattttgt atttatttat tttttaatta ttttgtgcag cgatgggggc   120
ggggggggggg gggcgcgcg ccaggcgggg cggggcgggg cgaggggcgg ggcggggcga   180
ggcggagagg tgcggcggca gccaatcaga gcgcgcgct ccgaaagttt ccttttatgg    240
cgaggcggcg gcggcggcgg ccctataaaa agcgaagcgc gcggcgggcg              290
```

| SEQ ID NO: 51 | moltype = DNA length = 960 |
|---|---|
| FEATURE | Location/Qualifiers |
| misc_feature | 1..960<br>note = Helper - Chicken beta actin intron - Enhance gene expression |
| source | 1..960<br>mol_type = other DNA<br>organism = synthetic construct |

SEQUENCE: 51

```
ggagtcgctg cgttgccttc gccccgtgcc ccgctccgcg ccgcctcgcg ccgcccgccc     60
cggctctgac tgaccgcgtt actcccacag gtgagcgggc gggacggccc ttctcctccg   120
ggctgtaatt agcgcttggt ttaatgacgg ctcgtttctt ttctgtggct gcgtgaaagc   180
cttaaagggc tccggagggg ccctttgtgc ggggggagcg gctcggggga gtgcgtgcgt   240
gtgtgtgtgc gtggggagcg ccgcgtgcg cccgcgctgc ccggcggctg tgagcgctgc   300
gggcgcggcg cggggctttg tgcgctccgc gtgtgcgcga ggggagcgcg gccggggcg   360
gtgccccgcg gtgcggggg gctgcgaggg gaacaaaggc tgcgtgcggg gtgtgtgcgt   420
ggggggggtga gcaggggtg tgggcgcggc ggtcgggctg taaccccccc ctgcacccc   480
ctccccgagt tgctgagcac ggcccggctt cgggtgcggg gctccgtgcg gggcgtggcc   540
cggggctcgc cgtgccgggc gggggtggc ggcaggtggg ggtgccgggc ggggcgggggc   600
cgcctcgggc cggggagggc tcgggggagg ggcgcggcgg ccccgagcg ccggcggctg   660
tcgaggcgcg gcgagccgca gccattgcct tttatggtaa tcgtgcgaga gggcgcaggg   720
acttcctttg tcccaaatct ggcggagccg aaatctggga ggcgccgcg cacccccct   780
agcgggcgcg ggcgaagcgg tgcggcgccg gcaggaagga aatgggcggg gagggccttc   840
gtgcgtcgcc gcgccgccgt ccccttctcc atctccagcc tcggggctgc cgcagggga   900
cggctgcctt cggggggggac ggggcagggc gggggttcggc ttctggcgtg tgaccggcgg   960
```

| SEQ ID NO: 52 | moltype = DNA length = 1503 |
|---|---|
| FEATURE | Location/Qualifiers |
| misc_feature | 1..1503<br>note = Helper - HIV Gag - Viral capsid |
| source | 1..1503<br>mol_type = other DNA<br>organism = synthetic construct |

SEQUENCE: 52

```
atgggtgcga gagcgtcagt attaagcggg ggagaattag atcgatggga aaaaattcgg     60
ttaaggccag ggggaaagaa aaaatataaa ttaaaacata tagtatgggc aagcagggag   120
ctagaacgat tcgcagttaa tcctggcctg ttagaaacat cagaaggctg tagacaaata   180
ctgggacagc tacaaccatc ccttcagaca ggatcagaag aacttagatc attatataat   240
acagtagcaa ccctctattg tgtgcatcaa aggatagaga taaaagacac caaggaagct   300
ttagacaaga tagaggaaga gcaaaacaaa agtaagaaaa agcacagca agcagcagct   360
gacacaggac acagcaatca ggtcagccaa aattacccta gtgcagaa catccaggg    420
caaatggtac atcaggccat atcacctaga acttttaaatg catgggtaaa agtagtagaa   480
gagaaggctt tcagcccaga agtgataccc atgttttcag cattatcaga aggagccacc   540
ccacaagatt taaacaccat gctaaacaca gtggggggac atcaagcagc catgcaaatg   600
ttaaaagaga ccatcaatga ggaagctgca gaatgggata gagtgcatcc agtgcatgca   660
gggcctattg caccaggcca gatgagagaa ccaaggggaa gtgacatagc aggaactact   720
agtacccttc aggaacaaat aggatggatg acacataatc cacctatccc agtaggagaa   780
atctataaaa gatggataat cctgggatta aataaaatag taagaatgta tagccctacc   840
agcattctgg acataagaca aggaccaaag gaacccttta gagactatgt agaccggttc   900
tataaaactc taagagccga gcaagcttca caagaggtaa aaaattggat gacagaaacc   960
ttgttggtcc aaaatgcgaa cccagattgt aagactattt taaaagcatt gggaccagga  1020
gcgacactag aagaaatgat gacagcatgt cagggagtgg ggggacccgg ccataaagca  1080
agagttttgg ctgaagcaat gagccaagta acaaatccag ctaccataat gatacagaaa  1140
ggcaattta ggaaccaaag aaagactgtt aagtgtttca attgtggcaa agaagggcac  1200
atagccaaaa attgcagggc ccctaggaaa aagggctgtt ggaaatgtgg aaaggaagga  1260
caccaaatga aagattgtac tgagagacag gctaattttt tagggaagat ctggccttcc  1320
cacaagggaa ggccagggaa ttttcttcag agcagaccag agccaacagc cccaccagaa  1380
gagagcttca ggtttgggga agagacaaca actccctctc agaagcagga gccgatagac  1440
aaggaactgt atcctttagc ttccctcaga tcactctttg gcagcgaccc ctcgtcacaa  1500
taa                                                                  1503
```

| SEQ ID NO: 53 | moltype = DNA length = 1872 |
|---|---|
| FEATURE | Location/Qualifiers |
| misc_feature | 1..1872<br>note = Helper - HIV Pol - Protease and reverse transcriptase |

```
source                  1..1872
                        mol_type = other DNA
                        organism = synthetic construct
SEQUENCE: 53
atgaatttgc caggaagatg gaaaccaaaa atgatagggg gaattggagg ttttatcaaa    60
gtaggacagt atgatcagat actcatagaa atctgcggac ataaagctat aggtacagta   120
ttagtaggac ctacacctgt caacataatt ggaagaaatc tgttgactca gattggctgc   180
actttaaatt ttcccattag tcctattgag actgtaccag taaaattaaa gccaggaatg   240
gatggcccaa aagttaaaca atggccattg acagaagaaa aaataaaagc attagtagaa   300
atttgtacag aaatggaaaa ggaaggaaaa atttcaaaaa ttgggcctga aaatccatac   360
aatactccag tatttgccat aaagaaaaaa gacagtacta atggagaaa attagtagat   420
ttcagagaac ttaataagag aactcaagat ttctgggaag ttcaattagg aataccacat   480
cctgcagggt taaaacagaa aaaatcagta acagtactgg atgtgggcga tgcatatttt   540
tcagttccct tagataaaga cttcaggaag tatactgcat ttaccatacc tagtataaac   600
aatgagacac cagggattag atatcagtac aatgtgcttc cacagggatg gaaaggatca   660
ccagcaatat tccagtgtag catgacaaaa atcttagagc cttttagaaa acaaaatcca   720
gacatagtca tctatcaata catggatgat ttgtatgtag gatctgactt agaaataggg   780
cagcatagaa caaaaataga ggaactgaga caacatctgt tgaggtgggg atttaccaca   840
ccagacaaaa aacatcagaa agaacctcca ttcctttgga tgggttatga actccatcct   900
gataaatgga cagtacagcc tatagtgctg ccagaaaagg acagctggac tgtcaatgac   960
atacagaaat tagtgggaaa attgaattgg gcaagtcaga tttatgcagg gattaaagta  1020
aggcaattat gtaaacttct tagggaacc aaagcactaa cagaagtagt accactaaca  1080
gaagaagcag agctagaact ggcagaaaac agggagattc taaaagaacc ggtacatgga  1140
gtgtattatg acccatcaaa agacttaata gcagaaatac agaagcaggg gcaaggccaa  1200
tggacatatc aaatttatca agagccattt aaaaatctga aaacaggaaa atatgcaaga  1260
atgaagggtg cccacactaa tgatgtgaaa caattaacag aggcagtaca aaaaatagcc  1320
acagaaagca tagtaatatg gggaaagact cctaaattta aattacccat acaaaaggaa  1380
acatgggaag catggtggac agagtattgg caagccacct ggattcctga gtgggagttt  1440
gtcaataccc ctcccttagt gaagttatgg taccagttag agaagaacc cataatagga  1500
gcagaaactt tctatgtaga tggggcagcc aatagggaaa ctaaattagg aaaagcagga  1560
tatgtaactg acagaggaag acaaaaagtt gtccccctaa cggacacaaa aaatcagaag  1620
actgagttac aagcaattca tctagctttg caggattcgg gattagaagt aaacatagtg  1680
acagactcac aatatgcatt gggaatcatt caagcacaac cagataagag tgaatcagag  1740
ttagtcagtc aaataataga gcagttaata aaaaaggaaa aagtctacct ggcatgggta  1800
ccagcacaca aaggaattgg aggaaatgaa caagtagatg ggttggtcag tgctggaatc  1860
aggaaagtac ta                                                     1872

SEQ ID NO: 54           moltype = DNA  length = 867
FEATURE                 Location/Qualifiers
misc_feature            1..867
                        note = Helper - HIV Integrase - Integration of viral RNA
source                  1..867
                        mol_type = other DNA
                        organism = synthetic construct
SEQUENCE: 54
tttttagatg gaatagataa ggcccaagaa gaacatgaga atatcacag taattggaga     60
gcaatggcta gtgattttaa cctaccacct gtagtagcaa aagaaatagt agccagctgt   120
gataaatgtc agctaaaagg ggaagccatg catggacaag tagactgtag cccaggaata   180
tggcagctag attgtacaca tttagaagga aaagttatct tggtagcagt tcatgtagcc   240
agtggatata tagaagcaga agtaattcca gcagagacag ggcaagaaac agcatacttc   300
ctcttaaaat tagcaggaag atggccagta aaaacagtac atacagacaa tggcagcaat   360
ttcaccagta ctacagttaa ggccgcctgt tggtgggcga ggatcaagca ggaatttggc   420
attccctaca atccccaaag tcaaggagta atagaatcta tgaataaaga attaaagaaa   480
attataggac aggtaagaga tcaggctgaa catcttaaga cagcagtaca atggcagta   540
ttcatccaca attttaaaag aaaagggggg attgggggt acagtgcagg ggaaagaata   600
gtagacataa tagcaacaga catacaaact aaagaattac aaaaacaaat tacaaaaatt   660
caaaattttc gggtttatta cagggacagc agagatccaa tttggaaagg accagcaaaa   720
ctcctctgga aaggtgaagg ggcagtagta atacaagata atagtgacat aaaagtagtg   780
ccaagaagaa aagcaaagat catcagggat tatggaaaac agatggcagg tgatgattgt   840
gtggcaagta gacaggatga ggattaa                                      867

SEQ ID NO: 55           moltype = DNA  length = 234
FEATURE                 Location/Qualifiers
misc_feature            1..234
                        note = Helper - HIV RRE - Binds Rev element
source                  1..234
                        mol_type = other DNA
                        organism = synthetic construct
SEQUENCE: 55
aggagctttg ttccttgggt tcttgggagc agcaggaagc actatgggcg cagcgtcaat    60
gacgctgacg gtacaggcca gacaattatt gtctggtata gtgcagcagc agaacaattt   120
gctgagggct attgaggcgc aacagcatct gttgcaactc acagtctggg gcatcaagca   180
gctccaggca agaatcctgg ctgtggaaag atacctaaag gatcaacagc tcct          234

SEQ ID NO: 56           moltype = DNA  length = 448
FEATURE                 Location/Qualifiers
misc_feature            1..448
                        note = Helper - Rabbit beta globin poly A - RNA stability
```

```
source                    1..448
                          mol_type = other DNA
                          organism = synthetic construct
SEQUENCE: 56
agatctttt  ccctctgcca  aaaattatgg  ggacatcatg  aagcccttg   agcatctgac   60
ttctggctaa  taaggaaat   ttattttcat  tgcaatagtg  tgttggaatt  ttttgtgtct  120
ctcactcgga  aggacatatg  ggagggcaaa  tcatttaaaa  catcagaatg  agtatttggt  180
ttagagtttg  gcaacatatg  ccatatgctg  gctgccatga  acaaaggtgg  ctataaagag  240
gtcatcagta  tatgaaacag  cccctgctg   tccattcct   attccataga  aaagccttga  300
cttgaggtta  gattttttt   atattttgtt  ttgtgttatt  tttttcttta  acatccctaa  360
aattttcctt  acatgttta   ctagccagat  ttttcctcct  ctcctgacta  ctcccagtca  420
tagctgtccc  tcttctctta  tgaagatc                                         448

SEQ ID NO: 57             moltype = DNA  length = 351
FEATURE                   Location/Qualifiers
misc_feature              1..351
                          note = Rev - RSV promoter - Transcription
source                    1..351
                          mol_type = other DNA
                          organism = synthetic construct
SEQUENCE: 57
atggcaggaa  gaagcggaga  cagcgacgaa  gaactcctca  aggcagtcag  actcatcaag   60
tttctctatc  aaagcaaccc  acctcccaat  cccgagggga  cccgacaggc  ccgaaggaat  120
agaagaagaa  ggtggagaga  gagacagaga  cagatccatt  cgattagtga  acggatcctt  180
agcacttatc  tgggacgatc  tgcggagcct  gtgcctcttc  agctaccacc  gcttgagaga  240
cttactcttg  attgtaacga  ggattgtgga  acttctggga  cgcaggggt   gggaagccct  300
caaatattgg  tggaatctcc  tacaatattg  gagtcaggag  ctaaagaata  g            351

SEQ ID NO: 58             moltype = DNA  length = 351
FEATURE                   Location/Qualifiers
misc_feature              1..351
                          note = Rev - HIV Rev- Nuclear export and stabilize viral
                            mRNA
source                    1..351
                          mol_type = other DNA
                          organism = synthetic construct
SEQUENCE: 58
atggcaggaa  gaagcggaga  cagcgacgaa  gaactcctca  aggcagtcag  actcatcaag   60
tttctctatc  aaagcaaccc  acctcccaat  cccgagggga  cccgacaggc  ccgaaggaat  120
agaagaagaa  ggtggagaga  gagacagaga  cagatccatt  cgattagtga  acggatcctt  180
agcacttatc  tgggacgatc  tgcggagcct  gtgcctcttc  agctaccacc  gcttgagaga  240
cttactcttg  attgtaacga  ggattgtgga  acttctggga  cgcaggggt   gggaagccct  300
caaatattgg  tggaatctcc  tacaatattg  gagtcaggag  ctaaagaata  g            351

SEQ ID NO: 59             moltype = DNA  length = 450
FEATURE                   Location/Qualifiers
misc_feature              1..450
                          note = Rev- Rabbit beta globin poly A- RNA stability
source                    1..450
                          mol_type = other DNA
                          organism = synthetic construct
SEQUENCE: 59
agatctttt  ccctctgcca  aaaattatgg  ggacatcatg  aagcccttg   agcatctgac   60
ttctggctaa  taaggaaat   ttattttcat  tgcaatagtg  tgttggaatt  ttttgtgtct  120
ctcactcgga  aggacatatg  ggagggcaaa  tcatttaaaa  catcagaatg  agtatttggt  180
ttagagtttg  gcaacatatg  cccatatgct  ggctgccatg  aacaaaggtt  ggctataaag  240
aggtcatcag  tatatgaaac  agccccctgc  tgtccattcc  ttattccata  gaaaagcctt  300
gacttgaggt  tagattttt   ttatatttg   ttttgtgtta  ttttttctt   taacatccct  360
aaaattttcc  ttcatgtttt  tactagccag  attttcctc   ctctcctgac  tactcccagt  420
catagctgtc  cctcttctct  tatggagatc                                       450

SEQ ID NO: 60             moltype = DNA  length = 577
FEATURE                   Location/Qualifiers
misc_feature              1..577
                          note = Envelope- CMV promoter- Transcription
source                    1..577
                          mol_type = other DNA
                          organism = synthetic construct
SEQUENCE: 60
acattgatta  ttgactagtt  attaatagta  atcaattacg  gggtcattag  ttcatagccc   60
atatatggag  ttccgcgtta  cataacttac  ggtaaatggc  ccgcctggct  gaccgcccaa  120
cgaccccgc   ccattgacgt  caataatgac  gtatgttccc  atagtaacgc  caatagggac  180
tttccattga  cgtcaatggg  tggagtattt  acggtaaact  gcccacttgg  cagtacatca  240
agtgtatcat  atgccaagta  cgccccctat  tgacgtcaat  gacggtaaat  ggcccgcctg  300
gcattatgcc  cagtacatga  ccttatggga  ctttcctact  tggcagtaca  tctacgtatt  360
agtcatcgct  attaccatgg  tgatgcggtt  ttggcagtac  atcaatgggc  gtggatagcg  420
gtttgactca  cggggatttc  caagtctcca  ccccattgac  gtcaatggga  gtttgttttg  480
gcaccaaaat  caacgggact  ttccaaaatg  tcgtaacaac  tccgcccat   tgacgcaaat  540
gggcggtagg  cgtgtacggt  gggaggtcta  tataagc                              577
```

```
SEQ ID NO: 61            moltype = DNA  length = 573
FEATURE                  Location/Qualifiers
misc_feature             1..573
                         note = Envelope- Beta globin intron- Enhance gene expression
source                   1..573
                         mol_type = other DNA
                         organism = synthetic construct
SEQUENCE: 61
gtgagtttgg ggaccttga  ttgttctttc ttttcgcta  ttgtaaaatt catgttatat   60
ggaggggca  aagttttcag  ggtgttgttt agaatgggaa gatgtccctt gtatcaccat  120
ggaccctcat gataattttg  tttctttcac tttctactct gttgacaacc attgtctcct  180
cttattttct tttcattttc  tgtaacttt  tcgttaaact ttagcttgca tttgtaacga  240
attttttaaat tcactttgt  ttatttgtca gattgtaagt acttctcta  atcacttttt  300
tttcaaggca atcagggtat attatattgt acttcagcac agttttagag aacaattgtt  360
ataattaaat gataaggtag  aatatttctg catataaatt ctggctggcg tggaaatatt  420
cttattggta gaaacaacta caccctggtc atcatcctgc ctttctcttt atggttacaa  480
tgatatacac tgtttgagat gaggataaaa tactctgagt ccaaaccggg cccctctgct  540
aaccatgttc atgccttctt ctcttttccta cag                               573

SEQ ID NO: 62            moltype = DNA  length = 1519
FEATURE                  Location/Qualifiers
misc_feature             1..1519
                         note = Envelope- VSV-G- Glycoprotein envelope-cell entry
source                   1..1519
                         mol_type = other DNA
                         organism = synthetic construct
SEQUENCE: 62
atgaagtgcc ttttgtactt agccttttta ttcattgggg tgaattgcaa gttcaccata   60
gtttttccac acaaccaaaa aggaaactgg aaaaatgttc cttctaatta ccattattgc  120
ccgtcaagct cagatttaaa ttggcataat gacttaatag gcacagcctt acaagtcaaa  180
atgcccaaga gtcacaaggc tattcaagca gacggttgga tgtgtcatgc ttccaaatgg  240
gtcactactt tgtgatttccg ctggtatgga ccgaagtata taacacattc catccgatcc  300
ttcactccat ctgtagaaca aacgaaggaa agcattgaac aaacgaaaca aggaactgg   360
ctgaatccag gcttccctcc tcaaagttgt ggatatgcaa ctgtgacgga tgccgaagca  420
gtgattgtcc aggtgactcc tcaccatgtg ctggttgatg aatacacagg agaatgggtt  480
gattcacagt tcatcaacgg aaaatgcagc aattacatat gccccactgt ccataactct  540
acaacctggc attctgacta taaggtcaaa gggctatgtg attctaacct catttccatg  600
gacatcacct tcttctcaga ggacggagag ctatcatccc tgggaaagga gggcacaggg  660
ttcagaagta actactttgc ttatgaaact ggaggcaagg cctgcaaaat gcaatactgc  720
aagcattggg gagtcagact cccatcaggt gtctggttcg agatggctga taaggatctc  780
tttgctgcag ccagattccc tgaatgccca gaagggtcaa gtatctctgc tccatctcag  840
acctcagtgg atgtaagtct aattcaggac gttgagagga tcttggatta ttccctctgc  900
caagaaacct ggagcaaaat cagagcgggt cttccaatct ctccagtgga tctcagctat  960
cttgctccta aaaacccagg aaccggtcct gctttcacca taatcaatgg taccctaaaa  1020
tactttgaga ccagatacat cagagtcgat attgctgctc caatcctctc aagaatggtc  1080
ggaatgatca gtgaactac  cacagaaagg gaactgtggc atgactgggc accatatgaa  1140
gacgtggaaa ttggacccaa tggagttctg aggaccagtt caggatataa gtttcctta   1200
tacatgattg acatggtat  gttggactcc gatcttcatc ttagctcaaa ggctcaggtg  1260
ttcgaacatc ctcacattca agacgctgct tcgaacttc  ctgatgatga gagtttatttt  1320
tttggtgata ctgggctatc caaaaatcca atcgagcttg tagaaggttg gttcagtagt  1380
tggaaaagct ctattgcctc ttttttcttt atcatagggt taatcattgg actattcttg  1440
gttctccgag ttggtatcca tctttgcatt aaattaaagc acaccaagaa agacagatt   1500
tatacagaca tagagatga                                                1519

SEQ ID NO: 63            moltype = DNA  length = 450
FEATURE                  Location/Qualifiers
misc_feature             1..450
                         note = Envelope- Rabbit beta globin poly A- RNA stability
source                   1..450
                         mol_type = other DNA
                         organism = synthetic construct
SEQUENCE: 63
agatcttttt ccctctgcca aaaattatgg ggacatcatg aagccccttg agcatctgac   60
ttctggctaa taaggaaat  ttattttcat tgcaatagtg tgttggaatt ttttgtgtct  120
ctcactcgga aggacatatg ggagggcaaa tcatttaaaa catcagaatg agtatttggt  180
ttagagtttg gcaacatatg cccatatgct ggctgccatg aacaaggtt  ggctataaag  240
aggtcatcag tatatgaaac agccccctgc tgtccattcc ttattccata gaaaagcctt  300
gacttgaggt tagatttttt ttatattttg ttttgtgtta tttttcctt  taacatcct   360
aaaattttcc ttacatgttt tactagccag attttttcctc ctctcctgac tactcccagt  420
catagctgtc cctcttctct tatggagatc                                    450

SEQ ID NO: 64            moltype = DNA  length = 1104
FEATURE                  Location/Qualifiers
misc_feature             1..1104
                         note = Promoter- EF-1
source                   1..1104
                         mol_type = other DNA
                         organism = synthetic construct
```

```
SEQUENCE: 64
ccggtgccta gagaaggtgg cgcggggtaa actgggaaag tgatgtcgtg tactggctcc      60
gccttttcc cgagggtggg ggagaaccgt atataagtgc agtagtcgcc gtgaacgttc      120
tttttcgcaa cgggtttgcc gccagaacac aggtaagtgc cgtgtgtggt tcccgcgggc    180
ctggcctctt tacgggttat ggcccttgcg tgccttgatt tacttccacg ccctggctg    240
cagtacgtga ttcttgatcc cgagcttcgg gttggaagtg ggtgggagag ttcgaggcct    300
tgcgcttaag gagccccttc gcctcgtgct tgagttgagg cctggcctgg gcgctggggc    360
cgccgcgtgc gaatctggtg gcaccttcgc gcctgtctcg ctgctttcga taagtctcta    420
gccatttaaa attttgatg acctgctgcg acgcttttt tctggcaaga tagtcttgta      480
aatgcgggcc aagatctgca cactggtatt tcggttttgg ggccgcggg cggcgacggg    540
gcccgtgcgt cccagcgcac atgttcggcg aggcggggcc tgcgagcgcg gccaccgaga    600
atcggacggg ggtagtctca agctggccgg cctgctctgg tgcctggcct cgcgccgccg    660
tgtatcgccc cgccctgggc ggcaaggctg gcccggtcgg caccagttgc gtgagcggaa    720
agatggccgc ttcccggccc tgctgcaggg agctcaaaat ggaggacgcg gcgctcggga    780
gagcgggcgg gtgagtcacc cacacaaagg aaaagggcct ttccgtcctc agccgtcgct    840
tcatgtgact ccacggagta ccgggcgccg tccaggcacc tcgattagtt ctcgagcttt    900
tggagtacgt cgtcttagg ttgggggag gggttttatg cgatggagtt tccccacact      960
gagtgggtgg agactgaagt taggccagct tggcacttga tgtaattctc cttgaatttt    1020
gcccttttg agtttggatc ttggttcatt ctcaagcctc agacagtggt tcaaagtttt    1080
tttcttccat ttcaggtgtc gtga                                           1104

SEQ ID NO: 65        moltype = DNA   length = 511
FEATURE              Location/Qualifiers
misc_feature         1..511
                     note = Promoter- PGK
source               1..511
                     mol_type = other DNA
                     organism = synthetic construct
SEQUENCE: 65
ggggttgggg ttgcgccttt tccaaggcag ccctgggttt gcgcagggac gcggctgctc       60
tgggcgtggt tccgggaaac gcagcggcgc cgaccctggg tctcgcacat tcttcacgtc     120
cgttcgcagc gtcaccccgga tcttcgccgc taccccttgtg ggccccccgg cgacgcttcc  180
tgctccgccc ctaagtcggg aaggttcctt gcggttcgcg cgtgccgga cgtgacaaac     240
ggaagccgca cgtctcacta gtaccctcgc agacggacag cgccagggag caatggcagc    300
gcgccgaccg cgatgggctg tggccaatag cggctgctca gcagggcgcg ccgagagcag    360
cggccgggaa ggggcggtgc gggaggcggg gtgtgggcg gtagtgtggg ccctgttcct    420
gcccgcgcgg tgttccgcat tctgcaagcc tccggagcgc acgtcggcag tcggctccct    480
cgttgaccga atcaccgacc tctctcccca g                                    511

SEQ ID NO: 66        moltype = DNA   length = 1162
FEATURE              Location/Qualifiers
misc_feature         1..1162
                     note = Promoter- UbC
source               1..1162
                     mol_type = other DNA
                     organism = synthetic construct
SEQUENCE: 66
gcgccgggtt ttggcgcctc ccgcggggcgc ccccctcctc acggcgagcg ctgccacgtc      60
agacgaaggg cgcaggagcg ttcctgatcc ttccgcccgg acgctcagga cagcggcccg    120
ctgctcataa gactcggcct tagaaccccca gtatcagcag aaggacattt taggacggga    180
cttgggtgac tctagggcac tggttttctt tccagagaga ggaacaggcg aggaaaagta    240
gtcccttctc ggcgattctg cggagggatc tccgtgggc ggtgaacgcc gatgattata    300
taaggacgcg ccgggtgtgg cacagctagt tccgtcgcag ccgggatttg ggtcgcggtt    360
cttgtttgtg gatcgctgtg atcgtcactt ggtgagttgc gggctgctgg gctggccggg    420
gctttcgtgg ccgccgggcc gctcggtggg acggaagcgt gtggagagac cgccaagggc    480
tgtagtctgg gtccgcgagc aaggttgccc tgaactgggg gttggggga gcgcacaaaa    540
tggcggctgt tcccgagtct tgaatggaag acgcttgtaa ggcgggctgt gaggtcgttg    600
aaacaaggtg gggggcatgg tgggcggcaa gaacccaagg tcttgaggcc ttcgctaatg    660
cgggaaagct cttattcggg tgagatgggc tgggccacca tctgggcacc ctgacgtgaa    720
gtttgtcact gactggagaa ctcgggttg tcgtctggtt gcgggggcgg cagttatgcg    780
gtgccgttgg gcagtgcacc cgtacctttg ggagcgcgcg cctcgtcgtg tcgtgacgtc    840
acccgttctg ttggcttata atgcaggtgg gggccacctg ccggtaggtg tgcggtaggc    900
ttttctccgt cgcaggacgc agggttcggg cctagggtag gctctcctga atcgacaggc    960
gccggaccct ctggtgaggg ggagataagt gaggcgtcag cggtttttatg cggttttatg   1020
tacctatctt cttaagtagc tgaagctccg gttttgaact atgcgctcgg ggttggcgag    1080
tgtgttttgt gaagtttttt aggcaccttt tgaaatgtaa tcatttgggt caatatgtaa    1140
ttttcagtgt tagactagta aa                                             1162

SEQ ID NO: 67        moltype = DNA   length = 120
FEATURE              Location/Qualifiers
misc_feature         1..120
                     note = Poly A- SV40
source               1..120
                     mol_type = other DNA
                     organism = synthetic construct
SEQUENCE: 67
gtttattgca gcttataatg gttacaaata aagcaatagc atcacaaatt tcacaaataa       60
agcattttt tcactgcatt ctagttgtgg tttgtccaaa ctcatcaatg tatcttatca     120
```

```
SEQ ID NO: 68            moltype = DNA   length = 227
FEATURE                  Location/Qualifiers
misc_feature             1..227
                         note = Poly A- bGH
source                   1..227
                         mol_type = other DNA
                         organism = synthetic construct
SEQUENCE: 68
gactgtgcct tctagttgcc agccatctgt tgtttgcccc tcccccgtgc cttccttgac    60
cctggaaggt gccactccca ctgtcctttc ctaataaaat gaggaaattg catcgcattg   120
tctgagtagg tgtcattcta ttctgggggg tggggtgggg caggacagca agggggagga   180
ttgggaagac aatagcaggc atgctgggga tgcggtgggc tctatgg               227

SEQ ID NO: 69            moltype = DNA   length = 1512
FEATURE                  Location/Qualifiers
misc_feature             1..1512
                         note = HIV Gag- Bal
source                   1..1512
                         mol_type = other DNA
                         organism = synthetic construct
SEQUENCE: 69
atgggtgcga gagcgtcagt attaagcggg ggagaattag ataggtggga aaaaattcgg    60
ttaaggccag ggggaaagaa aaaatataga ttaaaacata tagtatgggc aagcagggaa   120
ctagaaagat tcgcagtcaa tcctggcctg ttagaaacat cagaaggctg cagacaaata   180
ctgggacagc tacaaccatc ccttcagaca ggatcagaag aacttagatc attatataat   240
acagtagcaa ccctctattg tgtacatcaa aagatagagg taaaagacac caaggaagct   300
ttagacaaaa tagaggaaga gcaaaacaaa tgtaagaaaa aggcacagca agcagcagct   360
gacacaggaa acagcggtca ggtcagccaa aatttcccta tagtgcagaa cctccagggg   420
caaatggtac atcaggccat atcacctaga actttaaatg catgggtaaa agtaatagaa   480
gagaaagctt tcagcccaga gtaatacccc atgttttcag cattatcaga aggagccacc   540
ccacaagatt taaacaccat gctaaacaca gtggggggac atcaagcagc catgcaaatg   600
ttaaaagaac ccatcaatga ggaagctgca gatgggata gattgcatcc cgtgcaggca   660
gggcctgttg caccaggcca gataagagat ccaaggggaa gtgacatagc aggaactacc   720
agtacccttc aggaacaaat aggatggatg acaagtaatc cacctatccc agtaggagaa   780
atctataaaa gatggataat cctgggatta aataaaatag taaggatgta tagccctacc   840
agcattttgg acataagaca aggaccaaag gaacccttta gagactatgt agaccggttc   900
tataaaactc taagagccga gcaagcttca caggaggtaa aaaattggat gacagaaacc   960
ttgttggtcc aaaatgcgaa cccagattgt aagactatt taaaagcatt gggaccagca  1020
gctacactag aagaaatgat gacagcatgt cagggagtgg gaggacccag ccataaagca  1080
agaattttgg cagaagcaat gagccaagta acaaattcag ctaccataat gatgcagaaa  1140
ggcaatttta ggaaccaaag aaagattgtt aaatgtttca attgtggcaa agaagggcac  1200
atagccagaa actgcagggc ccctaggaaa aggggctgtt ggaaatgtgg aaggaagga  1260
caccaaatga aagactgtac tgagagacag gctaattttt tagggaaaat ctggccttcc  1320
cacaaaggaa ggccagggaa tttccttcag agcagaccag agccaacagc cccaccagcc  1380
ccaccagaag agagcttcag gtttggggaa gagacaacaa ctccctctca gaagcaggag  1440
ctgatagaca aggaactgta tcctttagct tccctcagat cactctttgg caacgacccc  1500
tcgtcacaat aa                                                     1512

SEQ ID NO: 70            moltype = DNA   length = 1872
FEATURE                  Location/Qualifiers
misc_feature             1..1872
                         note = HIV Pol- Bal
source                   1..1872
                         mol_type = other DNA
                         organism = synthetic construct
SEQUENCE: 70
atgaatttgc caggaagatg gaaaccaaaa atgataggg gaattggagg ttttatcaaa    60
gtaagacagt atgatcagat actcatagaa atctgtggac ataaagctat aggtacagta   120
ttaataggac ctacacctgt caacataatt ggaagaaatc tgttgactca gattggttgc   180
actttaaatt ttcccattag tcctattgaa actgtaccag taaaattaaa accaggaatg   240
gatggcccaa aagttaaaca atggccactg acagaagaaa aaataaaagc attaatggaa   300
atctgtacag aaatggaaaa ggaagggaaa atttcaaaaa ttgggcctga aaatccatac   360
aatactccag tatttgccat aaagaaaaaa gacagtacta atggagaaa attagtagat   420
ttcagagaac ttaataagag aactcaagac ttctgggaag tacaattagg aatacacatc   480
ccgcaggggt taaaaaagaa aaaatcagta acagtactgg atgtgggtga tgcatatttt   540
tcagttccct tagataaaga attcaggaag tatactgcat ttaccatacc tagtataaac   600
aatgaaacac cagggattag atatcagtac aatgtacttc cacagggatg gaaggatca   660
ccagcaatat tccaaagtag catgacaaga atcttagagc cttttagaaa acaaaatcca   720
gaaatagtga tctatcaata catggatgat ttgtatgtag gatctgactt agaaataggg   780
cagcatagaa caaaaataga ggaactgaga caacatctgt tgaggtgggg atttaccaca   840
ccagacaaaa aacatcagaa agaacctcca ttcctttgga tgggttatga actccatcct   900
gataaatgga cagtacagcc tatagtgctg ccagaaaaag acagctggac tgtcaatgac   960
atacagaagt tagtgggaaa attgaattgg gcaagtcaga tttacccagg aattaaagta  1020
aagcaattat gtaaactcct taggggaacc aaggcattaa caagaagta ccactaaca  1080
aaagaaacag agctagaact ggcagagaac agggaaattc taaaagaacc agtacatggg  1140
gtgtattatg acccatcaaa agacttaata gcagaaatac agaagcaggg gcaaggccaa  1200
tggacatatc aaatttatca agagccattt aaaaatctga aacaggaaa atatgcaaga  1260
atgaggggtg cccacactaa tgatgtaaaa caattaacag aggcagtgca aaaaataacc  1320
acagaaagca tagtaatatg gggaaagact cctaaattta aactacccat acaaaaagaa  1380
```

```
acatgggaaa catggtggac agagtattgg caagccacct ggattcctga gtgggagttt   1440
gtcaataccc ctcccttagt gaaattatgt taccagttag agaaagaacc cataatagga   1500
gcagaaacat tctatgtaga tggagcagct aaccgggaga ctaaattagg aaaagcagga   1560
tatgttacta acagaggaag acaaaaagtt gtctccctaa ctgacacaac aaatcagaag   1620
actgagttac aagcaattca tctagcttta caagattcag gattagaagt aaacatagta   1680
acagactcac aatatgcatt aggaatcatt caagcacaac cagataaaag tgaatcagag   1740
ttagtcagtc aaataataga acagttaata aaaaaggaaa aggtctacct ggcatgggta   1800
ccagcgcaca aaggaattgg aggaaatgaa caagtagata aattagtcag tactggaatc   1860
aggaaagtac ta                                                       1872

SEQ ID NO: 71          moltype = DNA   length = 867
FEATURE                Location/Qualifiers
misc_feature           1..867
                       note = HIV Integrase- Bal
source                 1..867
                       mol_type = other DNA
                       organism = synthetic construct
SEQUENCE: 71
tttttagatg gaatagatat agcccaagaa gaacatgaga aatatcacag taattggaga   60
gcaatggcta gtgattttaa cctgccacct gtggtagcaa aagaaatagt agccagctgt   120
gataaatgtc agctaaaagg agaagccatg catggacaag tagactgtag tccaggaata   180
tggcaactag attgtacaca tttagaagga aaaattatcc tggtagcagt tcatgtagcc   240
agtggatata tagaagcaga agttattcca gcagagacag ggcaggaaac agcatacttt   300
ctcttaaaat tagcaggaag atggccagta aaaacaatac atacagacaa tggcagcaat   360
ttcactagta ctacagtcaa ggccgcctgt tggtgggcgg ggatcaagca ggaatttggc   420
attccctaca atccccaaag tcagggagta gtagaatcta taaataaaga attaaagaaa   480
attataggac aggtaagaga tcaggctgaa catcttaaaa cagcagtaca aatggcagta   540
ttcatccaca attttaaaag aaaaggggg attgggggggt atagtgcagg ggaaagaata   600
gtagacataa tagcaacaga catacaaact aaagaattac aaaaacaaat tacaaaaatt   660
caaaattttc gggtttatta cagggacagc agagatccaa tttggaaagg accagcaaag   720
cttctctgga aaggtgaagg ggcagtagta atacaagata atagtgacat aaaagtagtg   780
ccaagaagaa aagcaaagat cattagggat tatggaaaac agatggcagg tgatgattgt   840
gtggcaagta gacaggatga ggattag                                       867

SEQ ID NO: 72          moltype = DNA   length = 1695
FEATURE                Location/Qualifiers
misc_feature           1..1695
                       note = Envelope- RD114
source                 1..1695
                       mol_type = other DNA
                       organism = synthetic construct
SEQUENCE: 72
atgaaactcc caacaggaat ggtcattta tgtagcctaa taatagttcg ggcagggttt   60
gacgacccccc gcaaggctat cgcattagta caaaacaac atggtaaacc atgcgaatgc   120
agcggagggc aggtatccga ggccccaccg aactccatcc aacaggtaac ttgcccaggc   180
aagacggcct acttaatgac caaccaaaaa tggaaatgca gagtcactcc aaaaaatctc   240
accccctagcg ggggagaact ccagaactgc ccctgtaaca cttttccagga ctcgatgcac   300
agttcttgtt atactgaata ccggcaatgc agggcgaata taagacata ctacacggcc   360
accttgctta aaatacggtc tgggagcctc aacgaggtac agatattaca aaaccccaat   420
cagctcctac agtccccttg tagggctct ataaatcagc ccgtttgctg gagtgccaca   480
gccccatcc atatctccga tggtggagga cccctcgata ctaagagagt gggtgacagtc   540
caaaaaaggc tagaacaaat tcataaggct atgcatcctg aacttcaata ccacccctta   600
gccctgccca aagtcagaga tgaccttagc cttgatgcac ggacttttga tatcctgaat   660
accactttta ggttactcca gatgtccaat tttagccttg cccaagattg ttggctctgt   720
ttaaaactag gtacccctac ccctcttgcg ataccccctc ctcttaac ctactccta   780
gcagactccc tagcgaatgc ctcctgtcag attatacctc ccctcttggt tcaaccgatg   840
cagttctcca actcgtcctg ttttatcttc ccctttcatta acgatacgga acaaatagac   900
ttaggtgcag tcacctttac taactgcacc tctgtagcca atgtcagtag tcctttatgt   960
gccctaaacg gtcagtcttt cctctgtgga aataacatgg catacacctca tttacccaa   1020
aactggacag gactttgcgt ccaagctcc ctcctcccgg acattgacat catcccgggg   1080
gatgagccga tccccattcc tgccattgat cattatatac atagacctaa acgagctgta   1140
cagttcatcc ctttactagc tggactggga atcaccgcag cattcaccac ggagctaca   1200
ggcctaggtg tctccgtcac ccagtataca aaattatccc atcagttaat atctgatgtc   1260
caagtcttat ccggtaccat acaagattta caagaccgta gctgaagta   1320
gttctccaaa ataggagggg actgaccta ctaacggcag aacaaggagg aatttgttta   1380
gccttacaag aaaaatgctg ttttatgct aacaagtcag gaattgtgag aaacaaaata   1440
agaaccctac aagaagaatt acaaaaacgc agggaaagcc tggcatccaa ccctctctgg   1500
accgggctgc agggctttct tccgtacctc ctacctctcc tgggaccct actcacctc   1560
ctactcatac taaccattgg gccatgcgtt tcaatcgat tggtccaatt tgttaaagac   1620
aggatctcag tggtccagge tctggttttg actcagcaat atcaccagct aaaacccata   1680
gagtacgagc catga                                                    1695

SEQ ID NO: 73          moltype = DNA   length = 2013
FEATURE                Location/Qualifiers
misc_feature           1..2013
                       note = Envelope- GALV
source                 1..2013
                       mol_type = other DNA
                       organism = synthetic construct
```

```
SEQUENCE: 73
atgcttctca cctcaagccc gcaccacctt cggcaccaga tgagtcctgg gagctggaaa    60
agactgatca tcctcttaag ctgcgtattc ggagacggca aaacgagtct gcagaataag   120
aaccccccacc agcctgtgac cctcacctgg caggtactgt cccaaactgg ggacgttgtc  180
tgggacaaaa aggcagtcca gccccctttgg acttggtggc cctctcttac acctgatgta  240
tgtgccctgg cggccggtct tgagtcctgg gatatcccgg gatccgatgt atcgtcctct   300
aaaagagtta gacctcctga ttcagactat actgccgctt ataagcaaat cacctgggga   360
gccataggt gcagctaccc tcgggctagg accaggatgg caaattcccc cttctacgtg   420
tgtccccgag ctggccgaac ccattcagaa gctaggaggt gtgggggct agaatcccta    480
tactgtaaag aatggagttg tgagaccacg ggtaccgttt attggcaacc caagtcctca   540
tgggacctca taactgtaaa atgggaccaa aatgtgaaat gggagcaaaa atttcaaaag   600
tgtgaacaaa ccggctggtg taaccccctc aagatagact tcacagaaaa aggaaaactc   660
tccagagatt ggataacgga aaaaacctgg gaattaaggt tctatgtata tggcaccccca  720
ggcatacagt tgactatccg cttagaggtc actaacatgc cggttgtggc agtgggccca   780
gaccctgtcc ttgcggaaca gggacctcct agcaagcccc tcactctccc tctctcccca   840
cggaaagcgc cgcccacccc tctacccccg gcggctagtg agcaaacccc tgcggtgcat   900
ggagaaactg ttaccctaaa ctctccgcct ccaccagtg gcgaccgact cttttggcctt   960
gtgcaggggg ccttcctaac cttgaatgct accaaccag gggccactaa tgtcttgctgg  1020
ctctgtttgg gcatgagccc ccttattat gaagggatag cctcttcagg agaggtcgct   1080
tatacctcca accatacccg atgccactgg ggggcccaag aaagcttac cctcactgag    1140
gtctccggac tcgggtcatg catagggaag gtgcctctta cccatcaaca tctttgcaac   1200
cagaccttac ccatcaattc ctctaaaaac catcagtatc tgctccctc aaaccatagc    1260
tggtgggcct gcagcactgg cctcacccc tgcctctcca cctcagtttt taatcagtct    1320
aaagacttct gtgtccaggt ccagctgatc ccccgcatct attaccattc tgaagaaacc   1380
ttgttacaag cctatgacaa atcacccccc aggtttaaaa gagagcctgc ctcacttacc   1440
ctagctgtct tcctggggtt agggattgcg gcaggtatag gtactggctc aaccgcccta   1500
attaaagggc ccatagacct cagcaaggc ctaaccagcc tccaaatcgc cattgacgct    1560
gacctccggg cccttcagga ctcaatcagc aagctagagg actcactgac ttccctatct   1620
gaggtagtac tccaaaatag gagaggcctt gacttactat tccttaaaga aggaggcctc   1680
tgcgcggccc taaaagaaga gtgctgtttt tatgtagacc actcaggtgc agtacgagac   1740
tccatgaaaa aacttaaaga aagactagat aaaagacagt tagagcgcca gaaaaaccaa   1800
aactggtatg aagggtggtt caataactcc ccttggttta ctaccctact atcaaccatc   1860
gctgggcccc tattgctcct ccttttgtta ctcactcttg ggcctgcat catcaataaa    1920
ttaatccaat tcatcaatga taggataagt gcagtcaaaa ttttagtcct tagacagaaa   1980
tatcagaccc tagataacga ggaaaacctt taa                                 2013

SEQ ID NO: 74         moltype = DNA   length = 1530
FEATURE               Location/Qualifiers
misc_feature          1..1530
                      note = Envelope- FUG
source                1..1530
                      mol_type = other DNA
                      organism = synthetic construct
SEQUENCE: 74
atggttccgc aggttctttt gtttgtactc cttctgggtt tttcgttgtg tttcgggaag    60
ttccccattt acacgatacc agacgaactt ggtccctgga gcctattga catacaccat    120
ctcagctgtc caaataacct ggttgtggag gatgaaggat gtaccaacct gtccgagttc   180
tcctacatgg aactcaaagt gggatacatc tcagccatca aagtgaacgg gttcacttgc   240
acaggtgttg tgacagaggc agagacctac accaactttg ttggttatgt cacaaccaca   300
ttcaagagaa agcatttccg ccccacccca gacgcatgta gagccgcgta taactggaag  360
atggccggtg accccagata tgaagagtcc ctacacaatc cataccccga ctaccactgg  420
cttcgaactg taagaaccac caaagagtcc ctcattatca tatccccaag tgtgacagat  480
ttggacccat atgacaaatc ccttcactca agggtcttcc ctgcggaaa gtgctcagga   540
ataacggtgt cctctaccta ctgctcaact aaccatgatt acaccatttg gatgcccgag  600
aatccgagac caggacacc ttgtgacatt tttaccaata gcagagggaa gagagcatcc   660
aacgggaaca agacttgcgg ctttgtggat gaaagaggcc tgtataagtc tctaaaagga   720
gcatgcaggc tcaagttatg tggagttctt ggacttagac ttatgdatgg aacatggtc    780
gcgatgcaaa catcagatga gaccaaatg tgccctccag atcagttggt gaatttgcac   840
gactttcgct cagacgagat cgagcatctc gttgtggagg agttagttaa gaaaagagag   900
gaatgtctgg atgcattaga gtccatcatg accaccaagt cagtaagttt cagacgtctc   960
agtcacctga gaaacttgt cccagggttt ggaaaagcat ataccatatt caacaaaacc   1020
ttgatggaga ctgatgctca ctacaagtca gtccggacct ggaatgagat catccccttca   1080
aaagggtgtt tgaaagttgg aggaaggtgc catcctcatg taaacggggg gtttttcaat   1140
ggtataatat tagggcctga cgaccatgtc ctaatcccag atgcaatc atccctcctc    1200
cagcaacata tggagttgtt ggaatcttca gttatcccc tgatgcaccc cctggcagac   1260
ccttctacag ttttcaaaga aggtgatgag gctgaggatt tgttgaagt tcacctcccc    1320
gatgtgtaca aacagatctc aggggttgac ctgggtctcc cgaactgggg aaagtatgta   1380
ttgatgactg caggggccat gattggcctg gtgttgatat ttttcccaat gacatggtgc   1440
agagttggta tccatctttg cattaaatta aagcacacca agaaaagaca gatttataca   1500
gacatagaga tgaaccgact tggaaagtaa                                     1530

SEQ ID NO: 75         moltype = DNA   length = 1497
FEATURE               Location/Qualifiers
misc_feature          1..1497
                      note = Envelope- LCMV
source                1..1497
                      mol_type = other DNA
                      organ

```
SEQUENCE: 75
atgggtcaga ttgtgacaat gtttgaggct ctgcctcaca tcatcgatga ggtgatcaac  60
attgtcatta ttgtgcttat cgtgatcacg ggtatcaagg ctgtctacaa ttttgccacc  120
tgtgggatat tcgcattgat cagtttccta cttctggctg gcaggtcctg tggcatgtac  180
ggtcttaagg gacccgacat ttacaaagga gtttaccaat ttaagtcagt ggagtttgat  240
atgtcacatc tgaacctgac catgcccaac gcatgttcag ccaacaactc ccaccattac  300
atcagtatgg ggacttctgg actagaattg accttcacca atgattccat catcagtcac  360
aacttttgca atctgacctc tgccttcaac aaaaagacct ttgaccacac actcatgagt  420
atagtttcga gcctacacct cagtatcaga gggaactcca actataaggc agtatcctgc  480
gacttcaaca atggcataac catccaatac aacttgacat tctcagatcg acaaagtgct  540
cagagccagt gtagaacctt cagaggtaga gtcctagata tgtttagaac tgccttcggg  600
gggaaataca tgaggagtgg ctggggctgg acaggctcag atggcaagac cacctggtgt  660
agccagacga gttaccaata cctgattata caaaatagaa cctgggaaaa ccactgcaca  720
tatgcaggtc cttttgggat gtccaggatt ctcctttccc aagagaagac taagttcttc  780
actaggagac tagcgggcac attcacctgg actttgtcag actcttcagg ggtggagaat  840
ccaggtggtt attgcctgac caaatggatg attcttgctg cagagcttaa gtgtttcggg  900
aacacagcag ttgcgaaatg caatgtaaat catgatgccg aattctgtga catgctgcga  960
ctaattgact acaacaaggc tgctttgagt aagttcaaag aggacgtaga atctgccttg  1020
cacttattca aaacaacagt gaattctttg atttcagatc aactactgat gaggaaccac  1080
ttgagagatc tgatgggggt gccatattgc aattactcaa agttttggta cctagaacat  1140
gcaaagaccg gcgaaactag tgtccccaag tgctggcttg tcaccaatgg ttcttactta  1200
aatgagaccc acttcagtga tcaaatcgaa caggaagccg ataacatgat tacagagatg  1260
ttgaggaagg attacataaa gaggcagggg agtacccccc tagcattgat ggaccttctg  1320
atgttttcca catctgcata tctagtcagc atcttcctgc accttgtcaa aataccaaca  1380
cacaggcaca taaaaggtgg ctcatgtcca aagccacacc gattaaccaa caaaggaatt  1440
tgtagttgtg gtgcatttaa ggtgcctggt gtaaaaaccg tctggaaaag acgctga     1497

SEQ ID NO: 76           moltype = DNA  length = 1692
FEATURE                 Location/Qualifiers
misc_feature            1..1692
                        note = Envelope- FPV
source                  1..1692
                        mol_type = other DNA
                        organism = synthetic construct
SEQUENCE: 76
atgaacactc aaatcctggt tttcgccctt gtggcagtca tccccacaaa tgcagacaaa  60
atttgtcttg gacatcatgc tgtatcaaat ggcaccaaag taaacacact cactgagaga  120
ggagtagaag ttgtcaatgc aacggaaaca gtggagcgga caaacatccc caaaatttgc  180
tcaaaaggga aaagaaccac tgatcttggc caatgcggac tgttagggac cattaccgga  240
ccacctcaat gcgaccaatt tctagaattt tcagctgatc taataatcga gagacgagaa  300
ggaaatgatg tttgttaccc ggggaagttt gttaatgaag aggcattgcg acaaatcctc  360
agaggatcag gtgggattga caaagaaaca atgggattca catatagtgg aataaggacc  420
aacggaacaa ctagtgcatg tagaagatca gggtcttcat tctatgcaga aatggagtgg  480
ctcctgtcaa atacagacaa tgctgctttc ccacaaatga caaaatcata caaaaacaca  540
aggagagaat cagctctgat agtctgggga atccaccatt caggatcaac caccgaacag  600
accaaactat atgggagtgg aaataaactg ataacagtcg ggagttccaa atatcatcaa  660
tcttttgtgc cgagtccagg aacacgaccg cagataaatg gccagtccgg acggattgat  720
tttcattggt tgatcttgga tcccaatgat acagttactt ttagtttcaa tggggctttc  780
atagctccaa atcgtgccag cttcttgagg ggaaagtcca tggggatcca gagcgatgtg  840
caggttgatg ccaattgcga aggggaatgc taccacagtg gagggactat aacaagcaga  900
ttgccttttc aaaacatcaa tagcagagca gttggcaaat gcccaagata tgtaaaacag  960
gaaagtttat tattggcaac tgggatgaag aacgttcccg aaccttccaa aaaaaggaaa  1020
aaaagaggcc tgtttggcgc tatagcaggg tttattgaaa atggttggga aggtctggtc  1080
gacgggtggt acggtttcag gcatcagaat gcacaaggag aaggaactgc agcagactac  1140
aaaagcaccc aatcggcaat tgatcagata accggaaagt taaatagact cattgagaaa  1200
accaaccagc aatttgagct aatagataat gaattcactg aggtggaaaa gcagattggc  1260
aatttaatta actggaccaa agactccatc acagaagtat ggtcttacaa tgctgaactt  1320
cttgtggcaa tggaaaacca gcacactatt gatttggctg attcagagat gaacaagctg  1380
tatgagcgag tgaggaaaca attaagggaa aatgctgaag aggatggcac tggttgcttt  1440
gaaatttttc ataaatgtga cgatgattgt atggctagta taaggaacaa tacttatgat  1500
cacagcaaat acagagaaga agcgatgcaa aatagaatac aaattgaccc agtcaaattg  1560
agtagtggct acaaagatgt gatactttgg tttagcttcg ggcatcatg ctttttgctt  1620
cttgccattg caatgggcct tgttttcata tgtgtgaaga acggaaacat gcggtgcact  1680
atttgtatat aa                                                       1692

SEQ ID NO: 77           moltype = DNA  length = 1266
FEATURE                 Location/Qualifiers
misc_feature            1..1266
                        note = Envelope- RRV
source                  1..1266
                        mol_type = other DNA
                        organism = synthetic construct
SEQUENCE: 77
agtgtaacag agcactttaa tgtgtataag gctactagac catacctagc acattgcgcc  60
gattgcgggg acgggtactt ctgctatagc ccagttgcta tcgaggagat ccgagatgag  120
gcgtctgatg gcatgcttaa gatccaagtc tccgcccaaa taggtctgga caaggcaggc  180
acccacgccc acacgaagct ccgatatatg gctggtcatg atgttcagga atctaagaga  240
gattccttga gggtgtacac gtccgcagcg tgctccatac atgggacgat gggacacttc  300
atcgtcgcac actgtccacc aggcgactac ctcaaggttt cgttcgagga cgcagattcg  360

```
cacgtgaagg catgtaaggt ccaatacaag cacaatccat tgccggtggg tagagagaag   420
ttcgtggtta gaccacactt tggcgtagag ctgccatgca cctcatacca gctgacaacg   480
gctcccaccg acgaggagat tgacatgcat acaccgccag atataccgga tcgcaccctg   540
ctatcacaga cggcgggcaa cgtcaaaata acagcaggcg gcaggactat caggtacaac   600
tgtacctgcg gccgtgacaa cgtaggcact accagtactg acaagaccat caacacatgc   660
aagattgacc aatgccatgc tgccgtcacc agccatgaca aatggcaatt tacctctcca   720
tttgttccca gggctgatca gacagctagg aaaggcaagg tacacgttcc gttccctctg   780
actaacgtca cctgccgagt gccgttggct cgagcgccgg atgccaccta tggtaagaag   840
gaggtgaccc tgagattaca cccagatcat ccgacgctct tctcctatag gagtttagga   900
gccgaaccgc acccgtacga ggaatgggtt gacaagttct ctgagcgcat catcccagtg   960
acggaagaag ggattgagta ccagtggggc aacaacccgc cggtctgcct gtgggcgcaa  1020
ctgacgaccg agggcaaacc ccatggctgg ccacatgaaa tcattcagta ctattatgga  1080
ctataccccg ccgccactat tgccgcagta tccggggcga gtctgatggc cctcctaact  1140
ctggcggcca catgctgcat gctggccacc gcgaggagaa agtgcctaac accgtacgcc  1200
ctgacgccag gagcggtggt accgttgaca ctggggctgc tttgctgcgc accgagggcg  1260
aatgca                                                             1266

SEQ ID NO: 78           moltype = DNA   length = 1266
FEATURE                 Location/Qualifiers
misc_feature            1..1266
                        note = Envelope- MLV 10A1
source                  1..1266
                        mol_type = other DNA
                        organism = synthetic construct
SEQUENCE: 78
agtgtaacag agcactttaa tgtgtataag gctactagac catacctagc acattgcgcc   60
gattgcgggg acgggtactt ctgctatagc ccagttgcta tcgaggagat ccgagatgag  120
gcgtctgatg gcatgcttaa gatccaagtc tccgcccaaa taggtctgga caaggcaggc  180
acccacgccc acacgaagct ccgatatatg gctggtcatg atgttcagga atctaagaga  240
gattccttga gggtgtacac gtccgcagcg tgctccatac atgggacgat gggacacttc  300
atcgtcgcac actgtccacc aggcgactac ctcaaggttt cgttcgagga cgcagattcc  360
cacgtgaagg catgtaaggt ccaatacaag cacaatccat tgccggtggg tagagagaag  420
ttcgtggtta gaccacactt tggcgtagag ctgccatgca cctcatacca gctgacaacg  480
gctcccaccg acgaggagat tgacatgcat acagcaggcg gcaggactat caggtacaac  540
ctatcacaga cggcgggcaa cgtcaaaata acagcaggcg gcaggactat caggtacaac  600
tgtacctgcg gccgtgacaa cgtaggcact accagtactg acaagaccat caacacatgc  660
aagattgacc aatgccatgc tgccgtcacc agccatgaca aatggcaatt tacctctcca  720
tttgttccca gggctgatca gacagctagg aaaggcaagg tacacgttcc gttccctctg  780
actaacgtca cctgccgagt gccgttggct cgagcgccgg atgccaccta tggtaagaag  840
gaggtgaccc tgagattaca cccagatcat ccgacgctct tctcctatag gagtttagga  900
gccgaaccgc acccgtacga ggaatgggtt gacaagttct ctgagcgcat catcccagtg  960
acggaagaag ggattgagta ccagtggggc aacaacccgc cggtctgcct gtgggcgcaa 1020
ctgacgaccg agggcaaacc ccatggctgg ccacatgaaa tcattcagta ctattatgga 1080
ctataccccg ccgccactat tgccgcagta tccggggcga gtctgatggc cctcctaact 1140
ctggcggcca catgctgcat gctggccacc gcgaggagaa agtgcctaac accgtacgcc 1200
ctgacgccag gagcggtggt accgttgaca ctggggctgc tttgctgcgc accgagggcg 1260
aatgca                                                            1266

SEQ ID NO: 79           moltype = DNA   length = 2030
FEATURE                 Location/Qualifiers
misc_feature            1..2030
                        note = Envelope- Ebola
source                  1..2030
                        mol_type = other DNA
                        organism = synthetic construct
SEQUENCE: 79
atgggtgtta caggaatatt gcagttacct cgtgatcgat tcaagaggac atcattcttt   60
ctttgggtaa ttatcctttt ccaaagaaca ttttccatcc cacttggagt catccacaat  120
agcacattac aggttagtga tgtcgacaaa ctggtttgtc gtgacaaact gtcatccaca  180
aatcaattga gatcagttgg actgaatctc gaagggaatg gagtggcaac tgacgtgcca  240
tctgcaacta aaagatgggg cttcaggtcc ggtgtcccac caaaggtggt caattatgaa  300
gctggtgaat gggctgaaaa ctgctacaat cttgaaatca aaaaacctga cgggagtgag  360
tgtctaccag cagcgccaga cgggattcgg ggcttccccc ggtgccggta tgtgcacaaa  420
gtatcaggaa cgggaccgtg tgccggagac tttgccttcc acaaagaggg tgctttcttc  480
ctgtatgacc gacttgcttc cacagttatc taccgaggaa cgactttcgc tgaaggtgtc  540
gttgcatttc tgatactgcc caagctaagg aaggactttc tcagctcaca ccccttgaga  600
gagccggtca atgcaacgga ggaccgtctc agtggctact attctaccac aattagatat  660
caagctaccg gttttggaac caatgagaca gagtatttgt tcgaggttga caatttgacc  720
tacgtccaac ttgaatcaag attcacacca cagtttctgc tgcagacaga caatatgcaa  780
tatacaagtg ggaaaggag caataccacg ggaaaactaa tttggaaggt caacccccga  840
attgatacaa caatcgggga gtgggccttc tgggaaacta aaaaaacctc actagaaaaa  900
ttcgcagtga gagttgtctt tcacagctg tatcaaacag agccaaaaac atcagtggtc 960
agagtccggc gcgaacttct tccgacccag ggaccaacac aacaactgaa gaccacaaaa 1020
tcatgaggac gggacagct cgcccagaca tttaagtgca gtcaagga agggaagctg 1080
cagtgtcgca tctgacaacc cttgccacaa tctccacgag tcctcaaccc ccacaaccaa 1140
accaggtcc ggacaacagc acccacaata cacccgtgta taacttgac atctctgagg 1200
caactcaagt tgaacaacat caccgcagaa cagacaacga cagcacagcc tcgactcc 1260
ccccgccac gaccgcagcc ggacccctaa aagcagagaa caccaacacg agcaagggta 1320
ccgacctcct ggaccccgcc accacaacaa gtccccaaaa ccacagcgag accgctggca 1380
```

```
acaacaacac tcatcaccaa gataccggag aagagagtgc cagcagcggg aagctaggct    1440
taattaccaa tactattgct ggagtcgcag gactgatcac aggcgggagg agagctcgaa    1500
gagaagcaat tgtcaatgct caacccaaat gcaaccctaa tttacattac tggactactc    1560
aggatgaagg tgctgcaatc ggactggcct ggataccata tttcgggcca gcagccgagg    1620
gaatttacat agaggggctg atgcacaatc aagatggttt aatctgtggg ttgagacagc    1680
tggccaacga gacgactcaa gctcttcaac tgttcctgag agccacaacc gagctacgca    1740
ccttttcaat cctcaaccgt aaggcaattg atttcttgct gcagcgatgg ggcggcacat    1800
gccacatttt gggaccggac tgctgtatcg aaccacatga ttggaccaag aacataacag    1860
acaaaattga tcagattatt catgattttg ttgataaaac ccttccggac caggggggaca    1920
atgacaattg gtggacagga tggagacaat ggataccggc aggtattgga gttacaggcg    1980
ttataattgc agttatcgct ttattctgta tatgcaaatt tgtcttttag                2030

SEQ ID NO: 80              moltype = DNA   length = 389
FEATURE                    Location/Qualifiers
misc_feature               1..389
                           note = Short WPRE sequence
source                     1..389
                           mol_type = other DNA
                           organism = synthetic construct
SEQUENCE: 80
aatcaacctc tggattacaa aatttgtgaa agattgactg atattcttaa ctatgttgct     60
ccttttacgc tgtgtggata tgctgcttta atgcctctgt atcatgctat tgcttcccgt    120
acggctttcg ttttctcctc cttgtataaa tcctggttgc tgtctcttta tgaggagttg    180
tggcccgttg tccgtcaacg tggcgtggtg tgctctgtgt ttgctgacgc aacccccact    240
ggctgggca ttgccaccac ctgtcaactc ctttctggga ctttcgcttt ccccctcccg     300
atcgccacgg cagaactcat cgccgcctgc cttgcccgct gctggacagg ggctaggttg    360
ctgggcactg ataattccgt ggtgttgtc                                       389

SEQ ID NO: 81              moltype = DNA   length = 31
FEATURE                    Location/Qualifiers
misc_feature               1..31
                           note = Primer
source                     1..31
                           mol_type = other DNA
                           organism = synthetic construct
SEQUENCE: 81
taagcagaat tcatgaattt gccaggaaga t                                     31

SEQ ID NO: 82              moltype = DNA   length = 36
FEATURE                    Location/Qualifiers
misc_feature               1..36
                           note = Primer
source                     1..36
                           mol_type = other DNA
                           organism = synthetic construct
SEQUENCE: 82
ccatacaatg aatggacact aggcggccgc acgaat                                36

SEQ ID NO: 83              moltype = DNA   length = 2745
FEATURE                    Location/Qualifiers
misc_feature               1..2745
                           note = Gag, Pol, Integrase fragment
source                     1..2745
                           mol_type = other DNA
                           organism = synthetic construct
SEQUENCE: 83
gaattcatga atttgccagg aagatggaaa ccaaaaatga tagggggaat tggaggtttt     60
atcaaagtaa gacagtatga tcagatactc atagaaatct gcggacataa agctataggt    120
acagtattag taggacctac acctgtcaac ataattggaa gaaatctgtt gactcagatt    180
ggctgcactt taaatttcc cattagtcct attgagactg taccagtaaa attaaagcca    240
ggaatggatg gcccaaaagt taaacaatgg ccattgacag aagaaaaaat aaaagcatta    300
gtagaaattt gtacagaaat ggaaaaggaa ggaaaaattt caaaaattgg gcctgaaaat    360
ccatacaata ctccagtatt tgccataaag aaaaaagaca gtactaaatg gagaaaatta    420
gtagatttca gagaacttaa taagagaact caagatttct gggaagttca attaggaata    480
ccacatcctg cagggttaaa acagaaaaaa tcagtaacag tactggatgt gggcgatgca    540
tatttttcag ttcccttaga taaagacttc aggaagtata ctgcatttac catacctagt    600
ataaacaatg agacaccagg gattagatat cagtacaatg tgcttccaca gggatggaaa    660
ggatcaccag caatattcca gtgtagcatg acaaaaatct tagagccttt tagaaaacaa    720
aatccagaca tagtcatcta tcaatacatg gatgatttgt atgtaggatc tgacttagaa    780
atagggcagc atagaacaaa aatagaggaa ctgagacaac atctgttgag gtggggattt    840
accacaccag acaaaaaaca tcagaaagaa cctccattcc tttggatggg ttatgaactc    900
catcctgata aatggacagt acagcctata gtgctgccag aaaaggacag ctggactgtc    960
aatgacatac agaaattagt gggaaaattg aattgggcaa gtcagattta tgcagggatt   1020
aaagtaaggc aattatgtaa acttcttagg ggaaccaaag cactaacaga agtagtacca   1080
ctaacagaaa agcagagct agaactggca gaaaacaggg agattctaaa agaaccggta   1140
catggagtgt attatgaccc atcaaaagac ttaatagcag aaatacagaa gcaggggcaa   1200
ggccaatgga catatcaaat ttatcaagag ccatttaaaa atctgaaaac aggaaagtat   1260
gcaagaatga agggtgccca cactaatgat gtgaaacaat taacagaggc agtacaaaaa   1320
atagccacag aaagcatagt aatatgggga aagactccta aatttaaatt acccatacaa   1380
```

```
aaggaaacat gggaagcatg gtggacagag tattggcaag ccacctggat tcctgagtgg 1440
gagtttgtca atacccctcc cttagtgaag ttatggtacc agttagaaga agaacccata 1500
ataggagcag aaactttcta tgtagatggg gcagccaata gggaaactaa attaggaaaa 1560
gcaggatatg taactgacag aggaagacaa aaagttgtcc ccctaacgga cacaacaaat 1620
cagaagactg agttacaagc aattcatcta gctttgcagg attcgggatt agaagtaaac 1680
atagtgacag actcacaata tgcattggga atcattcaag caccaccaga taagagtgaa 1740
tcagagttag tcagtcaaat aatagagcag ttaataaaaa aggaaaagt ctacctggca 1800
tgggtaccag cacacaaagg aattggagga aatgaacaag tagataaatt ggtcagtgct 1860
ggaatcagga aagtactatt tttagatgga atagataagg cccaagaaga acatgagaaa 1920
tatcacagta attggagagc aatggctagt gattttaacc taccacctgt agtagcaaaa 1980
gaaatagtag ccagctgtga taaatgtcag ctaaaagggg aagccatgca tggacaagta 2040
gactgtagcc caggaatatg gcagctagat tgtacacatt tagaaggaaa agttatcttg 2100
gtagcagttc atgtagccag tggatatata gaagcagaag taattccagc agagacaggg 2160
caagaaacag catacttcct cttaaaatta gcaggaagat ggccagtaaa aacagtacat 2220
acagacaatg gcagcaattt caccagtact acagttaagg ccgcctgttg gtgggcgggg 2280
atcaagcagg aatttggcat tccctacaat ccccaaagtc aaggagtaat agaatctatg 2340
aataaagaat taagaaaat tataggacag gtaagagatc aggctgaaca tcttaagaca 2400
gcagtacaaa tggcagtatt catccacaat tttaaaagaa aaggggggat tggggggtac 2460
agtgcagggg aaagaatagt agacataata gcaacagaca tacaaactaa agaattacaa 2520
aaacaaatta caaaaattca aaattttcgg gtttattaca gggacagcag agatccagtt 2580
tggaaaggac cagcaaagct cctctggaaa ggtgaagggg cagtagtaat acaagataat 2640
agtgacataa aagtagtgcc aagaagaaaa gcaaagatca tcaggggatta tggaaaacag 2700
atggcaggtg atgattgtgt ggcaagtaga caggatgagg attaa 2745

SEQ ID NO: 84           moltype = DNA    length = 1586
FEATURE                 Location/Qualifiers
misc_feature            1..1586
                        note = DNA Fragment containing Rev, RRE and rabbit beta
                         globin poly A
source                  1..1586
                        mol_type = other DNA
                        organism = synthetic construct
SEQUENCE: 84
tctagaatgg caggaagaag cggagacagc gacgaagagc tcatcagaac agtcagactc 60
atcaagcttc tctatcaaag caacccacct cccaatcccg aggggacccg acaggcccga 120
aggaatagaa gaagaaggtg gagagagaga cagagacaga tccattcgat tagtgaacgg 180
atccttggca cttatctggg acgatctgcg gagcctgtgc ctcttcagct accaccgctt 240
gagagactta ctcttgattg taacgaggat tgtggaactt ctgggacgca ggggggtggga 300
agccctcaaa tattggtgga atctcctaca atattggagt caggagctaa agaatagagg 360
agctttgttc cttgggttct tgggagcagc aggaagcact atgggcgcag cgtcaatgac 420
gctgacggta caggccagac aattattgtc tggtatagtg cagcagcaga caatttgct 480
gagggctatt gaggcgcaac agcatctgtt gcaactcaca gtctgggca tcaagcagct 540
ccaggcaaga atcctggctg tggaaagata cctaaaggat caacagctcc tagatctttt 600
tccctctgcc aaaaattatg gggacatcat gaagccccctt gagcatctga cttctggcta 660
ataaaggaaa tttatttca ttgcaatagt gtgttggaat tttttgtgtc tctcactcgg 720
aaggacatat ggagggcaa atcatttaaa acatcagaat gagtatttgg tttagagttt 780
ggcaacatat gccatatgct ggctgccatg aacaaaggta gctataaaga ggtcatcagt 840
atatgaaaca gccccctgct gtccattcct tattccatag aaaagccttg acttgaggtt 900
agattttttt tatattttgt tttgtgttat ttttttctt aacatcccta aaattttcct 960
tacatgtttt actagccaga ttttcctcc tctcctgact actcccagtc atagctgtcc 1020
ctcttctctt atgaagatcc ctcgacctgc agcccaagct tggcgtaatc atggtcatag 1080
ctgtttcctg tgtgaaattg ttatccgctc acaattccac acaacatacg agccggaagc 1140
ataaagtgta aagcctgggg tgcctaatga gtgagctaac tcacattaat tgcgttgcgc 1200
tcactgcccg ctttccagtc gggaaacctg tcgtgccagc ggatccgcat ctcaattagt 1260
cagcaaccat agtcccgccc ctaactccgc ccatcccgcc ctaactccgc ccagttccg 1320
cccattctcc gccccatggc tgactaattt tttttattta gcagaggcc gaggccgcct 1380
cggcctctga gctattccag aagtagtgag gaggcttttt tggaggccta ggcttttgca 1440
aaaagctaac ttgtttattg cagcttataa tggttacaaa taaagcaata gcatcacaaa 1500
tttcacaaat aaagcatttt ttcactgca ttctagttgt ggtttgtcca aactcatcaa 1560
tgtatcttat cagcggccgc cccggg                                      1586

SEQ ID NO: 85           moltype = DNA    length = 1614
FEATURE                 Location/Qualifiers
misc_feature            1..1614
                        note = DNA fragment containing the CAG
                         enhancer/promoter/intron sequence
source                  1..1614
                        mol_type = other DNA
                        organism = synthetic construct
SEQUENCE: 85
acgcgttagt tattaatagt aatcaattac ggggtcatta gttcatagcc catatatgga 60
gttccgcgtt acataactta cggtaaatgg cccgcctggc tgaccgccca acgacccccg 120
cccattgacg tcaataatga cgtatgttcc catagtaacg ccaatagga ctttccattg 180
acgtcaatgg gtggactatt tacggtaaac tgcccacttg gcagtacatc aagtgtatca 240
tatgccaagt acgcccccta ttgacgtcaa tgacggtaaa tggcccgcct ggcattatgc 300
ccagtacatg accttatggg actttcctac ttggcagtac atctacgtat tagtcatcgc 360
tattaccatg gtcgaggtg agccccacgt tctgcttcac tctccccatc tcccccccct 420
ccccaccccc aattttgtat ttatttattt tttaattatt ttgtgcagcg atggggggcgg 480
ggggggggggg ggcgcgcgcc aggcggggcg gggcggggcg aggggcggggg cggggcgagg 540
```

```
cggagaggtg cggcggcagc caatcagagc ggcgcgctcc gaaagtttcc ttttatggcg   600
aggcggcggc ggcggcggcc ctataaaaag cgaagcgcgc ggcgggcggg agtcgctgcg   660
ttgccttcgc cccgtgcccc gctccgcgcc gcctcgcgcc gcccgccccg gctctgactg   720
accgcgttac tcccacaggt gagcgggcgg gacggcccct ctcctccggg ctgtaattag   780
cgcttggttt aatgacggct cgtttctttt ctgtggcgtc gtgaaagcct taaagggctc   840
cgggagggcc cttgtgtcgg gggggagcgg ctccgggggt gcgtgcgtgt gtgtgtgcgt   900
ggggagcgcc gcgtgcggcc cgcgctgccc ggcggctgtg agcgctgcgg gcgcggcgcg   960
gggctttgtg cgctccgcgt gtgcgcgagg ggagcgcggc cggggcggt gccccgcggt   1020
gcgggggggc tgcgagggga acaaaggctg cgtgcgggt gtgtgcgtgg gggggtgagc   1080
aggggtgtg ggcgcggcgg tcgggctgta accccccct gcacccccct ccccgagttg   1140
ctgagcacgg cccggcttcg ggtgcgggc tccgtgcggg gcgtggccgcg gggctcgccg   1200
tgccgggcgg ggggtggcgg caggtggggg tgccgggcgg ggcggggccg cctcgggccg   1260
gggagggctc ggggagggg cgcggcggcc ccggagcgcc ggcggctgtc gaggcgcggc   1320
gagccgcagc cattgccttt tatggtaatc gtgcgagagg gcagggac ttcctttggc   1380
ccaaatctgg cggagccgaa atctgggagg cgccgccgca ccccctctag cgggcgcggg   1440
cgaagcggtg cggcgccggc aggaaggaaa tgggcgggga gggccttcgt gcgtcgccgc   1500
gccgccgtcc ccttctccat ctccagcctc ggggctgccg caggggacg gctgccttcg   1560
ggggggacgg ggcagggcgg ggttcggctt ctggcgtgtg accggcggga attc          1614

SEQ ID NO: 86              moltype = DNA   length = 1531
FEATURE                    Location/Qualifiers
misc_feature               1..1531
                           note = DNA fragment containing VSV-G
source                     1..1531
                           mol_type = other DNA
                           organism = synthetic construct
SEQUENCE: 86
gaattcatga agtgcctttt gtacttagcc tttttattca ttggggtgaa ttgcaagttc     60
accatagttt ttccacacaa ccaaaaagga aactggaaaa atgttccttc taattaccat    120
tattgcccgt caagctcaga tttaaattgg cataatgact taataggcac agccttacaa    180
gtcaaaatgc ccaagagtca caaggctatt caagcagacg gttggatgtg tcatgcttcc    240
aaatgggtca ctacttgtga tttccgctgg tatggaccga gtatataac acattccatc    300
cgatccttca ctccatctgt agaacaatgc aaggaaagca ttgaacaaac gaaacaagga    360
acttggctga atccaggctt ccctcctcaa agttgtggat atgcaactgt gacggatgcc    420
gaagcagtga ttgtccaggt gactcctcac catgtgctgg ttgatgaata cacaggagaa    480
tgggttgatt cacagttcat caacggaaaa tgcagcaatt acatatgccc cactgtccat    540
aactctacaa cctggcattc tgactataag gtcaaagggc tatgtgattc taacctcatt    600
tccatggaca tcaccttctt ctcagaggac ggagagctat catccctggg aaaggaggc    660
acagggttca gaagtaacta ctttgcttat gaaactgagg gcaaggcctg caaaatgcaa    720
tactgcaagc attgggggagt cagactccca tcaggtgtct ggttcgagat ggctgataag    780
gatctctttg ctgcagccag attccctgaa tgcccagaag gtcaagtat ctctgctcca    840
tctcagacct cagtggatgt aagtctaatt caggacgttg agaggatctt ggattattcc    900
ctctgccaag aaacctggag caaaatcaga gcgggtctc caatctctcc agtggatctc    960
agctatcttg ctcctaaaaa cccaggaacc ggtcctgctt tcaccataat caatggtacc   1020
ctaaaatact tgagaccag atacatcaga gtcgatattg ctgctccaat cctctcaaga   1080
atggtcgaa tgatcagtgg aactaccaca gaaagggaac tgtgggatga ctgggcacca   1140
tatgaagacg tggaaattgg acccaatgga gttctgagga ccagttcagg atataagttt   1200
ccttttataca tgattggaca tggtatgttg gactccgatc ttcatcttag ctcaaaggct   1260
caggtgttcg aacatcctca cattcaagac gctgcttcgc aacttcctga tgatgagagt   1320
ttatttttg gtgatactgg gctatccaaa aatccaatcg agcttgtaga aggttggttc   1380
agtagttgga aaagctctat tgcctctttt tctttatca tagggttaat cattggacta   1440
ttcttggttc tccgagttgg tatccatctt tgcattaaat taaagcacac caagaaaaga   1500
cagatttata cagacataga gatgagaatt c                                  1531

SEQ ID NO: 87              moltype = DNA   length = 1227
FEATURE                    Location/Qualifiers
misc_feature               1..1227
                           note = Helper plasmid containing RRE and rabbit beta globin
                            poly A
source                     1..1227
                           mol_type = other DNA
                           organism = synthetic construct
SEQUENCE: 87
tctagaagga gctttgttcc ttgggttctt gggagcagca ggaagcacta tgggcgcagc     60
gtcaatgacg ctgacggtac aggccagaca attattgtct ggtatagtgc agcagcagaa    120
caatttgctg agggctattg aggcgcaaca gcatctgttg caactcacag tctggggcat    180
caagcagctc caggcaagaa tcctggctgt ggaaagatac ctaaaggatc aacagctcct    240
agatcttttt ccctctgcca aaaattatgg ggacatcatg aagcccctg agcatctgac    300
ttctggctaa taaaggaaat ttatttcat tgcaatagtg tgttggaatt ttttgtgtct    360
ctcactcgga aggacatatg ggagggcaaa tcatttaaaa catcagaatg agtatttggt    420
ttagagtttg gcaacatatg ccatatgctg gctgccatga acaaaggtgg ctataaagag    480
gtcatcagta tatgaaacag ccccctgctg tccattcctt attccataga aaagccttga    540
cttgaggtta gatttttttt atattttgtt ttgtgttatt ttttcttta acatccctaa    600
aattttcctt acatgtttta ctagccagat ttttcctcct ctcctgacta ctcccagtca    660
tagctgtccc tcttctctta tgaagatccc tcgacctgca gcccaagctt ggcgtaatca    720
tggtcatagc tgtttcctgt gtgaaattgt tatccgctca caattccaca caacatacga    780
gccgaagca taaagtgtaa agcctgggt gcctaatgag tgagctaact cacattaatt    840
gcgttgcgct cactgcccgc tttccagtcg ggaaacctgt cgtgccagcg gatccgcatc    900
tcaattagtc agcaaccata gtcccgcccc taactccgcc catcccgccc ctaactccgc    960
```

```
ccagttccgc ccattctccg ccccatggct gactaatttt ttttatttat gcagaggccg    1020
aggccgcctc ggcctctgag ctattccaga agtagtgagg aggctttttt ggaggcctag    1080
gcttttgcaa aaagctaact tgtttattgc agcttataat ggttacaaat aaagcaatag    1140
catcacaaat ttcacaaata aagcattttt tcactgcat tctagttgtg gtttgtccaa     1200
actcatcaat gtatcttatc acccggg                                        1227

SEQ ID NO: 88          moltype = DNA   length = 884
FEATURE                Location/Qualifiers
misc_feature           1..884
                       note = RSV promoter and HIV Rev
source                 1..884
                       mol_type = other DNA
                       organism = synthetic construct
SEQUENCE: 88
caattgcgat gtacgggcca gatatacgcg tatctgaggg gactaggtg tgtttaggcg      60
aaaagcgggg cttcggttgt acgcggttag gagtccctc aggatatagt agtttcgctt    120
ttgcataggg aggggaaat gtagtcttat gcaatacact tgtagtcttg caacatggta    180
acgatgagtt agcaacatgc cttacaagga gagaaaaagc accgtgcatg ccgattggtg   240
gaagtaaggt ggtacgatcg tgccttatta ggaaggcaac agacaggtct gacatggatt   300
ggacgaacca ctgaattccg cattgcagag ataattgtat ttaagtgcct agctcgatac   360
aataaacgtc atttgaccat tcaccacatt ggtgtgcacc tccaagctcg agctcgttta   420
gtgaaccgtc agatcgcctg gagacgccat ccacgctgtt ttgacctcca tagaagacac   480
cgggaccgat ccagcctccc ctcgaagcta gcgattaggc atctcctatg gcaggaagaa   540
gcggagacag cgacgaagaa ctcctcaagg cagtcagact catcaagttt ctctatcaaa   600
gcaacccacc tcccaatccc gaggggaccc gacaggcccg aaggaataga agaagaaggt   660
ggagagagag acagagacag atccattcga ttagtgaacg gatccttagc acttatctgg   720
gacgatctgc ggagcctgtg cctcttcagc taccaccgct tgagagactt actcttgatt   780
gtaacgagga ttgtggaact tctgggacgc agggggtggg aagccctcaa atattggtgg   840
aatctcctac aatattggag tcaggagcta aagaatagtc taga                    884

SEQ ID NO: 89          moltype = DNA   length = 19
FEATURE                Location/Qualifiers
misc_feature           1..19
                       note = Target sequence
source                 1..19
                       mol_type = other DNA
                       organism = synthetic construct
SEQUENCE: 89
atggcaggaa gaagcggag                                                  19

SEQ ID NO: 90          moltype = DNA   length = 52
FEATURE                Location/Qualifiers
misc_feature           1..52
                       note = shRNA sequence
source                 1..52
                       mol_type = other DNA
                       organism = synthetic construct
SEQUENCE: 90
atggcaggaa gaagcggagt tcaagagact ccgcttcttc ctgccatttt tt             52

SEQ ID NO: 91          moltype = DNA   length = 279
FEATURE                Location/Qualifiers
misc_feature           1..279
                       note = H1 promoter and shRT sequence
source                 1..279
                       mol_type = other DNA
                       organism = synthetic construct
SEQUENCE: 91
gaacgctgac gtcatcaacc cgctccaagg aatcgcgggc ccagtgtcac taggcgggaa     60
cacccagcgc gcgtgcgccc tggcaggaag atggctgtga gggacagggg agtggcgccc   120
tgcaatattt gcatgtcgct atgtgttctg ggaaatcacc ataaacgtga aatgtctttg   180
gatttgggaa tcttataagt tctgtatgag accacttgga tccgcggaga cagcgacgaa   240
gagcttcaag agagctcttc gtcgctgtct ccgcttttt                          279

SEQ ID NO: 92          moltype = DNA   length = 275
FEATURE                Location/Qualifiers
misc_feature           1..275
                       note = H1 CCR5 sequence
source                 1..275
                       mol_type = other DNA
                       organism = synthetic construct
SEQUENCE: 92
gaacgctgac gtcatcaacc cgctccaagg aatcgcgggc ccagtgtcac taggcgggaa     60
cacccagcgc gcgtgcgccc tggcaggaag atggctgtga gggacagggg agtggcgccc   120
tgcaatattt gcatgtcgct atgtgttctg ggaaatcacc ataaacgtga aatgtctttg   180
gatttgggaa tcttataagt tctgtatgag accacttgga tccgtgtcaa gtccaatcta   240
tgttcaagag acatagattg gacttgacac ttttt                              275

SEQ ID NO: 93          moltype = DNA   length = 20
```

```
FEATURE                 Location/Qualifiers
misc_feature            1..20
                        note = Primer
source                  1..20
                        mol_type = other DNA
                        organism = synthetic construct
SEQUENCE: 93
aggaattgat ggcgagaagg                                               20

SEQ ID NO: 94           moltype = DNA   length = 24
FEATURE                 Location/Qualifiers
misc_feature            1..24
                        note = Primer
source                  1..24
                        mol_type = other DNA
                        organism = synthetic construct
SEQUENCE: 94
ccccaaagaa ggtcaaggta atca                                          24

SEQ ID NO: 95           moltype = DNA   length = 18
FEATURE                 Location/Qualifiers
misc_feature            1..18
                        note = Primer
source                  1..18
                        mol_type = other DNA
                        organism = synthetic construct
SEQUENCE: 95
agcgcggcta cagcttca                                                 18

SEQ ID NO: 96           moltype = DNA   length = 20
FEATURE                 Location/Qualifiers
misc_feature            1..20
                        note = Primer
misc_feature            20
                        note = n = p
source                  1..20
                        mol_type = other DNA
                        organism = synthetic construct
SEQUENCE: 96
ggcgacgtag cacagcttcn                                               20

SEQ ID NO: 97           moltype = DNA   length = 20
FEATURE                 Location/Qualifiers
misc_feature            1..20
                        note = AGT103 CCR5 miR30
source                  1..20
                        mol_type = other DNA
                        organism = synthetic construct
SEQUENCE: 97
tgtaaactga gcttgctcta                                               20

SEQ ID NO: 98           moltype = DNA   length = 20
FEATURE                 Location/Qualifiers
misc_feature            1..20
                        note = AGT103-R5-1
source                  1..20
                        mol_type = other DNA
                        organism = synthetic construct
SEQUENCE: 98
tgtaaactga gcttgctcgc                                               20

SEQ ID NO: 99           moltype = DNA   length = 19
FEATURE                 Location/Qualifiers
misc_feature            1..19
                        note = AGT103-R5-2
source                  1..19
                        mol_type = other DNA
                        organism = synthetic construct
SEQUENCE: 99
catagattgg acttgacac                                                19

SEQ ID NO: 100          moltype = DNA   length = 642
FEATURE                 Location/Qualifiers
misc_feature            1..642
                        note = CAG promoter
source                  1..642
                        mol_type = other DNA
                        organism = synthetic construct
```

```
SEQUENCE: 100
tagttattaa tagtaatcaa ttacggggtc attagttcat agcccatata tggagttccg    60
cgttacataa cttacggtaa atggcccgcc tggctgaccg cccaacgacc cccgcccatt   120
gacgtcaata atgacgtatg ttcccatagt aacgccaata gggactttcc attgacgtca   180
atgggtggac tatttacggt aaactgccca cttggcagta catcaagtgt atcatatgcc   240
aagtacgccc cctattgacg tcaatgacgg taaatggccc gcctggcatt atgcccagta   300
catgacctta tgggactttc ctacttggca gtacatctac gtattagtca tcgctattac   360
catgggtcga ggtgagcccc acgttctgct tcactctccc catctccccc cctcccccac   420
ccccaatttt gtatttattt attttttaat tattttgtgc agcgatgggg gcgggggggg   480
ggggggcgcg cgccaggcgg ggcggggcgg ggcgagggc gggcggggc gaggcggaga   540
ggtgcgcgg cagccaatca gagcggcgcg ctccgaaagt ttcctttttat ggcgaggcgg   600
cggcggcggc ggccctataa aaagcgaagc gcgcggcggg cg                      642

SEQ ID NO: 101          moltype = DNA   length = 217
FEATURE                 Location/Qualifiers
misc_feature            1..217
                        note = H1 element
source                  1..217
                        mol_type = other DNA
                        organism = synthetic construct
SEQUENCE: 101
gaacgctgac gtcatcaacc cgctccaagg aatcgcgggc ccagtgtcac taggcgggaa    60
cacccagcgc gcgtgcgccc tggcaggaag atggctgtga gggacagggg agtggcgccc   120
tgcaatattt gcatgtcgct atgtgttctg ggaaatcacc ataaacgtga aatgtctttg   180
gatttgggaa tcttataagt tctgtatgag accactt                            217

SEQ ID NO: 102          moltype = DNA   length = 250
FEATURE                 Location/Qualifiers
misc_feature            1..250
                        note = 3' LTR
source                  1..250
                        mol_type = other DNA
                        organism = synthetic construct
SEQUENCE: 102
tggaagggct aattcactcc caacgaagat aagatctgct ttttgcttgt actgggtctc    60
tctggttaga ccagatctga gcctgggagc tctctggcta actagggaac ccactgctta   120
agcctcaata aagcttgcct tgagtgcttc aagtagtgtg tgcccgtctg ttgtgtgact   180
ctggtaacta gagatccctc agaccctttt agtcagtgtg gaaaatctct agcagtagta   240
gttcatgtca                                                          250

SEQ ID NO: 103          moltype = DNA   length = 243
FEATURE                 Location/Qualifiers
misc_feature            1..243
                        note = 7SK promoter
source                  1..243
                        mol_type = other DNA
                        organism = synthetic construct
SEQUENCE: 103
ctgcagtatt tagcatgccc cacccatctg caaggcattc tggatagtgt caaaacagcc    60
ggaaatcaag tccgtttatc tcaaacttta gcatttgggg aataaatgat atttgctatg   120
ctggttaaat tagattttag ttaaatttcc tgctgaagct ctagtacgat aagcaacttg   180
acctaagtgt aaagttgaga tttccttcag gtttatatag cttgtgcgcc gcctggctac   240
ctc                                                                 243

SEQ ID NO: 104          moltype = DNA   length = 132
FEATURE                 Location/Qualifiers
misc_feature            1..132
                        note = miR155 Tat
source                  1..132
                        mol_type = other DNA
                        organism = synthetic construct
SEQUENCE: 104
ctggaggctt gctgaaggct gtatgctgtc cgcttcttcc tgccataggg ttttggccac    60
tgactgaccc tatgggggaag aagcggacag acacaaggc ctgttactag cactcacatg   120
gaacaaatgg cc                                                       132

SEQ ID NO: 105          moltype = DNA   length = 1110
FEATURE                 Location/Qualifiers
misc_feature            1..1110
                        note = Elongation Factor-1 alpha (EF1-alpha) promoter with
                         3 prime restriction recognition site
source                  1..1110
                        mol_type = other DNA
                        organism = synthetic construct
SEQUENCE: 105
ccggtgccta gagaaggtgg cgcggggtaa actgggaaag tgatgtcgtg tactggctcc    60
gcctttttcc cgagggtggg ggagaaccgt atataagtgc agtagtcgcc gtgaacgttc   120
tttttcgcaa cgggtttgcc gccagaacac aggtaagtgc cgtgtgtggt tcccgcgggc   180
ctggcctctt tacgggttat ggcccttgcg tgccttgaat tacttccacg cccctggctg   240
```

```
cagtacgtga ttcttgatcc cgagcttcgg gttggaagtg ggtgggagag ttcgaggcct   300
tgcgcttaag gagcccccttc gcctcgtgct tgagttgagg cctggcctgg gcgctgggggc 360
cgccgcgtgc gaatctggtg gcaccttcgc gcctgtctcg ctgctttcga taagtctcta   420
gccatttaaa attttgatg  acctgctgcg acgctttttt tctggcaaga tagtcttgta   480
aatgcgggcc aagatctgca cactggtatt tcggttttg  gggccgcggg cggcgacggg   540
gcccgtgcgt cccagcgcac atgttcggcg aggcggggcc tgcgagcgcg gccaccgaga   600
atcgacggg  ggtagtctca agctggccgg cctgctctgg tgcctggcct cgcgccgccg   660
tgtatcgccc cgccctgggc ggcaaggctg gcccggtcgg caccagttgc gtgagcggaa   720
agatggccgc ttcccggccc tgctgcaggg agctcaaaat ggaggacgcg gcgctcggga   780
gagcgggcgg gtgagtcacc cacacaaagg aaaagggcct ttccgtcctc agccgtcgct   840
tcatgtgact ccacggagta ccgggcgccg tccaggcacc tcgattagtt ctcgagcttt   900
tggagtacgt cgtctttagg ttgggggggag gggttttatg cgatggagtt tccccacact  960
gagtgggtgg agactgaagt taggccagct tggcacttga tgtaattctc cttggaattt  1020
gcccttttg  agtttggatc ttggttcatt ctcaagcctc agacagtggt tcaaagtttt  1080
tttcttccat ttcaggtgtc gtgatgtaca                                   1110

SEQ ID NO: 106         moltype = DNA  length = 122
FEATURE                Location/Qualifiers
misc_feature           1..122
                       note = miR-21 Vif coding sequence with 5 prime restriction
                         recognition site
source                 1..122
                       mol_type = other DNA
                       organism = synthetic construct
SEQUENCE: 106
cccgggcatc tccatggctg taccaccttg tcggggatg  tgtacttctg aacttgtgtt    60
gaatctcatg gagttcagaa gaacacatcc gcactgacat tttggtatct ttcatctgac   120
ca                                                                  122

SEQ ID NO: 107         moltype = DNA  length = 119
FEATURE                Location/Qualifiers
misc_feature           1..119
                       note = miR-185 Tat coding sequence with 5 prime restriction
                         recognition site
source                 1..119
                       mol_type = other DNA
                       organism = synthetic construct
SEQUENCE: 107
gctagcgggc ctggctcgag caggggcga  gggattccgc ttcttcctgc catagcgtgg    60
tcccctcccc tatggcaggc agaagcggca ccttccctcc caatgaccgc gtcttcgtc    119

SEQ ID NO: 108         moltype = DNA  length = 113
FEATURE                Location/Qualifiers
misc_feature           1..113
                       note = miR-185 Tat coding sequence
source                 1..113
                       mol_type = other DNA
                       organism = synthetic construct
SEQUENCE: 108
gggcctggct cgagcagggg gcgagggatt ccgcttcttc ctgccatagc gtggtcccct    60
cccctatggc aggcagaagc ggcaccttcc ctcccaatga ccgcgtcttc gtc          113
```

PRE-IMMUNIZATION AND IMMUNOTHERAPY

CROSS-REFERENCE TO RELATED APPLICATIONS

This application is a continuation of U.S. patent application Ser. No. 18/108,148 filed on Feb. 10, 2023, entitled "HIV PRE-IMMUNIZATION AND IMMUNOTHERAPY," which is a continuation of U.S. patent application Ser. No. 17/175,278 filed on Feb. 12, 2021, entitled "HIV PRE-IMMUNIZATION AND IMMUNOTHERAPY," which is a continuation of U.S. patent application Ser. No. 16/593,882 filed on Oct. 4, 2019, entitled "HIV PRE-IMMUNIZATION AND IMMUNOTHERAPY," which is a continuation of U.S. patent application Ser. No. 16/218,010 filed on Dec. 12, 2018, entitled "HIV PRE-IMMUNIZATION AND IMMUNOTHERAPY," which is a continuation of U.S. patent application Ser. No. 16/011,550 filed on Jun. 18, 2018, entitled "HIV PRE-IMMUNIZATION AND IMMUNOTHERAPY" which is a continuation of U.S. patent application Ser. No. 15/668,223 filed on Aug. 3, 2017, entitled "HIV PRE-IMMUNIZATION AND IMMUNOTHERAPY" which is a continuation of International Application No. PCT/US17/13019 filed on Jan. 11, 2017, entitled "HIV PRE-IMMUNIZATION AND IMMUNOTHERAPY" which claims priority to: U.S. Provisional Patent Application No. 62/360,185 filed on Jul. 8, 2016 entitled "HIV PRE-IMMUNIZATION AND IMMUNOTHERAPY", U.S. Provisional Patent Application No. 62/385,864 filed on Sep. 9, 2016 entitled "HIV PRE-IMMUNIZATION AND IMMUNOTHERAPY", and U.S. Provisional Patent Application No. 62/409,270 filed on Oct. 17, 2016 entitled "HIV PRE-IMMUNIZATION AND IMMUNOTHERAPY," the disclosures of which are incorporated herein by reference.

FIELD OF THE INVENTION

The present invention relates generally to the field of immunization and immunotherapy for the treatment and prevention of HIV. In particular, the disclosed methods of treatment and prevention relate to the administration of viral vectors and systems for the delivery of genes and other therapeutic, diagnostic, or research uses.

BACKGROUND OF THE INVENTION

Combination antiretroviral therapy (cART) (also known as Highly Active Antiretroviral Therapy or HAART) limits HIV-1 replication and retards disease progression, but drug toxicities and the emergence of drug-resistant viruses are challenges for long-term control in HIV-infected persons. Additionally, traditional antiretroviral therapy, while successful at delaying the onset of AIDS or death, has yet to provide a functional cure. Alternative treatment strategies are needed.

Intense interest in immunotherapy for HIV infection has been precipitated by emerging data indicating that the immune system has a major, albeit usually insufficient, role in limiting HIV replication. Virus-specific T-helper cells, which are critical to maintenance of cytolytic T cell (CTL) function, likely play a role. Viremia is also influenced by neutralizing antibodies, but they are generally low in magnitude in HIV infection and do not keep up with evolving viral variants in vivo.

Together this data indicates that increasing the strength and breadth of HIV-specific cellular immune responses might have a clinical benefit through so-called HIV immunotherapy. Some studies have tested vaccines against HIV, but success has been limited to date. Additionally, there has been interest in augmenting HIV immunotherapy by utilizing gene therapy techniques, but as with other immunotherapy approaches, success has been limited.

Viral vectors can be used to transduce genes into target cells owing to specific virus envelope-host cell receptor interactions and viral mechanisms for gene expression. As a result, viral vectors have been used as vehicles for the transfer of genes into many different cell types including whole T cells or other immune cells as well as embryos, fertilized eggs, isolated tissue samples, tissue targets in situ and cultured cells. The ability to introduce and express foreign or altered genes in a cell is useful for therapeutic interventions such as gene therapy, somatic cell reprogramming of induced pluripotent stem cells, and various types of immunotherapy.

Gene therapy is one of the ripest areas of biomedical research with the potential to create new therapeutics that may involve the use of viral vectors. In view of the wide variety of potential genes available for therapy, an efficient means of delivering these genes is needed to fulfill the promise of gene therapy as a means of treating infectious and non-infectious diseases. Several viral systems including murine retrovirus, adenovirus, parvovirus (adeno-associated virus), vaccinia virus, and herpes virus have been proposed as therapeutic gene transfer vectors.

There are many factors that must be considered when developing viral vectors, including tissue tropism, stability of virus preparations, stability and control of expression, genome packaging capacity, and construct-dependent vector stability. In addition, in vivo application of viral vectors is often limited by host immune responses against viral structural proteins and/or transduced gene products.

Thus, toxicity and safety are key hurdles that must be overcome for viral vectors to be used in vivo for the treatment of subjects. There are numerous historical examples of gene therapy applications in humans that have met with problems associated with the host immune responses against the gene delivery vehicles or the therapeutic gene products. Viral vectors (e.g., adenovirus) which co-transduce several viral genes together with one or more therapeutic gene(s) are particularly problematic.

Although lentiviral vectors do not generally induce cytotoxicity and do not elicit strong host immune responses, some lentiviral vectors such as HIV-1, which carry several immunostimulatory gene products, have the potential to cause cytotoxicity and induce strong immune responses in vivo. However, this may not be a concern for lentiviral derived transducing vectors that do not encode multiple viral genes after transduction. Of course, this may not always be the case, as sometimes the purpose of the vector is to encode a protein that will provoke a clinically useful immune response.

Another important issue related to the use of lentiviral vectors is that of possible cytopathogenicity upon exposure to some cytotoxic viral proteins. Exposure to certain HIV-1 proteins may induce cell death or functional unresponsiveness in T cells. Likewise, the possibility of generating replication-competent, virulent virus by recombination is often a concern. Accordingly, there remains a need for improved treatments of HIV.

SUMMARY OF THE INVENTION

In one aspect, a method of treating cells infected with HIV is provided. The method variously includes contacting peripheral blood mononuclear cells (PBMC) isolated from a subject infected with HIV with a therapeutically effective amount of a stimulatory agent, wherein the contacting is carried out ex vivo; transducing the PBMC ex vivo with a viral delivery system encoding at least one genetic element; and culturing the transduced PBMC for a sufficient period of time to ensure adequate transduction. In embodiments, the transduced PBMC may be cultured from about 1 to about 35 days. The method may further include infusing the transduced PBMC into a subject. The subject may be a human. The stimulatory agent may include any agent suitable for stimulating a T cell response in a subject. In embodiments, the stimulatory agent is a peptide or mixture of peptides, and in embodiments includes a gag peptide. The stimulatory agent may also include a vaccine. The vaccine may be a HIV vaccine, and in embodiments, the HIV vaccine is a MVA/HIV62B vaccine or a variant thereof. In embodiments, the viral delivery system includes a lentiviral particle. In embodiments, the at least one genetic element includes a small RNA capable of inhibiting production of chemokine receptor CCR5. In further embodiments, the at least one genetic element includes at least one small RNA capable of targeting an HIV RNA sequence. In further embodiments, the at least one genetic element may include a small RNA capable of inhibiting production of chemokine receptor CCR5 and at least one small RNA capable of targeting an HIV RNA sequence. The HIV RNA sequence includes any HIV sequence suitable for targeting by a viral delivery system. In embodiments, the HIV RNA sequence includes one or more of a HIV Vif sequence, a HIV Tat sequence, or a variant thereof. The at least one genetic element includes any genetic element capable of being expressed by a viral delivery system. In embodiments, the at least one genetic element includes a microRNA or a shRNA. In further embodiments, the at least one genetic element comprises a microRNA cluster.

In another aspect, the at least one genetic element includes a microRNA having at least 80%, or at least 85%, or at least 90%, or at least 95% percent identity with AGGTATATTGCTGTTGACAGTGAGCGACTGTAAACT-GAGCTTGCTCTACTGTGAAGCC ACAGATGGGT-AGAGCAAGCACAGTTTACCGCTGCC-TACTGCCTCGGACTTCAAGGGG CTT (SEQ ID NO: 1). In a preferred embodiment, the at least one genetic element comprises: AGGTATATTGCTGTTGACAGT-GAGCGACTGTAAACTGAGCTTGCTCTACTGT-GAAGCC ACAGATGGGTAGAGCAAGCACAGTT-TACCGCTGCCTACTGCCTCGGACTTCAAGGGG CTT (SEQ ID NO: 1).

In another aspect, the at least one genetic element includes a microRNA having at least 80%, or at least 85%, or at least 90%, or at least 95% percent identity with CATCTC-CATGGCTGTACCACCTTGTCGGGG-GATGTGTACTTCTGAACTTGTGTTGAAT CTCATG-GAGTTCAGAAGAACACATCCGCACTGACATTTG-GTATCTTTCATCTGACCA (SEQ ID NO: 2); or at least 80%, or at least 85%, or at least 90%, or at least 95% percent identity with GGGCCTGGCTCGAGCAGGGGGCGAGG-GATTCCGCTTCTTCCTGCCATAGCGTGG TCCCCTCCCC-TATGGCAGGCAGAAGCGGCACCTTCCCTCC-CAATGACCGCGTCTTCGT CG (SEQ ID NO: 3). In a preferred embodiment, the at least one genetic element includes CATCTCCATGGCTGTACCACCTTGTCGGGG-GATGTGTACTTCTGAACTTGTGTTGAAT CTCATG-GAGTTCAGAAGAACACATCCGCACTGACAT-TTTGGTATCTTTCATCTGACCA (SEQ ID NO: 2); or GGGCCTGGCTCGAGCAGGGGGCGAGGGAT-TCCGCTTCTTC CTGCCATAGCGTGGTCCCCTCCCC-TATGGCAGGCAGAAGCGGCACCTTCCCTCCCAAT GACCGCGTCTTCGTCG (SEQ ID NO: 3).

In another aspect, the microRNA cluster includes a sequence having at least 80%, or at least 85%, or at least 90%, or at least 95% percent identity with AGGTATAT-TGCTGTTGACAGTGAGCGACTGTAAACT-GAGCTTGCTCTACTGTGAAGCC ACAGATGGG-TAGAGCAAGCACAGTTTACCGCTGCC-TACTGCCTCGGACTTCAAGGGG CTTCCCGGG-CATCTCCATGGCTGTACCACCTTGTCGGGG-GATGTGTACTTCTGAACTT GTGTTGAATCTCATGGAGTTCAGAAGAACA-CATCCGCACTGACATTTTGGTATCTTTC ATCTGACCAGCTAGCGGGCCTGGCTCGAGCAGG-GGGCGAGGGATTCCGCTTCTTCCT GCCAT-AGCGTGGTCCCCTCCCC-TATGGCAGGCAGAAGCGGCACCTTCCCTCC-CAATGA CCGCGTCTTCGTC (SEQ ID NO: 31). In a preferred embodiment, the microRNA cluster includes: AGGTATATTGCTGTTGACAGT-GAGCGACTGTAAACTGAGCTTGCTCT ACTGT-GAAGCCACAGATGGGTAGAGCAAGCACAGTT-TACCGCTGCCTACTGCCTCGG ACTTCAAGGGGCTTCCCGGGCATCTC-CATGGCTGTACCACCTTGTCGGGGGATGTGTA CTTCTGAACTTGTGTTGAATCTCATG-GAGTTCAGAAGAACACATCCGCACTGACATTT TGGTATCTTT-CATCTGACCAGCTAGCGGGCCTGGCTCGAGCAG-GGGGCGAGGGATTC CGCTTCTTCCTGCCAT-AGCGTGGTCCCCTCCCC-TATGGCAGGCAGAAGCGGCACCTTC CCTCC-CAATGACCGCGTCTTCGTC (SEQ ID NO: 31).

In another aspect, a method of treating HIV infection in a subject is disclosed. The method variously includes immunizing the subject with an effective amount of a first stimulatory agent; removing leukocytes from the subject and obtaining peripheral blood mononuclear cells (PBMC). The method further includes contacting the PBMC ex vivo with a therapeutically effective amount of a second stimulatory agent; transducing the PBMC ex vivo with a viral delivery system encoding at least one genetic element; and culturing the transduced PBMC for a sufficient period of time to ensure adequate transduction. In embodiments, the transduced PBMC may be cultured from about 1 to about 35 days. In embodiments, the method further involves infusing the transduced PBMC into a subject. The subject may be a human. The first and second stimulatory agents may be the same or different. The first and second stimulatory agents may include one or more of a peptide or mixture of peptides. In embodiments, at least one of the first and second stimulatory agents includes a gag peptide. The at least one of the first and second stimulatory agents may include a vaccine. The vaccine may be a HIV vaccine, and in a preferred embodiment, the HIV vaccine is a MVA/HIV62B vaccine or a variant thereof. In a preferred embodiment, the viral delivery system includes a lentiviral particle. In embodiments, the at least one genetic element includes a small RNA capable of inhibiting production of chemokine receptor CCR5. In embodiments, the at least one genetic element includes at least one small RNA capable of targeting an HIV RNA sequence. In embodiments, the at least one genetic element includes a small RNA capable of inhibiting production of chemokine receptor CCR5 and at least one small RNA capable of targeting an HIV RNA sequence. The HIV RNA sequence may include a HIV Vif sequence, a HIV Tat sequence, or a variant thereof. The at least one genetic element may include a microRNA or a shRNA. In a preferred embodiment, the at least one genetic element comprises a microRNA cluster.

In another aspect, the at least one genetic element includes a microRNA having at least 80%, or at least 85%, or at least 90%, or at least 95% percent identity with AGGTATATTGCTGTTGACAGTGAGCGACTGTAAACTGAGCTTGCTCTACTGTGAAGCC ACAGATGGGTAGAGCAAGCACAGTTTACCGCTGCCTACTGCCTCGGACTTCAAGGGG CTT (SEQ ID NO: 1). In a preferred embodiment, the at least one genetic element comprises: AGGTATATTGCTGTTGACAGTGAGCGACTGTAAACTGAGCTTGCTCTACTGTGAAGCC ACAGATGGGTAGAGCAAGCACAGTTTACCGCTGCCTACTGCCTCGGACTTCAAGGGG CTT (SEQ ID NO: 1).

In another aspect, the at least one genetic element includes a microRNA having at least 80%, or at least 85%, or at least 90%, or at least 95% percent identity with CATCTCCATGGCTGTACCACCTTGTCGGGGGATGTGTACTTCTGAACTTGTGTTGAAT CTCATGGAGTTCAGAAGAACACATCCGCACTGACATTTTGGTATCTTTCATCTGACCA (SEQ ID NO: 2); or at least 80%, or at least 85%, or at least 90%, or at least 95% percent identity with GGGCCTGGCTCGAGCAGGGGGCGAGGGATTCCGCTTCTTCCTGCCATAGCGTGG TCCCCTCCCCTATGGCAGGCAGAAGCGGCACCTTCCCTCCCAATGACCGCGTCTTCGT CG (SEQ ID NO: 3). In a preferred embodiment, the at least one genetic element includes CATCTCCATGGCTGTACCACCTTGTCGGGGGATGTGTACTTCTGAACTTGTGTTGAAT CTCATGGAGTTCAGAAGAACACATCCGCACTGACATTTTGGTATCTTTCATCTGACCA (SEQ ID NO: 2); or GGGCCTGGCTCGAGCAGGGGGCGAGGGATTCCGCTTCTTC CTGCCATAGCGTGGTCCCCTCCCCTATGGCAGGCAGAAGCGGCACCTTCCCTCCCAAT GACCGCGTCTTCGTCG (SEQ ID NO: 3).

In another aspect, the microRNA cluster includes a sequence having at least 80%, or at least 85%, or at least 90%, or at least 95% percent identity with AGGTATATTGCTGTTGACAGTGAGCGACTGTAAACTGAGCTTGCTCTACTGTGAAGCC ACAGATGGGTAGAGCAAGCACAGTTTACCGCTGCCTACTGCCTCGGACTTCAAGGGG CTTCCCGGGCATCTCCATGGCTGTACCACCTTGTCGGGGGATGTGTACTTCTGAACTT GTGTTGAATCTCATGGAGTTCAGAAGAACACATCCGCACTGACATTTTGGTATCTTTC ATCTGACCAGCTAGCGGGCCTGGCTCGAGCAGGGGGCGAGGGATTCCGCTTCTTCCT GCCATAGCGTGGTCCCCTCCCCTATGGCAGGCAGAAGCGGCACCTTCCCTCCCAATGA CCGCGTCTTCGTC (SEQ ID NO: 31). In a preferred embodiment, the microRNA cluster includes: AGGTATATTGCTGTTGACAGTGAGCGACTGTAAACTGAGCTTGCTCT ACTGTGAAGCCACAGATGGGTAGAGCAAGCACAGTTTACCGCTGCCTACTGCCTCGG ACTTCAAGGGGCTTCCCGGGCATCTCCATGGCTGTACCACCTTGTCGGGGGATGTGTA CTTCTGAACTTGTGTTGAATCTCATGGAGTTCAGAAGAACACATCCGCACTGACATTT TGGTATCTTTCATCTGACCAGCTAGCGGGCCTGGCTCGAGCAGGGGGCGAGGGATTC CGCTTCTTCCTGCCATAGCGTGGTCCCCTCCCCTATGGCAGGCAGAAGCGGCACCTTC CCTCCCAATGACCGCGTCTTCGTC (SEQ ID NO: 31).

In another aspect, a lentiviral vector is disclosed. The lentiviral vector includes at least one encoded genetic element, wherein the at least one encoded genetic element comprises a small RNA capable of inhibiting production of chemokine receptor CCR5. The at least one encoded genetic element may also comprise at least one small RNA capable of targeting an HIV RNA sequence. In another aspect, the at least one encoded genetic element comprises a small RNA capable of inhibiting production of chemokine receptor CCR5 and at least one small RNA capable of targeting an HIV RNA sequence. The HIV RNA sequence may include a HIV Vif sequence, a HIV Tat sequence, or a variant thereof. The at least one encoded genetic element may include a microRNA or a shRNA. The at least one encoded genetic element may include a microRNA cluster.

In another aspect, the at least one genetic element includes a microRNA having at least 80%, or at least 85%, or at least 90%, or at least 95% percent identity with AGGTATATTGCTGTTGACAGTGAGCGACTGTAAACTGAGCTTGCTCTACTGTGAAGCC ACAGATGGGTAGAGCAAGCACAGTTTACCGCTGCCTACTGCCTCGGACTTCAAGGGG CTT (SEQ ID NO: 1). In a preferred embodiment, the at least one genetic element comprises: AGGTATATTGCTGTTGACAGTGAGCGACTGTAAACTGAGCTTGCTCTACTGTGAAGCC ACAGATGGGTAGAGCAAGCACAGTTTACCGCTGCCTACTGCCTCGGACTTCAAGGGG CTT (SEQ ID NO: 1).

In another aspect, the at least one genetic element includes a microRNA having at least 80%, or at least 85%, or at least 90%, or at least 95% percent identity with CATCTCCATGGCTGTACCACCTTGTCGGGGGATGTGTACTTCTGAACTTGTGTTGAAT CTCATGGAGTTCAGAAGAACACATCCGCACTGACATTTTGGTATCTTTCATCTGACCA (SEQ ID NO: 2); or at least 80%, or at least 85%, or at least 90%, or at least 95% percent identity with GGGCCTGGCTCGAGCAGGGGGCGAGGGATTCCGCTTCTTCCTGCCATAGCGTGG TCCCCTCCCCTATGGCAGGCAGAAGCGGCACCTTCCCTCCCAATGACCGCGTCTTCGT CG (SEQ ID NO: 3). In a preferred embodiment, the at least one genetic element includes CATCTCCATGGCTGTACCACCTTGTCGGGGGATGTGTACTTCTGAACTTGTGTTGAAT CTCATGGAGTTCAGAAGAACACATCCGCACTGACATTTTGGTATCTTTCATCTGACCA (SEQ ID NO: 2); or GGGCCTGGCTCGAGCAGGGGGCGAGGGATTCCGCTTCTTC CTGCCATAGCGTGGTCCCCTCCCCTATGGCAGGCAGAAGCGGCACCTTCCCTCCCAAT GACCGCGTCTTCGTCG (SEQ ID NO: 3).

In another aspect, the microRNA cluster includes a sequence having at least 80%, or at least 85%, or at least 90%, or at least 95% percent identity with AGGTATATTGCTGTTGACAGTGAGCGACTGTAAACTGAGCTTGCTCTACTGTGAAGCC ACAGATGGGTAGAGCAAGCACAGTTTACCGCTGCCTACTGCCTCGGACTTCAAGGGG CTTCCCGGGCATCTCCATGGCTGTACCACCTTGTCGGGGGATGTGTACTTCTGAACTT GTGTTGAATCTCATGGAGTTCAGAAGAACACATCCGCACTGACATTTTGGTATCTTTC ATCTGACCAGCTAGCGGGCCTGGCTCGAGCAGGGGGCGAGGGATTCCGCTTCTTCCT GCCATAGCGTGGTCCCCTCCCCTATGGCAGGCAGAAGCGGCACCTTCCCTCCCAATGA CCGCGTCTTCGTC (SEQ ID NO: 31). In a preferred embodiment, the microRNA cluster includes: AGGTATATTGCTGTTGACAGTGAGCGACTGTAAACT GAGCTTGCTCT ACTGTGAAGCCACA-
GATGGGTAGAGCAAGCACAGTTTACCGCTGCCTA-
CTGCCTCGG ACTTCAAGGGGCTTCCCGGG-
CATCTCCATGGCTGTACCACCTTGTCGGGG-
GATGTGTA CTTCTGAACTTGTGTTGAATCTCATG-
GAGTTCAGAAGAACACATCCGCACTGACATTT
TGGTATCTTT-
CATCTGACCAGCTAGCGGGCCTGGCTCGAGCAG-
GGGGCGAGGGATTC CGCTTCTTCCTGCCAT-
AGCGTGGTCCCCTCCCC-
TATGGCAGGCAGAAGCGGCACCTTC CCTCC-
CAATGACCGCGTCTTCGTC (SEQ ID NO: 31).

In another aspect, a lentiviral vector system for expressing a lentiviral particle is disclosed. The system includes a lentiviral vector as described herein; an envelope plasmid for expressing an envelope protein preferably optimized for infecting a cell; and at least one helper plasmid for expressing genes of interest. In embodiments, the genes of interest include one or more of gag, pol, and rev genes. In embodiments, the lentiviral vector, the envelope plasmid, and the at least one helper plasmid are transfected into a packaging cell line. In further embodiments, a lentiviral particle is produced by the packaging cell line. In embodiments, the lentiviral particle is capable of modulating production of a target of interest. In embodiments, the target of interest is any of chemokine receptor CCR5 or an HIV RNA sequence. The system may further include a first helper plasmid and a second helper plasmid. In embodiments, a first helper plasmid expresses the gag and pol genes, and a second helper plasmid expressesthe rev gene.

In another aspect, a lentiviral particle capable of infecting a cell is provided. The lentiviral particle includes an envelope protein preferably optimized for infecting a cell, and a lentiviral vector as described herein. In embodiments, the envelope protein may be optimized for infecting a T cell. In a preferred embodiment, the envelope protein is optimized for infecting a CD4+ T cell.

In another aspect, a modified cell is provided. The modified cell includes any cell capable of being infected with a lentiviral vector system for use in accordance with present aspects and embodiments. In embodiments, the cell is a CD4+ T cell that is infected with a lentiviral particle. In embodiments, the CD4+ T cell also has been selected to recognize an HIV antigen. In embodiments, the HIV antigen includes a gag antigen. In embodiments, the CD4+ T cell expresses a decreased level of CCR5 following infection with the lentiviral particle.

In another aspect, a method of selecting a subject for a therapeutic treatment regimen is provided. The method variously includes immunizing the subject with an effective amount of a first stimulatory agent; removing leukocytes from the subject and purifying peripheral blood mononuclear cells (PBMC) and determining a first quantifiable measurement associated with at least one factor associated with the PBMC; contacting the PBMC ex vivo with a therapeutically effective amount of a second stimulatory agent, and determining a second measurement associated with the at least one factor associated with the PBMC, whereby when the second quantifiable measurement is higher than the first quantifiable measurement, the subject is selected for the treatment regimen. The at least one factor may include any of T cell proliferation or IFN gamma production.

The foregoing general description and following brief description of the drawings and detailed description are exemplary and explanatory and are intended to provide further explanation of the invention as claimed. Other objects, advantages, and novel features will be readily apparent to those skilled in the art from the following brief description of the drawings and detailed description of the invention.

BRIEF DESCRIPTION OF THE DRAWINGS

FIG. 6 depicts exemplary vector sequences. Positive (i.e., genomic) strand sequences of the promoter and miR cluster were developed for inhibiting the spread of CCR5-tropic HIV strains. Sequences that are not underlined comprise the EF-1alpha promoter of transcription (SEQ ID NO: 105) that was selected as being a preferable promoter for this miR cluster. Sequences that are underlined show the miR cluster consisting of miR30 CCR5 (SEQ ID NO: 1), miR21 Vif (SEQ ID NO: 2), and miR185 Tat (SEQ ID NO: 108) (as shown collectively in SEQ ID NO: 33).

FIG. 7 depicts exemplary lentiviral vector constructs according to various aspects of this disclosure.

FIG. 8A shows CCR5 expression in AGTc120 cells with or without AGT103 lentivirus vector. FIG. 8B shows the sensitivity of transduced AGTc120 cells to infection with a HIV BaL virus stock that was expressing green fluorescent protein (GFP) fused to the Nef gene of HIV.

FIG. 9A shows screening data for potential candidates. FIG. 9B shows CCR5 knock-down data following transduction with CCR5 shRNA-1 (SEQ ID NO: 16).

FIG. 10A shows knock-down data for the rev/tat target gene. FIG. 10B shows knock-down data for the gag target gene.

In FIG. 12A, tat knock-down data is shown. In FIG. 12B, vif knock-down data is shown.

FIG. 18A shows an exemplary schedule of treatment. FIG. 18B shows IFN-gamma production in CD4-gated T cells, as described herein. FIG. 18C shows IFN-gamma production and GFP expression in CD4-gated T cells, as described herein. FIG. 18D shows frequency of HIV-specific CD4+ T cells, as described herein. FIG. 18E shows IFN-gamma production from PBMCs post-vaccination, as described herein.

FIG. 19A shows dose response data for increasing amounts of AGT103-GFP. FIG. 19B shows normally distributed populations in terms of CCR5 expression. FIG. 19C shows percentage inhibition of CCR5 expression with increasing doses of AGT103-GFP.

FIG. 20A shows frequency of transduced cells (GFP-positive) by FACS, as described herein. FIG. 20B shows number of vector copies per cell, as described herein.

FIG. 23A shows CD4 and CD8 expression profiles for cell populations, as described herein. FIG. 23B shows CD4 and CD8 expression profiles for cell populations, as described herein. FIG. 23C shows IFN-gamma and CD4 expression profiles for cell populations, as described herein. FIG. 23D shows IFN-gamma and GFP expression profiles for cell populations, as described herein.

DETAILED DESCRIPTION

Overview

Disclosed herein are methods and compositions for treating and/or preventing human immunodeficiency virus (HIV) disease to achieve a functional cure. The methods and compositions include integrating lentivirus, non-integrating lentivirus, and related viral vector technology as described below.

Figure 1:
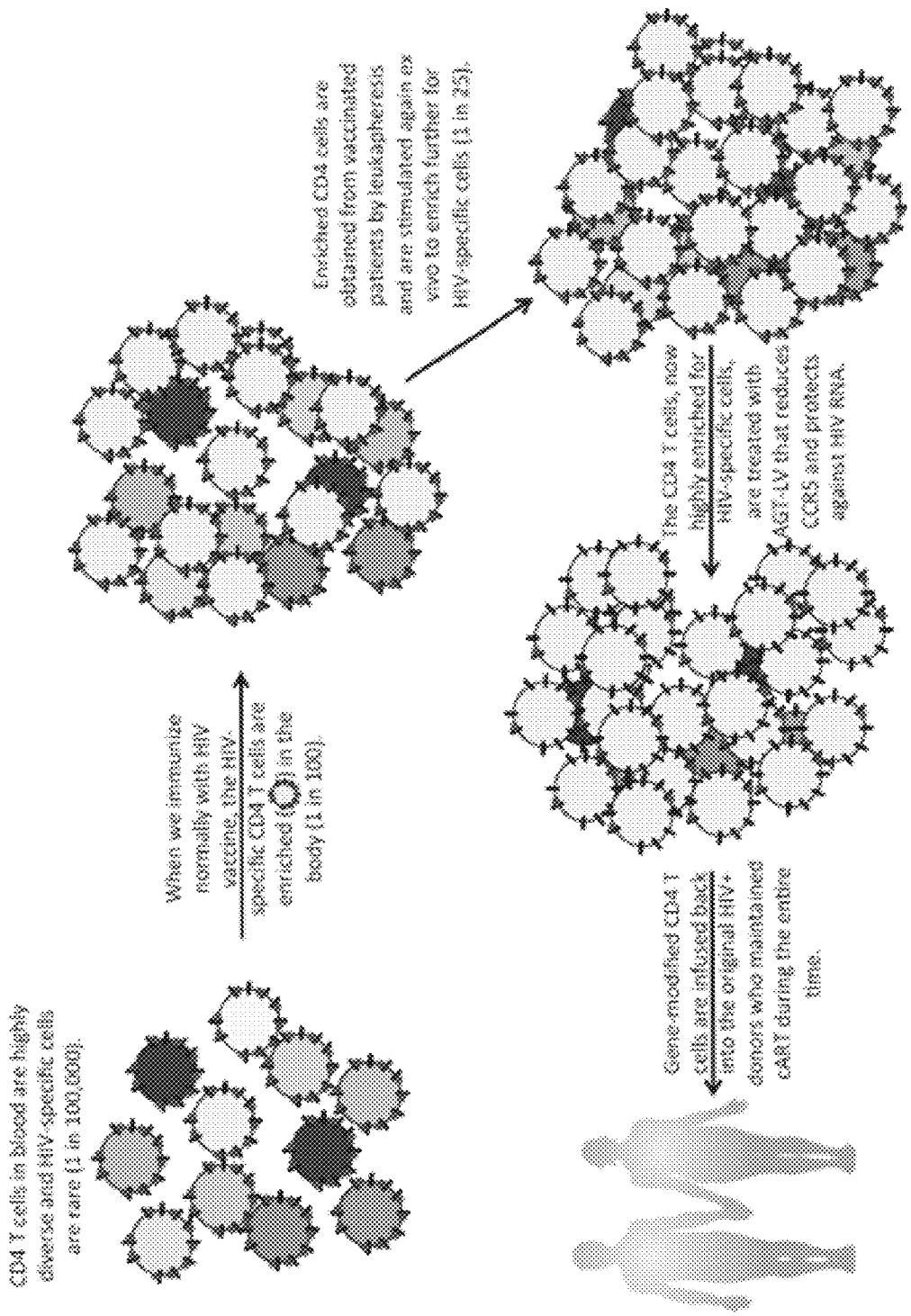
FIG. 1 depicts a flow diagram of an ex vivo treatment method of the present disclosure.

Disclosed herein are therapeutic viral vectors (e.g., lentiviral vectors), immunotherapies, and methods for their use for treating HIV infection. In embodiments, methods and compositions for achieving a functional cure for HIV infection are provided. As depicted in FIG. 1 herein, the various aspects and embodiments include a first stimulation event, for example a first therapeutic immunization with vaccines intended to produce strong immune responses against HIV in HIV-infected patients, for example with stable suppression of viremia due to daily administration of HAART. In embodiments, the first stimulation event enriches the fraction of HIV-specific CD4 T cells. This is followed by (1) isolating peripheral leukocytes by leukapheresis or purifying PBMC from venous blood, (2) a second stimulating event, for example re-stimulating CD4 T cells ex vivo with a suitable stimulatory agent, such as any vaccine or protein, for example, HIV or HIV-related peptides, (3) performing therapeutic lentivirus transduction, ex vivo T cell culture, and (4) re-infusion back into the original patient.

Figure 2:
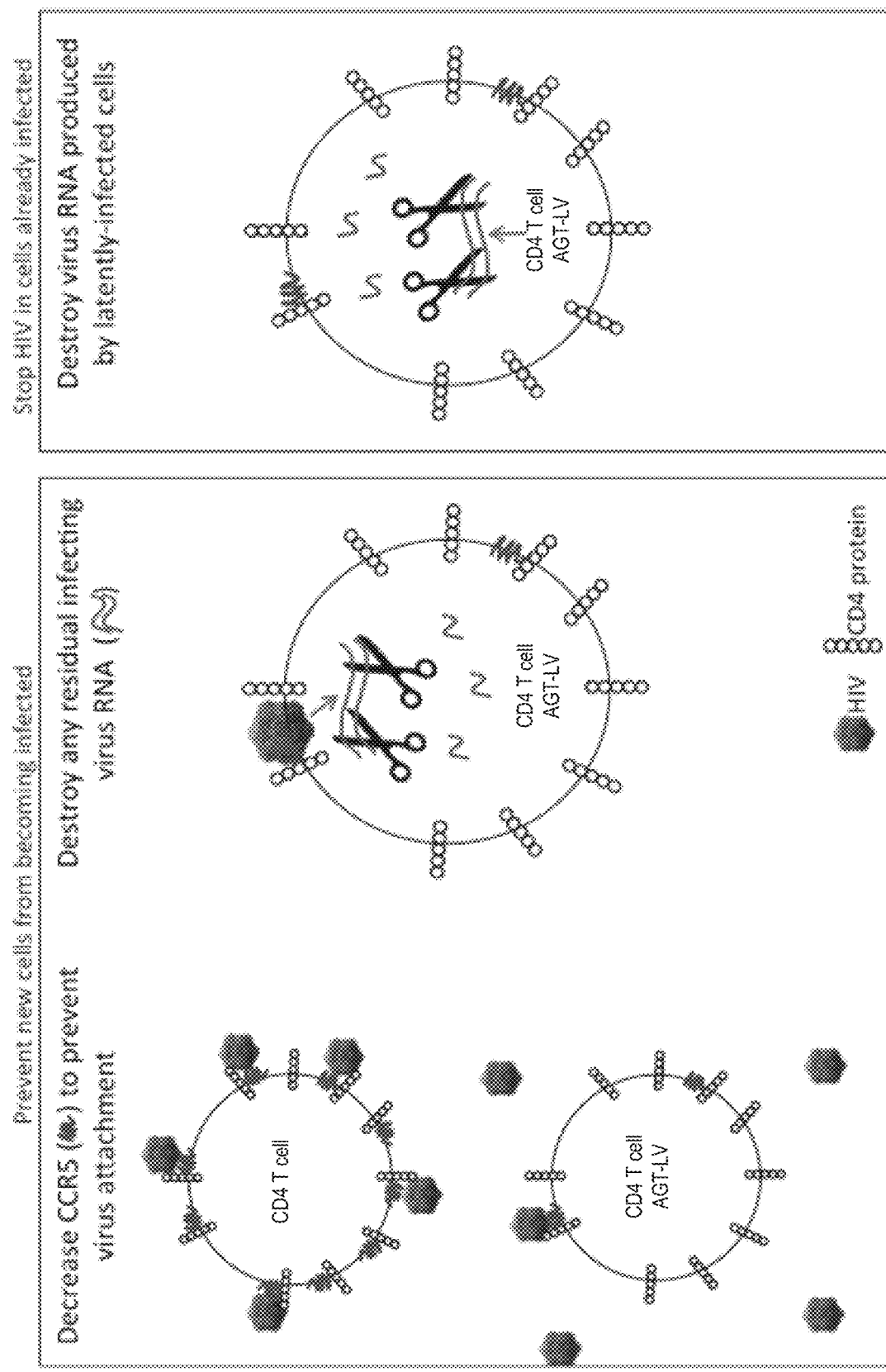
FIG. 2 depicts CD4+ T cell alteration and prevention of new infection in accordance with the present disclosure.

The various methods and compositions can be used to prevent new cells, such as CD4+ T cells, from becoming infected with HIV. For example as illustrated in FIG. 2, to prevent new cells from becoming infected, CCR5 expression can be targeted to prevent virus attachment. Further, destruction of any residual infecting viral RNA can also be targeted. In respect of the foregoing, and in reference to FIG. 2 herein, compositions and methods are provided to stop the HIV viral cycle in cells that have already become infected with HIV. To stop the HIV viral cycle, viral RNA produced by latently-infected cells, such as latently-infected CD4+ T cells, is targeted.

Previous efforts to achieve a cure for HIV have fallen short due to, among others, the failure to obtain sufficient numbers of HIV-specific CD4 T cells with protective genetic modifications. When this number is below a critical threshold, a functional cure as described herein is not achieved. For example, upon termination of antiretroviral therapy HIV re-emergence generally follows. Thereafter, patients often experience rapid destruction of HIV-specific CD4 T cells, and also followed by return to progression of disease despite prior genetic therapy. By employing therapeutic immunization in accordance with the compositions and methods described herein, a new HIV treatment regimen has been developed including, in various embodiments, a functional cure.

Definitions and Interpretation

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. Generally, nomenclature used in connection with, and techniques of, cell and tissue culture, molecular biology, immunology, microbiology, genetics and protein and nucleic acid chemistry and hybridization described herein are those well-known and commonly used in the art. The methods and techniques of the present disclosure are generally performed according to conventional methods well-known in the art and as described in various general and more specific references that are cited and discussed throughout the present specification unless otherwise indicated. See, e.g.: Sambrook J. & Russell D. Molecular Cloning: A Laboratory Manual, 3rd ed., Cold Spring Harbor Laboratory Press, Cold Spring Harbor, N.Y. (2000); Ausubel et al., Short Protocols in Molecular Biology: A Compendium of Methods from Current Protocols in Molecular Biology, Wiley, John & Sons, Inc. (2002); Harlow and Lane Using Antibodies: A Laboratory Manual; Cold Spring Harbor Laboratory Press, Cold Spring Harbor, N.Y. (1998); and Coligan et al., Short Protocols in Protein Science, Wiley, John & Sons, Inc. (2003). Any enzymatic reactions or purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those well-known and commonly used in the art.

As used herein, the term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

As used herein, the terms "administration of" or "administering" an active agent means providing an active agent of the invention to the subject in need of treatment in a form that can be introduced into that individual's body in a therapeutically useful form and therapeutically effective amount.

As used herein, the term "AGT103" refers to a particular embodiment of a lentiviral vector that contains a miR30-CCR5/miR21-Vif/miR185-Tat microRNA cluster sequence, as detailed herein.

As used herein, the term "AGT103T" refers to a cell that has been transduced with a lentivirus that contains the AGT103 lentiviral vector.

Throughout this specification and claims, the word "comprise," or variations such as "comprises" or "comprising," will be understood to imply the inclusion of a stated integer or group of integers but not the exclusion of any other integer or group of integers. Further, as used herein, the term "includes" means includes without limitation.

As used herein, the term "engraftment" refers to the ability for one skilled in the art to determine a quantitative level of sustained engraftment in a subject following infusion of a cellular source (see for e.g.: Rosenberg et al., *N. Engl. J. Med.* 323:570-578 (1990); Dudley el al., *J. Immunother.* 24:363-373 (2001); Yee et al., *Curr. Opin. Immunol.* 13:141-146 (2001); Rooney et al., *Blood* 92:1549-1555 (1998)).

The terms, "expression," "expressed," or "encodes" refer to the process by which polynucleotides are transcribed into mRNA and/or the process by which the transcribed mRNA is subsequently being translated into peptides, polypeptides, or proteins. Expression may include splicing of the mRNA in a eukaryotic cell or other forms of post-transcriptional modification or post-translational modification.

The term "functional cure", as referenced above, and further defined herein, refers to a state or condition wherein HIV+ individuals who previously required ongoing HIV therapies such as CART or HAART, may survive with low or undetectable virus replication using lower doses, intermittent doses, or discontinued dosing of such HIV therapies. An individual may be said to have been "functionally cured" while still requiring adjunct therapy to maintain low level virus replication and slow or eliminate disease progression. A possible outcome of a functional cure is the eventual eradication of all or virtually all HIV such that no recurrence is detected within a specified time frame, for example, 1 month, 3 months, 6 months, 1 year, 3 years, and 5 years, and all other time frames as may be defined.

The term "HIV vaccine" encompasses immunogens plus vehicle plus adjuvant intended to elicit HIV-specific immune responses. The term "HIV vaccine" is within the meaning of the term "stimulatory agent" as described herein. A "HIV vaccine" may include purified or whole inactivated virus particles that may be HIV or a recombinant virus vectors capable of expressing HIV proteins, protein fragments or peptides, glycoprotein fragments or glycopeptides, in addition to recombinant bacterial vectors, plasmid DNA or RNA capable of directing cells to producing HIV proteins, glycoproteins or protein fragments able to elicit specific immunity. Alternately, specific methods for immune stimulation including anti-CD3/CD28 beads, T cell receptor-specific antibodies, mitogens, superantigens and other chemical or biological stimuli may be used to activate dendritic, T or B cells for the purposes of enriching HIV-specific CD4 T cells prior to transduction or for in vitro assay of lentivirus-transduced CD4 T cells. Activating substances may be soluble, polymeric assemblies, liposome or endosome-based or linked to beads. Cytokines including interleukin-2, 6, 7, 12, 15, 23 or others may be added to improve cellular responses to stimuli and/or improve the survival of CD4 T cells throughout the culture and transduction intervals. Alternately, and without limiting any of the foregoing, the term "HIV vaccine" encompasses the MVA/HIV62B vaccine and variants thereof. The MVA/HIV62B vaccine is a known highly attenuated double recombinant MVA vaccine. The MVA/HIV62B vaccine was constructed through the insertion of HIV-1 gag-pol and env sequences into the known MVA vector (see: for e.g.: Goepfert et al. (2014) J. Infect. Dis. 210 (1): 99-110, and see WO2006026667, both of which are incorporated herein by reference). The term "HIV vaccine" also includes any one or more vaccines provided in Table 1, below.

TABLE 1

| IAVI Clinical Trial ID* | Prime** |
|---|---|
| HVTN 704 AMP | VRC-HIVMAB060-00-AB |
| VAC89220HPX2004 | Ad26.Mos.HIV Trivalent |
| 01-I-0079 | VRC4302 |
| 04/400-003-04 | APL 400-003 GENEVAX-HIV |
| 10-1074 | 10-1074 |
| 87 I-114 | gp160 Vaccine (Immuno-AG) |
| 96-I-0050 | APL 400-003 GENEVAX-HIV |
| ACTG 326; PACTG 326 | ALVAC vCP1452 |
| Ad26.ENVA.01 | Ad26.EnvA-01 |
| Ad26.ENVA.01 Mucosal/IPCAVD003 | Ad26.EnvA-01 |
| Ad5HVR48.ENVA.01 | Ad5HVR48.ENVA.01 |
| ANRS VAC 01 | ALVAC vCP125 |
| ANRS VAC 02 | rgp 160 + peptide V3 ANRS VAC 02 |
| ANRS VAC 03 | ALVAC-HIV MN120TMG strain (vCP205) |
| ANRS VAC 04 | LIPO-6 |
| ANRS VAC 04 bis | LIPO-6 |
| ANRS VAC 05 | ALVAC vCP125 |
| ANRS VAC 06 | ALVAC vCP125 |
| ANRS VAC 07 | ALVAC vCP300 |
| ANRS VAC 08 | ALVAC-HIV MN120TMG strain (vCP205) |

TABLE 1-continued

| IAVI Clinical Trial ID* | Prime** |
|---|---|
| ANRS VAC 09 | ALVAC-HIV MN120TMG strain (vCP205) |
| ANRS VAC 09 bis | LIPO-6 |
| ANRS VAC 10 | ALVAC vCP1452 |
| ANRS VAC 12 | LPHIV1 |
| ANRS VAC 14 | gp160 MN/LAI |
| ANRS VAC 16 | LPHIV1 |
| ANRS VAC 17 | LIPO-6 |
| ANRS VAC 18 | LIPO-5 |
| APL 400-003RX101 | APL 400-003 GENEVAX-HIV |
| AVEG 002 | HIVAC-1e |
| AVEG 002A | HIVAC-1e |
| AVEG 002B | HIVAC-1e |
| AVEG 003 | VaxSyn gp160 Vaccine (MicroGeneSys) |
| AVEG 003A | VaxSyn gp160 Vaccine (MicroGeneSys) |
| AVEG 003B | VaxSyn gp160 Vaccine (MicroGeneSys) |
| AVEG 004 | gp160 Vaccine (Immuno-AG) |
| AVEG 004A | gp160 Vaccine (Immuno-AG) |
| AVEG 004B | gp160 Vaccine (Immuno-AG) |
| AVEG 005A/B | Env 2-3 |
| AVEG 005C | Env 2-3 |
| AVEG 006X; VEU 006 | MN rgp120 |
| AVEG 007A/B | rgp120/HIV-1 SF-2 |
| AVEG 007C | rgp120/HIV-1 SF-2 |
| AVEG 008 | HIVAC-1e |
| AVEG 009 | MN rgp120 |
| AVEG 010 | HIVAC-1e |
| AVEG 011 | UBI HIV-1 Peptide Immunogen, Multivalent |
| AVEG 012A/B | ALVAC vCP125 |
| AVEG 013A | gp160 Vaccine (Immuno-AG) |
| AVEG 013B | gp160 Vaccine (Immuno-AG) |
| AVEG 014A/B | TBC-3B |
| AVEG 014C | TBC-3B |
| AVEG 015 | rgp120/HIV-1 SF-2 |
| AVEG 016 | MN rgp120 |
| AVEG 016A | MN rgp120 |
| AVEG 016B | MN rgp120 |
| AVEG 017 | UBI HIV-1 Peptide Vaccine, Microparticulate Monovalent |
| AVEG 018 | UBI HIV-1 Peptide Vaccine, Microparticulate Monovalent |
| AVEG 019 | p17/p24:Ty- VLP |
| AVEG 020 | gp120 C4-V3 |
| AVEG 021 | P3C541b Lipopeptide |
| AVEG 022 | ALVAC-HIV MN120TMG strain (vCP205) |
| AVEG 022A | ALVAC-HIV MN120TMG strain (vCP205) |
| AVEG 023 | UBI HIV-1 Peptide Immunogen, Multivalent |
| AVEG 024 | rgp120/HIV-1 SF-2 |
| AVEG 026 | ALVAC vCP300 |
| AVEG 027 | ALVAC-HIV MN120TMG strain (vCP205) |
| AVEG 028 | *Salmonella typhi* CVD 908-HIV-1 LAI gp 120 |
| AVEG 029 | ALVAC-HIV MN120TMG strain (vCP205) |
| AVEG 031 | APL 400-047 |
| AVEG 032 | ALVAC-HIV MN120TMG strain (vCP205) |
| AVEG 033 | ALVAC-HIV MN120TMG strain (vCP205) |
| AVEG 034/034A | ALVAC vCP1433 |
| AVEG 036 | MN rgp120 |
| AVEG 038 | ALVAC-HIV MN120TMG strain (vCP205) |
| AVEG 201 | rgp120/HIV-1 SF-2 |
| AVEG 202/HIVNET 014 | ALVAC-HIV MN120TMG strain (vCP205) |
| C060301 | GTU-MultiHIV |
| C86P1 | HIV gp140 ZM96 |
| Cervico-vaginal CN54gp140-hsp70 Conjugate Vaccine (TL01) | CN54gp140 |
| CM235 and SF2gp120 | CM235 (ThaiE) gp120 plus SF2(B) gp120 |
| CM235gp120 and SF2gp120 | CM235 (ThaiE) gp120 plus SF2(B) gp120 |
| CombiHIVvac (KombiVIChvak) | CombiHIVvac |
| CRC282 | P2G12 |
| CRO2049/CUT*HIVAC001 | GTU-MultiHIV |
| CUTHIVAC002 | DNA-C CN54ENV |
| DCVax-001 | DCVax-001 |
| DNA-4 | DNA-4 |
| DP6?001 | DP6?001 DNA |
| DVP-1 | EnvDNA |
| EN41-UGR7C | EN41-UGR7C |
| EnvDNA | EnvDNA |
| EnvPro | EnvPro |
| EuroNeut41 | EN41-FPA2 |
| EV01 | NYVAC-C |

TABLE 1-continued

| IAVI Clinical Trial ID* | Prime** |
|---|---|
| EV02 (EuroVacc 02) | DNA-C |
| EV03/ANRSVAC20 | DNA-C |
| Extention HVTN 073E/SAAVI 102 | Sub C gp140 |
| F4/AS01 | F4/AS01 |
| FIT Biotech | GTU-Nef |
| Guangxi CDC DNA vaccine | Chinese DNA |
| HGP-30 memory responses | HGP-30 |
| HIV-CORE002 | ChAdV63.HIVconsv |
| HIV-POL-001 | MVA-mBN32 |
| HIVIS 01 | HIVIS-DNA |
| HIVIS 02 | MVA-CMDR |
| HIVIS 03 | HIVIS-DNA |
| HIVIS 05 | HIVIS-DNA |
| HIVIS06 | HIVIS-DNA |
| HIVIS07 | HIVIS-DNA |
| HIVNET 007 | ALVAC-HIV MN120TMG strain (vCP205) |
| HIVNET 026 | ALVAC vCP1452 |
| HPTN 027 | ALVAC-HIV vCP1521 |
| HVRF-380-131004 | Vichrepol |
| HVTN 039 | ALVAC vCP1452 |
| HVTN 040 | AVX101 |
| HVTN 041 | rgp120w61d |
| HVTN 042/ANRS VAC 19 | ALVAC vCP1452 |
| HVTN 044 | VRC-HIVDNA009-00-VP |
| HVTN 045 | pGA2/JS7 DNA |
| HVTN 048 | EP HIV-1090 |
| HVTN 049 | Gag and Env DNA/PLG microparticles |
| HVTN 050/Merck 018 | MRKAd5 HIV-1 gag |
| HVTN 052 | VRC-HIVDNA009-00-VP |
| HVTN 054 | VRC-HIVADV014-00-VP |
| HVTN 055 | TBC-M335 |
| HVTN 056 | MEP |
| HVTN 057 | VRC-HIVDNA009-00-VP |
| HVTN 059 | AVX101 |
| HVTN 060 | HIV-1 gag DNA |
| HVTN 063 | HIV-1 gag DNA |
| HVTN 064 | EP HIV-1043 |
| HVTN 065 | pGA2/JS7 DNA |
| HVTN 067 | EP-1233 |
| HVTN 068 | VRC-HIVADV014-00-VP |
| HVTN 069 | VRC-HIVDNA009-00-VP |
| HVTN 070 | PENNVAX-B |
| HVTN 071 | MRKAd5 HIV-1 gag |
| HVTN 072 | VRC-HIVDNA044-00-VP |
| HVTN 073 | SAAVI DNA-C2 |
| HVTN 076 | VRC-HIVDNA016-00-VP |
| HVTN 077 | VRC-HIVADV027-00-VP |
| HVTN 078 | NYVAC-B |
| HVTN 080 | PENNVAX-B |
| HVTN 082 | VRC-HIVDNA016-00-VP |
| HVTN 083 | VRC-HIVADV038-00-VP |
| HVTN 084 | VRC-HIVADV054-00-VP |
| HVTN 085 | VRC-HIVADV014-00-VP |
| HVTN 086, SAAVI 103 | SAAVI MVA-C |
| HVTN 087 | HIV-MAG |
| HVTN 088 | Oligomeric gp140/MF59 |
| HVTN 090 | VSV-Indiana HIV gag vaccine |
| HVTN 092 | DNA-HIV-PT123 |
| HVTN 094 | GEO-D03 |
| HVTN 096 | DNA-HIV-PT123 |
| HVTN 097 | ALVAC-HIV vCP1521 |
| HVTN 098 | PENNVAX-GP |
| HVTN 100 | ALVAC-HIV-C (vCP2438) |
| HVTN 101 | DNA-HIV-PT123 |
| HVTN 102 | DNA-HIV-PT123 |
| HVTN 104 | VRC-HIVMAB060-00-AB |
| HVTN 105 | AIDSVAX B/E |
| HVTN 106 | DNA Nat-B env |
| HVTN 110 | Ad4-mgag |
| HVTN 112 | HIV-1 nef/tat/vif, env pDNA vaccine |
| HVTN 114; GOVX-B11 | AIDSVAX B/E |
| HVTN 116 | VRC-HIVMAB060-00-AB |
| HVTN 203 | ALVAC vCP1452 |
| HVTN 204 | VRC-HIVDNA016-00-VP |
| HVTN 205 | pGA2/JS7 DNA |
| HVTN 502/Merck 023 (Step Study) | MRKAd5 HIV-1 gag/pol/nef |
| HVTN 503 (Phambili) | MRKAd5 HIV-1 gag/pol/nef |
| HVTN 505 | VRC-HIVDNA016-00-VP |

TABLE 1-continued

| IAVI Clinical Trial ID* | Prime** |
|---|---|
| HVTN 702 | ALVAC-HIV-C (vCP2438) |
| HVTN 703 AMP | VRC-HIVMAB060-00-AB |
| HVTN 908 | pGA2/JS7 DNA |
| IAVI 001 | DNA.HIVA |
| IAVI 002 | DNA.HIVA |
| IAVI 003 | MVA.HIVA |
| IAVI 004 | MVA.HIVA |
| IAVI 005 | DNA.HIVA |
| IAVI 006 | DNA.HIVA |
| IAVI 008 | MVA.HIVA |
| IAVI 009 | DNA.HIVA |
| IAVI 010 | DNA.HIVA |
| IAVI 011 | MVA.HIVA |
| IAVI 016 | MVA.HIVA |
| IAVI A001 | tgAAC09 |
| IAVI A002 | tgAAC09 |
| IAVI A003 | AAV1-PG9 |
| IAVI B001 | Ad35-GRIN/ENV |
| IAVI B002 | Adjuvanted GSK investigational HIV vaccine formulation 1 |
| IAVI B003 | Ad26.EnvA-01 |
| IAVI B004 | HIV-MAG |
| IAVI C001 | ADVAX |
| IAVI C002 | ADMVA |
| IAVI C003 | ADMVA |
| IAVI C004/DHO-614 | ADVAX |
| IAVI D001 | TBC-M4 |
| IAVI N004 HIV-CORE 004 | Ad35-GRIN |
| IAVI P001 | ADVAX |
| IAVI P002 | ADVAX |
| IAVI R001 | rcAd26.MOS1.HIVEnv |
| IAVI S001 | SeV-G |
| IAVI V001 | VRC-HIVDNA016-00-VP |
| IAVI V002 | VRC-HIVDNA016-00-VP |
| IDEA EV06 | DNA-HIV-PT123 |
| IHV01 | Full-Length Single Chain (FLSC) |
| IMPAACT P1112 | VRC-HIVMAB060-00-AB |
| IPCAVD006 | MVA mosaic |
| IPCAVD008 | Trimeric gp140 |
| IPCAVD009 | Ad26.Mos.HIV Trivalent |
| IPCAVD010 | Ad26.Mos.HIV Trivalent |
| ISS P-001 | Tat vaccine |
| ISS P-002 | Tat vaccine |
| LFn-p24 vaccine | LFn-p24 |
| MCA-0835 | 3BNC117 |
| Merck V520-007 | Ad-5 HIV-1 gag (Merck) |
| MRC V001 | rgp120w61d |
| MRK Ad5 | Ad-5 HIV-1 gag (Merck) |
| MRKAd5 + ALVAC | MRKAd5 HIV-1 gag |
| Mucovac2 | CN54gp140 |
| MV1-F4 | Measles Vector - GSK |
| MYM-V101 | Virosome-Gp41 |
| NCHECR-AE1 | pHIS-HIV-AE |
| PACTG 230 | AIDSVAX B/E |
| PAVE100 | VRC-HIVDNA016-00-VP |
| PEACHI-04 | ChAdV63.HIVconsv |
| PedVacc001 & PedVacc002 | MVA.HIVA |
| PolyEnv1 | PolyEnv1 |
| PXVX-HIV-100-001 | Ad4-mgag |
| RISVAC02 | MVA-B |
| RisVac02 boost | MVA-B |
| RV 124 | ALVAC-HIV MN120TMG strain (vCP205) |
| RV 132 | ALVAC-HIV vCP1521 |
| RV 135 | ALVAC-HIV vCP1521 |
| RV 138; B011 | ALVAC-HIV MN120TMG strain (vCP205) |
| RV 144 | ALVAC-HIV vCP1521 |
| RV 151/WRAIR 984 | LFn-p24 |
| RV 156 | VRC-HIVDNA009-00-VP |
| RV 156A | VRC-HIVDNA009-00-VP |
| RV 158 | MVA-CMDR |
| RV 172 | VRC-HIVDNA016-00-VP |
| RV 305 | ALVAC-HIV vCP1521 |
| RV 306 | ALVAC-HIV vCP1521 |
| RV 328 | AIDSVAX B/E |
| RV 365 | MVA-CMDR |
| RV262 | Pennvax-G |
| SG06RS02 | HIV gp140 ZM96 |
| TAB9 | TAB9 |

TABLE 1-continued

| IAVI Clinical Trial ID* | Prime** |
|---|---|
| TaMoVac II | HIVIS-DNA |
| TAMOVAC-01-MZ | HIVIS-DNA |
| Tiantan vaccinia HIV Vaccine | Chinese DNA |
| Tiantan vaccinia HIV Vaccine and DNA | Chinese DNA |
| TMB-108 | Ibalizumab |
| UBI HIV-1 MN China | UBI HIV-1 Peptide Immunogen, Multivalent |
| UBI HIV-1MN octameric - Australia study | UBI HIV-1 Peptide Immunogen, Multivalent |
| UBI V106 | UBI HIV-1 Peptide Vaccine, Microparticulate Monovalent |
| UCLA MIG-001 | TBC-3B |
| UCLA MIG-003 | ALVAC-HIV MN120TMG strain (vCP205) |
| UKHVCSpoke003 | DNA - CN54ENV and ZM96GPN |
| V24P1 | HIV p24/MF59 Vaccine |
| V3-MAPS | V3-MAPS |
| V520-016 | MRKAd5 HIV-1 gag/pol/nef |
| V520-027 | MRKAd5 HIV-1 gag/pol/nef |
| V526-001 MRKAd5 and MRKAd6 HIV-1 Trigene Vaccines | MRKAd5 HIV-1 gag/pol/nef |
| VAX 002 | AIDSVAX B/B |
| VAX 003 | AIDSVAX B/E |
| VAX 004 | AIDSVAX B/B |
| VRC 004 (03-I-0022) | VRC-HIVDNA009-00-VP |
| VRC 006 (04-I-0172) | VRC-HIVADV014-00-VP |
| VRC 007 (04-I-0254) | VRC-HIVDNA016-00-VP |
| VRC 008 (05-I-0148) | VRC-HIVDNA016-00-VP |
| VRC 009 (05-I-0081) | VRC-HIVDNA009-00-VP |
| VRC 010 (05-I-0140) | VRC-HIVADV014-00-VP |
| VRC 011(06-I-0149) | VRC-HIVDNA016-00-VP |
| VRC 012 (07-I-0167) | VRC-HIVADV027-00-VP |
| VRC 015 (08-I-0171) | VRC-HIVADV014-00-VP |
| VRC 016 | VRC-HIVDNA016-00-VP |
| VRC 602 | VRC-HIVMAB060-00-AB |
| VRC 607 | VRCHIVMAB080-00-AB |
| VRC01LS | VRCHIVMAB080-00-AB |
| VRI01 | MVA-B |
| X001 | CN54gp140 |

*IAVI is the International AIDS Vaccine Initiative, whose clinical trials database is publicly available at http://www.iavi.org/trials-database/trials.
**As used herein, the term "Prime" refers to the composition initially used as an immunological inoculant in a given clinical trial as referenced in Table 1 herein.

The term "in vivo" refers to processes that occur in a living organism. The term "ex vivo" refers to processes that occur outside of a living organism. For example, in vivo treatment refers to treatment that occurs within a patient's body, while ex vivo treatment is one that occurs outside of a patient's body, but still uses or accesses or interacts with tissues from that patient. Thereafter, an ex vivo treatment step may include a subsequent in vivo treatment step.

The term "miRNA" refers to a microRNA, and also may be referred to herein as "miR". The term "microRNA cluster" refers to at least two microRNAs that are situate on a vector in close proximity to each other and are co-expressed.

The term "packaging cell line" refers to any cell line that can be used to express a lentiviral particle.

The term "percent identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of ordinary skill in the art) or by visual inspection. Depending on the application, the "percent identity" can exist over a region of the sequence being compared, e.g., over a functional domain, or, alternatively, exist over the full length of the two sequences to be compared. For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information website.

The percent identity between two nucleotide sequences can be determined using the GAP program in the GCG software package (available at www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* (48): 444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences of the present disclosure can further be used as a "query sequence" to perform a search against public databases to, for example, identify related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, word length=12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. To obtain gapped alignments for comparison purposes, Gapped BLAST can be utilized as described in Altschul et al., (1997) *Nucleic Acids Res.* 25 (17): 3389-3402. When utilizing BLAST and Gapped BLAST programs, the default parameters of the respective programs (e.g., XBLAST and NBLAST) can be used. See www.ncbi.nlm.nih.gov.

As used herein, "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

As used herein, a "pharmaceutically acceptable carrier" refers to, and includes, any and all solvents, dispersion media, coatings, antibacterial and antifungal agents, isotonic and absorption delaying agents, and the like that are physiologically compatible. The compositions can include a pharmaceutically acceptable salt or a acid addition salt or a base addition salt (see, e.g., Berge et al. (1977) *J Pharm Sci* 66:1-19).

As used herein, the term "SEQ ID NO" is synonymous with the term "Sequence ID No."

As used herein, "small RNA" refers to non-coding RNA that are generally less than about 200 nucleotides or less in length and possess a silencing or interference function. In other embodiments, the small RNA is about 175 nucleotides or less, about 150 nucleotides or less, about 125 nucleotides or less, about 100 nucleotides or less, or about 75 nucleotides or less in length. Such RNAs include microRNA (miRNA), small interfering RNA (siRNA), double stranded RNA (dsRNA), and short hairpin RNA (shRNA). "Small RNA" of the disclosure should be capable of inhibiting or knocking-down gene expression of a target gene, for example through pathways that result in the destruction of the target gene mRNA.

As used herein, the term "stimulatory agent" refers to any exogenous agent that can stimulate an immune response, and includes, without limitation, a vaccine, a HIV vaccine, and HIV or HIV-related peptides. A stimulatory agent can preferably stimulate a T cell response.

As used herein, the term "subject" includes a human patient but also includes other mammals. The terms "subject," "individual," "host," and "patient" may be used interchangeably herein.

The term "therapeutically effective amount" refers to a sufficient quantity of the active agents of the present invention, in a suitable composition, and in a suitable dosage form to treat or prevent the symptoms, progression, or onset of the complications seen in patients suffering from a given ailment, injury, disease, or condition. The therapeutically effective amount will vary depending on the state of the patient's condition or its severity, and the age, weight, etc., of the subject to be treated. A therapeutically effective amount can vary, depending on any of a number of factors, including, e.g., the route of administration, the condition of the subject, as well as other factors understood by those in the art.

As used herein, the term "therapeutic vector" is synonymous with a lentiviral vector such as the AGT103 vector.

The term "treatment" or "treating" generally refers to an intervention in an attempt to alter the natural course of the subject being treated, and can be performed either for prophylaxis or during the course of clinical pathology. Desirable effects include, but are not limited to, preventing occurrence or recurrence of disease, alleviating symptoms, suppressing, diminishing or inhibiting any direct or indirect pathological consequences of the disease, ameliorating or palliating the disease state, and causing remission or improved prognosis.

The term "vaccine", which is used interchangeably with the term "therapeutic vaccine" refers to an exogenous agent that can elicit an immune response in an individual and includes, without limitation, purified proteins, inactivated viruses, virally vectored proteins, bacterially vectored proteins, peptides or peptide fragents, or virus-like particles (VLPs).

Description of Aspects of the Disclosure

As detailed herein, in one aspect, a method of treating cells infected with HIV is provided. The method generally includes contacting peripheral blood mononuclear cells (PBMC) isolated from a subject infected with HIV with a therapeutically effective amount of a stimulatory agent, wherein the contacting step is carried out ex vivo; transducing the PBMC ex vivo with a viral delivery system encoding at least one genetic element; and culturing the transduced PBMC for a period of time sufficient to achieve such transduction. In embodiments, the transduced PBMC are cultured from about 1 to about 35 days. The method may further include infusing the transduced PBMC into a subject. The subject may be a human. The stimulatory agent may include a peptide or mixture of peptides, and in a preferred embodiment includes a gag peptide. The stimulatory agent may include a vaccine. The vaccine may be a HIV vaccine, and in a preferred embodiment, the HIV vaccine is a MVA/HIV62B vaccine or a variant thereof. In a preferred embodiment, the viral delivery system includes a lentiviral particle. In embodiments, the at least one genetic element may include a small RNA capable of inhibiting production of chemokine receptor CCR5. In embodiments, the at least one genetic element includes at least one small RNA capable of targeting an HIV RNA sequence. In other embodiments, the at least one genetic element includes a small RNA capable of inhibiting production of chemokine receptor CCR5 and at least one small RNA capable of targeting an HIV RNA sequence. The HIV RNA sequence may include a HIV Vif sequence, a HIV Tat sequence, or variants thereof. The at least one genetic element may include at least one of a microRNA or a shRNA. In a preferred embodiment, the at least one genetic element comprises a microRNA cluster.

In another aspect, the at least one genetic element includes a microRNA having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with AGGTATATTGCTGTTGACAGT-GAGCGACTGTAAACTGAGCTTGCTCTACTGT-GAAGCC ACAGATGGGTAGAGCAAGCACAGTT-TACCGCTGCCTACTGCCTCGGACTTCAAGGGG CTT (SEQ ID NO: 1). In a preferred embodiment, the at least one genetic element comprises: AGGTATAT-TGCTGTTGACAGTGAGCGACTGTAAACT-GAGCTTGCTCTACTGTGAAGCC ACA-GATGGGTAGAGCAAGCACAGTTTACCGCTGCCTA-CTGCCTCGGACTTCAAGGGG CTT (SEQ ID NO: 1).

In another aspect, the at least one genetic element includes a microRNA having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with CATCTCCATGGCTGTAC-CACCTTGTCGGGGGATGTGTACTTCT-GAACTTGTGTTGAAT CTCATG-GAGTTCAGAAGAACACATCCGCACTGACATTTTG-GTATCTTTCATCTGACCA (SEQ ID NO: 2); or at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with GGGCCTGGCTCGAGCAGGGGGCGAGGGAT-TCCGCTTCTTCCTGCCATAGCGTGG TCCCCTCCCC-TATGGCAGGCAGAAGCGGCACCTTCCCTCC-CAATGACCGCGTCTTCGT CG (SEQ ID NO: 3). In a preferred embodiment, the at least one genetic element includes CATCTCCATGGCTGTACCACCTTGTCGGGG-GATGTGTACTTCTGAACTTGTGTTGAAT CTCATG-GAGTTCAGAAGAACACATCCGCACTGACAT-TTTGGTATCTTTCATCTGACCA (SEQ ID NO: 2); or GGGCCTGGCTCGAGCAGGGGGCGAGGGAT-TCCGCTTCTTC CTGCCATAGCGTGGTCCCCTCCCC-TATGGCAGGCAGAAGCGGCACCTTCCCTCCCAAT GACCGCGTCTTCGTCG (SEQ ID NO: 3).

In another aspect, the microRNA cluster includes a sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with AGGTATATTGCTGTTGACAGT-GAGCGACTGTAAACTGAGCTTGCTCTACTGT-GAAGCC ACAGATGGGTAGAGCAAGCACAGTT-TACCGCTGCCTACTGCCTCGGACTTCAAGGGG CTTCCCGGGCATCTCCATGGCTGTAC-CACCTTGTCGGGGGATGTGTACTTCTGAACTT GTGTTGAATCTCATGGAGTTCAGAAGAACA-CATCCGCACTGACATTTTGGTATCTTTC ATCTGACCAGCTAGCGGGCCTGGCTCGAGCAGG-GGGCGAGGGATTCCGCTTCTTCCT GCCAT-AGCGTGGTCCCCTCCCC-TATGGCAGGCAGAAGCGGCACCTTCCCTCC-CAATGA CCGCGTCTTCGTC (SEQ ID NO: 31). In a preferred embodiment, the microRNA cluster includes: AGGTATATTGCTGTTGACAGT-GAGCGACTGTAAACTGAGCTTGCTCT ACTGT-GAAGCCACAGATGGGTAGAGCAAGCACAGTT-TACCGCTGCCTA-CTGCCTCGG ACTTCAAGGGGCTTCCCGGG-CATCTCCATGGCTGTACCACCTTGTCGGGG-GATGTGTA CTTCTGAACTTGTGTTGAATCTCATG-GAGTTCAGAAGAACACATCCGCACTGACATTT TGGTATCTTT-CATCTGACCAGCTAGCGGGCCTGGCTCGAGCAG-GGGGCGAGGGATTC CGCTTCTTCCTGCCAT-AGCGTGGTCCCCTCCCC-TATGGCAGGCAGAAGCGGCACCTTC CCTCC-CAATGACCGCGTCTTCGTC (SEQ ID NO: 31).

In another aspect, a method of treating HIV infection in a subject is disclosed. The method generally includes immunizing the subject with an effective amount of a first stimulatory agent; removing leukocytes from the subject and purifying peripheral blood mononuclear cells (PBMC). The method further includes contacting the PBMC ex vivo with a therapeutically effective amount of a second stimulatory agent; transducing the PBMC ex vivo with a viral delivery system encoding at least one genetic element; and culturing the transduced PBMC for a period of time sufficient to achieve transduction. The method may further include further enrichment of the PBMC, for example, by preferably enriching the PBMC for CD4+ T cells. In embodiments, the transduced PBMC are cultured from about 1 to about 35 days. The method may further involve infusing the transduced PBMC into a subject. The subject may be a human. The first and second stimulatory agents may be the same or different from each other. The at least one of the first and second stimulatory agents may include a peptide or mixture of peptides. In embodiments, at least one of the first and second stimulatory agents includes a gag peptide. The at least one of the first and second stimulatory agents may include a vaccine. The vaccine may be a HIV vaccine, and in a preferred embodiment, the HIV vaccine is a MVA/HIV62B vaccine or a variant thereof. In embodiments, the first stimulatory agent is a HIV vaccine and the second stimulatory agent is a gag peptide.

In embodiments, the viral delivery system includes a lentiviral particle. In embodiments, the at least one genetic element includes a small RNA capable of inhibiting production of chemokine receptor CCR5. In embodiments, the at least one genetic element includes at least one small RNA capable of targeting an HIV RNA sequence. In embodiments, the at least one genetic element includes a small RNA capable of inhibiting production of chemokine receptor CCR5 and at least one small RNA capable of targeting an HIV RNA sequence. The HIV RNA sequence may include a HIV Vif sequence, a HIV Tat sequence, or variants thereof. The at least one genetic element may include a microRNA or a shRNA, or a cluster thereof. In a preferred embodiment, the at least one genetic element comprises a microRNA cluster.

In another aspect, the at least one genetic element includes a microRNA having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with AGGTATATTGCTGTTGACAGT-GAGCGACTGTAAACTGAGCTTGCTCTACTGT-GAAGCC ACAGATGGGTAGAGCAAGCACAGTT-TACCGCTGCCTACTGCCTCGGACTTCAAGGGG CTT (SEQ ID NO: 1). In a preferred embodiment, the at least one genetic element comprises: AGGTATAT-TGCTGTTGACAGTGAGCGACTGTAAACT-GAGCTTGCTCTACTGTGAAGCC ACA-GATGGGTAGAGCAAGCACAGTTTACCGCTGCCTA-CTGCCTCGGACTTCAAGGGG CTT (SEQ ID NO: 1).

In another aspect, the at least one genetic element includes a microRNA having at least 80%, or at least 85%, or at least 90%, or at least 95% percent identity with CATCTCCATGGCTGTACCACCTTGTCGGGGGATGTGTACTTCTGAACTTGTGTTGAAT CTCATGGAGTTCAGAAGAACACATCCGCACTGACATTTTGGTATCTTTCATCTGACCA (SEQ ID NO: 2); or at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, with at least 95% or more percent identity GGGCCTGGCTCGAGCAGGGGGCGAGGGATTCCGCTTCTTCCTGCCATAGCGTGG TCCCCTCCCCTATGGCAGGCAGAAGCGGCACCTTCCCTCCCAATGACCGCGTCTTCGT CG (SEQ ID NO: 3). In a preferred embodiment, the at least one genetic element includes CATCTCCATGGCTGTACCACCTTGTCGGGGGATGTGTACTTCTGAACTTGTGTTGAAT CTCATGGAGTTCAGAAGAACACATCCGCACTGACATTTTGGTATCTTTCATCTGACCA (SEQ ID NO: 2); or GGGCCTGGCTCGAGCAGGGGGCGAGGGATTCCGCTTCTTC CTGCCATAGCGTGGTCCCCTCCCCTATGGCAGGCAGAAGCGGCACCTTCCCTCCCAAT GACCGCGTCTTCGTCG (SEQ ID NO: 3).

In another aspect, the microRNA cluster includes a sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with AGGTATATTGCTGTTGACAGTGAGCGACTGTAAACTGAGCTTGCTCTACTGTGAAGCC ACAGATGGGTAGAGCAAGCACAGTTTACCGCTGCCTACTGCCTCGGACTTCAAGGGG CTTCCCGGGCATCTCCATGGCTGTACCACCTTGTCGGGGGATGTGTACTTCTGAACTT GTGTTGAATCTCATGGAGTTCAGAAGAACACATCCGCACTGACATTTTGGTATCTTTC ATCTGACCAGCTAGCGGGCCTGGCTCGAGCAGGGGGCGAGGGATTCCGCTTCTTCCT GCCATAGCGTGGTCCCCTCCCCTATGGCAGGCAGAAGCGGCACCTTCCCTCCCAATGA CCGCGTCTTCGTC (SEQ ID NO: 31). In a preferred embodiment, the microRNA cluster includes: AGGTATATTGCTGTTGACAGTGAGCGACTGTAAACTGAGCTTGCTCT ACTGTGAAGCCACAGATGGGTAGAGCAAGCACAGTTTACCGCTGCCTACTGCCTCGG ACTTCAAGGGGCTTCCCGGGCATCTCCATGGCTGTACCACCTTGTCGGGGGATGTGTA CTTCTGAACTTGTGTTGAATCTCATGGAGTTCAGAAGAACACATCCGCACTGACATTT TGGTATCTTTCATCTGACCAGCTAGCGGGCCTGGCTCGAGCAGGGGGCGAGGGATTC CGCTTCTTCCTGCCATAGCGTGGTCCCCTCCCCTATGGCAGGCAGAAGCGGCACCTTC CCTCCCAATGACCGCGTCTTCGTC (SEQ ID NO: 31).

In another aspect, a lentiviral vector is disclosed. The lentiviral vector includes at least one encoded genetic element, wherein the at least one encoded genetic element comprises a small RNA capable of inhibiting production of chemokine receptor CCR5 or at least one small RNA capable of targeting an HIV RNA sequence. In another aspect a lentiviral vector is disclosed in the at least one encoded genetic element comprises a small RNA capable of inhibiting production of chemokine receptor CCR5 and at least one small RNA capable of targeting an HIV RNA sequence. The HIV RNA sequence may include a HIV Vif sequence, a HIV Tat sequence, or a variant thereof. The at least one encoded genetic element may include a microRNA or a shRNA. The at least one encoded genetic element may include a microRNA cluster.

In another aspect, the at least one genetic element includes a microRNA having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with AGGTATATTGCTGTTGACAGTGAGCGACTGTAAACTGAGCTTGCTCTACTGTGAAGCC ACAGATGGGTAGAGCAAGCACAGTTTACCGCTGCCTACTGCCTCGGACTTCAAGGGG CTT (SEQ ID NO: 1). In a preferred embodiment, the at least one genetic element comprises: AGGTATATTGCTGTTGACAGTGAGCGACTGTAAACTGAGCTTGCTCTACTGTGAAGCC ACAGATGGGTAGAGCAAGCACAGTTTACCGCTGCCTACTGCCTCGGACTTCAAGGGG CTT (SEQ ID NO: 1).

In another aspect, the at least one genetic element includes a microRNA having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with CATCTCCATGGCTGTACCACCTTGTCGGGGGATGTGTACTTCTGAACTTGTGTTGAAT CTCATGGAGTTCAGAAGAACACATCCGCACTGACATTTTGGTATCTTTCATCTGACCA (SEQ ID NO: 2); or at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with GGGCCTGGCTCGAGCAGGGGGCGAGGGATTCCGCTTCTTCCTGCCATAGCGTGG TCCCCTCCCCTATGGCAGGCAGAAGCGGCACCTTCCCTCCCAATGACCGCGTCTTCGT CG (SEQ ID NO: 3). In a preferred embodiment, the at least one genetic element includes CATCTCCATGGCTGTACCACCTTGTCGGGGGATGTGTACTTCTGAACTTGTGTTGAAT CTCATGGAGTTCAGAAGAACACATCCGCACTGACATTTTGGTATCTTTCATCTGACCA (SEQ ID NO: 2); or GGGCCTGGCTCGAGCAGGGGGCGAGGGATTCCGCTTCTTC CTGCCATAGCGTGGTCCCCTCCCCTATGGCAGGCAGAAGCGGCACCTTCCCTCCCAAT GACCGCGTCTTCGTCG (SEQ ID NO: 3).

In another aspect, the microRNA cluster includes a sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with AGGTATATTGCTGTTGACAGTGAGCGACTGTAAACTGAGCTTGCTCTACTGTGAAGCC ACAGATGGGTAGAGCAAGCACAGTTTACCGCTGCCTACTGCCTCGGACTTCAAGGGG CTTCCCGGGCATCTCCATGGCTGTACCACCTTGTCGGGGGATGTGTACTTCTGAACTT GTGTTGAATCTCATGGAGTTCAGAAGAACACATCCGCACTGACATTTTGGTATCTTTC ATCTGACCAGCTAGCGGGCCTGGCTCGAGCAGGGGGCGAGGGATTCCGCTTCTTCCT GCCATAGCGTGGTCCCCTCCCCTATGGCAGGCAGAAGCGGCACCTTCCCTCCCAATGA CCGCGTCTTCGTC (SEQ ID NO: 31). In a preferred embodiment, the microRNA cluster includes: AGGTATATTGCTGTTGACAGT GAGCGACTGTAAACTGAGCTTGCTCT ACTGTGAAGCCACAGATGGGTAGAGCAAGCACAGTTTACCGCTGCCTACTGCCTCGG ACTTCAAGGGGCTTCCCGGGCATCTC-CATGGCTGTACCACCTTGTCGGGGGATGTGTACTTCTGAACTTGTGTTGAATCTCATG-GAGTTCAGAAGAACACATCCGCACTGACATTTTGGTATCTTT-CATCTGACCAGCTAGCGGGCCTGGCTCGAGCAGG-GGGCGAGGGATTC CGCTTCTTCCTGCCAT-AGCGTGGTCCCCTCCCC-TATGGCAGGCAGAAGCGGCACCTTC CCTCC-CAATGACCGCGTCTTCGTC (SEQ ID NO: 31).

In another aspect, a lentiviral vector system for expressing a lentiviral particle is provided. The system includes a lentiviral vector as described herein; at least one envelope plasmid for expressing an envelope protein preferably optimized for infecting a cell; and at least one helper plasmid for expressing a gene of interest, for example any of gag, pol, and rev genes, wherein when the lentiviral vector, the at least one envelope plasmid, and the at least one helper plasmid are transfected into a packaging cell, wherein a lentiviral particle is produced by the packaging cell, wherein the lentiviral particle is capable of modulating a target sequence of interest, for example inhibiting production of chemokine receptor CCR5 or targeting an HIV RNA sequence.

In another aspect, a lentiviral particle capable of infecting a cell is disclosed. The lentiviral particle includes at least one envelope protein preferably optimized for infecting a cell, and a lentiviral vector as described herein. The envelope protein may be optimized for infecting a T cell. In a preferred embodiment, the envelope protein is optimized for infecting a CD4+ T cell.

In another aspect, a modified cell is disclosed. In embodiments, the modified cell is a CD4+ T cell. In embodiments, the CD4+ T cell isinfected with a lentiviral particle as described herein. In embodiments, the CD4+ T cell also has been selected to recognize an HIV antigen based on the prior immunization with a stimulatory agent. In a further preferred embodiment, the HIV antigen that is recognized by the CD4+ T cell includes a gag antigen. In a further preferred embodiment, the CD4+ T cell expresses a decreased level of CCR5 following infection with the lentiviral particle.

In another aspect, a method of selecting a subject for a therapeutic treatment regimen is disclosed. The method generally includes immunizing the subject with an effective amount of a first stimulatory agent; removing leukocytes from the subject and purifying peripheral blood mononuclear cells (PBMC) and determining a first quantifiable measurement associated with at least one factor associated with the PBMC; contacting the PBMC ex vivo with a therapeutically effective amount of a second stimulatory agent, and determining a second measurement associated with the at least one factor associated with the PBMC, whereby when the second quantifiable measurement is different (e.g., higher) than the first quantifiable measurement, the subject is selected for the treatment regimen. The at least one factor may be T cell proliferation or IFN gamma production.

Human Immunodeficiency Virus (HIV)

Human Immunodeficiency Virus, which is also commonly referred to as "HIV", is a retrovirus that causes acquired immunodeficiency syndrome (AIDS) in humans. AIDS is a condition in which progressive failure of the immune system allows life-threatening opportunistic infections and cancers to thrive. Without treatment, average survival time after infection with HIV is estimated to be 9 to 11 years, depending upon the HIV subtype. Infection with HIV occurs by the transfer of bodily fluids, including but not limited to blood, semen, vaginal fluid, pre-ejaculate, saliva, tears, lymph or cerebro-spinal fluid, or breast milk. HIV may be present in an infected individual as both free virus particles and within infected immune cells.

HIV infects vital cells in the human immune system such as helper T cells, although tropism can vary among HIV subtypes. Immune cells that may be specifically susceptible to HIV infection include but are not limited to CD4+ T cells, macrophages, and dendritic cells. HIV infection leads to low levels of CD4+ T cells through a number of mechanisms, including but not limited to apoptosis of uninfected bystander cells, direct viral killing of infected cells, and killing of infected CD4+ T cells by CD8 cytotoxic lymphocytes that recognize infected cells. When CD4+ T cell numbers decline below a critical level, cell-mediated immunity is lost, and the body becomes progressively more susceptible to opportunistic infections and cancer.

Structurally, HIV is distinct from many other retroviruses. The RNA genome consists of at least seven structural landmarks (LTR, TAR, RRE, PE, SLIP, CRS, and INS), and at least nine genes (gag, pol, env, tat, rev, nef, vif, vpr, vpu, and sometimes a tenth tev, which is a fusion of tat, env and rev), encoding 19 proteins. Three of these genes, gag, pol, and env, contain information needed to make the structural proteins for new virus particles.

HIV replicates primarily in CD4 T cells, and causes cellular destruction or dysregulation to reduce host immunity. Because HIV establishes infection as an integrated provirus and may enter a state of latency wherein virus expression in a particular cell decreases below the level for cytopathology affecting that cell or detection by the host immune system, HIV is difficult to treat and has not been eradicated even after prolonged intervals of highly active antiretroviral therapy (HAART). In the vast majority of cases, HIV infection causes fatal disease although survival may be prolonged by HAART.

A major goal in the fight against HIV is to develop strategies for curing disease. Prolonged HAART has not accomplished this goal, so investigators have turned to alternative procedures. Early efforts to improve host immunity by therapeutic immunization (using a vaccine after infection has occurred) had marginal or no impact. Likewise, treatment intensification had moderate or no impact.

Some progress has been made using genetic therapy, but positive results are sporadic and found only among rare human beings carrying defects in one or both alleles of the gene encoding CCR5 (chemokine receptor), which plays a critical role in viral penetration of host cells. However, many investigators are optimistic that genetic therapy holds the best promise for eventually achieving an HIV cure.

As disclosed herein, the methods and compositions of the invention are able to achieve a functional cure that may or may not include complete eradication of all HIV from the body. As mentioned above, a functional cure is defined as a state or condition wherein HIV+ individuals who previously required HAART, may survive with low or undetectable virus replication and using lower or intermittent doses of HAART, or are potentially able to discontinue HAART altogether. As used herein, a functional cure may still possibly require adjunct therapy to maintain low level virus replication and slow or eliminate disease progression. A possible outcome of a functional cure is the eventual eradication of HIV to prevent all possibility of recurrence.

The primary obstacles to achieving a functional cure lie in the basic biology of HIV itself. Virus infection deletes CD4 T cells that are critical for nearly all immune functions. Most importantly, HIV infection and depletion of CD4 T cells requires activation of individual cells. Activation is a specific mechanism for individual CD4 T cell clones that recognize pathogens or other molecules, using a rearranged T cell receptor.

In the case of HIV, infection activates a population of HIV-specific T cells that become infected and are consequently depleted before other T cells that are less specific for the virus, which effectively cripples the immune system's defense against the virus. The capacity for HIV-specific T cell responses is rebuilt during prolonged HAART; however, when HAART is interrupted the rebounding virus infection repeats the process and again deletes the virus-specific cells, resetting the clock on disease progression.

Clearly, a functional cure is only possible if enough HIV-specific CD4 T cells are protected to allow for a host's native immunity to confront and control HIV once HAART is interrupted. In one embodiment, the present invention provides methods and compositions for improving the effectiveness of genetic therapy to provide a functional cure of HIV disease. In another embodiment, the present invention provides methods and compositions for enhancing host immunity against HIV to provide a functional cure. In yet another embodiment, the present invention provides methods and compositions for enriching HIV-specific CD4 T cells in a patient to achieve a functional cure.

In one embodiment of the invention, treatment results in enriching a subject's HIV-specific CD4 T cells by about 100%, about 200%, about 300%, about 400%, about 500%, about 600%, about 700%, about 800%, about 900%, or about 1000%.

Gene Therapy

Viral vectors are used to deliver genetic constructs to host cells for the purposes of disease therapy or prevention.

Genetic constructs can include, but are not limited to, functional genes or portions of genes to correct or complement existing defects, DNA sequences encoding regulatory proteins, DNA sequences encoding regulatory RNA molecules including antisense, short homology RNA, long non-coding RNA, small interfering RNA or others, and decoy sequences encoding either RNA or proteins designed to compete for critical cellular factors to alter a disease state. Gene therapy involves delivering these therapeutic genetic constructs to target cells to provide treatment or alleviation of a particular disease.

There are multiple ongoing efforts to utilize genetic therapy in the treatment of HIV disease, but thus far, the results have been poor. A small number of treatment successes were obtained in rare HIV patients carrying a spontaneous deletion of the CCR5 gene (an allele known as CCR5delta32).

Lentivirus-delivered nucleases or other mechanisms for gene deletion/modification may be used to lower the overall expression of CCR5 and/or help to lower HIV replication. At least one study has reported having success in treating the disease when lentivirus was administered in patients with a genetic background of CCR5delta32. However, this was only one example of success, and many other patients without the CCR5delta32 genotype have not been treated as successfully. Consequently, there is a substantial need to improve the performance of viral genetic therapy against HIV, both in terms of performance for the individual viral vector construct and for improved use of the vector through a strategy for achieving functional HIV cure.

For example, some existing therapies rely on zinc finger nucleases to delete a portion of CCR5 in an attempt to render cells resistant to HIV infection. However, even after optimal treatment, only 30% of T cells had been modified by the nuclease at all, and of those that were modified, only 10% of the total CD4 T cell population had been modified in a way that would prevent HIV infection. In contrast, the disclosed methods result in virtually every cell carrying a lentivirus transgene having a reduction in CCR5 expression below the level needed to allow HIV infection.

For the purposes of the disclosed methods, gene therapy can include, but is not limited to, affinity-enhanced T cell receptors, chimeric antigen receptors on CD4 T cells (or alternatively on CD8 T cells), modification of signal transduction pathways to avoid cell death cause by viral proteins, increased expression of HIV restriction elements including TREX, SAMHD1, MxA or MxB proteins, APOBEC complexes, TRIM5-alpha complexes, tetherin (BST2), and similar proteins identified as being capable of reducing HIV replication in mammalian cells.

Immunotherapy

Historically, vaccines have been a go-to weapon against deadly infectious diseases, including smallpox, polio, measles, and yellow fever. Unfortunately, there is no currently approved vaccine for HIV. The HIV virus has unique ways of evading the immune system, and the human body seems incapable of mounting an effective immune response against it. As a result, scientists do not have a clear picture of what is needed to provide protection against HIV.

However, immunotherapy may provide a solution that was previously unaddressed by conventional vaccine approaches. Immunotherapy, also called biologic therapy, is a type of treatment designed to boost the body's natural defenses to fight infections or cancer. It uses materials either made by the body or in a laboratory to improve, target, or restore immune system function.

In some embodiments of the disclosed invention, immunotherapeutic approaches may be used to enrich a population of HIV-specific CD4 T cells for the purpose of increasing the host's anti-HIV immunity. In some embodiments of the disclosed invention, integrating or non-integrating lentivirus vectors may be used to transduce a host's immune cells for the purposes of increasing the host's anti-HIV immunity. In yet another embodiment of the invention, a vaccine comprising HIV proteins including but not limited to a killed particle, a virus-like particle, HIV peptides or peptide fragments, a recombinant viral vector, a recombinant bacterial vector, a purified subunit or plasmid DNA combined with a suitable vehicle and/or biological or chemical adjuvants to increase a host's immune responses may be used to enrich the population of virus-specific T cells or antibodies, and these methods may be further enhanced through the use of HIV-targeted genetic therapy using lentivirus or other viral vector.

Methods

In one aspect, the disclosure provides methods for using viral vectors to achieve a functional cure for HIV disease. The methods generally include immunotherapy to enrich the proportion of HIV-specific CD4 T cells, followed by lentivirus transduction to deliver inhibitors of HIV and CCR5 and CXCR4 as required.

In one embodiment, the methods include a first stimulation event to enrich a proportion of HIV-specific CD4 T cells. The first stimulation can include administration of one or more of any agent suitable for enriching a patient's HIV-specific CD4+ T cells including but not limited to a vaccine.

Therapeutic vaccines can include one or more HIV protein with protein sequences representing the predominant viral types of the geographic region where treatment is occurring. Therapeutic vaccines will include purified proteins, inactivated viruses, virally vectored proteins, bacterially vectored proteins, peptides or peptide fragments, virus-like particles (VLPs), biological or chemical adjuvants including cytokines and/or chemokines, vehicles, and methods for immunization. Vaccinations may be administered according to standard methods known in the art and HIV patients may continue antiretroviral therapy during the interval of immunization and subsequent ex vivo lymphocyte culture including lentivirus transduction.

In some embodiments, HIV+ patients are immunized with an HIV vaccine, increasing the frequency of HIV-specific CD4 T cells by about 2, about 25, about 250, about 500, about 750, about 1000, about 1250, or about 1500-fold (or any amount in between these values). The vaccine may be any clinically utilized or experimental HIV vaccine, including the disclosed lentiviral, other viral vectors or other bacterial vectors used as vaccine delivery systems. In another embodiment, the vectors encode virus-like particles (VLPs) to induce higher titers of neutralizing antibodies. In another embodiment, the vectors encode peptides or peptide fragments associated with HIV including but not limited to gag, pol, and env, tat, rev, nef, vif, vpr, vpu, and tev, as well as LTR, TAR, RRE, PE, SLIP, CRS, and INS. Alternatively, the HIV vaccine used in the disclosed methods may comprise purified proteins, inactivated viruses, virally vectored proteins, bacterially vectored proteins, peptides or peptide fragments, virus-like particles (VLPs), or biological or chemical adjuvants including cytokines and/or chemokines.

In one embodiment, the methods include ex vivo re-stimulation of CD4 T cells from persons or patients previously immunized by therapeutic vaccination, using purified proteins, inactivated viruses, virally vectored proteins, bacterially vectored proteins, biological or chemical adjuvants including cytokines and/or chemokines, vehicles, and methods for re-stimulation. Ex vivo re-stimulation may be performed using the same vaccine or immune stimulating compound used for in vivo immunization, or it may be performed using a different vaccine or immune stimulating compound than those used for in vivo immunization. Moreover, in some embodiments, the patient does not require prior therapeutic vaccination or re-stimulation of CD4 T cells if the individual has sufficiently high antigen-specific CD4 T cell responses to HIV proteins. In these embodiments, such a patient may only require administration of the disclosed viral vectors to achieve a functional cure.

In embodiments, peripheral blood mononuclear cells (PBMCs) are obtained by leukapheresis and treated ex vivo to obtain about $1 \times 10^{10}$ CD4 T cells of which about 0.1%, about 1%, about 5% or about 10% or about 30% are both HIV-specific in terms of antigen responses, and HIV-resistant by virtue of carrying the therapeutic transgene delivered by the disclosed lentivirus vector. Alternatively, about $1 \times 10^7$, about $1 \times 10^8$, about $1 \times 10^9$, about $1 \times 10^{10}$, about $1 \times 10^{11}$, or about $1 \times 10^{12}$ CD4 T cells may be isolated for re-stimulation. Any suitable amount of CD4 T cells are isolated for ex vivo re-stimulation.

The isolated CD4 T cells can be cultured in appropriate medium throughout re-stimulation with HIV vaccine antigens, which may include antigens present in the prior therapeutic vaccination. Antiretroviral therapeutic drugs including inhibitors of reverse transcriptase, protease or integrase may be added to prevent virus re-emergence during prolonged ex vivo culture. CD4 T cell re-stimulation is used to enrich the proportion of HIV-specific CD4 T cells in culture. The same procedure may also be used for analytical objectives wherein smaller blood volumes with peripheral blood mononuclear cells obtained by purification, are used to identify HIV-specific T cells and measure the frequency of this sub-population.

The PBMC fraction may be enriched for HIV-specific CD4 T cells by contacting the cells with HIV proteins matching or complementary to the components of the vaccine previously used for in vivo immunization. Ex vivo re-stimulation can increase the relative frequency of HIV-specific CD4 T cells by about 5, about 10, 25, about 50, about 75, about 100, about 125, about 150, about 175, or about 200-fold.

The methods additionally include combining in vivo therapeutic immunization and ex vivo re-stimulation of CD4 T cells with ex vivo lentiviral transduction and culturing.

Thus, in one embodiment, the re-stimulated PBMC fraction that has been enriched for HIV-specific CD4 T cells can be transduced with therapeutic anti-HIV lentivirus or other vectors and maintained in culture for a sufficient period of time for such transduction, for example from about 1 to about 21 days, including up to about 35 days. Alternatively, the cells may be cultured for about 1-about 18 days, about 1-about 15 days, about 1-about 12 days, about 1-about 9 days, or about 3-about 7 days. Thus, the transduced cells may be cultured for about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, or about 35 days.

In further embodiments, once the transduced cells have been cultured for a sufficient period of time, transduced CD4 T cells are infused back into the original patient. Infusion can be performed using various devices and methods known in the art. In some embodiments, infusion may be accompanied by pre-treatment with cyclophosphamide or similar compounds to increase the efficiency of re-engraftment.

In some embodiments, a CCR5-targeted therapy may be added to a subject's antiretroviral therapy regimen, which was continued throughout the treatment process. Examples of CCR5-targeted therapies include but are not limited to Maraviroc (a CCR5 antagonist) or Rapamycin (immunosuppressive agent that lowers CCR5). In some embodiments, the antiretroviral therapy may be ceased and the subject can be tested for virus rebound. If no rebound occurs, adjuvant therapy can also be removed and the subject can be tested again for virus rebound.

In various embodiments, continued virus suppression with reduced or no antiretroviral therapy including cART or HAART, and reduced or no adjuvant therapy for about 26 weeks can be considered a functional cure for HIV. Other definitions of a functional cure are described herein.

The lentiviral and other vectors used in the disclosed methods may encode at least one, at least two, at least three, at least four, or at least five genes, or at least six genes, or at least seven genes, or at least eight genes, or at least nine genes, or at least ten genes, or at least eleven genes, or at least twelve genes of interest. Given the versatility and therapeutic potential of HIV-targeted gene therapy, a viral vector of the invention may encode genes or nucleic acid sequences that include but are not limited to (i) an antibody directed to an antigen associated with an infectious disease or a toxin produced by the infectious pathogen, (ii) cytokines including interleukins that are required for immune cell growth or function and may be therapeutic for immune dysregulation encountered in HIV and other chronic or acute human viral or bacterial pathogens, (iii) factors that suppress the growth of HIV in vivo including CD8 suppressor factors, (iv) mutations or deletions of chemokine receptor CCR5, mutations or deletions of chemokine receptor CXCR4, or mutations or deletions of chemokine receptor CXCR5, (v) antisense DNA or RNA against specific receptors or peptides associated with HIV or host protein associated with HIV, (vi) small interfering RNA against specific receptors or peptides associated with HIV or host protein associated with HIV, or (vii) a variety of other therapeutically useful sequences that may be used to treat HIV or AIDS.

Additional examples of HIV-targeted gene therapy that can be used in the disclosed methods include, but are not limited to, affinity-enhanced T cell receptors, chimeric antigen receptors on CD4 T cells (or alternatively on CD8 T cells), modification of signal transduction pathways to avoid cell death cause by viral proteins, increased expression of HIV restriction elements including TREX, SAMHD1, MxA or MxB proteins, APOBEC complexes, TRIM5-alpha complexes, tetherin (BST2), and similar proteins identified as being capable of reducing HIV replication in mammalian cells.

In some embodiments, a patient may be undergoing cART or HAART concurrently while being treated according to the methods of the invention. In other embodiments, a patient may undergo CART or HAART before or after being treated according to the methods of the invention. In some embodiments, cART or HAART is maintained throughout treatment according to the methods of the invention and the patient may be monitored for HIV viral burden in blood and frequency of lentivirus-transduced CD4 T cells in blood. Preferably, a patient receiving cART or HAART prior to being treated according to the methods of the invention is able to discontinue or reduce cART or HAART following treatment according to the methods of the invention.

For efficacy purposes, the frequency of transduced, HIV-specific CD4 T cells, which is a novel surrogate marker for gene therapy effects, may be determined, as discussed in more detail herein.

Compositions

In various aspects, the disclosure provides lentiviral vectors capable of delivering genetic constructs to inhibit HIV penetration of susceptible cells. For instance, one mechanism of action in accordance herein is to reduce mRNA levels for CCR5 and/or CXCR4 chemokine receptors for reducing the rates for viral entry into susceptible cells.

Alternatively, the disclosed lentiviral vectors are capable of inhibiting the formation of HIV-infected cells by reducing the stability of incoming HIV genomic RNA. And in yet another embodiment, the disclosed lentivirus vectors are capable of preventing HIV production from a latently infected cell, wherein the mechanism of action is to cause instability of viral RNA sequences through the action of inhibitory RNA including short-homology, small-interfering or other regulatory RNA species.

The therapeutic lentiviruses disclosed generally comprise at least one of two types of genetic cargo. First, the lentiviruses may encode genetic elements that direct expression of small RNA capable of inhibiting the production of chemokine receptors CCR5 and/or CXCR4 that are important for HIV penetration of susceptible cells. The second type of genetic cargo includes constructs capable of expressing small RNA molecules targeting HIV RNA sequences for the purpose of preventing reverse transcription, RNA splicing, RNA translation to produce proteins, or packaging of viral genomic RNA for particle production and spreading infection. An exemplary structure is diagrammed in FIG. 3.

Figure 3:
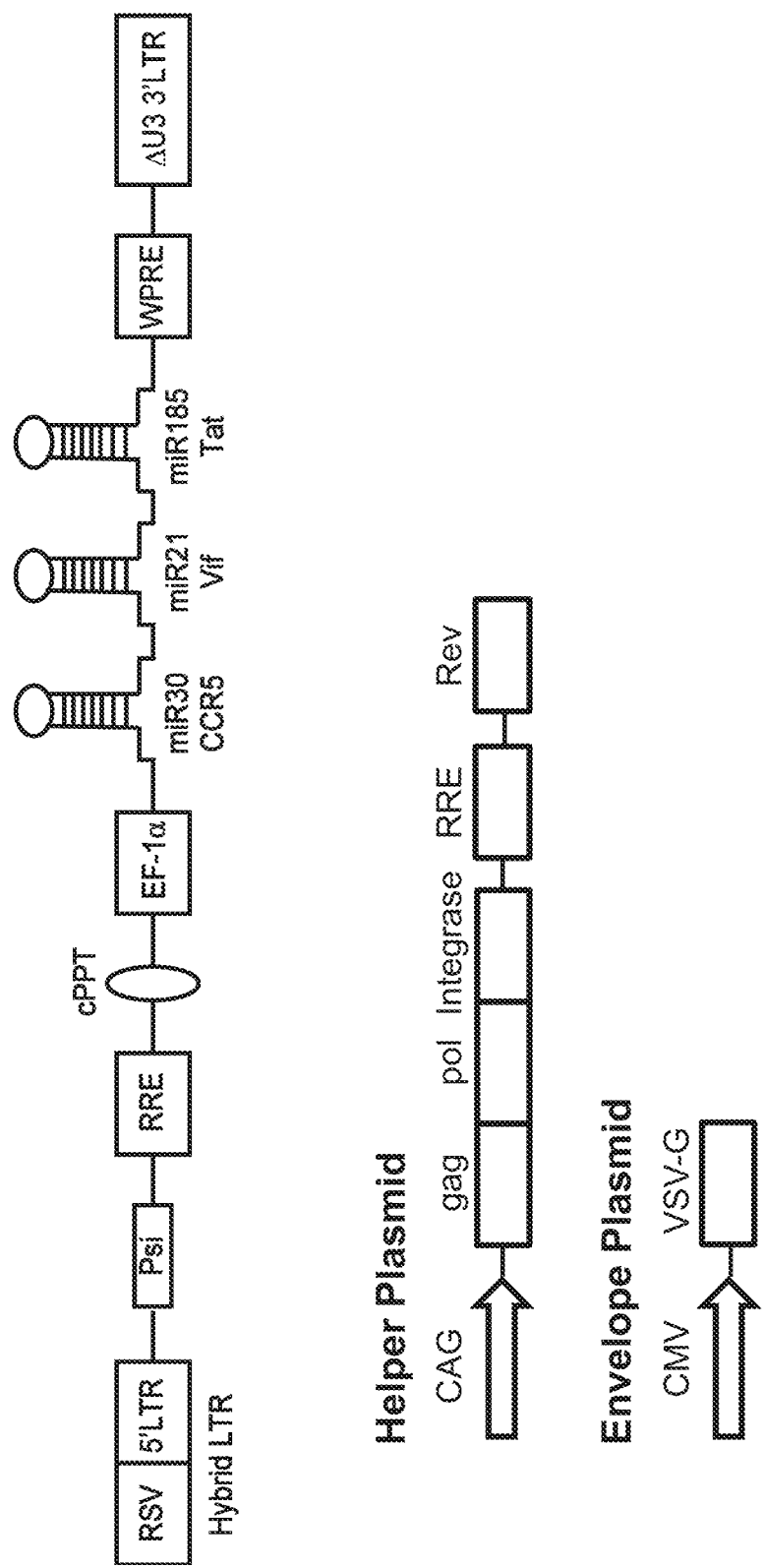
FIG. 3 depicts an exemplary lentiviral vector system comprised of a therapeutic vector, a helper plasmid, and an envelope plasmid. The therapeutic vector shown here is a preferred therapeutic vector, which is also referred to herein as AGT103, and contains miR30CCR5-miR21 Vif-miR185-Tat.

As shown in FIG. 3 (top panel), an exemplary construct may comprise numerous sections or components. For example, in one embodiment, an exemplary LV construct may comprise the following sections or components:

RSV—a Rous Sarcoma virus long terminal repeat;

5'LTR—a portion of an HIV long terminal repeat that can be truncated to prevent replication of the vector after chromosomal integration;

Psi—a packaging signal that allows for incorporation of the vector RNA genome into viral particles during packaging;

RRE—a Rev Responsive element can be added to improve expression from the transgene by mobilizing RNA out of the nucleus and into the cytoplasm of cells;

cPPT—a Poly purine tract that facilitates second strand DNA synthesis prior to integration of the transgene into the host cell chromosome;

Promoter—a promoter initiates RNA transcription from the integrated transgene to express micro-RNA clusters (or other genetic elements of the construct), and in some embodiments, the vectors may use an EF-1 promoter;

Anti-CCR5—a micro RNA targeting messenger RNA for the host cell factor CCR5 to reduce its expression on the cell surface;

Anti-Rev/Tat—a micro RNA targeting HIV genomic or messenger RNA at the junction between HIV Rev and Tat coding regions, which is sometimes designated miRNA Tat or given a similar description in this application;

Anti-Vif—a micro RNA targeting HIV genomic or messenger RNA within the Vif coding region;

WPRE—a woodchuck hepatitis virus post-transcriptional regulatory element is an additional vector component that can be used to facilitate RNA transport of the nucleus; and deltaU3 3'LTR—a modified version of a HIV 3' long terminal repeat where a portion of the U3 region has been deleted to improve safety of the vector.

One of ordinary skill in the art will recognize that the above components are merely examples, and that such components may be reorganized, substituted with other elements, or otherwise changed, so long as the construct is able to prevent expression of HIV genes and decrease the spread of infection.

Vectors of the invention may include either or both of the types of genetic cargo discussed above (i.e., genetic elements that direct expression of a gene or small RNAs, such as siRNA, shRNA, or miRNA that can prevent translation or transcription), and the vectors of the invention may also encode additionally useful products for the purpose of treatment or diagnosis of HIV. For instance, in some embodiments, these vectors may also encode green fluorescent protein (GFP) for the purpose of tracking the vectors or antibiotic resistance genes for the purposes of selectively maintaining genetically-modified cells in vivo.

The combination of genetic elements incorporated into the disclosed vectors is not particularly limited. For example, a vector herein may encode a single small RNA, two small RNAs, three small RNA, four small RNAs, five small RNAs, six small RNAs, seven small RNAs, eight small RNAs, nine small RNAs, or ten small RNAs, or eleven small RNAs, or twelve small RNAs. Such vectors may additionally encode other genetic elements to function in concert with the small RNAs to prevent expression and infection of HIV.

Those of ordinary skill in the art will understand that the therapeutic lentivirus may substitute alternate sequences for the promoter region, targeting of regulatory RNA, and types of regulatory RNA. Further, the therapeutic lentivirus of the disclosure may comprise changes in the plasmids used for packaging the lentivirus particles; these changes are required to increase levels of production in vitro.

Lentiviral Vector System

A lentiviral virion (particle) in accordance with various aspects and embodiments herein is expressed by a vector system encoding the necessary viral proteins to produce a virion (viral particle). In various embodiments, one vector containing a nucleic acid sequence encoding the lentiviral pol proteins is provided for reverse transcription and integration, operably linked to a promoter. In another embodiment, the pol proteins are expressed by multiple vectors. In other embodiments, vectors containing a nucleic acid sequence encoding the lentiviral Gag proteins for forming a viral capsid, operably linked to a promoter, are provided. In embodiments, this gag nucleic acid sequence is on a separate vector than at least some of the pol nucleic acid sequence. In other embodiments, the gag nucleic acid is on a separate vector from all the pol nucleic acid sequences that encode pol proteins.

Numerous modifications can be made to the vectors herein, which are used to create the particles to further minimize the chance of obtaining wild type revertants. These include, but are not limited to deletions of the U3 region of the LTR, tat deletions and matrix (MA) deletions. In embodiments, the gag, pol and env vector(s) do not contain nucleotides from the lentiviral genome that package lentiviral RNA, referred to as the lentiviral packaging sequence.

The vector(s) forming the particle preferably do not contain a nucleic acid sequence from the lentiviral genome that expresses an envelope protein. Preferably, a separate vector that contains a nucleic acid sequence encoding an envelope protein operably linked to a promoter is used. This env vector also does not contain a lentiviral packaging sequence. In one embodiment the env nucleic acid sequence encodes a lentiviral envelope protein.

In another embodiment the envelope protein is not from the lentivirus, but from a different virus. The resultant particle is referred to as a pseudotyped particle. By appropriate selection of envelopes one can "infect" virtually any cell. For example, one can use an env gene that encodes an envelope protein that targets an endocytic compartment such as that of the influenza virus, VSV-G, alpha viruses (Semliki forest virus, Sindbis virus), arenaviruses (lymphocytic choriomeningitis virus), flaviviruses (tick-borne encephalitis virus, Dengue virus, hepatitis C virus, GB virus), rhabdoviruses (vesicular stomatitis virus, rabies virus), paramyxoviruses (mumps or measles) and orthomyxoviruses (influenza virus). Other envelopes that can preferably be used include those from Moloney Leukemia Virus such as MLV-E, MLV-A and GALV. These latter envelopes are particularly preferred where the host cell is a primary cell. Other envelope proteins can be selected depending upon the desired host cell. For example, targeting specific receptors such as a dopamine receptor can be used for brain delivery. Another target can be vascular endothelium. These cells can be targeted using a filovirus envelope. For example, the GP of Ebola, which by post-transcriptional modification become the GP, and GP2 glycoproteins. In another embodiment, one can use different lentiviral capsids with a pseudotyped envelope (for example, FIV or SHIV [U.S. Pat. No. 5,654, 195]). A SHIV pseudotyped vector can readily be used in animal models such as monkeys.

Lentiviral vector systems as provided herein typically include at least one helper plasmid comprising at least one of a gag, pol, or rev gene. Each of the gag, pol and rev genes may be provided on individual plasmids, or one or more genes may be provided together on the same plasmid. In one embodiment, the gag, pol, and rev genes are provided on the same plasmid (e.g., FIGS. 4A-4B). In another embodiment, the gag and pol genes are provided on a first plasmid and the rev gene is provided on a second plasmid (e.g., FIGS. 5A-5B). Accordingly, both 3-vector and 4-vector systems can be used to produce a lentivirus as described herein. In embodiments, the therapeutic vector, at least one envelope plasmid and at least one helper plasmid are transfected into a packaging cell, for example a packaging cell line. A non-limiting example of a packaging cell line is the 293T/17 HEK cell line. When the therapeutic vector, the envelope plasmid, and at least one helper plasmid are transfected into the packaging cell line, a lentiviral particle is ultimately produced.

In another aspect, a lentiviral vector system for expressing a lentiviral particle is disclosed. The system includes a lentiviral vector as described herein; an envelope plasmid for expressing an envelope protein optimized for infecting a cell; and at least one helper plasmid for expressing gag, pol, and rev genes, wherein when the lentiviral vector, the envelope plasmid, and the at least one helper plasmid are transfected into a packaging cell line, a lentiviral particle is produced by the packaging cell line, wherein the lentiviral particle is capable of inhibiting production of chemokine receptor CCR5 or targeting an HIV RNA sequence.

In another aspect, the lentiviral vector, which is also referred to herein as a therapeutic vector, includes the following elements: hybrid 5' long terminal repeat (RSV/5' LTR) (SEQ ID NOS: 34-35), Psi sequence (RNA packaging site) (SEQ ID NO: 36), RRE (Rev-response element) (SEQ ID NO: 37), cPPT (polypurine tract) (SEQ ID NO: 38), EF-1α promoter (SEQ ID NO: 4), miR30CCR5 (SEQ ID NO: 1), miR21Vif (SEQ ID NO: 2), miR185Tat (SEQ ID NO: 3), Woodchuck Post-Transcriptional Regulatory Element (WPRE) (SEQ ID NOS: 32 or 80), and AU3 3' LTR (SEQ ID NO: 39). In another aspect, sequence variation, by way of substitution, deletion, addition, or mutation can be used to modify the sequences references herein.

In another aspect, a helper plasmid includes the following elements: CAG promoter (SEQ ID NO: 41); HIV component gag (SEQ ID NO: 43); HIV component pol (SEQ ID NO: 44); HIV Int (SEQ ID NO: 45); HIV RRE (SEQ ID NO: 46); and HIV Rev (SEQ ID NO: 47). In another aspect, the helper plasmid may be modified to include a first helper plasmid for expressing the gag and pol genes, and a second and separate plasmid for expressing the rev gene. In another aspect, sequence variation, by way of substitution, deletion, addition, or mutation can be used to modify the sequences references herein.

In another aspect, an envelope plasmid includes the following elements: RNA polymerase II promoter (CMV) (SEQ ID NO: 60) and vesicular stomatitis virus G glycoprotein (VSV-G) (SEQ ID NO: 62). In another aspect, sequence variation, by way of substitution, deletion, addition, or mutation can be used to modify the sequences references herein.

In various aspects, the plasmids used for lentiviral packaging are modified by substitution, addition, subtraction or mutation of various elements without loss of vector function. For example, and without limitation, the following elements can replace similar elements in the plasmids that comprise the packaging system: Elongation Factor-1 (EF-1), phosphoglycerate kinase (PGK), and ubiquitin C (UbC) promoters can replace the CMV or CAG promoter. SV40 poly A and bGH poly A can replace the rabbit beta globin poly A. The HIV sequences in the helper plasmid can be constructed from different HIV strains or clades. The VSV-G glycoprotein can be substituted with membrane glycoproteins from feline endogenous virus (RD114), gibbon ape leukemia virus (GALV), Rabies (FUG), lymphocytic choriomeningitis virus (LCMV), influenza A fowl plague virus (FPV), Ross River alphavirus (RRV), murine leukemia virus 10A1 (MLV), or Ebola virus (EboV).

Various lentiviral packaging systems can be acquired commercially (e.g., Lenti-vpak packaging kit from OriGene Technologies, Inc., Rockville, MD), and can also be designed as described herein. Moreover, it is within the skill of a person ordinarily skilled in the art to substitute or modify aspects of a lentiviral packaging system to improve any number of relevant factors, including the production efficiency of a lentiviral particle.

Bioassays

In various aspects, the present invention includes bioassays for determining the success of HIV treatment for achieving a functional cure. These assays provide a method for measuring the efficacy of the disclosed methods of immunization and treatment by measuring the frequency of transduced, HIV specific CD4 T cells in a patient. HIV-specific CD4 T cells are recognizable because, among others, they proliferate, change the composition of cell surface markers, induce signaling pathways including phosphorylation, and/or express specific marker proteins that may be cytokines, chemokines, caspases, phosphorylated signaling molecules or other cytoplasmic and/or nuclear components. Specific responding CD4 T cells are recognized for example, using labeled monoclonal antibodies or specific in situ amplification of mRNA sequences, that allow sorting of HIV-specific cells using flow cytometry sorting, magnetic bead separation or other recognized methods for antigen-specific CD4 T cell isolation. The isolated CD4 T cells are tested to determine the frequency of cells carrying integrated therapeutic lentivirus. Single cell testing methods may also be used including microfluidic separation of individual cells that are coupled with mass spectrometry, PCR, ELISA or antibody staining to confirm responsiveness to HIV and presence of integrated therapeutic lentivirus.

Thus, in various embodiments, following application of a treatment according to the invention (e.g., (a) immunization, (b) ex vivo leukocyte/lymphocyte culture; (c) re-stimulation with purified proteins, inactivated viruses, virally vectored proteins, bacterially vectored proteins, biological or chemical adjuvants including cytokines and/or chemokines, vehicles; and (d) infusion of the enriched, transduced T cells), a patient may be subsequently assayed to determine the efficacy of the treatment. A threshold value of target T cells in the body may be established to measure a functional cure at a determined value, for example, at about $1 \times 10^8$ HIV-specific CD4 T cells bearing genetic modification from therapeutic lentivirus. Alternatively, the threshold value may be about $1 \times 10^5$, about $1 \times 10^6$, about $1 \times 10^7$, about $1 \times 10^8$, about $1 \times 10^9$, or about $1 \times 10^{10}$ CD4 T cells in the body of the patient.

HIV-specific CD4 T cells bearing genetic modification from therapeutic lentivirus can be determined using any suitable method, such as but not limited to flow cytometry, cell sorting, FACS analysis, DNA cloning, PCR, RT-PCR or Q-PCR, ELISA, FISH, western blotting, southern blotting, high throughput sequencing, RNA sequencing, oligonucleotide primer extension, or other methods known in the art.

While methods for defining antigen specific T cells with genetic modifications are known in the art, utilizing such methods to combine identifying HIV-specific T cells with integrated or non-integrated gene therapy constructs as a standard measure for efficacy is a novel concept in the field of HIV treatment, as described variously herein.

Doses and Dosage Forms

The disclosed methods and compositions can be used for treating HIV+ patients during various stages of their disease. Accordingly, dosing regimens may vary based upon the condition of the patient and the method of administration.

In various embodiments, HIV-specific vaccines for the initial in vivo immunization are administered to a subject in need in varying doses. In general, vaccines delivered by intramuscular injection include about 10 µg to about 300 µg, about 25 µg to about 275 µg, about 50 µg to about 250 µg, about 75 µg to about 225, or about 100 µg to about 200 µg of HIV protein, either total virus protein prepared from inactivated virus particles, virus-like particles or purified virus protein from recombinant systems or purified from virus preparations. Recombinant viral or bacterial vectors may be administered by any and all of the routes described. Intramuscular vaccines will include about 1 µg to about 100 µg, about 10 µg to about 90 µg, about 20 µg to about 80 µg, about 30 µg to about 70 µg, about 40 µg to about 60 µg, or about 50 µg of suitable adjuvant molecules and be suspended in oil, saline, buffer or water in volumes of 0.1 to 5 ml per injection dose, and may be soluble or emulsion preparations. Vaccines delivered orally, rectally, bucally, at genital mucosal or intranasally, including some virally-vectored or bacterially-vectored vaccines, fusion proteins, liposome formulations or similar preparations, may contain higher amounts of virus protein and adjuvant. Dermal, sub-dermal or subcutaneous vaccines utilize protein and adjuvant amounts more similar to oral, rectal or intranasal-delivered vaccines. Depending on responses to the initial immunization, vaccination may be repeated 1-5 times using the same or alternate routes for delivery. Intervals may be of 2-24 weeks between immunizations. Immune responses to vaccination are measured by testing HIV-specific antibodies in serum, plasma, vaginal secretions, rectal secretions, saliva or bronchoalveolar lavage fluids, using ELISA or similar methodology. Cellular immune responses are tested by in vitro stimulation with vaccine antigens followed by staining for intracellular cytokine accumulation followed by flow cytometry or similar methods including lymphoproliferation, expression of phosphorylated signaling proteins or changes in cell surface activation markers. Upper limits of dosing may be determined based on the individual patient and will depend on toxicity/safety profiles for each individual product or product lot.

Immunization may occur once, twice, three times, or repeatedly. For instance, an agent for HIV immunization may be administered to a subject in need once a week, once every other week, once every three weeks, once a month, every other month, every three months, every six months, every nine months, once a year, every eighteen months, every two years, every 36 months, or every three years.

Immunization will generally occur at least once before ex vivo expansion and enrichment of CD4 T cells, and immunization may occur once, twice, three times, or more after ex vivo leukocyte/lymphocyte culture/re-stimulation and infusion.

In one embodiment, HIV-vaccines for immunization are administered as a pharmaceutical composition. In one embodiment, the pharmaceutical composition comprising an HIV vaccineis formulated in a wide variety of nasal, pulmonary, oral, topical, or parenteral dosage forms for clinical application. Each of the dosage forms can comprise various disintegrating agents, surfactants, fillers, thickeners, binders, diluents such as wetting agents or other pharmaceutically acceptable excipients. The pharmaceutical composition comprising an HIV vaccine can also be formulated for injection.

HIV vaccine compositions for the purpose of immunization can be administered using any pharmaceutically acceptable method, such as intranasal, buccal, sublingual, oral, rectal, ocular, parenteral (intravenously, intradermally, intramuscularly, subcutaneously, intracisternally, intraperitoneally), pulmonary, intravaginal, locally administered, topically administered, topically administered after scarification, mucosally administered, via an aerosol, or via a buccal or nasal spray formulation.

Further, the HIV vaccine compositions can be formulated into any pharmaceutically acceptable dosage form, such as a solid dosage form, tablet, pill, lozenge, capsule, liquid dispersion, gel, aerosol, pulmonary aerosol, nasal aerosol, ointment, cream, semi-solid dosage form, and a suspension. Further, the composition may be a controlled release formulation, sustained release formulation, immediate release formulation, or any combination thereof. Further, the composition may be a transdermal delivery system.

In another embodiment, the pharmaceutical composition comprising an HIV vaccine is formulated in a solid dosage form for oral administration, and the solid dosage form can be powders, granules, capsules, tablets or pills. In yet another embodiment, the solid dosage form includes one or more excipients such as calcium carbonate, starch, sucrose, lactose, microcrystalline cellulose or gelatin. In addition, the solid dosage form can include, in addition to the excipients, a lubricant such as talc or magnesium stearate. In some embodiments, the oral dosage form is in immediate release or a modified release form. Modified release dosage forms include controlled or extended release, enteric release, and the like. The excipients used in the modified release dosage forms are commonly known to a person of ordinary skill in the art.

In a further embodiment, the pharmaceutical composition comprising a HIV vaccine is formulated as a sublingual or buccal dosage form. Such dosage forms comprise sublingual tablets or solution compositions that are administered under the tongue and buccal tablets that are placed between the cheek and gum.

In yet a further embodiment, the pharmaceutical composition comprising an HIV vaccine is formulated as a nasal dosage form. Such dosage forms of the present invention comprise solution, suspension, and gel compositions for nasal delivery.

In one embodiment, the pharmaceutical composition is formulated in a liquid dosage form for oral administration, such as suspensions, emulsions or syrups. In other embodiments, the liquid dosage form can include, in addition to commonly used simple diluents such as water and liquid paraffin, various excipients such as humectants, sweeteners, aromatics or preservatives. In particular embodiments, the composition comprising HIV vaccine or a pharmaceutically acceptable salt thereof is formulated to be suitable for administration to a pediatric patient.

In one embodiment, the pharmaceutical composition is formulated in a dosage form for parenteral administration, such as sterile aqueous solutions, suspensions, emulsions, non-aqueous solutions or suppositories. In other embodiments, the non-aqueous solutions or suspensions includes propyleneglycol, polyethyleneglycol, vegetable oils such as olive oil or injectable esters such as ethyl oleate. As a base for suppositories, witepsol, macrogol, tween 61, cacao oil, laurin oil or glycerinated gelatin can be used.

The dosage of the pharmaceutical composition can vary depending on the patient's weight, age, gender, administration time and mode, excretion rate, and the severity of disease.

For the purposes of re-stimulation, lymphocytes, PBMCs, and/or CD4 T cells are generally removed from a patient and isolated for re-stimulation and culturing. The isolated cells may be contacted with the same HIV vaccine or activating agent used for immunization or a different HIV vaccine or activating agent. In one embodiment, the isolated cells are contacted with about 10 ng to 5 µg of an HIV vaccine or activating agent per about $10^6$ cells in culture (or any other suitable amount). More specifically, the isolated cells may be contacted with about 50 ng, about 100 ng, about 200 ng, about 300 ng, about 400 ng, about 500 ng, about 600 ng, about 700 ng, about 800 ng, about 900 ng, about 1 µg, about 1.5 µg, about 2 µg, about 2.5 µg, about 3 µg, about 3.5 µg, about 4 µg, about 4.5 µg, or about 5 µg of an HIV vaccine or activating agent per about $10^6$ cells in culture.

Activating agents or vaccines are generally used once for each in vitro cell culture but may be repeated after intervals of about 15 to about 35 days. For example, a repeat dosing could occur at about 15, about 16, about 17, about 18, about 19, about 20, about 21, about 22, about 23, about 24, about 25, about 26, about 27, about 28, about 29, about 30, about 31, about 32, about 33, about 34, or about 35 days.

Figure 4A:
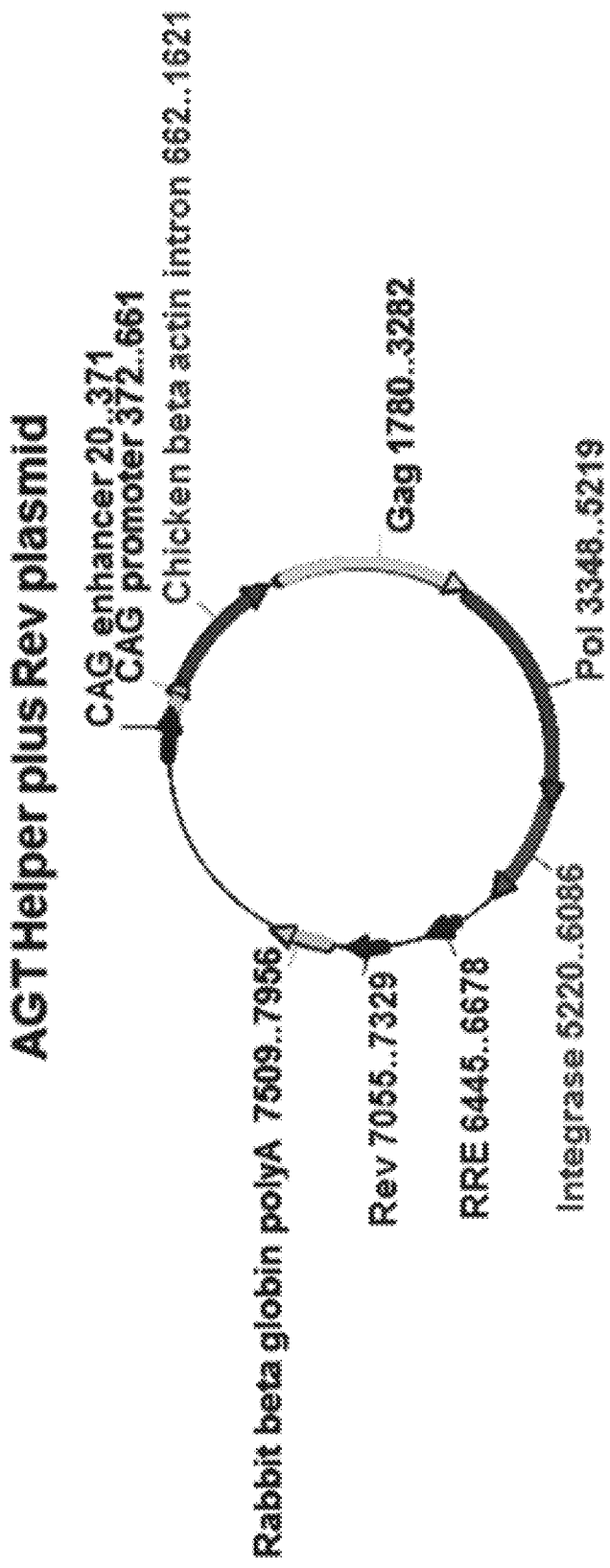
FIGS. 4A-4C depict an exemplary 3-vector lentiviral vector system in a circularized form.
Figure 4B:
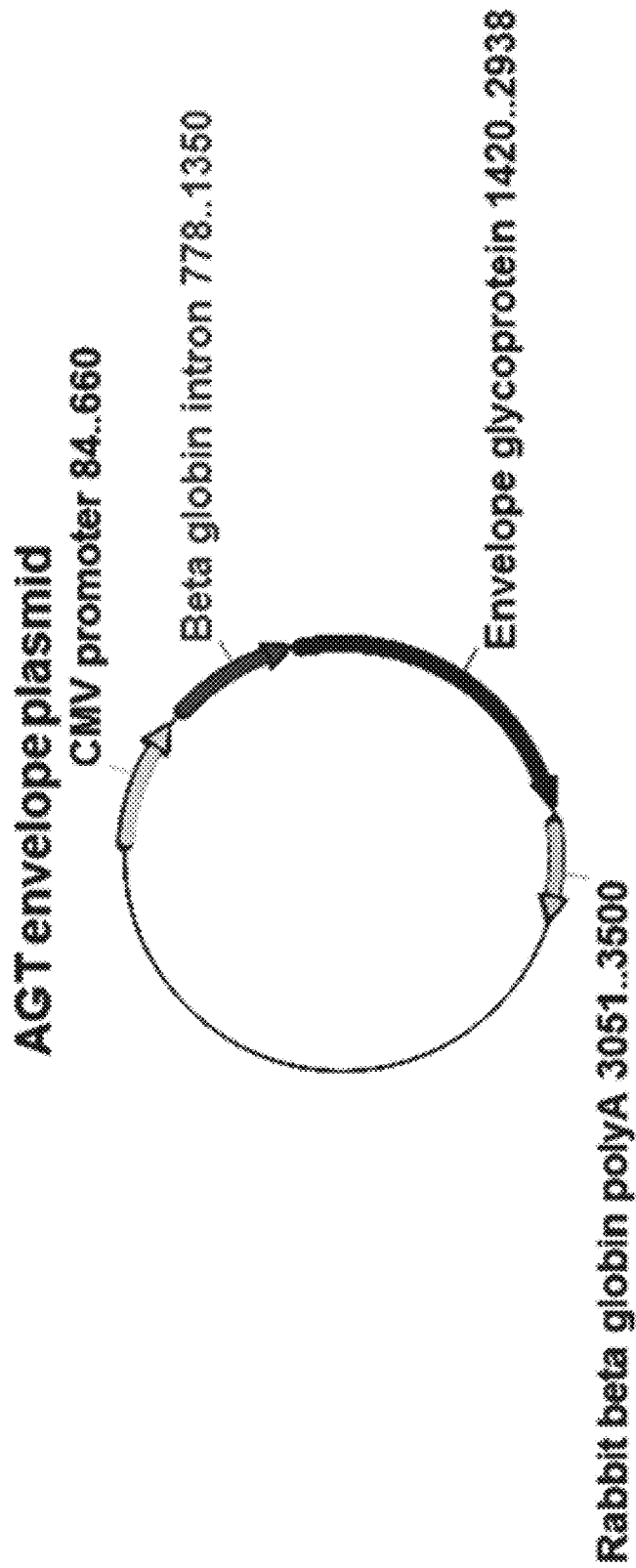
Figure 4C:
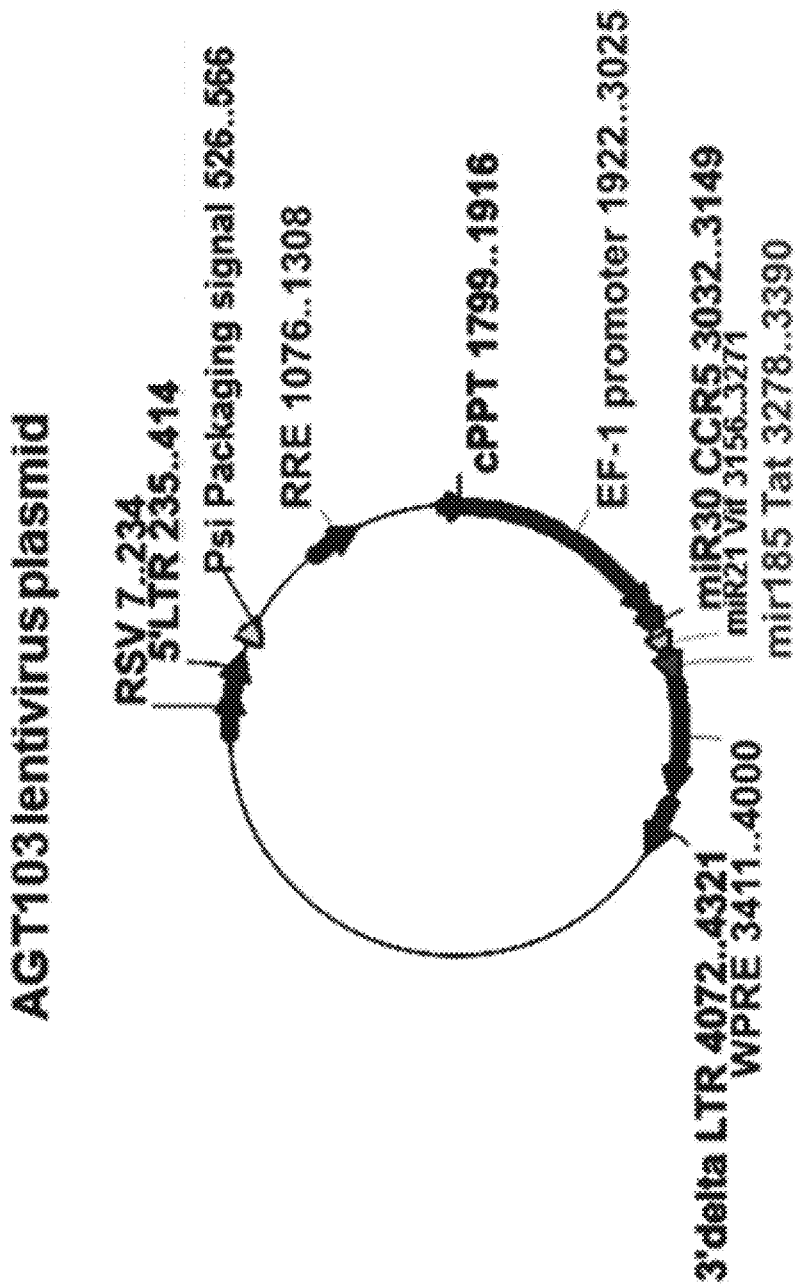

For transduction of the enriched, re-stimulated cells, the cells may be transduced with lentiviral vectors or with other known vector systems as disclosed, for example, in FIGS. 4A-4C. The cells being transduced may be contacted with about 1-1,000 viral genomes (measured by RT-PCR assay of culture fluids containing lentivirus vector) per target cell in culture (or any other suitable amount). Lentivirus transduction may be repeated 1-5 times using the same range of 1-1,000 viral genomes per target cell in culture.

Cellular Enrichment

In various embodiments, cells such as T cells are obtained from an HIV infected patient and cultured. Culturing can occur in multiwell plates in a culture medium comprising conditioned media ("CM"). The levels of supernatant $p24^{gag}$ ("p24") and viral RNA levels may be assessed by standard means. Those patients whose CM-cultured cells have peak p24 supernatant levels of less than 1 ng/ml may be suitable patients for large-scale T-cell expansion in CM with or without the use of additional anti-viral agents. Additionally, different drugs or drug combinations of interest may be added to different wells and the impact on virus levels in the sample may be assessed by standard means. Those drug combinations providing adequate viral suppression are therapeutically useful combinations. It is within the capacity of a competent technician to determine what constitutes adequate viral suppression in relation to a particular subject. In order to test the effectiveness of drugs of interest in limiting viral expansion, additional factors such as anti-CD3 antibodies may be added to the culture to stimulate viral production. Unlike culture methods for HIV infected cell samples known in the art, CM allows the culture of T cells for periods of over two months, thereby providing an effective system in which to assay long term drug effectiveness.

This approach allows the inhibition of gene expression driven by the HIV LTR promoter region in a cell population by the culture of cells in a medium comprising the CM. Culture in CM4 likely inhibits HIV LTR driven gene expression by altering one or more interactions between transcription mediating proteins and HIV gene expression regulatory elements. Transcription-mediating proteins of interest include host cell encoded proteins such as AP-1, NFkappaB, NF-AT, IRF, LEF-1 and Sp1, and the HIV encoded protein Tat. HIV gene expression regulatory elements of interest include binding sites for AP-1, NFkappaB, NF-AT, IRF, LEF-1 and Sp1, as well as the transacting responsive element ("TAR") which interacts with Tat.

In a preferred embodiment, the HIV infected cells are obtained from a subject with susceptible transcription mediating protein sequences and susceptible HIV regulatory element sequences. In a more preferred embodiment, the HIV infected cells are obtained from a subject having wild-type transcription-mediating protein sequences and wild-type HIV regulatory sequences.

Another method of enriching T Cells utilizes immunoaffinity-based selection. This method includes the simultaneous enrichment or selection of a first and second population of cells, such as a CD4+ and CD8+ cell population. Cells containing primary human T cells are contacted with a first immunoaffinity reagent that specifically binds to CD4 and a second immunoaffinity reagent that specifically binds to CD8 in an incubation composition, under conditions whereby the immunoaffinity reagents specifically bind to CD4 and CD8 molecules, respectively, on the surface of cells in the sample. Cells bound to the first and/or the second immunoaffinity reagent are recovered, thereby generating an enriched composition comprising CD4+ cells and CD8+ cells. This approach may include incubation of the composition with a concentration of the first and/or second immunoaffinity reagent that is at a sub-optimal yield concentration. Notably, in some embodiments, transduced cells are a mixed T cell population, and in other embodiments transduced cells are not a mixed T cell population.

In some embodiments, immunoaffinity-based selection is used where the solid support is a sphere, such as a bead, such as a microbead or nanobead. In other embodiments, the bead can be a magnetic bead. In another embodiment, the antibody contains one or more binding partners capable of forming a reversible bond with a binding reagent immobilized on the solid surface, such as a sphere or chromatography matrix, wherein the antibody is reversibly mobilized to the solid surface. In some embodiments, cells expressing a cell surface marker bound by the antibody on said solid surface are capable of being recovered from the matrix by disruption of the reversible binding between the binding reagent and binding partner. In some embodiments, the binding reagent is streptavidin or is a streptavidin analog or mutant.

Stable transduction of primary cells of the hematopoietic system and/or hematopoietic stem cells may be obtained by contacting, in vitro or ex vivo, the surface of the cells with both a lentiviral vector and at least one molecule which binds the cell surface. The cells may be cultured in a ventilated vessel comprising two or more layers under conditions conducive to growth and/or proliferation. In some embodiments, this approach may be used in conjunction with non-CD4+ T cell depletion and/or broad polyclonal expansion.

In another approach to T cell enrichment, PBMCs are stimulated with a peptide and enriched for cells secreting a cytokine, such as interferon-gamma. This approach generally involves stimulating a mixture of cells containing T cells with antigen, and effecting a separation of antigen-stimulated cells according to the degree to which they are labeled with the product. Antigen stimulation is achieved by exposing the cells to at least one antigen under conditions effective to elicit antigen-specific stimulation of at least one T cell. Labeling with the product is achieved by modifying the surface of the cells to contain at least one capture moiety, culturing the cells under conditions in which the product is secreted, released and specifically bound ("captured" or "entrapped") to said capture moiety; and labeling the captured product with a label moiety, where the labeled cells are not lysed as part of the labeling procedure or as part of the separation procedure. The capture moiety may incorporate detection of cell surface glycoproteins CD3 or CD4 to refine the enrichment step and increase the proportion of antigen-specific T cells in general, of CD4+ T cells in specific.

The following examples are given to illustrate aspects of the present invention. It should be understood, however, that the invention is not to be limited to the specific conditions or details described in these examples. All printed publications referenced herein are specifically incorporated by reference.

EXAMPLES

Example 1: Development of a Lentiviral Vector System

A lentiviral vector system was developed as summarized in FIG. 3 (linear form) and FIGS. 4A-C (circularized form). Referring first to the top portion of FIG. 3, a representative therapeutic vector has been designed and produced with the following elements being from left to right: hybrid 5' long terminal repeat (RSV/5' LTR) (SEQ ID NOS: 34-35), Psi sequence (RNA packaging site) (SEQ ID NO: 36), RRE (Rev-response element) (SEQ ID NO: 37), cPPT (polypurine tract) (SEQ ID NO: 38), EF-1a promoter (SEQ ID NO: 4), miR30CCR5 (SEQ ID NO: 1), miR21Vif (SEQ ID NO: 2), miR185Tat (SEQ ID NO: 3), Woodchuck Post-Transcriptional Regulatory Element (WPRE) (SEQ ID NOS: 32 or 80), and AU3 3' LTR (SEQ ID NO: 39). The therapeutic vector detailed in FIG. 3 is also referred to herein as AGT103.

Referring next to the middle portion of FIG. 3, a helper plasmid has been designed and produced with the following elements being from left to right: CAG promoter (SEQ ID NO: 41); HIV component gag (SEQ ID NO: 43); HIV component pol (SEQ ID NO: 44); HIV Int (SEQ ID NO: 45); HIV RRE (SEQ ID NO: 46); and HIV Rev (SEQ ID NO: 47).

Referring next to the lower portion of FIG. 3, an envelope plasmid has been designed and produced with the following elements being from left to right: RNA polymerase II promoter (CMV) (SEQ ID NO: 60) and vesicular stomatitis virus G glycoprotein (VSV-G) (SEQ ID NO: 62).

Lentiviral particles were produced in 293T/17 HEK cells (purchased from American Type Culture Collection, Manassas, VA) following transfection with the therapeutic vector, the envelope plasmid, and the helper plasmid (as shown in FIG. 3). The transfection of 293T/17 HEK cells, which produced functional viral particles, employed the reagent Poly(ethylenimine) (PEI) to increase the efficiency of plasmid DNA uptake. The plasmids and DNA were initially added separately in culture medium without serum in a ratio of 3:1 (mass ratio of PEI to DNA). After 2-3 days, cell medium was collected and lentiviral particles were purified by high-speed centrifugation and/or filtration followed by anion-exchange chromatography. The concentration of lentiviral particles can be expressed in terms of transducing units/ml (TU/ml). The determination of TU was accomplished by measuring HIV p24 levels in culture fluids (p24 protein is incorporated into lentiviral particles), measuring the number of viral DNA copies per cell by quantitative PCR, or by infecting cells and using light (if the vectors encode luciferase or fluorescent protein markers).

As mentioned above, a 3-vector system (i.e., a 2-vector lentiviral packaging system) was designed for the production of lentiviral particles. A schematic of the 3-vector system is shown in FIGS. 4A-4C. The schematic of FIGS. 4A-4C is a circularized version of the linear system previously described in FIG. 3. Briefly, and with reference to FIGS. 4A-4C, FIG. 4A depicts a helper plasmid, which, in this case, includes Rev. The vector appearing in FIG. 4B is the envelope plasmid. The vector appearing in FIG. 4C is the previously described therapeutic vector.

Referring more specifically to FIG. 4A, the Helper plus Rev plasmid includes a CAG enhancer (SEQ ID NO: 40); a CAG promoter (SEQ ID NO: 41); a chicken beta actin intron (SEQ ID NO: 42); a HIV gag (SEQ ID NO: 43); a HIV Pol (SEQ ID NO: 44); a HIV Int (SEQ ID NO: 45); a HIV RRE (SEQ ID NO: 46); a HIV Rev (SEQ ID NO: 47); and a rabbit beta globin poly A (SEQ ID NO: 48).

The Envelope plasmid of FIG. 4B includes a CMV promoter (SEQ ID NO: 60); a beta globin intron (SEQ ID NO: 61); a VSV-G (SEQ ID NO: 62); and a rabbit beta globin poly A (SEQ ID NO: 63).

Synthesis of a 2-Vector Lentiviral Packaging System Including Helper (Plus Rev) and Envelope Plasmids.

Materials and Methods:

Construction of the helper plasmid: The helper plasmid was constructed by initial PCR amplification of a DNA fragment from the pNL4-3 HIV plasmid (NIH Aids Reagent Program) containing Gag, Pol, and Integrase genes. Primers were designed to amplify the fragment with EcoRI and NotI restriction sites which could be used to insert at the same sites in the pCDNA3 plasmid (Invitrogen). The forward primer was (5'-TAAGCAGAATTC ATGAATTTGCCAG-GAAGAT-3') (SEQ ID NO: 81) and reverse primer was (5'-CCATACAAT-GAATGGACACTAGGCGGCCGCACGAAT-3') (SEQ ID NO: 82). The sequence for the Gag, Pol, Integrase fragment was as follows:

```
                                        (SEQ ID NO: 83)
GAATTCATGAATTTGCCAGGAAGATGGAAACCAAAAATGATAGGGGGAAT

TGGAGGTTTTATCAAAGTAAGACAGTATGATCAGATACTCATAGAAATCT

GCGGACATAAAGCTATAGGTACAGTATTAGTAGGACCTACACCTGTCAAC

ATAATTGGAAGAAATCTGTTGACTCAGATTGGCTGCACTTTAAATTTTCC

CATTAGTCCTATTGAGACTGTACCAGTAAAATTAAAGCCAGGAATGGATG

GCCCAAAAGTTAAACAATGGCCATTGACAGAAGAAAAAATAAAAGCATTA

GTAGAAATTTGTACAGAAATGGAAAAGGAAGGAAAAATTTCAAAAATTGG

GCCTGAAAATCCATACAATACTCCAGTATTTGCCATAAAGAAAAAAGACA

GTACTAAATGGAGAAAATTAGTAGATTTCAGAGAACTTAATAAGAGAACT

CAAGATTTCTGGGAAGTTCAATTAGGAATACCACATCCTGCAGGGTTAAA

ACAGAAAAAATCAGTAACAGTACTGGATGTGGGCGATGCATATTTTTCAG

TTCCCTTAGATAAAGACTTCAGGAAGTATACTGCATTTACCATACCTAGT

ATAAACAATGAGACACCAGGGATTAGATATCAGTACAATGTGCTTCCACA

GGGATGGAAAGGATCACCAGCAATATTCCAGTGTAGCATGACAAAAATCT

TAGAGCCTTTTAGAAAACAAAATCCAGACATAGTCATCTATCAATACATG

GATGATTTGTATGTAGGATCTGACTTAGAAATAGGGCAGCATAGAACAAA

AATAGAGGAACTGAGACAACATCTGTTGAGGTGGGGATTTACCACACCAG

ACAAAAAACATCAGAAAGAACCTCCATTCCTTTGGATGGGTTATGAACTC

CATCCTGATAAATGGACAGTACAGCCTATAGTGCTGCCAGAAAAGGACAG

CTGGACTGTCAATGACATACAGAAATTAGTGGGAAAATTGAATTGGGCAA

GTCAGATTTATGCAGGGATTAAAGTAAGGCAATTATGTAAACTTCTTAGG

GGAACCAAAGCACTAACAGAAGTAGTACCACTAACAGAAGAAGCAGAGCT

AGAACTGGCAGAAAACAGGGAGATTCTAAAAGAACCGGTACATGGAGTGT

ATTATGACCCATCAAAAGACTTAATAGCAGAAATACAGAAGCAGGGGCAA

GGCCAATGGACATATCAAATTTATCAAGAGCCATTTAAAAATCTGAAAAC

AGGAAAGTATGCAAGAATGAAGGGTGCCCACACTAATGATGTGAAACAAT

TAACAGAGGCAGTACAAAAAATAGCCACAGAAAGCATAGTAATATGGGGA

AAGACTCCTAAATTTAAATTACCCATACAAAAGGAAACATGGGAAGCATG

GTGGACAGAGTATTGGCAAGCCACCTGGATTCCTGAGTGGGAGTTTGTCA

ATACCCCTCCCTTAGTGAAGTTATGGTACCAGTTAGAGAAAGAACCCATA

ATAGGAGCAGAAACTTTCTATGTAGATGGGGCAGCCAATAGGGAAACTAA

ATTAGGAAAAGCAGGATATGTAACTGACAGAGGAAGACAAAAAGTTGTCC

CCCTAACGGACACAACAAATCAGAAGACTGAGTTACAAGCAATTCATCTA

GCTTTGCAGGATTCGGGATTAGAAGTAAACATAGTGACAGACTCACAATA

TGCATTGGGAATCATTCAAGCACAACCAGATAAGAGTGAATCAGAGTTAG

TCAGTCAAATAATAGAGCAGTTAATAAAAAAGGAAAAAGTCTACCTGGCA

TGGGTACCAGCACACAAAGGAATTGGAGGAAATGAACAAGTAGATAAATT

GGTCAGTGCTGGAATCAGGAAAGTACTATTTTTAGATGGAATAGATAAGG

CCCAAGAAGAACATGAGAAATATCACAGTAATTGGAGAGCAATGGCTAGT

GATTTTAACCTACCACCTGTAGTAGCAAAAGAAATAGTAGCCAGCTGTGA

TAAATGTCAGCTAAAAGGGGAAGCCATGCATGGACAAGTAGACTGTAGCC

CAGGAATATGGCAGCTAGATTGTACACATTTAGAAGGAAAAGTTATCTTG

GTAGCAGTTCATGTAGCCAGTGGATATATAGAAGCAGAAGTAATTCCAGC

AGAGACAGGGCAAGAAACAGCATACTTCCTCTTAAAATTAGCAGGAAGAT

GGCCAGTAAAAACAGTACATACAGACAATGGCAGCAATTTCACCAGTACT

ACAGTTAAGGCCGCCTGTTGGTGGGCGGGATCAAGCAGGAATTTGGCAT

TCCCTACAATCCCCAAAGTCAAGGAGTAATAGAATCTATGAATAAAGAAT

TAAAGAAAATTATAGGACAGGTAAGAGATCAGGCTGAACATCTTAAGACA

GCAGTACAAATGGCAGTATTCATCCACAATTTTAAAAGAAAAGGGGGGAT

TGGGGGGTACAGTGCAGGGGAAAGAATAGTAGACATAATAGCAACAGACA

TACAAACTAAAGAATTACAAAAACAAATTACAAAAATTCAAAATTTTCGG

GTTTATTACAGGGACAGCAGAGATCCAGTTTGGAAAGGACCAGCAAAGCT

CCTCTGGAAAGGTGAAGGGGCAGTAGTAATACAAGATAATAGTGACATAA
```

-continued
AAGTAGTGCCAAGAAGAAAAGCAAAGATCATCAGGGATTATGGAAAACAG

ATGGCAGGTGATGATTGTGTGGCAAGTAGACAGGATGAGGATTAA

Next, a DNA fragment containing the Rev, RRE, and rabbit beta globin poly A sequence with XbaI and XmaI flanking restriction sites was synthesized by MWG Operon. The DNA fragment was then inserted into the plasmid at the XbaI and XmaI restriction sites The DNA sequence was as follows:

(SEQ ID NO: 84)
TCTAGAATGGCAGGAAGAAGCGGAGACAGCGACGAAGAGCTCATCAGAA

CAGTCAGACTCATCAAGCTTCTCTATCAAAGCAACCCACCTCCCAATCC

CGAGGGGACCCGACAGGCCCGAAGGAATAGAAGAAGAAGGTGGAGAGAG

AGACAGAGACAGATCCATTCGATTAGTGAACGGATCCTTGGCACTTATC

TGGGACGATCTGCGGAGCCTGTGCCTCTTCAGCTACCACCGCTTGAGAG

ACTTACTCTTGATTGTAACGAGGATTGTGGAACTTCTGGGACGCAGGGG

GTGGGAAGCCCTCAAATATTGGTGGAATCTCCTACAATATTGGAGTCAG

GAGCTAAAGAATAGAGGAGCTTTGTTCCTTGGGTTCTTGGGAGCAGCAG

GAAGCACTATGGGCGCAGCGTCAATGACGCTGACGGTACAGGCCAGACA

ATTATTGTCTGGTATAGTGCAGCAGCAGAACAATTTGCTGAGGGCTATT

GAGGCGCAACAGCATCTGTTGCAACTCACAGTCTGGGGCATCAAGCAGC

TCCAGGCAAGAATCCTGGCTGTGGAAAGATACCTAAAGGATCAACAGCT

CCTAGATCTTTTTCCCTCTGCCAAAAATTATGGGGACATCATGAAGCCC

CTTGAGCATCTGACTTCTGGCTAATAAAGGAAATTTATTTTCATTGCAA

TAGTGTGTTGGAATTTTTTGTGTCTCTCACTCGGAAGGACATATGGGAG

GGCAAATCATTTAAAACATCAGAATGAGTATTTGGTTTAGAGTTTGGCA

ACATATGCCATATGCTGGCTGCCATGAACAAAGGTGGCTATAAAGAGGT

CATCAGTATATGAAACAGCCCCCTGCTGTCCATTCCTTATTCCATAGAA

AAGCCTTGACTTGAGGTTAGATTTTTTTTATATTTTGTTTTGTGTTATT

TTTTTCTTTAACATCCCTAAAATTTTCCTTACATGTTTTACTAGCCAGA

TTTTTCCTCCTCTCCTGACTACTCCCAGTCATAGCTGTCCCTCTTCTCT

TATGAAGATCCCTCGACCTGCAGCCCAAGCTTGGCGTAATCATGGTCAT

AGCTGTTTCCTGTGTGAAATTGTTATCCGCTCACAATTCCACACAACAT

ACGAGCCGGAAGCATAAAGTGTAAAGCCTGGGGTGCCTAATGAGTGAGC

TAACTCACATTAATTGCGTTGCGCTCACTGCCCGCTTTCCAGTCGGGAA

ACCTGTCGTGCCAGCGGATCCGCATCTCAATTAGTCAGCAACCATAGTC

CCGCCCCTAACTCCGCCCATCCCGCCCCTAACTCCGCCCAGTTCCGCCC

ATTCTCCGCCCCATGGCTGACTAATTTTTTTTATTTATGCAGAGGCCGA

GGCCGCCTCGGCCTCTGAGCTATTCCAGAAGTAGTGAGGAGGCTTTTTT

GGAGGCCTAGGCTTTTGCAAAAAGCTAACTTGTTTATTGCAGCTTATAA

TGGTTACAAATAAAGCAATAGCATCACAAATTTCACAAATAAAGCATTT

TTTTCACTGCATTCTAGTTGTGGTTTGTCCAAACTCATCAATGTATCTT

ATCAGCGGCCGCCCCGGG

Finally, the CMV promoter of pCDNA3.1 was replaced with the CAG enhancer/promoter plus a chicken beta actin intron sequence. A DNA fragment containing the CAG enhancer/promoter/intron sequence with MluI and EcoRI flanking restriction sites was synthesized by MWG Operon. The DNA fragment was then inserted into the plasmid at the MluI and EcoRI restriction sites. The DNA sequence was as follows:

(SEQ ID NO: 85)
ACGCGTTAGTTATTAATAGTAATCAATTACGGGGTCATTAGTTCATAGC

CCATATATGGAGTTCCGCGTTACATAACTTACGGTAAATGGCCCGCCTG

GCTGACCGCCCAACGACCCCCGCCCATTGACGTCAATAATGACGTATGT

TCCCATAGTAACGCCAATAGGGACTTTCCATTGACGTCAATGGGTGGAC

TATTTACGGTAAACTGCCCACTTGGCAGTACATCAAGTGTATCATATGC

CAAGTACGCCCCCTATTGACGTCAATGACGGTAAATGGCCCGCCTGGCA

TTATGCCCAGTACATGACCTTATGGGACTTTCCTACTTGGCAGTACATC

TACGTATTAGTCATCGCTATTACCATGGGTCGAGGTGAGCCCCACGTTC

TGCTTCACTCTCCCCATCTCCCCCCCCTCCCCACCCCCAATTTTGTATT

TATTTATTTTTTAATTATTTTGTGCAGCGATGGGGGCGGGGGGGGGGG

GGCGCGCGCCAGGCGGGGCGGGGCGGGCGAGGGGCGGGGCGGGGCGAG

GCGGAGAGGTGCGGCGGCAGCCAATCAGAGCGGCGCGCTCCGAAAGTTT

CCTTTTATGGCGAGGCGGCGGCGGCGGCGGCCCTATAAAAAGCGAAGCG

CGCGGCGGGCGGGAGTCGCTGCGTTGCCTTCGCCCCGTGCCCCGCTCCG

CGCCGCCTCGCGCCGCCCGCCCCGGCTCTGACTGACCGCGTTACTCCCA

CAGGTGAGCGGGCGGGACGGCCCTTCTCCTCCGGGCTGTAATTAGCGCT

TGGTTTAATGACGGCTCGTTTCTTTTCTGTGGCTGCGTGAAAGCCTTAA

AGGGCTCCGGGAGGGCCCTTTGTGCGGGGGGAGCGGCTCGGGGGGTGC

GTGCGTGTGTGTGCGTGGGGAGCGCCGCGTGCGGCCCGCGCTGCCCG

GCGGCTGTGAGCGCTGCGGGCGCGGCGCGGGGCTTTGTGCGCTCCGCGT

GTGCGCGAGGGGAGCGCGCCGGGGGCGGTGCCCCGCGGTGCGGGGGGG

CTGCGAGGGGAACAAAGGCTGCGTGCGGGGTGTGTGCGTGGGGGGTGA

GCAGGGGGTGTGGGCGCGGCGGTCGGGCTGTAACCCCCCCCTGCACCCC

CCTCCCCGAGTTGCTGAGCACGGCCCGGCTTCGGGTGCGGGGCTCCGTG

CGGGGCGTGGCGCGGGGCTCGCCGTGCCGGGCGGGGGTGGCGGCAGGT

GGGGGTGCCGGGCGGGCGGGCCGCCTCGGGCCGGGAGGGCTCGGGG

GAGGGGCGCGGCGGCCCCGGAGCGCCGGCGGCTGTCGAGGCGCGGCGAG

CCGCAGCCATTGCCTTTTATGGTAATCGTGCGAGAGGGCGCAGGGACTT

CCTTTGTCCCAAATCTGGCGGAGCCGAAATCTGGGAGGCGCCGCCGCAC

CCCCTCTAGCGGGCGCGGGCGAAGCGGTGCGGCGCCGGCAGGAAGGAAA

TGGGCGGGAGGGCCTTCGTGCGTCGCCGCGCCGCCGTCCCCTTCTCCA

TCTCCAGCCTCGGGGCTGCCGCAGGGGGACGGCTGCCTTCGGGGGGGAC

GGGGCAGGGCGGGGTTCGGCTTCTGGCGTGTGACCGGCGGGAATTC

Construction of the USE-G Envelope Plasmid:
The vesicular stomatitis Indiana virus glycoprotein (VSV-G) sequence was synthesized by MWG Operon with flanking EcoRI restriction sites. The DNA fragment was then inserted into the pCDNA3.1 plasmid (Invitrogen) at the EcoRI restriction site and the correct orientation was determined by sequencing using a CMV specific primer. The DNA sequence was as follows:

(SEQ ID NO: 86)
GAATTCATGAAGTGCCTTTTGTACTTAGCCTTTTTATTCATTGGGGTGA

ATTGCAAGTTCACCATAGTTTTTCCACACAACCAAAAAGGAAACTGGAA

AAATGTTCCTTCTAATTACCATTATTGCCCGTCAAGCTCAGATTTAAAT

TGGCATAATGACTTAATAGGCACAGCCTTACAAGTCAAAATGCCCAAGA

GTCACAAGGCTATTCAAGCAGACGGTTGGATGTGTCATGCTTCCAAATG

GGTCACTACTTGTGATTTCCGCTGGTATGGACCGAAGTATATAACACAT

TCCATCCGATCCTTCACTCCATCTGTAGAACAATGCAAGGAAAGCATTG

AACAAACGAAACAAGGAACTTGGCTGAATCCAGGCTTCCCTCCTCAAAG

TTGTGGATATGCAACTGTGACGGATGCCGAAGCAGTGATTGTCCAGGTG

ACTCCTCACCATGTGCTGGTTGATGAATACACAGGAGAATGGGTTGATT

CACAGTTCATCAACGGAAAATGCAGCAATTACATATGCCCCACTGTCCA

TAACTCTACAACCTGGCATTCTGACTATAAGGTCAAAGGGCTATGTGAT

TCTAACCTCATTTCCATGGACATCACCTTCTTCTCAGAGGACGGAGAGC

TATCATCCCTGGGAAAGGAGGGCACAGGGTTCAGAAGTAACTACTTTGC

TTATGAAACTGGAGGCAAGGCCTGCAAAATGCAATACTGCAAGCATTGG

GGAGTCAGACTCCCATCAGGTGTCTGGTTCGAGATGGCTGATAAGGATC

TCTTTGCTGCAGCCAGATTCCCTGAATGCCCAGAAGGGTCAAGTATCTC

TGCTCCATCTCAGACCTCAGTGGATGTAAGTCTAATTCAGGACGTTGAG

AGGATCTTGGATTATTCCCTCTGCCAAGAAACCTGGAGCAAAATCAGAG

CGGGTCTTCCAATCTCTCCAGTGGATCTCAGCTATCTTGCTCCTAAAAA

CCCAGGAACCGGTCCTGCTTTCACCATAATCAATGGTACCCTAAAATAC

TTTGAGACCAGATACATCAGAGTCGATATTGCTGCTCCAATCCTCTCAA

GAATGGTCGGAATGATCAGTGGAACTACCACAGAAAGGGAACTGTGGGA

TGACTGGGCACCATATGAAGACGTGGAAATTGGACCCAATGGAGTTCTG

AGGACCAGTTCAGGATATAAGTTTCCTTTATACATGATTGGACATGGTA

TGTTGGACTCCGATCTTCATCTTAGCTCAAAGGCTCAGGTGTTCGAACA

TCCTCACATTCAAGACGCTGCTTCGCAACTTCCTGATGATGAGAGTTTA

TTTTTTGGTGATACTGGGCTATCCAAAAATCCAATCGAGCTTGTAGAAG

GTTGGTTCAGTAGTTGGAAAAGCTCTATTGCCTCTTTTTTCTTTATCAT

AGGGTTAATCATTGGACTATTCTTGGTTCTCCGAGTTGGTATCCATCTT

TGCATTAAATTAAAGCACACCAAGAAAAGACAGATTTATACAGACATAG

AGATGAGAATTC

Figure 5A:
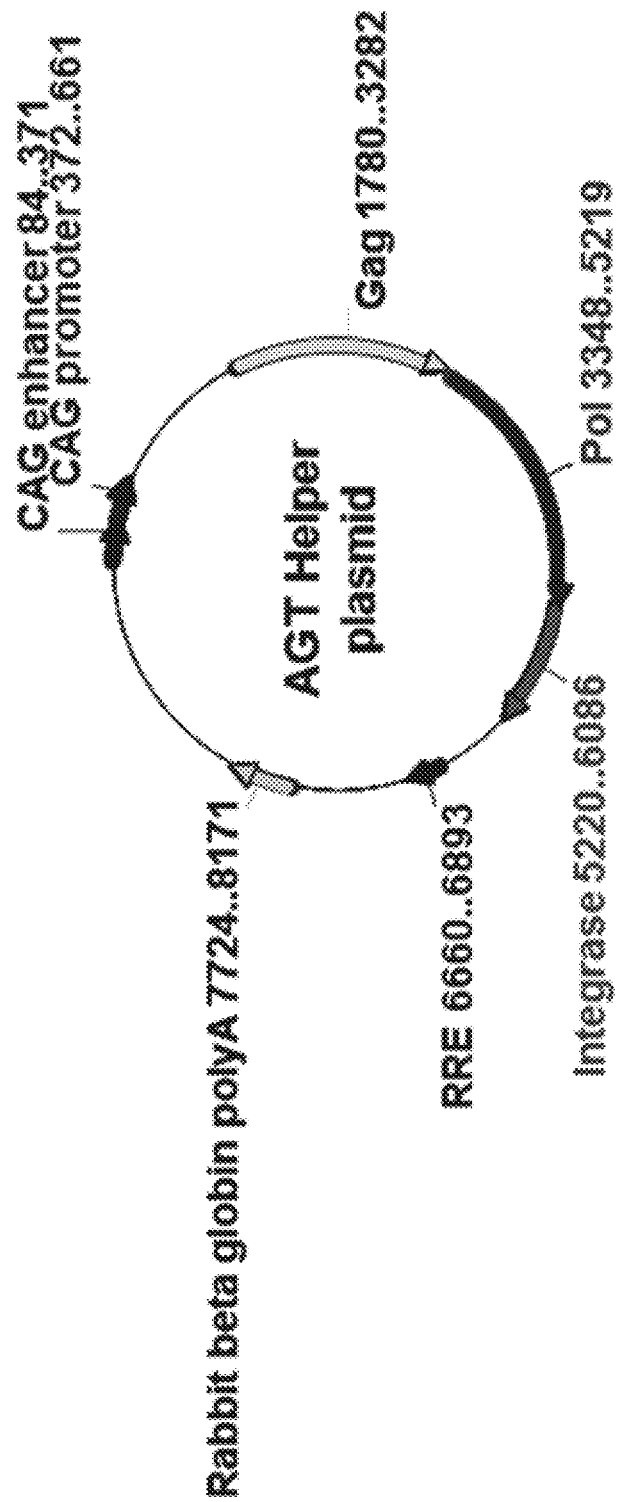
FIGS. 5A-5D depict an exemplary 4-vector lentiviral vector system in a circularized form.
Figure 5B:
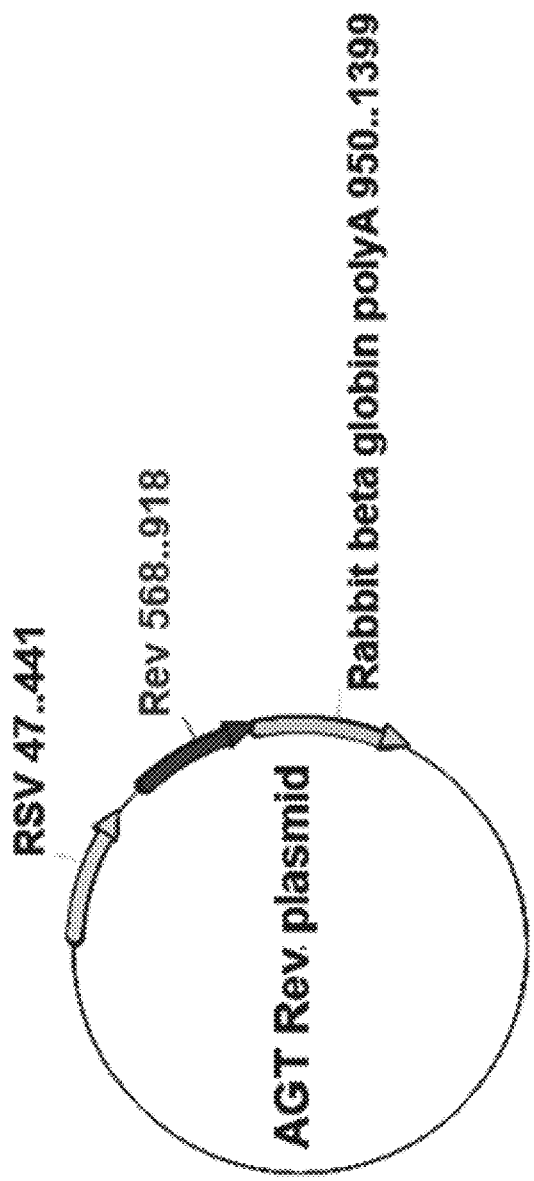
Figure 5C:
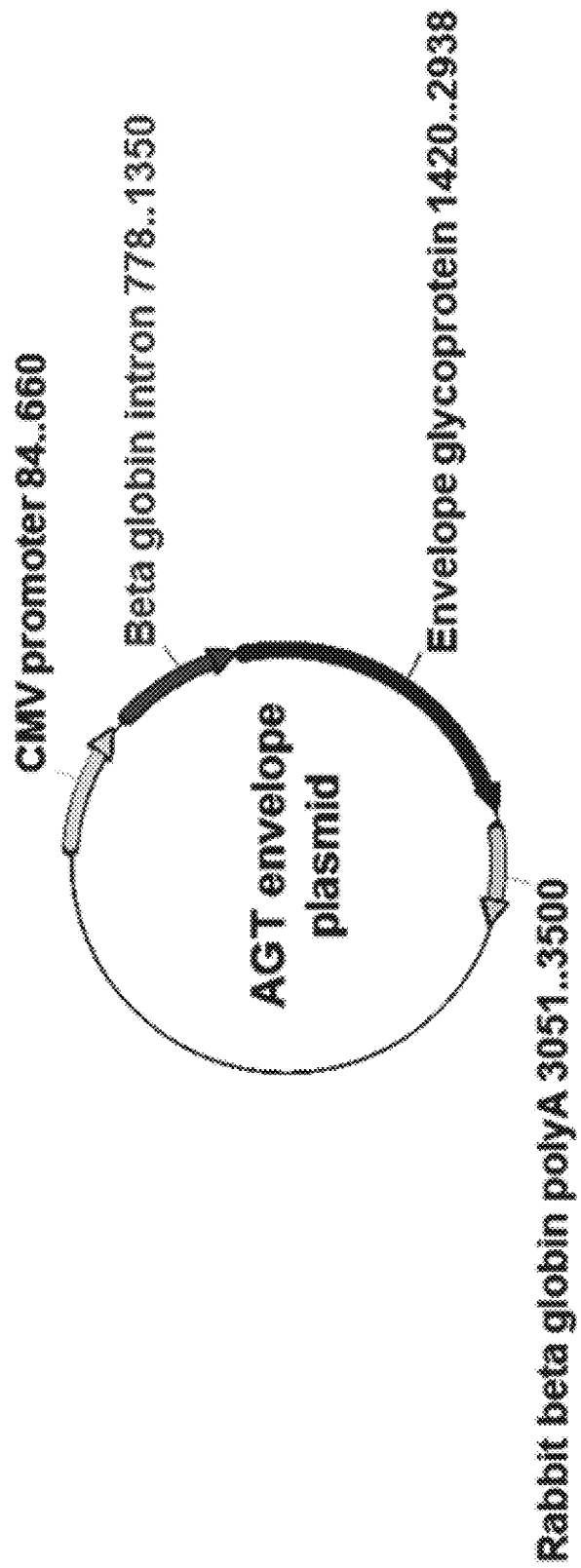
Figure 5D:
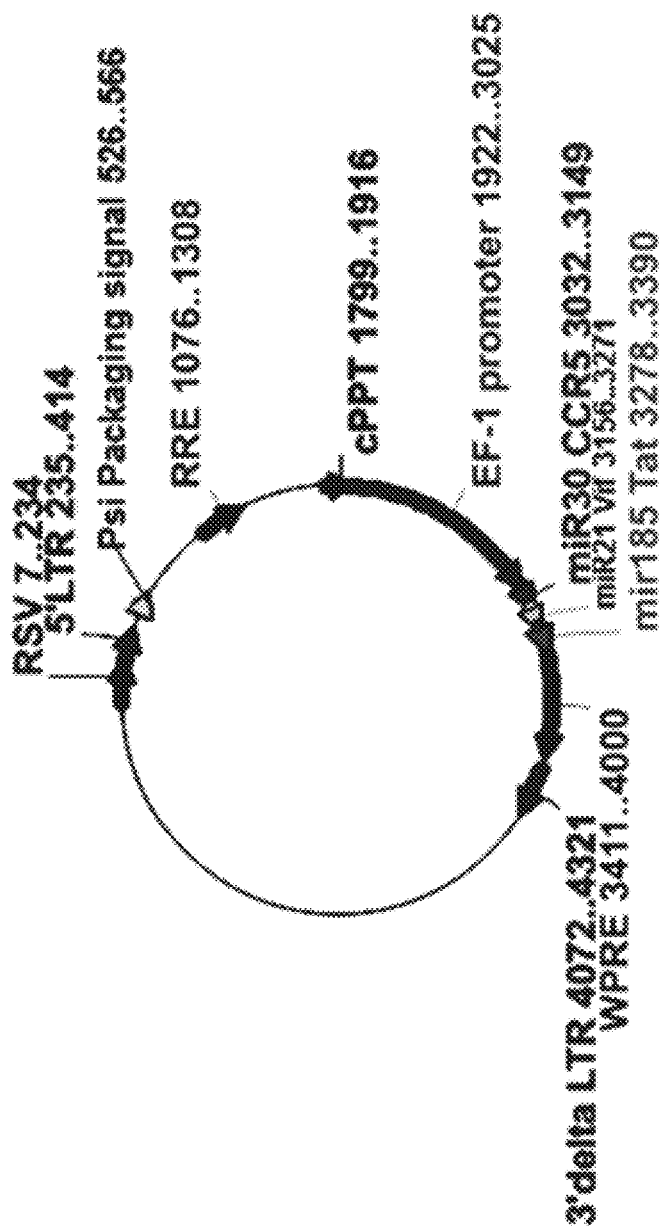

A 4-vector system (i.e., a 3-vector lentiviral packaging system) has also been designed and produced using the methods and materials described herein. A schematic of the 4-vector system is shown in FIGS. 5A-5D. Briefly, and with reference to FIG. 5, the vector of FIG. 5A is a helper plasmid, which, in this case, does not include Rev. The vector depicted in FIG. 5B is a separate Rev plasmid. The vector depicted in FIG. 5C is the envelope plasmid. The vector depicted in FIG. 5D is the previously described therapeutic vector.

Referring, in part, to FIG. 5A, the Helper plasmid includes a CAG enhancer (SEQ ID NO: 49); a CAG promoter (SEQ ID NO: 50); a chicken beta actin intron (SEQ ID NO: 51); a HIV gag (SEQ ID NO: 52); a HIV Pol (SEQ ID NO: 53); a HIV Int (SEQ ID NO: 54); a HIV RRE (SEQ ID NO: 55); and a rabbit beta globin poly A (SEQ ID NO: 56).

The Rev plasmid depicted in FIG. 5B includes a RSV promoter (SEQ ID NO: 57); a HIV Rev (SEQ ID NO: 58); and a rabbit beta globin poly A (SEQ ID NO: 59).

The Envelope plasmid depicted in FIG. 5C includes a CMV promoter (SEQ ID NO: 60); a beta globin intron (SEQ ID NO: 61); a VSV-G (SEQ ID NO: 62); and a rabbit beta globin poly A (SEQ ID NO: 63).

Synthesis of a 3-Vector Lentiviral Packaging System Including Helper, Rev, and Envelope Plasmids.

Materials and Methods:

Construction of the Helper Plasmid without Rev:

The Helper plasmid without Rev was constructed by inserting a DNA fragment containing the RRE and rabbit beta globin poly A sequence. This sequence was synthesized by MWG Operon with flanking XbaI and XmaI restriction sites. The RRE/rabbit poly A beta globin sequence was then inserted into the Helper plasmid at the XbaI and XmaI restriction sites. The DNA sequence is as follows:

(SEQ ID NO: 87)
TCTAGAAGGAGCTTTGTTCCTTGGGTTCTTGGGAGCAGCAGGAAGCACT

ATGGGCGCAGCGTCAATGACGCTGACGGTACAGGCCAGACAATTATTGT

CTGGTATAGTGCAGCAGCAGAACAATTTGCTGAGGGCTATTGAGGCGCA

ACAGCATCTGTTGCAACTCACAGTCTGGGGCATCAAGCAGCTCCAGGCA

AGAATCCTGGCTGTGGAAAGATACCTAAAGGATCAACAGCTCCTAGATC

TTTTTCCCTCTGCCAAAAATTATGGGGACATCATGAAGCCCCTTGAGCA

TCTGACTTCTGGCTAATAAAGGAAATTTATTTTCATTGCAATAGTGTGT

TGGAATTTTTTGTGTCTCTCACTCGGAAGGACATATGGGAGGGCAAATC

ATTTAAAACATCAGAATGAGTATTTGGTTTAGAGTTTGGCAACATATGC

CATATGCTGGCTGCCATGAACAAAGGTGGCTATAAAGAGGTCATCAGTA

TATGAAACAGCCCCCTGCTGTCCATTCCTTATTCCATAGAAAAGCCTTG

ACTTGAGGTTAGATTTTTTTATATTTTGTTTTGTGTTATTTTTTCTT

TAACATCCCTAAAATTTTCCTTACATGTTTTACTAGCCAGATTTTTCCT

CCTCTCCTGACTACTCCCAGTCATAGCTGTCCCTCTTCTCTTATGAAGA

TCCCTCGACCTGCAGCCCAAGCTTGGCGTAATCATGGTCATAGCTGTTT

CCTGTGTGAAATTGTTATCCGCTCACAATTCCACACAACATACGAGCCG

GAAGCATAAAGTGTAAAGCCTGGGGTGCCTAATGAGTGAGCTAACTCAC

ATTAATTGCGTTGCGCTCACTGCCCGCTTTCCAGTCGGGAAACCTGTCG

TGCCAGCGGATCCGCATCTCAATTAGTCAGCAACCATAGTCCCGCCCCT

AACTCCGCCCATCCCGCCCCTAACTCCGCCCAGTTCCGCCCATTCTCCG

CCCCATGGCTGACTAATTTTTTTTATTTATGCAGAGGCCGAGGCCGCCT

CGGCCTCTGAGCTATTCCAGAAGTAGTGAGGAGGCTTTTTTGGAGGCCT

```
                                    -continued
AGGCTTTTGCAAAAAGCTAACTTGTTTATTGCAGCTTATAATGGTTACA

AATAAAGCAATAGCATCACAAATTTCACAAATAAAGCATTTTTTTCACT

GCATTCTAGTTGTGGTTTGTCCAAACTCATCAATGTATCTTATCACCCG

GG
```

Construction of the Rev Plasmid:

The RSV promoter and HIV Rev sequence was synthesized as a single DNA fragment by MWG Operon with flanking MfeI and XbaI restriction sites. The DNA fragment was then inserted into the pCDNA3.1 plasmid (Invitrogen) at the MfeI and XbaI restriction sites in which the CMV promoter is replaced with the RSV promoter. The DNA sequence was as follows:

```
                                              (SEQ ID NO: 88)
CAATTGCGATGTACGGGCCAGATATACGCGTATCTGAGGGGACTAGGGT

GTGTTTAGGCGAAAAGCGGGGCTTCGGTTGTACGCGGTTAGGAGTCCCC

TCAGGATATAGTAGTTTCGCTTTTGCATAGGGAGGGGGAAATGTAGTCT

TATGCAATACACTTGTAGTCTTGCAACATGGTAACGATGAGTTAGCAAC

ATGCCTTACAAGGAGAGAAAAAGCACCGTGCATGCCGATTGGTGGAAGT

AAGGTGGTACGATCGTGCCTTATTAGGAAGGCAACAGACAGGTCTGACA

TGGATTGGACGAACCACTGAATTCCGCATTGCAGAGATAATTGTATTTA

AGTGCCTAGCTCGATACAATAAACGCCATTTGACCATTCACCACATTGG

TGTGCACCTCCAAGCTCGAGCTCGTTTAGTGAACCGTCAGATCGCCTGG

AGACGCCATCCACGCTGTTTTGACCTCCATAGAAGACACCGGGACCGAT

CCAGCCTCCCCTCGAAGCTAGCGATTAGGCATCTCCTATGGCAGGAAGA

AGCGGAGACAGCGACGAAGAACTCCTCAAGGCAGTCAGACTCATCAAGT

TTCTCTATCAAAGCAACCCACCTCCCAATCCCGAGGGGACCCGACAGGC

CCGAAGGAATAGAAGAAGAAGGTGGAGAGAGAGACAGAGACAGATCCAT

TCGATTAGTGAACGGATCCTTAGCACTTATCTGGGACGATCTGCGGAGC

CTGTGCCTCTTCAGCTACCACCGCTTGAGAGACTTACTCTTGATTGTAA

CGAGGATTGTGGAACTTCTGGGACGCAGGGGGTGGGAAGCCCTCAAATA

TTGGTGGAATCTCCTACAATATTGGAGTCAGGAGCTAAAGAATAGTCTA

GA
```

The plasmids for the 2-vector and 3-vector packaging systems could be modified with similar elements and the intron sequences could potentially be removed without loss of vector function. For example, the following elements could replace similar elements in the 2-vector and 3-vector packaging system:

Promoters: Elongation Factor-1 (EF-1) (SEQ ID NO: 64), phosphoglycerate kinase (PGK) (SEQ ID NO: 65), and ubiquitin C (UbC) (SEQ ID NO: 66) can replace the CMV (SEQ ID NO: 60) or CAG promoter (SEQ ID NO: 100). These sequences can also be further varied by addition, substitution, deletion or mutation.

Poly A sequences: SV40 poly A (SEQ ID NO: 67) and bGH poly A (SEQ ID NO: 68) can replace the rabbit beta globin poly A (SEQ ID NO: 48). These sequences can also be further varied by addition, substitution, deletion or mutation.

HIV Gag, Pol, and Integrase sequences: The HIV sequences in the Helper plasmid can be constructed from different HIV strains or clades. For example, HIV Gag (SEQ ID NO: 69); HIV Pol (SEQ ID NO: 70); and HIV Int (SEQ ID NO: 71) from the Bal strain can be interchanged with the gag, pol, and int sequences contained in the helper/helper plus Rev plasmids as outlined herein. These sequences can also be further varied by addition, substitution, deletion or mutation.

Envelope: The VSV-G glycoprotein can be substituted with membrane glycoproteins from feline endogenous virus (RD114) (SEQ ID NO: 72), gibbon ape leukemia virus (GALV) (SEQ ID NO: 73), Rabies (FUG) (SEQ ID NO: 74), lymphocytic choriomeningitis virus (LCMV) (SEQ ID NO: 75), influenza A fowl plague virus (FPV) (SEQ ID NO: 76), Ross River alphavirus (RRV) (SEQ ID NO: 77), murine leukemia virus 10A1 (MLV) (SEQ ID NO: 78), or Ebola virus (EboV) (SEQ ID NO: 79). Sequences for these envelopes are identified in the sequence portion herein. Further, these sequences can also be further varied by addition, substitution, deletion or mutation.

In summary, the 3-vector versus 4-vector systems can be compared and contrasted, in part, as follows. The 3-vector lentiviral vector system contains: 1. Helper plasmid: HIV Gag, Pol, Integrase, and Rev/Tat; 2. Envelope plasmid: VSV-G/FUG envelope; and 3. Therapeutic vector: RSV 5'LTR, Psi Packaging Signal, Gag fragment, RRE, Env fragment, cPPT, WPRE, and 3'delta LTR. The 4-vector lentiviral vector system contains: 1. Helper plasmid: HIV Gag, Pol, and Integrase; 2. Rev plasmid: Rev; 3. Envelope plasmid: VSV-G/FUG envelope; and 4. Therapeutic vector: RSV 5'LTR, Psi Packaging Signal, Gag fragment, RRE, Env fragment, cPPT, WPRE, and 3'delta LTR. Sequences corresponding with the above elements are identified in the sequence listings portion herein.

Example 2: Development of an Anti-HIV Lentivirus Vector

The purpose of this example was to develop an anti-HIV lentivirus vector.

Inhibitory RNA Designs. The sequence of Homo sapiens chemokine C-C motif receptor 5 (CCR5) (GC03P046377) mRNA was used to search for potential siRNA or shRNA candidates to knockdown CCR5 levels in human cells. Potential RNA interference sequences were chosen from candidates selected by siRNA or shRNA design programs such as from the Broad Institute or the BLOCK-IT RNAi Designer from Thermo Scientific. Individual selected shRNA sequences were inserted into lentiviral vectors immediately 3' to a RNA polymerase III promoter such as H1, U6, or 7SK to regulate shRNA expression. These lentivirus-shRNA constructs were used to transduce cells and measure the change in specific mRNA levels. The shRNA most potent for reducing mRNA levels were embedded individually within a microRNA backbone to allow for expression by either the CMV or EF-1alpha RNA polymerase II promoters. The microRNA backbone was selected from mirbase.org. RNA sequences were also synthesized as synthetic siRNA oligonucleotides and introduced directly into cells without using a lentiviral vector.

The genomic sequence of Bal strain of human immunodeficiency virus type 1 (HIV-1 85US BaL, accession number AY713409) was used to search for potential siRNA or shRNA candidates to knockdown HIV replication levels in human cells. Based on sequence homology and experience, the search focused on regions of the Tat and Vif genes of HIV although an individual of skill in the art will understand that use of these regions is non-limiting and other potential targets might be selected. Importantly, highly conserved regions of gag or pol genes could not be targeted by shRNA because these same sequences were present in the packaging system complementation plasmids needed for vector manufacturing. As with the CCR5 (NM 000579.3, NM 001100168.1-specific) RNAs, potential HIV-specific RNA interference sequences were chosen from candidates selected by siRNA or shRNA design programs such as from the Gene-E Software Suite hosted by the Broad Institute (broadinstitute.org/mai/public) or the BLOCK-IT RNAi Designer from Thermo Scientific (rnadesigner.thermofisher.com/rnaiexpress/setOption.do?designOption=shrna&pid=67126273607 06061801). Individual selected shRNA sequences were inserted into lentiviral vectors immediately 3' to a RNA polymerase III promoter such as H1, U6, or 7SK to regulate shRNA expression. These lentivirus-shRNA constructs were used to transduce cells and measure the change in specific mRNA levels. The shRNA most potent for reducing mRNA levels were embedded individually within a microRNA backbone to allow for expression by either the CMV or EF-1alpha RNA polymerase II promoters Vector Constructions. For CCR5, Tat or Vif shRNA, oligonucleotide sequences containing BamHI and EcoRI restriction sites were synthesized by Eurofins MWG Operon, LLC. Overlapping sense and antisense oligonucleotide sequences were mixed and annealed during cooling from 70 degrees Celsius to room temperature. The lentiviral vector was digested with the restriction enzymes BamHI and EcoRI for one hour at 37 degrees Celsius. The digested lentiviral vector was purified by agarose gel electrophoresis and extracted from the gel using a DNA gel extraction kit from Invitrogen. The DNA concentrations were determined and vector to oligo (3:1 ratio) were mixed, allowed to anneal, and ligated. The ligation reaction was performed with T4 DNA ligase for 30 minutes at room temperature. 2.5 microliters of the ligation mix were added to 25 microliters of STBL3 competent bacterial cells. Transformation was achieved after heat-shock at 42 degrees Celsius. Bacterial cells were spread on agar plates containing ampicillin and drug-resistant colonies (indicating the presence of ampicillin-resistance plasmids) were recovered, purified and expanded in LB broth. To check for insertion of the oligo sequences, plasmid DNA were extracted from harvested bacteria cultures with the Invitrogen DNA mini prep kit. Insertion of the shRNA sequence in the lentiviral vector was verified by DNA sequencing using a specific primer for the promoter used to regulate shRNA expression. Exemplary vector sequences that were determined to restrict HIV replication can be found in FIG. 6. For example, the shRNA sequences with the highest activity against CCR5, Tat or Vif gene expression were then assembled into a microRNA (miR) cluster under control of the EF-1alpha promoter. The promoter and miR sequences are depicted in FIG. 6.

Further, and using standard molecular biology techniques (e.g., Sambrook; Molecular Cloning: A Laboratory Manual, 4$^{th}$ Ed.) as well as the techniques described herein, a series of lentiviral vectors have been developed as depicted in FIG. 7 herein.

Vector 1 was developed and contains, from left to right: a long terminal repeat (LTR) portion (SEQ ID NO: 35); a H1 element (SEQ ID NO: 101); a shCCR5 (SEQ ID NOS: 16, 18, 20, 22, or 24-Y); a posttranscriptional regulatory element of woodchuck hepatitis virus (WPRE) (SEQ ID NOS: 32, 80); and a long terminal repeat portion (SEQ ID NO: 102).

Vector 2 was developed and contains, from left to right: a long terminal repeat (LTR) portion (SEQ ID NO: 35); a H1 element (SEQ ID NO: 101); a shRev/Tat (SEQ ID NO: 10); a H1 element (SEQ ID NO: 101); a shCCR5 (SEQ ID NOS: 16, 18, 20, 22, or 24); a posttranscriptional regulatory element of woodchuck hepatitis virus (WPRE) (SEQ ID NOS: 32, 80); and a long terminal repeat portion (SEQ ID NO: 102).

Vector 3 was developed and contains, from left to right: a long terminal repeat (LTR) portion (SEQ ID NO: 35); a H1 element (SEQ ID NO: 101); a shGag (SEQ ID NO: 12); a H1 element (SEQ ID NO: 101); a shCCR5 (SEQ ID NOS: 16, 18, 20, 22, or 24); a posttranscriptional regulatory element of woodchuck hepatitis virus (WPRE) (SEQ ID NOS: 32, 80); and a long terminal repeat portion (SEQ ID NO: 102).

Vector 4 was developed and contains, from left to right: a long terminal repeat (LTR) portion (SEQ ID NO: 35); a 7SK element (SEQ ID NO: 103); a shRev/Tat (SEQ ID NO: 10); a H1 element (SEQ ID NO: 101); a shCCR5 (SEQ ID NOS: 16, 18, 20, 22, or 24); a posttranscriptional regulatory element of woodchuck hepatitis virus (WPRE) (SEQ ID NOS: 32, 80); and a long terminal repeat portion (SEQ ID NO: 102).

Vector 5 was developed and contains, from left to right: a long terminal repeat (LTR) portion (SEQ ID NO: 35); a EF1 element (SEQ ID NO: 4); miR30CCR5 (SEQ ID NO: 1); MiR21 Vif (SEQ ID NO: 2); miR185Tat (SEQ ID NO: 3); a posttranscriptional regulatory element of woodchuck hepatitis virus (WPRE) (SEQ ID NOS: 32, 80); and a long terminal repeat portion (SEQ ID NO: 102).

Vector 6 was developed and contains, from left to right: a long terminal repeat (LTR) portion (SEQ ID NO: 35); a EF1 element (SEQ ID NO: 4); miR30CCR5 (SEQ ID NO: 1); MiR21 Vif (SEQ ID NO: 2); miR155Tat (SEQ ID NO: 104); a posttranscriptional regulatory element of woodchuck hepatitis virus (WPRE) (SEQ ID NOS: 32, 80); and a long terminal repeat portion (SEQ ID NO: 102).

Vector 7 was developed and contains, from left to right: a long terminal repeat (LTR) portion (SEQ ID NO: 35); a EF1 element (SEQ ID NO: 4); miR30CCR5 (SEQ ID NO: 1); MiR21 Vif (SEQ ID NO: 2); miR185Tat (SEQ ID NO: 3); a posttranscriptional regulatory element of woodchuck hepatitis virus (WPRE) (SEQ ID NOS: 32, 80); and a long terminal repeat portion (SEQ ID NO: 102).

Vector 8 was developed and contains, from left to right: a long terminal repeat (LTR) portion (SEQ ID NO: 35); a EF1 element (SEQ ID NO: 4); miR30CCR5 (SEQ ID NO: 1); MiR21 Vif (SEQ ID NO: 2); miR185Tat (SEQ ID NO: 3); and a long terminal repeat portion (SEQ ID NO: 102).

Vector 9 was developed and contains, from left to right: a long terminal repeat (LTR) portion (SEQ ID NO: 35); a CD4 element (SEQ ID NO: 30); miR30CCR5 (SEQ ID NO: 1); miR21 Vif (SEQ ID NO: 2); miR185Tat (SEQ ID NO: 3); a posttranscriptional regulatory element of woodchuck hepatitis virus (WPRE) (SEQ ID NOS: 32, 80); and a long terminal repeat portion (SEQ ID NO: 102).

Development of Vectors

It should be noted that not all vectors developed for these experiments necessarily worked as might be predicted. More specifically, a lentivirus vector against HIV might include three main components: 1) inhibitory RNA to reduce the level of HIV binding proteins (receptors) on the target cell surface to block initial virus attachment and penetration; 2) overexpression of the HIV TAR sequence that will sequester viral Tat protein and decrease its ability to transactivate viral gene expression; and 3) inhibitory RNA that attack important and conserved sequences within the HIV genome.

With respect to the first point above, a key cell surface HIV binding protein is the chemokine receptor CCR5. HIV particles attach to susceptible T cells by binding to the CD4 and CCR5 cell surface proteins. Because CD4 is an essential glycoprotein on the cell surface that is important for the immunological function of T cells, this was not chosen as a target to manipulate its expression levels. However, people born homozygous for null mutations in the CCR5 gene and completely lacking receptor expression, live normal lives save for enhanced susceptibility to a few infectious diseases and the possibility of developing rare autoimmunity. Thus, modulating CCR5 was determined to be a relatively safe approach and was a primary target in the development of anti-HIV lentivirus vectors.

With respect to the second point above, the viral TAR sequence is a highly structured region of HIV genomic RNA that binds tightly to viral Tat protein. The Tat: TAR complex is important for efficient generation of viral RNA. Overexpression of the TAR region was envisioned as a decoy molecule that would sequester Tat protein and decrease the levels of viral RNA. However, TAR proved toxic to most mammalian cells including cells used for manufacturing lentivirus particles. Further, TAR was inefficient for inhibiting viral gene expression in other laboratories and has been discarded as a viable component in HIV gene therapy.

In various embodiments, viral gene sequences have been identified that meet 3 criteria: i) Sequences that are reasonably conserved across a range of HIV isolates representative of the epidemic in a geographic region of interest; ii) reduction in RNA levels due to the activity of an inhibitory RNA in a viral vector will reduce the corresponding protein levels by an amount sufficient to meaningfully reduce HIV replication; and iii) the viral gene sequence(s) targeted by inhibitory RNA are not present in the genes required for packaging and assembling viral vector particles during manufacturing. In various embodiments, a sequence at the junction of HIV Tat and Rev genes and a second sequence within the HIV Vif gene have been targeted by inhibitory RNA. The Tat/Rev targeting has an additional benefit of reducing HIV envelope glycoprotein expression because this region overlaps with the envelope gene in the HIV genome.

Various methods for vector development and testing relies first on identifying suitable targets (as described herein) followed by constructing plasmid DNAs expressing individual or multiple inhibitory RNA species for testing in cell models, and finally constructing lentivirus vectors containing inhibitory RNA with proven anti-HIV function. The lentivirus vectors are tested for toxicity, yield during in vitro production, and effectiveness against HIV in terms of reducing CCR5 expression levels or lowering viral gene products to inhibit virus replication.

Table 2 below demonstrates progression through multiple versions of inhibitory constructs until arriving at a clinical candidate. Initially, shRNA (short homology RNA) molecules were designed and expressed from plasmid DNA constructs.

Plasmids 1-4, as detailed in Table 2 below, tested shRNA sequences against Gag, Pol and RT genes of HIV. While each shRNA was active for suppressing viral protein expression in a cell model, there were two important problems that prevented further development. First, the sequences were targeted to a laboratory isolate of HIV that was not representative of Clade B HIV strains currently circulating in North America and Europe. Second, these shRNA targeted critical components in the lentivirus vector packaging system and would severely reduce vector yield during manufacturing. Plasmid 5, as detailed in Table 2, was selected to target CCR5 and provided a lead candidate sequence. Plasmids 6, 7, 8, 9, 10, and 11, as detailed in Table 2, incorporated the TAR sequence and it was found they produced unacceptable toxicity for mammalian cells including cells used for lentivirus vector manufacturing. Plasmid 2, as detailed in Table 2, identified a lead shRNA sequence capable of reducing Tat RNA expression. Plasmid 12, as detailed in Table 2, demonstrated the effectiveness of shCCR5 expressed as a microRNA (miR) in a lentiviral vector and confirmed it should be in the final product. Plasmid 13, as detailed in Table 2, demonstrated the effectiveness of a sh Vif expressed as a microRNA (miR) in a lentiviral vector and confirmed it should be in the final product. Plasmid 14, as detailed in Table 2, demonstrated the effectiveness of shTat expressed as a microRNA (miR) in a lentiviral vector and confirmed it should be in the final product. Plasmid 15, as detailed in Table 2, contained the miR CCR5, miR Tat and miR Vif in the form of a miR cluster expressed from a single promoter. These miR do not target critical components in the lentivirus vector packaging system and proved to have negligible toxicity for mammalian cells. The miR within the cluster were equally effective to individual miR that were tested previously, and the overall impact was a substantial reduction in replication of a CCR5-tropic HIV BaL strain.

TABLE 2

Development of HIV Vectors

| | Internal Code | Material | Description | Remarks | Decision |
|---|---|---|---|---|---|
| 1 | SIH-H1-shRT-1,3 | Lentiviral vector | shRNA construct for RT of LAI strain | Wrong target, lab virus, no virus test | Abandon |
| 2 | SIH-H1-shRT43 (Tat/Rev NL4-3) | Lentiviral vector | H1 promoter shRNA Tat/Rev overlap | Tat protein knock-down >90% | Lead |

Vector Construction: For Rev/Tat (RT) shRNA, oligonucleotide sequences containing BamHI and EcoRI restriction sites were synthesized by MWG Operon. Two different Rev/Tat target sequences were tested for their ability to decrease Tat mRNA expression. The RT1,3 target sequence is (5'-ATGGCAGGAAGAAGCGGAG-3') (SEQ ID NO: 89) and shRNA sequence is (5'-ATGGCAGGAAGAAGCGGAGTTCAAGAGACTCCGCTTCTTCCTGCCATTTTTT-3')

TABLE 2-continued

Development of HIV Vectors

| Internal Code | Material | Description | Remarks | Decision |
|---|---|---|---|---|

(SEQ ID NO: 90). The RT43 sequence is (5'-GCGGAGACAGCGACGAAGAGC-3') (SEQ ID NO: 9) and shRNA sequence is (5'-GCGGAGACAGCGACGAAGAGCTTCAAGAGAGCTCTTCGTCGCTGTCTCCGCTTTTT-3') (SEQ ID NO: 10). Oligonucleotide sequences were inserted into the pSIH lentiviral vector (System Biosciences).
Functional test for shRNA against Rev/Tat: The ability of the vector to reduce Tat expression was tested using a luciferase reporter plasmid which contained the Rev/Tat target sequences inserted into the 3'-UTR (untranslated region of the mRNA). Either the shRT1,3 or shRT43 plasmid was co-transfected with the plasmid containing luciferase and the Rev/Tar target sequence. There was a 90% reduction in light emission indicating strong function of the shRT43 shRNA sequence but less than 10% with the shRT1,3 plasmid.
Conclusion: The SIH-H1-shRT43 was superior to SIH-H1-shRT-1,3 in terms of reducing mRNA levels in the Luciferase assay system. This indicates potent inhibitory activity of the shRT43 sequence and it was selected as a lead candidate for further development.

| 3 | SIH-H1-shGag-1 | Lentiviral vector | shRNA construct for LAI Gag | Inhibits Gag expression but will inhibit packaging | Abandon |

Vector Construction: For Gag shRNA, oligonucleotide sequences containing BamHI and EcoRI restriction sites were synthesized by MWG Operon. A Gag target sequence was tested for their ability to decrease Gag mRNA expression. The Gag target sequence is (5'-GAAGAAATGATGACAGCAT-3') (SEQ ID NO: 11) and shRNA sequence is (5'-GAAGAAATGATGACAGCATTTCAAGAGAATGCTGTCATCATTTCTTCTTTTT-3') (SEQ ID NO: 12). Oligonucleotide sequences were inserted into the pSIH lentiviral vector (System Biosciences).
Functional test for shRNA against Gag: The ability of the vector to reduce Gag expression was tested using a luciferase reporter plasmid which contained the Gag target sequences inserted into the 3'-UTR (untranslated region of the mRNA). The Gag plasmid was co-transfected with the plasmid containing luciferase and the Gag target sequence. There was nearly a 90% reduction in light emission indicating a strong effect of the shGag shRNA sequence.
Conclusion: This shRNA sequence is potent against HIV Gag expression but was abandoned. The lentivirus packaging system requires production of Gag from the helper plasmid and shRNA inhibition of Gag will reduce lentivirus vector yield. This shRNA sequence could be used as an oligonucleotide inhibitor of HIV or incorporated into an alternate viral vector packaging system that uses a different vector genome or is modified to resist inhibition by this shRNA.

| 4 | SIH-H1-shPol-1 | Lentiviral vector | shRNA construct for Pol | Inhibits Pol expression but will inhibit packaging | Abandon |

Vector Construction: A Pol shRNA was constructed with oligonucleotide sequences containing BamHI and EcoRI restriction sites that were synthesized by MWG Operon. A Pol target sequence was tested for its ability to decrease Pol mRNA expression. The Pol target sequence is (5'-CAGGAGCAGATGATACAG-3') (SEQ ID NO: 13) and shRNA sequence is (5'-CAGGAGATGATACAGTTCAAGAGACTGTATCATCTGCTCCTGTTTTT-3') (SEQ ID NO: 14). Oligonucleotide sequences were inserted into the pSIH lentiviral vector (System Biosciences).
Functional tests for shRNA against HIV Pol: The ability of the vector to reduce Pol expression was tested using a luciferase reporter plasmid which contained the Pol target sequences inserted into the 3'-UTR (untranslated region of the mRNA). The Pol plasmid was co-transfected with the plasmid containing luciferase and the Pol target sequence. There was a 60% reduction in light emission indicating a strong effect of the shPol shRNA sequence.
Conclusion: This shRNA sequence is potent against HIV Pol expression but was abandoned. The lentivirus packaging system requires production of Pol from the helper plasmid and shRNA inhibition of Pol will reduce lentivirus vector yield. This shRNA sequence could be used as an oligonucleotide inhibitor of HIV or incorporated into an alternate viral vector packaging system that uses a different vector genome or is modified to resist inhibition by this shRNA.

| 5 | SIH-H1-shCCR5-1 | Lentiviral vector | shRNA construct for CCR5 | Best of 5 candidates, Extracellular CCR5 protein reduction >90% | Lead |

Vector Construction: A CCR5 shRNA was constructed with oligonucleotide sequences containing BamHI and EcoRI restriction sites that were synthesized by MWG Operon. Oligonucleotide sequences were inserted into the pSIH lentiviral vector (System Biosciences). The CCR5 target sequence #1, which focuses on CCR5 gene sequence 1 (SEQ ID NO: 25), is (5'-GTGTCAAGTCCAATCTATG-3') (SEQ ID NO: 15) and the shRNA sequence is (5'-GTGTCAAGTCCAATCTATGTTCAAGAGACATAGATTGGACTTGACACTTTTT-3') (SEQ ID NO: 16). The CCR5 target sequence #2, which focuses on CCR5 gene sequence 2 (SEQ ID NO: 26), is (5'-GAGCATGACTGACATCTAC-3') (SEQ ID NO: 17) and the shRNA sequence is (5'-GAGCATGACTGACATCTACTTCAAGAGAGTAGATGTCAGTCATGCTCTTTTT-3') (SEQ ID NO: 18). The CCR5 target sequence #3, which focuses on CCR5 gene sequence 3 (SEQ ID NO: 27), is (5'-GTAGCTCTAACAGGTTGGA-3') (SEQ ID NO: 19) and the shRNA sequence is (5'-GTAGCTCTAACAGGTTGGATTCAAGAGATCCAACCTGTTAGAGCTACTTTTT-3')

TABLE 2-continued

Development of HIV Vectors

| Internal Code | Material | Description | Remarks | Decision |
|---|---|---|---|---|

(SEQ ID NO: 20). The CCR5 target sequence #4, which focuses on CCR5 gene sequence 4 (SEQ ID NO: 28, is (5'-GTTCAGAAACTACCTCTTA-3') (SEQ ID NO: 21) and the shRNA sequence is (5'-GTTCAGAAACTACCTCTTATTCAAGAGATAAGAGGTAGTTTCTGAACTTTTT-3') (SEQ ID NO: 22). The CCR5 target sequence #5, which focuses on CCR5 gene sequence 5 (SEQ ID NO: 29), is (5'-GAGCAAGCTCAGTTTACACC-3') (SEQ ID NO: 23) and the shRNA sequence is (5'-GAGCAAGCTCAGTTTACACCTTCAAGAGAGGTGTAAACTGAGCTTGCTCTTTTT-3') (SEQ ID NO: 24).
Functional test for shRNA against CCR5: The ability of a CCR5 shRNA sequence to knock-down CCR5 RNA expression was initially tested by co-transfecting each of the lentiviral plasmids, in separate experiments for each plasmid, containing one of the five CCR5 target sequences with a plasmid expressing the human CCR5 gene. CCR5 mRNA expression was then assessed by qPCR analysis using CCR5-specific primers.
Conclusion: Based on the reduction in CCR5 mRNA levels the shRNACCR5-1 was most potent for reducing CCR5 gene expression. This shRNA was selected as a lead candidate.

| Internal Code | | Material | Description | Remarks | Decision |
|---|---|---|---|---|---|
| 6 | SIH-U6-TAR | Lentiviral vector | U6 promoter-TAR | Toxic to cells | Abandon |
| 7 | SIH-U6-TAR-H1-shCCR5 | Lentiviral vector | U6 promoter-TAR-H1-shCCR5 | Toxic to cells | Abandon |
| 8 | U6-TAR-H1-shRT | Lentiviral vector | U6 promoter-TAR-H1-RT | Suppress HIV, toxic to cells, poor packaging | Abandon |
| 9 | U6-TAR-7SK-shRT | Lentiviral vector | Change shRNA promoter to 7SK | Toxic, poor packaging | Abandon |
| 10 | U6-TAR-H1-shRT-H1-shCCR5 | Lentiviral vector | U6 promoter-TAR-H1-RT-H1-shCCR5 | Toxic, poor packaging, H1 repeats | Abandon |
| 11 | U6-TAR-7SK-shRT-H1-CCR5 | Lentiviral vector | Change shRNA promoter to 7SK | Toxic, poor packaging | Abandon |

Vector Construction: A TAR decoy sequence containing flanking KpnI restriction sites was synthesized by MWG operon and inserted into the pSIH lentiviral vector (System Biosciences) at the KpnI site. In this vector, TAR expression is regulate id by the U6 promoter. The TAR decoy sequence is (5'-CTTGCAATGATGTCGTAATTTGCGTCTTACCTCGTTCTCGACAGCGACCAGATCTGAGCCTGGGAGCTCTCTGGCTGTCAGTAAGCTGGTACAGAAGGTTGACGAAATTCTTACTGAGCAAGAAA-3') (SEQ ID NO: 8). Expression of the TAR decoy sequence was determined by qPCR analysis using specific primers for the TAR sequence. Additional vectors were constructed also containing the TAR sequence. The H1 promoter and shRT sequence was inserted in this vector in the XhoI site. The H1 shRT sequence (5'-GAACGCTGACGTCATCAACCCGCTCCAAGGAATCGCGGGCCCAGTGTCACTAGGCGGGAACACCCAGCGCGCGTGCGCCCTGGCAGGAAGATGGCTGTGAGGGACAGGGGAGTGGCGCCCTGCAATATTTGCATGTCGCTATGTGTTCTGGGAAATCACCATAAACGTGAAATGTCTTTGGATTTGGGAATCTTATAAGTTCTGTATGAGACCACTTGGATCCGCGGAGACAGCGACGAAGAGCTTCAAGAGAGCTCTTCGTCGCTGTCCGCTTTTT-3') (SEQ ID NO: 91). This vector could express TAR and knockdown RT. The 7SK promoter was also substituted for the H1 promoter to regulate shRT expression. Another vector was constructed containing U6 TAR, H1 shRT, and H1 shCCR5. The H1 shCCR5 sequence was inserted into the SpeI site of the plasmid containing U6 TAR and H1 shRT. The H1 CCR5 sequence is (5'-GAACGCTGACGTCATCAACCCGCTCCAAGGAATCGCGGGCCCAGTGTCACTAGGCGGGAACACCCAGCGCGCGTGCGCCCTGGCAGGAAGATGGCTGTGAGGGACAGGGGAGTGGCGCCCTGCAATATTTGCATGTCGCTATGTGTTCTGGGAAATCACCATAAACGTGAAATGTCTTTGGATTTGGGAATCTTATAAGTTCTGTATGAGACCACTTGGATCCGTGTCAAGTCCAATCTATGTTCAAGAGACATAGATTGGACTTGACACTTTTT-3') (SEQ ID NO: 92).
The 7SK promoter was also substituted for the H1 promoter to regulate shRT expression.
Functional test for TAR decoy activity: We tested the effect of SIH-U6-TAR on packaging efficiency. When TAR sequence was included, the yield of vector in the SIH packaging system was reduced substantially.
Conclusion: Lentivirus vectors expressing the TAR decoy sequence are unsuitable for commercial development due to low vector yields. These constructs were abandoned.

| | | | | | |
|---|---|---|---|---|---|
| 12 | shCCR5 | Lentiviral vector | microRNA sequence | Extracellular CCR5 protein reduction >90% | Lead |

Vector Construction: A CCR5 microRNA was constructed with oligonucleotide sequences containing BsrGI and NotI restriction sites that were synthesized by MWG Operon. Oligonucleotide sequences were inserted into the pCDH lentiviral vector (System Biosciences),

TABLE 2-continued

Development of HIV Vectors

| Internal Code | Material | Description | Remarks | Decision |
|---|---|---|---|---|

The EF-1 promoter was substituted for a CMV promoter that was used in the plasmid construct Test Material 5. The EF-1 promoter was synthesized by MWG Operon containing flanking ClaI and BsrGI restriction sites and inserted into the pCDH vector containing shCCR5-1. The EF-1 promoter sequence is (5'-CCGGTGCCTAGAGAAGGTGGCGCGGGGTAAACTGGGAAAGTGATGTCGTGTACTG
GCTCCGCCTTTTTCCCGAGGGTGGGGGAGAACCGTATATAAGTGCAGTAGTCGCCG
TGAACGTTCTTTTTCGCAACGGGTTTGCCGCCAGAACACAGGTAAGTGCCGTGTGT
GGTTCCCGCGGGCCTGGCCTCTTTACGGGTTATGGCCCTTGCGTGCCTTGAATTACT
TCCACGCCCCTGGCTGCAGTACGTGATTCTTGATCCCGAGCTTCGGGTTGGAAGTGG
GTGGGAGAGTTCGAGGCCTTGCGCTTAAGGAGCCCCTTCGCCTCGTGCTTGAGTTG
AGGCCTGGCCTGGGCGCTGGGGCCGCCGCGTGCGAATCTGGTGGCACCTTCGCGCC
TGTCTCGCTGCTTTCGATAAGTCTCTAGCCATTTAAAATTTTTGATGACCTGCTGCG
ACGCTTTTTTTCTGGCAAGATAGTCTTGTAAATGCGGGCCAAGATCTGCACACTGGT
ATTTCGGTTTTTGGGGCCGCGGGCGGCGACGGGGCCCGTGCGTCCCAGCGCACATG
TTCGGCGAGGCGGGGCCTGCGAGCGCGGCCACCGAGAATCGGACGGGGGTAGTCT
CAAGCTGGCCGGCCTGCTCTGGTGCCTGGCCTCGCGCCGCCGTGTATCGCCCCGCCC
TGGGCGGCAAGGCTGGCCCGGTCGGCACCAGTTGCGTGAGCGGAAAGATGGCCGC
TTCCCGGCCCTGCTGCAGGGAGCTCAAAATGGAGGACGCGGCGCTCGGGAGAGCG
GGCGGGTGAGTCACCCACACAAAGGAAAAGGGCCTTTCCGTCCTCAGCCGTCGCTT
CATGTGACTCCACGGAGTACCGGGCGCCGTCCAGGCACCTCGATTAGTTCTCGAGC
TTTTGGAGTACGTCGTCTTTAGGTTGGGGGGAGGGGTTTTATGCGATGGAGTTTCCC
CACACTGAGTGGGTGGAGACTGAAGTTAGGCCAGCTTGGCACTTGATGTAATTCTC
CTTGGAATTTGCCCTTTTTGAGTTTGGATCTTGGTTCATTCTCAAGCCTCAGACAGT
GGTTCAAAGTTTTTTCTTCCATTTCAGGTGTCGTGA-3') (SEQ ID NO: 4).
Functional test for lentivirus CDH-shCCR5-1: The ability of the miR CCR5 sequences to knock-down CCR5 expression was determined by transducing CEM-CCR5 T cells and measuring cell surface CCR5 expression after staining with a fluorescently-labeled monoclonal antibody against CCR5 and measuring the intensity of staining, that is directly proportional to the number of cell surface CCR5 molecules, by analytical flow cytometry. The most effective shRNA sequence for targeting CCR5 was CCR5 shRNA sequence #1. However, the most effective CCR5 targeting sequence for constructing the synthetic microRNA sequence was overlapping with CCR5 sequence #5; this conclusion was based on sequence alignments and experience with miRNA construction. Finally, the miR30 hairpin sequence was used to construct the synthetic miR30 CCR5 sequence which is (5'-
AGGTATATTGCTGTTGACAGTGAGCGACTGTAAACTGAGCTTGCTCTACTGTGAAG
CCACAGATGGGTAGAGCAAGCACAGTTTACCGCTGCCTACTGCCTCGGACTTCAAG
GGGCTT-3') (SEQ ID NO: 1). The miR CCR5 target sequence is (5'-
GAGCAAGCTCAGTTTACA-3') (SEQ ID NO: 5). At multiplicity of infection equal to 5, generating on average 1.25 genome copies of integrated lentivirus per cell, CCR5 expression levels were reduce by ≥90% indicating potent inhibition of CCR5 mRNA by the miR30CCR5 micro RNA construct in a lentivirus vector.
Conclusion: The miR30CCR5 construct is potent for reducing CCR5 cell surface expression and is a lead candidate for a therapeutic lentivirus for HIV.

| 13 | shVif | Lentiviral vector | microRNA sequence | Vif protein reduction >80% | Lead |

Vector Construction: A Vif microRNA was constructed with oligonucleotide sequences containing BsrGI and NotI restriction sites that were synthesized by MWG Operon. Oligonucleotide sequences were inserted into the pCDH lentiviral vector (System Biosciences) containing an EF-1 promoter. Based on sequence alignments and experience with constructing synthetic miRNA, the miR21 hairpin sequence was used to construct the synthetic miR21 Vif sequence which is (5'-CATCTCCATGGCTGTACCACCTTGTCGGGGATGTGTACTTCTGAACTTGTGTTGAA
TCTCATGGAGTTCAGAAGAACACATCCGCACTGACATTTTGGTATCTTTCATCTGAC
CA-3') (SEQ ID NO: 2). The miR Vif target sequence is (5'-
GGGATGTGTACTTCTGAACTT-3') (SEQ ID NO: 6).
Functional test for potency of miR21Vif: The ability of the miR Vif sequence to knock-down Vif expression was determined by measuring Vif protein expression by immunoblot analysis using an anti-Vif monoclonal antibody to identify the Vif protein.
Conclusion: the miR21Vif reduced Vif protein expression by ≥10-fold as determined by quantitative image analysis of immunoblot data. This was sufficient to justify miR21 Vif as a lead candidate for our therapeutic lentivirus.

| 14 | shTat | Lentiviral vector | microRNA sequence | Tat RNA reduction >80% | Lead |

Vector Construction: A Tat microRNA was constructed with oligonucleotide sequences containing BsrGI and NotI restriction sites that were synthesized by MWG Operon. The microRNA cluster was inserted into the pCDH lentiviral vector (System Biosciences) containing an EF-1 promoter. Based on sequence alignments and experience in the construction of synthetic miRNA, the miR185 hairpin sequence was selected for constructing a synthetic miR185 Tat sequence which is (5'-
GGGCCTGGCTCGAGCAGGGGGCGAGGGATTCCGCTTCTTCCTGCCATAGCGTGGTC
CCCTCCCCTATGGCAGGCAGAAGCGGCACCTTCCCTCCCAATGACCGCGTCTTCGTC
G-3'). The miR Tat target sequence is (5'-TCCGCTTCTTCCTGCCATAG-3') (SEQ ID NO: 3).

TABLE 2-continued

Development of HIV Vectors

| Internal Code | Material | Description | Remarks | Decision |
|---|---|---|---|---|
| | | | Functional test for potency of miR185Tat: The ability of miR Tat to knock-down Tat expression was determined by measuring Tat mRNA expression by RT-PCR analysis using Tat specific primers. We compared the miR185Tat (SEQ ID NO: 108) with a similar miR155Tat on the basis of reducing the relative levels of Tat mRNA. Conclusion: The miR185Tat (SEQ ID NO: 108) was approximately twice as potent for reducing Tat mRNA compared to miR155Tat, and was selected as the lead candidate for our therapeutic lentivirus. | | |
| 15 | shCCR5-shVif-shTat | Lentiviral vector | microRNA cluster sequence | CCR5 reduction >90%, Vif protein reduction >80%, Tat RNA reduction >80%, >95% inhibition of HIV replication | Candidate |
| | | | Vector Construction: A miR30CCR5 miR21Vif miR185Tat microRNA cluster sequence was constructed with a synthetic DNA fragment containing BsrGI and NotI restriction sites that was synthesized by MWG Operon. The DNA fragment was inserted into the pCDH lentiviral vector (System Biosciences) containing the EF-1 promoter. The miR cluster sequence is (5'-AGGTATATTGCTGTTGACAGTGAGCGACTGTAAACTGAGCTTGCTCTACTGTGAAG CCACAGATGGGTAGAGCAAGCACAGTTTACCGCTGCCTACTGCCTCGGACTTCAAG GGGCTTCCCGGGCATCTCCATGGCTGTACCACCTTGTCGGGGATGTGTACTTCTGA ACTTGTGTTGAATCTCATGGAGTTCAGAAGAACACATCCGCACTGACATTTTGGTAT CTTTCATCTGACCAGCTAGCGGGCCTGGCTCGAGCAGGGGGCGAGGGATTCCGCTT CTTCCTGCCATAGCGTGGTCCCCTCCCCTATGGCAGGCAGAAGCGGCACCTTCCCTC CCAATGACCGCGTCTTCGTC-3') (SEQ ID NO: 31) and incorporates Test Material 12, Test Material 13 and Test Material 14 into a single cluster that can be expressed under control of the EF-1 promoter. Functional test for potency of the Lentivirus Vector AGT 103 containing the microRNA cluster of miR30CCR5, miR2IVif andmiR185Tat: The AGT103 vector was tested for potency against CCR5 using the assay for reduction in cell surface CCR5 expression (Test Material 12). The AGT 103 vector was tested for potency against Vif using the assay for reduction in cell surface Vif expression (Test Material 13). The AGT103 vector was tested for potency against Tat using the assay for reduction in cell surface Tat expression (Test Material 14). Conclusion: Potency for reducing CCR5 expression by the miRNA cluster was similar to potency observed for the miR30CCR5 alone. Potency for reducing Vif expression by the miRNA cluster was similar to potency observed for the miR21 Vif alone. Potency for reducing Tat expression by the miRNA cluster was similar to potency observed for the miR185Tat alone. The miRNA cluster is potent for reducing cell surface CCR5 levels and for inhibiting two HIV genes. Thus, AGT 103 containing this miRNA cluster was selected as the therapeutic vector construct for our HIV functional cure program. | | |

Functional Assays. Individual lentivirus vectors containing CCR5, Tat or Vif shRNA sequences and, for experimental purposes, expressing green fluorescent protein (GFP) under control of the CMV Immediate Early Promoter, and designated AGT103/CMV-GFP were tested for their ability to knockdown CCR5, Tat or Vif expression. Mammalian cells were transduced with lentiviral particles either in the presence or absence of polybrene. Cells were collected after 2-4 days; protein and RNA were analyzed for CCR5, Tat or Vif expression. Protein levels were tested by Western blot assay or by labeling cells with specific fluorescent antibodies (CCR5 assay), followed by analytical flow cytometry comparing modified and unmodified cell fluorescence using either the CCR5-specific or isotype control antibodies.

Starting Testing of Lentivirus. T cell culture medium was made using RPMI 1640 supplemented with 10% FBS and 1% penicillin-streptomycin. Cytokine stocks of IL2 10,000 units/ml, IL-12 1 µg/ml, IL-7 1 µg/ml, IL-15 1 µg/ml were also prepared in advance.

Prior to transduction with the lentivirus, an infectious viral titer was determined and used to calculate the amount of virus to add for the proper multiplicity of infection (MOI).

Day 0-12: Antigen-specific enrichment. On day 0, cryopreserved PBMC were thawed, washed with 10 ml 37° C. medium at 1200 rpm for 10 minutes and resuspended at a concentration of $2\times10^6$/ml in 37° C. medium. The cells were cultured at 0.5 ml/well in a 24-well plate at 37° C. in 5% CO2. To define the optimal stimulation conditions, cells were stimulated with combinations of reagents as listed in Table 3 below:

TABLE 3

| 1 | 2 | 3 | 4 | 5 | 6 |
|---|---|---|---|---|---|
| IL-2 + IL-12 | IL-7 + IL-15 | Peptides + IL-2 + IL-12 | Peptides + IL-7 + IL-15 | MVA + IL-2 + IL-12 | MVA + IL-7 + IL-15 |

Final concentrations: IL-2=20 units/ml, IL-12=10 ng/ml, IL-7=10 ng/ml, IL-15=10 ng/ml, peptides=5 µg/ml individual peptide, MVA MOI=1.

On days 4 and 8, 0.5 ml fresh medium and cytokine at listed concentrations (all concentrations indicate the final concentration in the culture) were added to the stimulated cells.

Day 12-24: non-specific expansion and lentivirus transduction. On day 12, the stimulated cells were removed from the plate by pipetting and resuspended in fresh T cell culture medium at a concentration of 1×10⁶/ml. The resuspended cells were transferred to T25 culture flasks and stimulated with DYNABEADS® Human T-Activator CD3/CD28 following the manufacturer's instruction plus cytokine as listed above; flasks were incubated in the vertical position.

On day 14, AGT103/CMV-GFP was added at MOI 20 and cultures were returned to the incubator for 2 days. At this time, cells were recovered by pipetting, collected by centrifugation at 1300 rpm for 10 minutes, resuspended in the same volume of fresh medium, and centrifuged again to form a loose cell pellet. That cell pellet was resuspended in fresh medium with the same cytokines used in previous steps, with cells at $0.5 \times 10^6$ viable cells per ml.

From days 14 to 23, the number of the cells was evaluated every 2 days and the cells were diluted to $0.5 \times 10^6$/ml with fresh media. Cytokines were added every time.

On day 24, the cells were collected and the beads were removed from the cells. To remove the beads, cells were transferred to a suitable tube that was placed in the sorting magnet for 2 minutes. Supernatant containing the cells was transferred to a new tube. Cells were then cultured for 1 day in fresh medium at $1 \times 10^6$/ml. Assays were performed to determine the frequencies of antigen-specific T cells and lentivirus transduced cells.

To prevent possible viral outgrowth, amprenavir (0.5 ng/ml) was added to the cultures on the first day of stimulation and every other day during the culture.

Examine antigen-specific T cells by intracellular cytokine staining for IFN-gamma. Cultured cells after peptide stimulation or after lentivirus transduction at $1 \times 10^6$ cells/ml were stimulated with medium alone (negative control), Gag peptides (5 µg/ml individual peptide), or PHA (5 µg/ml, positive control). After 4 hours, BD GolgiPlug™ (1:1000, BD Biosciences) was added to block Golgi transport. After 8 hours, cells were washed and stained with extracellular (CD3, CD4 or CD8; BD Biosciences) and intracellular (IFN-gamma; BD Biosciences) antibodies with BD Cytofix/Cytoperm™ kit following the manufacturer's instruction. Samples were analyzed on a BD FACSCalibur™ Flow Cytometer. Control samples labeled with appropriate isotype-matched antibodies were included in each experiment. Data were analyzed using Flowjo software.

Lentivirus transduction rate was determined by the frequency of GFP+ cells. The transduced antigen-specific T cells are determined by the frequency of CD3+CD4+GFP+ IFN gamma+ cells; tests for CD3+CD8+GFP+IFN gamma+ cells are included as a control.

These results indicate that CD4 T cells, the target T cell population, can be transduced with lentiviruses that are designed to specifically knock down the expression of HIV-specific proteins, thus producing an expandable population of T cells that are immune to the virus. This example serves as a proof of concept indicating that the disclosed lentiviral constructs can be used in combination with vaccination to produce a functional cure in HIV patients.

Example 4: CCR5 Knockdown with Experimental Vectors

AGTc120 is a Hela cell line that stably expresses large amounts of CD4 and CCR5. AGTc120 was transduced with or without LV-CMV-mCherry (the red fluorescent protein mCherry expressed under control of the CMV Immediate Early Promoter) or AGT103/CMV-mCherry. Gene expression of the mCherry fluorescent protein was controlled by a CMV (cytomegalovirus immediate early promoter) expression cassette. The LV-CMV-mCherry vector lacked a microRNA cluster, while AGT103/CMV-mCherry expressed therapeutic miRNA against CCR5, Vif, and Tat.

Figure 8A:
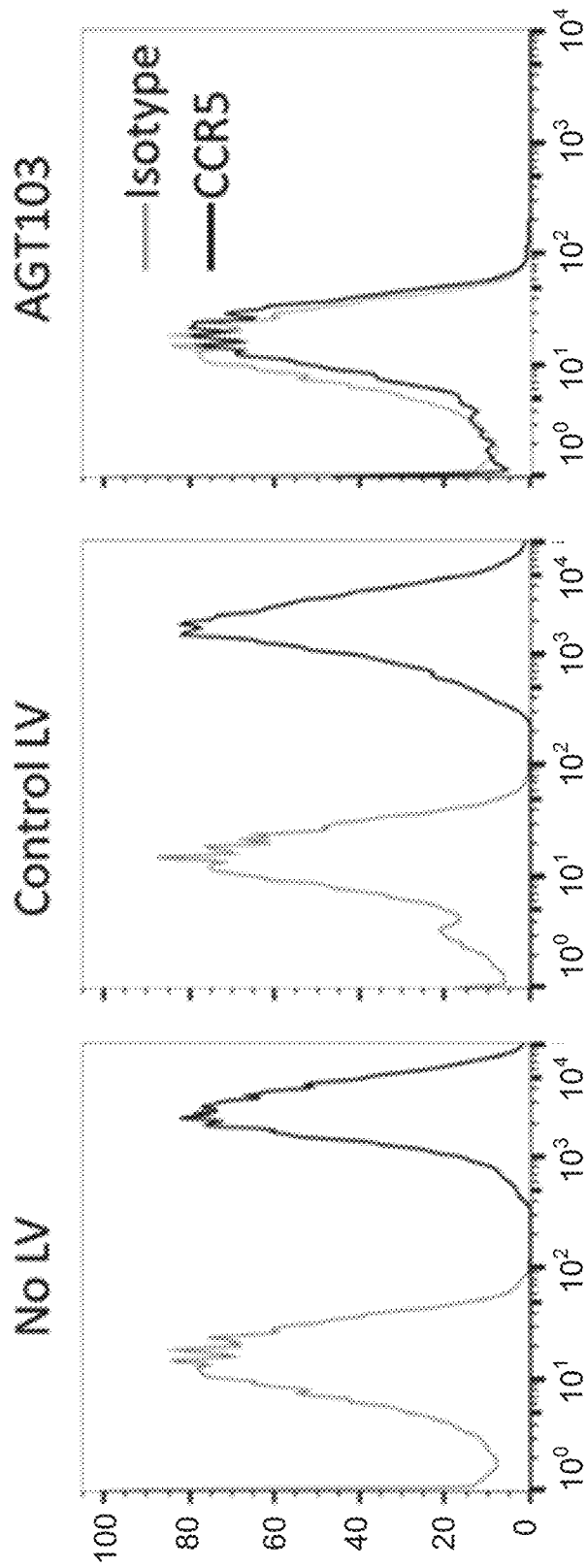
FIGS. 8A-8B show knockdown of CCR5 by an experimental vector and corresponding prevention of R5-tropic HIV infection in AGTc120 cells.

As shown in FIG. 8A, transduction efficiency was >90%. After 7 days, cells were collected and stained with fluorescent monoclonal antibody against CCR5 and subjected to analytical flow cytometry. Isotype controls are shown in gray on these histograms plotting Mean Fluorescence Intensity of CCR5 APC (x axis) versus cell number normalized to mode (y axis). After staining for cell surface CCR5, cells treated with no lentivirus or control lentivirus (expressing only the mCherry marker) showed no changes in CCR5 density while AGT103 (right section) reduced CCR5 staining intensity to nearly the levels of isotype control. After 7 days, cells were infected with or without R5-tropic HIV reporter virus Bal-GFP. 3 days later, cells were collected and analyzed by flow cytometry. More than 90% of cells were transduced. AGT103-CMV/CMVmCherry reduced CCR5 expression in transduced AGTc120 cells and blocked R5-tropic HIV infection compared with cells treated with the Control vector.

Figure 8B:
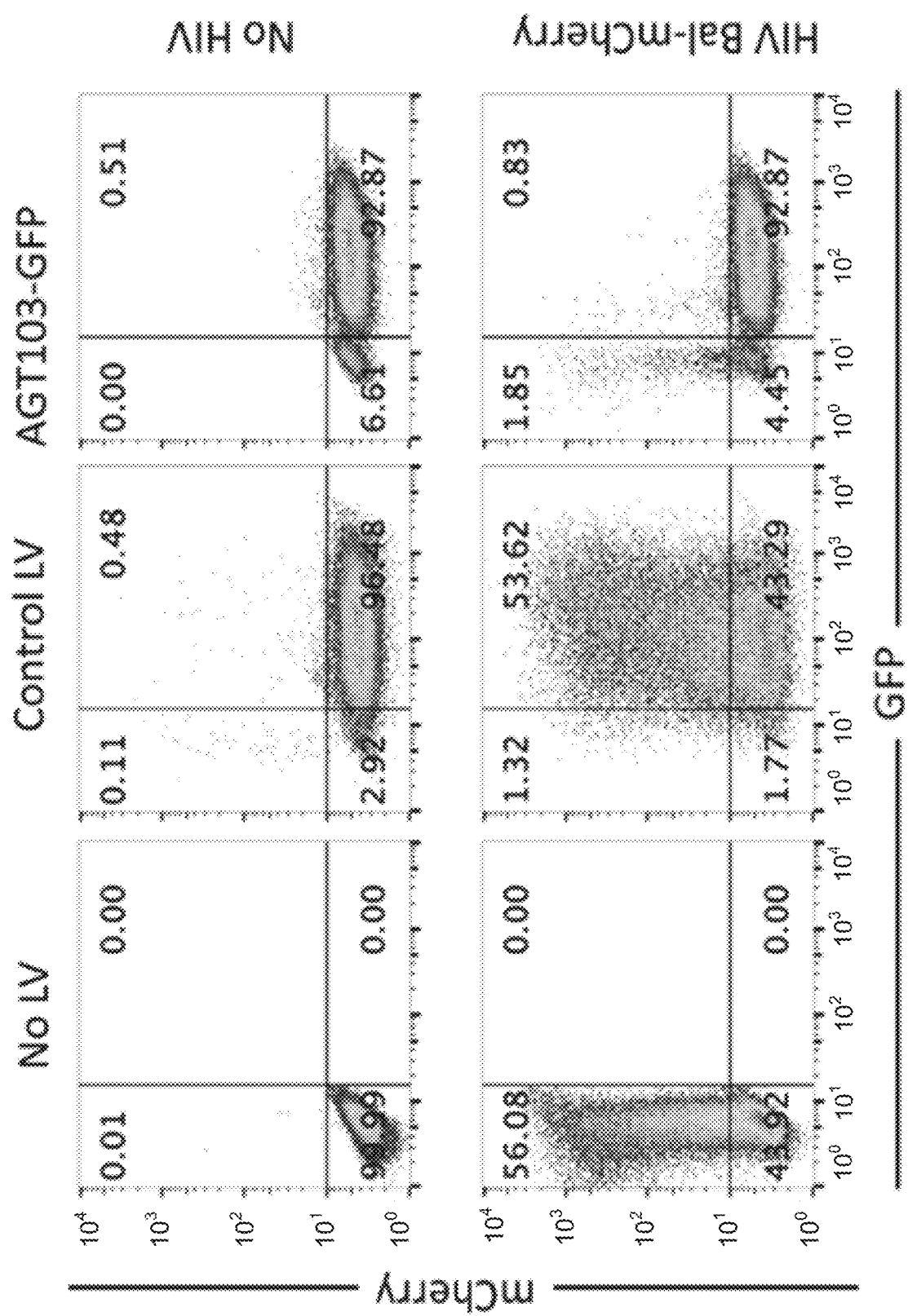

FIG. 8B shows the relative insensitivity of transfected AGTc120 cells to infection with HIV. As above, the lentivirus vectors express mCherry protein and a transduced cell that was also infected with HIV (expressing GFP) would appear as a double positive cell in the upper right quadrant of the false color flow cytometry dot plots. In the absence of HIV (upper panels), there were no GFP+ cells under any condition. After HIV infection (lower panels), 56% of cells were infected in the absence of lentivirus transduction and 53.6% of cells became infected in AGTc120 cells transduced with the LV-CMV-mCherry. When cells were transduced with the therapeutic AGT103/CMV-mCherry vector, only 0.83% of cells appeared in the double positive quadrant indicating they were transduced and infected.

Dividing 53.62 (proportion of double positive cells with control vector) by 0.83 (the proportion of double positive cells with the therapeutic vector) shows that AGT103 provided greater than 65-fold protection against HIV in this experimental system.

Example 5: Regulation of CCR5 Expression by shRNA Inhibitor Sequences in a Lentiviral Vector Inhibitory RNA Design. The sequence of *Homo sapiens* chemokine receptor CCR5 (CCR5, NC 000003.12) was used to search for potential siRNA or shRNA candidates to knockdown CCR5 levels in human cells. Potential RNA interference sequences were chosen from candidates selected by siRNA or shRNA design programs such as from the Broad Institute or the BLOCK-IT RNA iDesigner from Thermo Scientific. A shRNA sequence may be inserted into a plasmid immediately after a RNA polymerase III promoter such as H1, U6, or 7SK to regulate shRNA expression. The shRNA sequence may also be inserted into a lentiviral vector using similar promoters or embedded within a microRNA backbone to allow for expression by an RNA polymerase II promoter such as CMV or EF-1 alpha. The RNA sequence may also be synthesized as a siRNA oligonucleotide and utilized independently of a plasmid or lentiviral vector.

Plasmid Construction. For CCR5 shRNA, oligonucleotide sequences containing BamHI and EcoRI restriction sites were synthesized by MWG Operon. Oligonucleotide sequences were annealed by incubating at 70° C. then cooled to room temperature. Annealed oligonucleotides were digested with the restriction enzymes BamHI and EcoRI for one hour at 37° C., then the enzymes were inactivated at 70° C. for 20 minutes. In parallel, plasmid DNA was digested with the restriction enzymes BamHI and EcoRI for one hour at 37° C. The digested plasmid DNA was purified by agarose gel electrophoresis and extracted from the gel using a DNA gel extraction kit from Invitrogen. The DNA concentration was determined and the plasma to oligonucleotide sequence was ligated in the ratio 3:1 insert to vector. The ligation reaction was done with T4 DNA ligase for 30 minutes at room temperature. 2.5 uL of the ligation mix were added to 25 μL of STBL3 competent bacterial cells. Transformation required heat shock at 42° C. Bacterial cells were spread on agar plates containing ampicillin and colonies were expanded in L broth. To check for insertion of the oligo sequences, plasmid DNA was extracted from harvested bacterial cultures using the Invitrogen DNA Miniprep kit and tested by restriction enzyme digestion. Insertion of the shRNA sequence into the plasmid was verified by DNA sequencing using a primer specific for the promoter used to regulate shRNA expression.

Functional Assay for CCR5 mRNA Reduction: The assay for inhibition of CCR5 expression required co-transfection of two plasmids. The first plasmid contains one of five different shRNA sequences directed against CCR5 mRNA. The second plasmid contains the cDNA sequence for human CCR5 gene. Plasmids were co-transfected into 293T cells. After 48 hours, cells were lysed and RNA was extracted using the RNeasy kit from Qiagen. cDNA was synthesized from RNA using a Super Script Kit from Invitrogen. The samples were then analyzed by quantitative RT-PCR using an Applied Biosystems Step One PCR machine. CCR5 expression was detected with SYBR Green from Invitrogen using the forward primer (5'-AGGAATT-GATGGCGAGAAGG-3') (SEQ ID NO: 93) and reverse primer (5'-CCCCAAAGAAGGTCAAGGTAATCA-3') (SEQ ID NO: 94) with standard conditions for polymerase chain reaction analysis. The samples were normalized to the mRNA for beta actin gene expression using the forward primer (5'-AGCGCGGCTACAGCTTCA-3') (SEQ ID NO: 95) and reverse primer (5'-GGCGACGTAGCACAGCTTCP-3') (SEQ ID NO: 96) with standard conditions for polymerase chain reaction analysis. The relative expression of CCR5 mRNA was determined by its Ct value normalized to the level of actin messenger RNA for each sample. The results are shown in FIGS. 9A-9B.

Figure 9A:
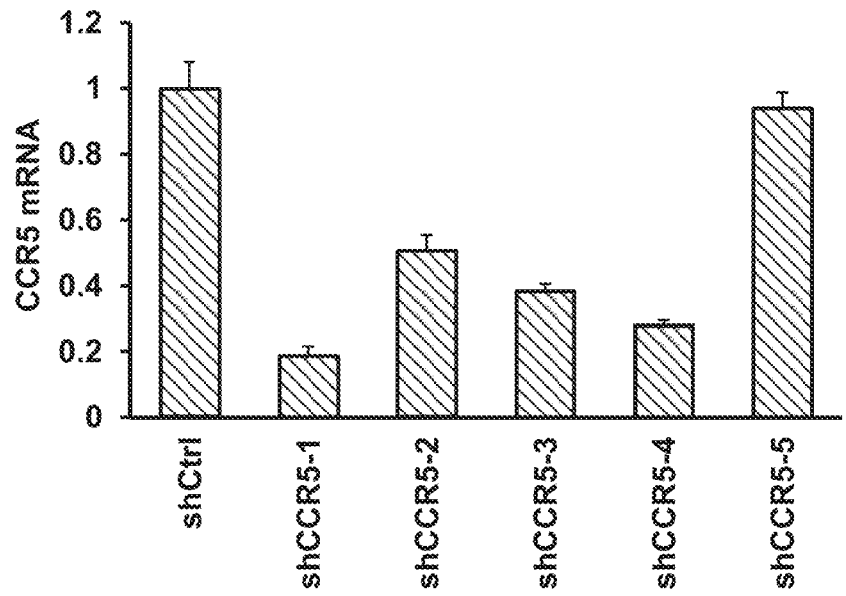
FIGS. 9A-9B depict data demonstrating regulation of CCR5 expression by shRNA inhibitor sequences in a lentiviral vector of the present disclosure.
Figure 9B:
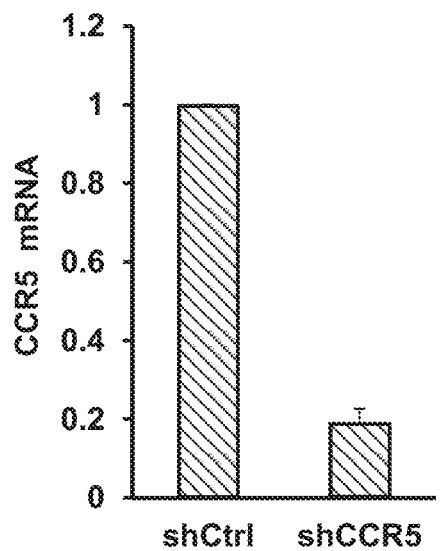

As shown in FIG. 9A, CCR5 knock-down was tested in 293T cells by co-transfection of the CCR5 shRNA construct and a CCR5-expressing plasmid. Control samples were transfected with a scrambled shRNA sequence that did not target any human gene and the CCR5-expressing plasmid. After 60 hours post-transfection, samples were harvested and CCR5 mRNA levels were measured by quantitative PCR. Further, as shown in FIG. 9B, CCR5 knock-down after transduction with lentivirus expressing CCR5 shRNA-1 (SEQ ID NO: 16).

Example 6: Regulation of HIV Components by shRNA Inhibitor Sequences in a Lentiviral Vector Inhibitory RNA Design.

```
The sequences of HIV type 1 Rev/Tat
(5'-GCGGAGACAGCGACGAAGAGC-3') (SEQ ID NO: 9) and
Gag (5'-GAAGAAATGATGACAGCAT-3') (SEQ ID NO: 11)
were used to design:
Rev/Tat:
(5'GCGGAGACAGCGACGAAGAGCTTCAAGAGAGCTCTTCGTCGCTGTCT
CCGCTTTTT-3') (SEQ ID NO: 10)
``` and

```
Gag:
(5'GAAGAAATGATGACAGCATTTCAAGAGAATGCTGTCATCATTTCTTC
TTTTT-3')
```

(SEQ ID NO: 12) shRNA that were synthesized and cloned into plasmids as described above.

Plasmid Construction. The Rev/Tat or Gag target sequences were inserted into the 3'UTR (untranslated region) of the firefly luciferase gene used commonly as a reporter of gene expression in cells or tissues. Additionally, one plasmid was constructed to express the Rev/Tat shRNA and a second plasmid was constructed to express the Gag shRNA. Plasmid constructions were as described above.

Functional assay for shRNA targeting of Rev Tat or Gag mRNA: Using plasmid co-transfection we tested whether a shRNA plasmid was capable of degrading luciferase messenger RNA and decreasing the intensity of light emission in co-transfected cells. A shRNA control (scrambled sequence) was used to establish the maximum yield of light from luciferase transfected cells. When the luciferase construct containing a Rev/Tat target sequence inserted into the 3'-UTR (untranslated region of the mRNA) was co-transfected with the Rev/Tat shRNA sequence there was nearly a 90% reduction in light emission indicating strong function of the shRNA sequence. A similar result was obtained when a luciferase construct containing a Gag target sequence in the 3'-UTR was co-transfected with the Gag shRNA sequence. These results indicate potent activity of the shRNA sequences.

Figure 10A:
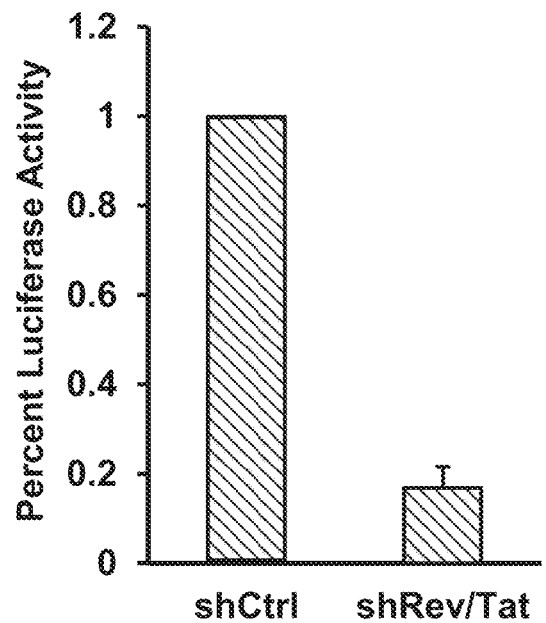
FIGS. 10A-10B depict data demonstrating regulation of HIV components by shRNA inhibitor sequences in a lentiviral vector of the present disclosure.
Figure 10B:
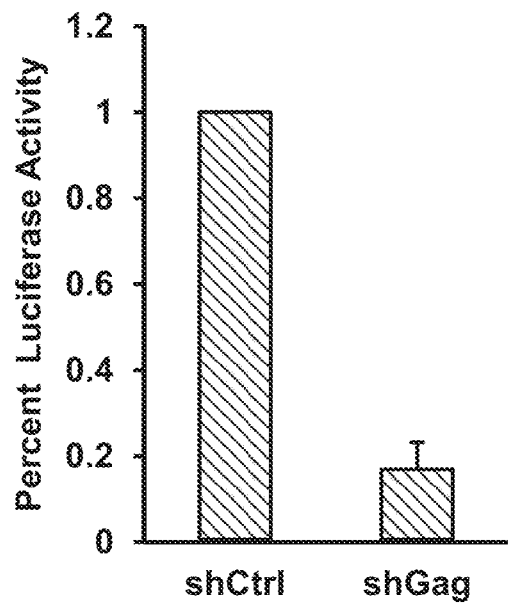

As shown in FIG. 10A, knock-down of the Rev/Tat target gene was measured by a reduction of luciferase activity, which was fused with the target mRNA sequence in the 3'UTR, by transient transfection in 293T cells. As shown in FIG. 10B, knock-down of the Gag target gene sequence fused with the luciferase gene. The results are displayed as the mean+SD of three independent transfection experiments, each in triplicate.

Example 7: AGT103 Decreases Expression of Tat and Vif

Cells were transfected with exemplary vector AGT103/CMV-GFP. AGT103 and other exemplary vectors are defined in Table 3 below.

TABLE 3

| Vector Designation | Composition |
|---|---|
| AGT103 | EF1-miR30CCR5-miR21Vif-miR185-Tat-WPRE |
| Control-mCherry | CMV-mCherry |
| AGT103/CMV-mCherry | CMV-mCherry-EF1-miR30CCR5-miR21Vif-miR185-Tat-WPRE-CMV-mCherry |
| Control-GFP | CMV-mCherry |
| AGT103/CMV-GFP | CMV-GFP-EF1-miR30CCR5-miR21Vif-miR185-Tat-WPRE- |

Figure 11:
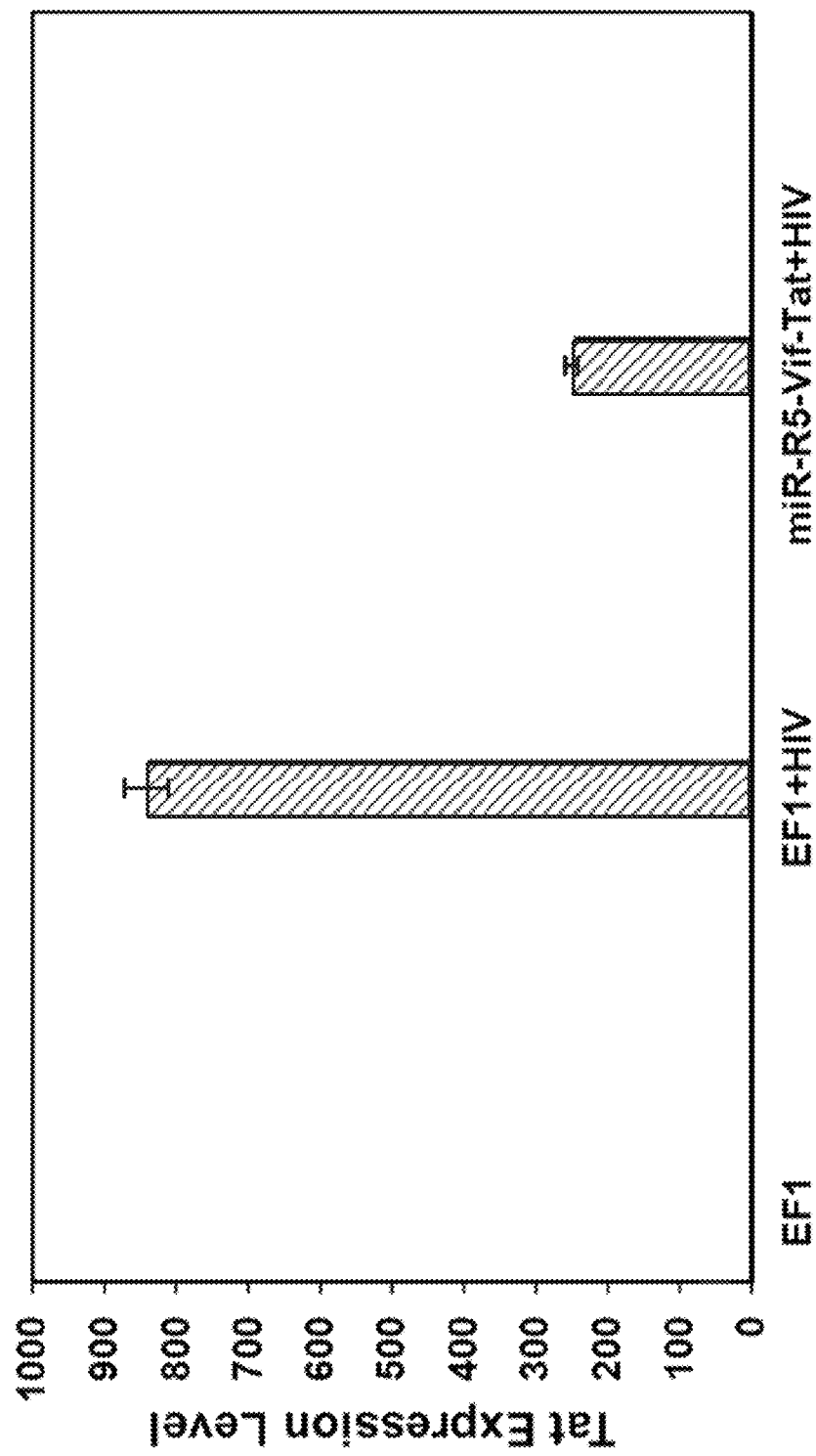
FIG. 11 depicts data demonstrating that AGT103 reduces expression of Tat protein expression in cells transfected with an HIV expression plasmid, as described herein.

Abbreviations:
EF-1: elongation factor 1 transcriptional promoter
miR30CCR5—synthetic microRNA capable of reducing CCR5 protein on cell surfaces
miR21Vif—synthetic microRNA capable of reducing levels of HIV RNA and Vif protein expression
miR185Tat—synthetic micro RNA capable of reducing levels of HIV RNA and Tat protein expression
CMV—Immediate early transcriptional promoter from human cytomegalovirus
mCherry—coding region for the mCherry red fluorescent protein
GFP—coding region for the green fluorescent protein
WPRE—Woodchuck hepatitis virus post transcriptional regulatory element A T lymphoblastoid cell line (CEM; CCRF-CEM; American Type Culture Collection Catalogue number CCL 119) was transduced with AGT103/CMV-GFP. 48 hours later the cells were transfected with an HIV expression plasmid encoding the entire viral sequence. After 24 hours, RNA was extracted from cells and tested for levels of intact Tat sequences using reverse transcriptase polymerase chain reaction. Relative expression levels for intact Tat RNA were reduced from approximately 850 in the presence of control lentivirus vector, to approximately 200 in the presence of AGT103/CMV-GFP for a total reduction of >4 fold, as shown in FIG. 11.

Example 8: Regulation of HIV Components by Synthetic MicroRNA Sequences in a Lentiviral Vector Inhibitory RNA Design. The sequence of HIV-1 Tat and Vif genes were used to search for potential siRNA or shRNA candidates to knockdown Tat or Vif levels in human cells. Potential RNA interference sequences were chosen from candidates selected by siRNA or shRNA design programs such as from the Broad Institute or the BLOCK-IT RNA iDesigner from Thermo Scientific. The selected shRNA sequences most potent for Tat or Vif knockdown were embedded within a microRNA backbone to allow for expression by an RNA polymerase II promoter such as CMV or EF-I alpha. The RNA sequence may also be synthesized as a siRNA oligonucleotide and used independently of a plasmid or lentiviral vector.

Plasmid Construction. The Tat target sequence (5'-TCCGCTTCTTCCTGCCATAG-3') (SEQ ID NO: 7) was incorporated into the miR185 backbone to create a Tat miRNA (5'-GGGCCTGGCTCGAGCAGGGGGCGAGG-GATTCCGCTTCTTCCTGCCATAGCGTGGTCCC CTCCCC-TATGGCAGGCAGAAGCGGCACCTTCCCTCC-CAATGACCGCGTCTTCGTCG-3') (SEQ ID NO: 3) that was inserted into a lentivirus vector and expressed under control of the EF-1 alpha promoter. Similarly, the Vif target sequence (5'-GGGATGTGTACTTCTGAACTT-3') (SEQ ID NO: 6) was incorporated into the miR21 backbone to create a Vif miRNA (5'-CATCTCCATGGCTGTAC-CACCTTGTCGGGGGATGTGTACTTCT-GAACTTGTGTTGAAT CTCATG-GAGTTCAGAAGAACACATCCGCACTGACATTTTG-GTATCTTTCATCTGACCA-3') (SEQ ID NO: 2) that was inserted into a lentivirus vector and expressed under control of the EF-1 alpha promoter. The resulting Vif/Tat miRNA-expressing lentivirus vectors were produced in 293T cells using a lentiviral vector packaging system. The Vif and Tat miRNA were embedded into a microRNA cluster consisting of miR CCR5, miR Vif, and miR Tat all expressed under control of the EF-1 promoter.

Functional assay for miR185Tat inhibition of Tat mRNA accumulation. A lentivirus vector expressing miR 185 Tat (LV-EF1-miR-CCR5-Vif-Tat) was used at a multiplicity of infection equal to 5 for transducing 293T cells. 24 hours after transduction the cells were transfected with a plasmid expressing HIV strain NL4-3 (pNL4-3) using Lipofectamine2000 under standard conditions. 24 hours later RNA was extracted and levels of Tat messenger RNA were tested by RT-PCR using Tat-specific primers and compared to actin mRNA levels for a control.

Functional assay for miR21 Vif inhibition of Vif protein accumulation. A lentivirus vector expressing miR21 Vif (LV-EF1-miR-CCR5-Vif-Tat) was used at a multiplicity of infection equal to 5 for transducing 293T cells. 24 hours after transduction, the cells were transfected with a plasmid expressing HIV strain NL4-3 (pNL4-3) using Lipofectamine2000. 24 hours later cells were lysed and total soluble protein was tested to measure the content of Vif protein. Cell lysates were separated by SDS-PAGE according to established techniques. The separated proteins were transferred to nylon membranes and probed with a Vif-specific monoclonal antibody or actin control antibody.

Figure 12A:
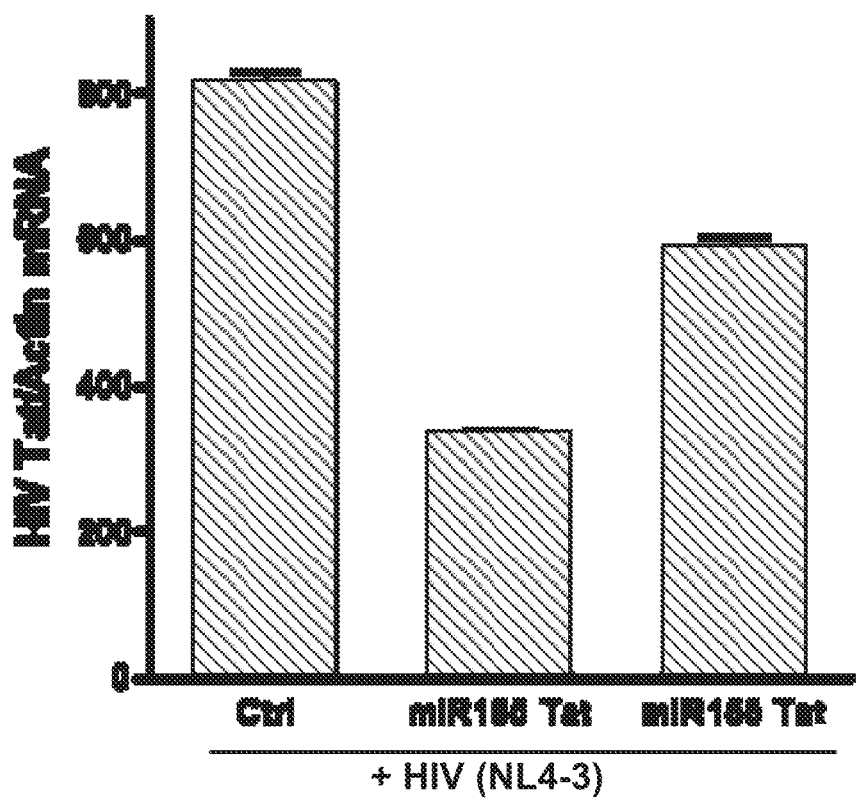
FIGS. 12A-12B depict data demonstrating regulation of HIV components by synthetic microRNA sequences in a lentiviral vector of the present disclosure.
Figure 12B:
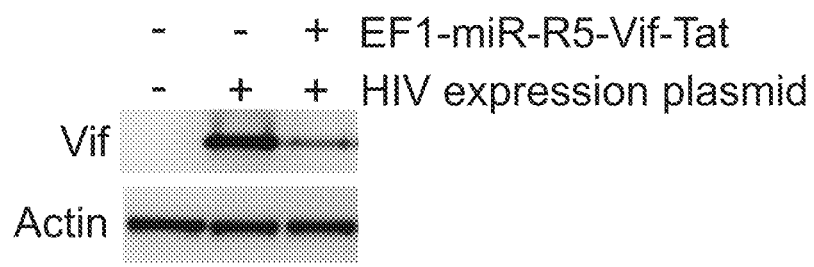

As shown in FIG. 12A, Tat knock-down was tested in 293T cells transduced with either a control lentiviral vector or a lentiviral vector expressing either synthetic miR 185 Tat or miR155 Tat microRNA. After 24 hours, the HIV vector pNL4-3 was transfected with Lipofectamine2000 for 24 hours and then RNA was extracted for qPCR analysis with primers for Tat. As shown in FIG. 12B, Vif knock-down was tested in 293T cells transduced with either a control lentiviral vector or a lentiviral vector expressing a synthetic miR21 Vif microRNA. After 24 hours, the HIV vector pNL4-3 was transfected with Lipofectamine2000 for 24 hours and then protein was extracted for immunoblot analysis with an antibody for HIV Vif.

Figure 13:
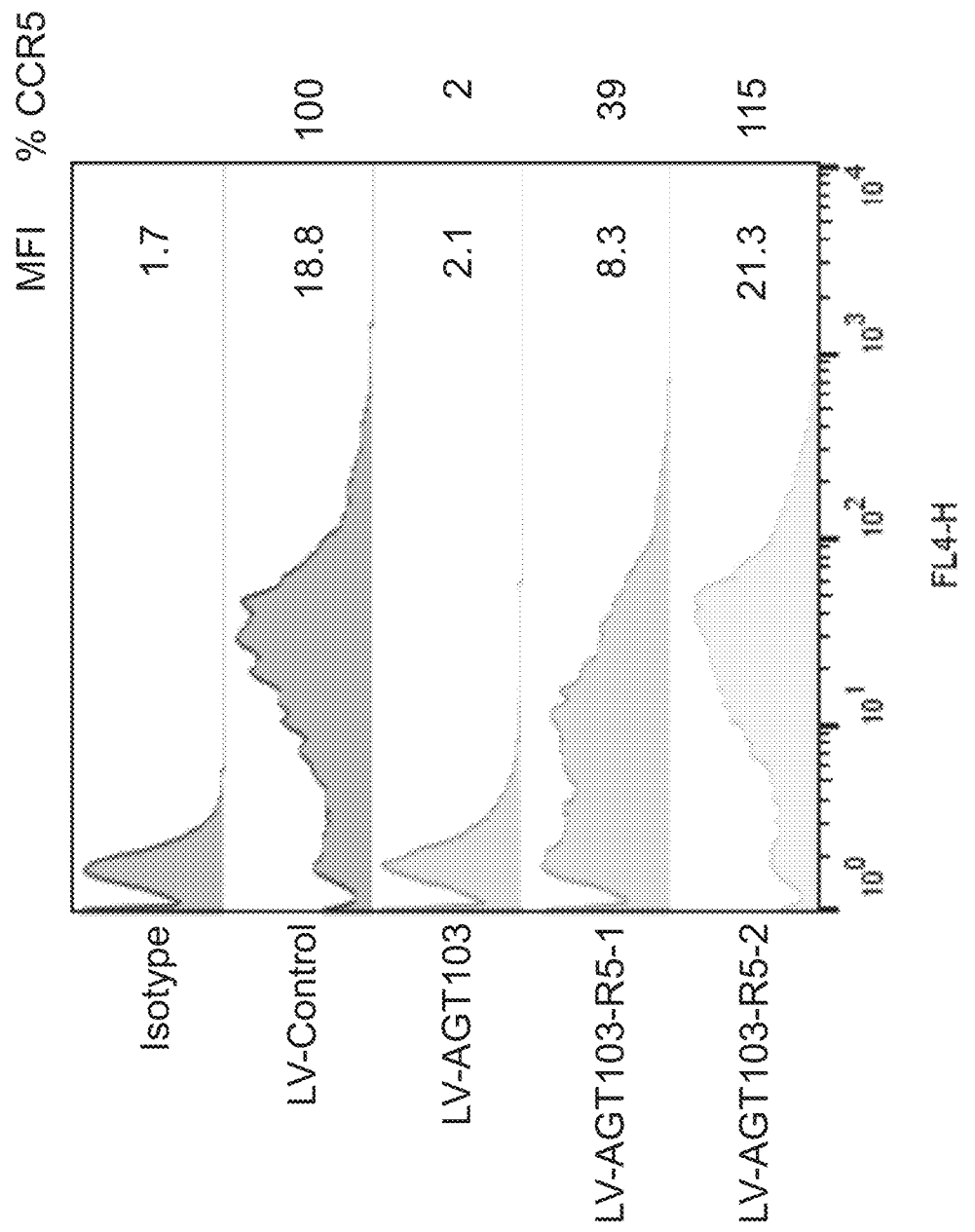
FIG. 13 depicts data demonstrating regulation of CCR5 expression by synthetic microRNA sequences in a lentiviral vector of the present disclosure.

Example 9: Regulation of CCR5 Expression by Synthetic microRNA Sequences in a Lentiviral Vector CEM-CCR5 cells were transduced with a lentiviral vector containing a synthetic miR30 sequence for CCR5 (AGT103: TGTAAACTGAGCTTGCTCTA (SEQ ID NO: 97), AGT103-R5-1: TGTAAACTGAGCTTGCTCGC (SEQ ID NO: 98), or AGT103-R5-2: CATAGATTGGACTTGACAC (SEQ ID NO: 99). After 6 days, CCR5 expression was determined by FACS analysis with an APC-conjugated CCR5 antibody and quantified by mean fluorescence intensity (MFI). CCR5 levels were expressed as % CCR5 with LV-Control set at 100%. The target sequence of AGT103 and AGT103-R5-1 is in the same region as CCR5 target sequence #5. The target sequence of AGT103-R5-2 is the same as CCR5 target sequence #1. AGT103 (2% of total CCR5) is most effective at reducing CCR5 levels as compared with AGT103-R5-1 (39% of total CCR5) and AGT103-R5-2 which does not reduce CCR5 levels. The data is demonstrated in FIG. 13 herein.

Example 10: Regulation of CCR5 Expression by Synthetic microRNA Sequences in a Lentiviral Vector Containing Either a Long or Short WPRE Sequence Vector Construction. Lentivirus vectors often require an RNA regulatory element for optimal expression of therapeutic genes or genetic constructs. A common choice is to use the Woodchuck hepatitis virus post transcriptional regulatory element (WPRE). We compared AGT103 that contains a full-length WPRE:

(SEQ ID NO: 32)
(5'AATCAACCTCTGATTACAAAATTTGTGAAAGATTGACTGGTATTCT

TAACTATGTTGCTCCTTTTACGCTATGTGGATACGCTGCTTTAATGCCT

TTGTATCATGCTATTGCTTCCCGTATGGCTTTCATTTTCTCCTCCTTGT

ATAAATCCTGGTTGCTGTCTCTTTATGAGGAGTTGTGGCCCGTTGTCAG

GCAACGTGGCGTGGTGTGCACTGTGTTTGCTGACGCAACCCCCACTGGT

-continued

```
TGGGGCATTGCCACCACCTGTCAGCTCCTTTCCGGGACTTTCGCTTTCC

CCCTCCCTATTGCCACGGCGGAACTCATCGCCGCCTGCCTTGCCCGCTG

CTGGACAGGGGCTCGGCTGTTGGGCACTGACAATTCCGTGGTGTTGTCG

GGGAAATCATCGTCCTTTCCTTGGCTGCTCGCCTGTGTTGCCACCTGGA

TTCTGCGCGGGACGTCCTTCTGCTACGTCCCTTCGGCCCTCAATCCAGC

GGACCTTCCTTCCCGCGGCCTGCTGCCGGCTCTGCGGCCTCTTCCGCGT

CTTCGCCTTCGCCCTCAGACGAGTCGGATCTCCCTTTGGGCCGCCTCCC

CGCCT-3')
``` with a modified AGT103 vector containing a shortened WPRE element (SEQ ID NO: 80)
```
(5'AATCAACCTCTGGATTACAAAATTTGTGAAAGATTGACTGATATTC

TTAACTATGTTGCTCCTTTTACGCTGTGTGGATATGCTGCTTTAATGCC

TCTGTATCATGCTATTGCTTCCCGTACGGCTTTCGTTTTCTCCTCCTTG

TATAAATCCTGGTTGCTGTCTCTTTATGAGGAGTTGTGGCCCGTTGTCC

GTCAACGTGGCGTGGTGTGCTCTGTGTTTGCTGACGCAACCCCCACTGG

CTGGGGCATTGCCACCACCTGTCAACTCCTTTCTGGGACTTTCGCTTTC

CCCCTCCCGATCGCCACGGCAGAACTCATCGCCGCCTGCCTTGCCCGCT

GCTGGACAGGGGCTAGGTTGCTGGGCACTGATAATTCCGTGGTGTTGT

C-3').
```

Functional assay for modulating cell surface ('C'R5 expression as a function of long versus short WPRE element in the vector sequence. AGT103 containing long or short WPRE elements were used for transducing CEM-CCR5 T cells a multiplicity of infection equal to 5. Six days after transduction cells were collected and stained with a monoclonal antibody capable of detecting cell surface CCR5 protein. The antibody was conjugated to a fluorescent marker and the intensity of staining is directly proportional to the level of CCR5 on the cell surface. A control lentivirus had no effect on cell surface CCR5 levels resulting in a single population with a mean fluorescence intensity of 73.6 units. The conventional AGT103 with a long WPRE element reduced CCR5 expression to a mean fluorescence intensity level of 11 units. AGT103 modified to incorporate a short WPRE element resulted in a single population of cells with mean fluorescence intensity of 13 units. Accordingly, substituting a short WPRE element had little or no effect on the capacity for AGT103 to reduce cell surface CCR5 expression.

Figure 14:
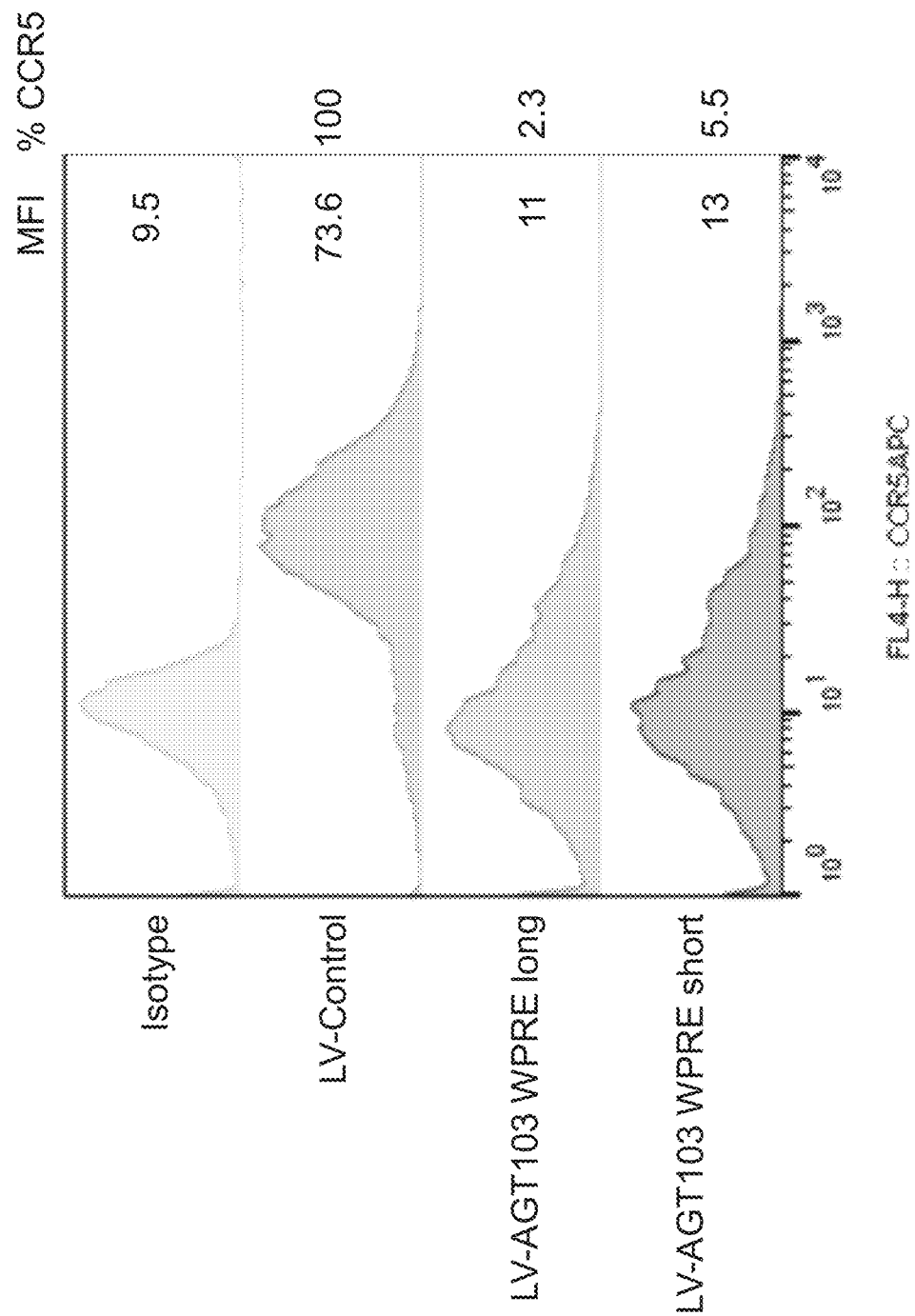
FIG. 14 depicts data demonstrating regulation of CCR5 expression by synthetic microRNA sequences in a lentiviral vector of the present disclosure containing either a long or short WPRE sequence.

As shown in FIG. 14, CEM-CCR5 cells were transduced with AGT103 containing either a long or short WPRE sequence. After 6 days, CCR5 expression was determined by FACS analysis with an APC-conjugated CCR5 antibody and quantified as mean fluorescence intensity (MFI). CCR5 levels were expressed as % CCR5 with LV-Control set at 100%. The reduction in CCR5 levels was similar for AGT103 with either the short (5.5% of total CCR5) or long (2.3% of total CCR5) WPRE sequence.

Example 11: Regulation of CCR5 Expression by Synthetic microRNA Sequences in a Lentiviral Vector with or without a WPRE Sequence Vector construction. In order to test whether WPRE was required for AGT103 down regulation of CCR5 expression we constructed a modified vector without WPRE element sequences.

Functional assay for modulating cell surface CCR5 expression as a function of including or not including a long WPRE element in the AGT103 vector. In order to test whether WPRE was required for AGT103 modulation of CCR5 expression levels we transduced CEM-CCR5 T cells with AGT103 or a modified vector lacking WPRE using a multiplicity of infection equal to 5. Six days after transduction cells were collected and stained with a monoclonal antibody capable of recognizing cell surface CCR5 protein. The monoclonal antibody was directly conjugated to a fluorescent marker and the intensity of staining is directly proportional to the number of CCR5 molecules per cell surface. A lentivirus control vector had no effect on cell surface CCR5 levels resulting in a uniform population with mean fluorescence intensity of 164. The lentivirus vector (AGT103 with a long WPRE and also expressing GFP marker protein), AGT103 lacking GFP but containing a long WPRE element, or AGT103 lacking both GFP and WPRE all were similarly effective for modulating cell surface CCR5 expression. After removing GFP, AGT103 with or without WPRE elements were indistinguishable in terms of their capacity for modulating cell surface CCR5 expression.

Figure 15:
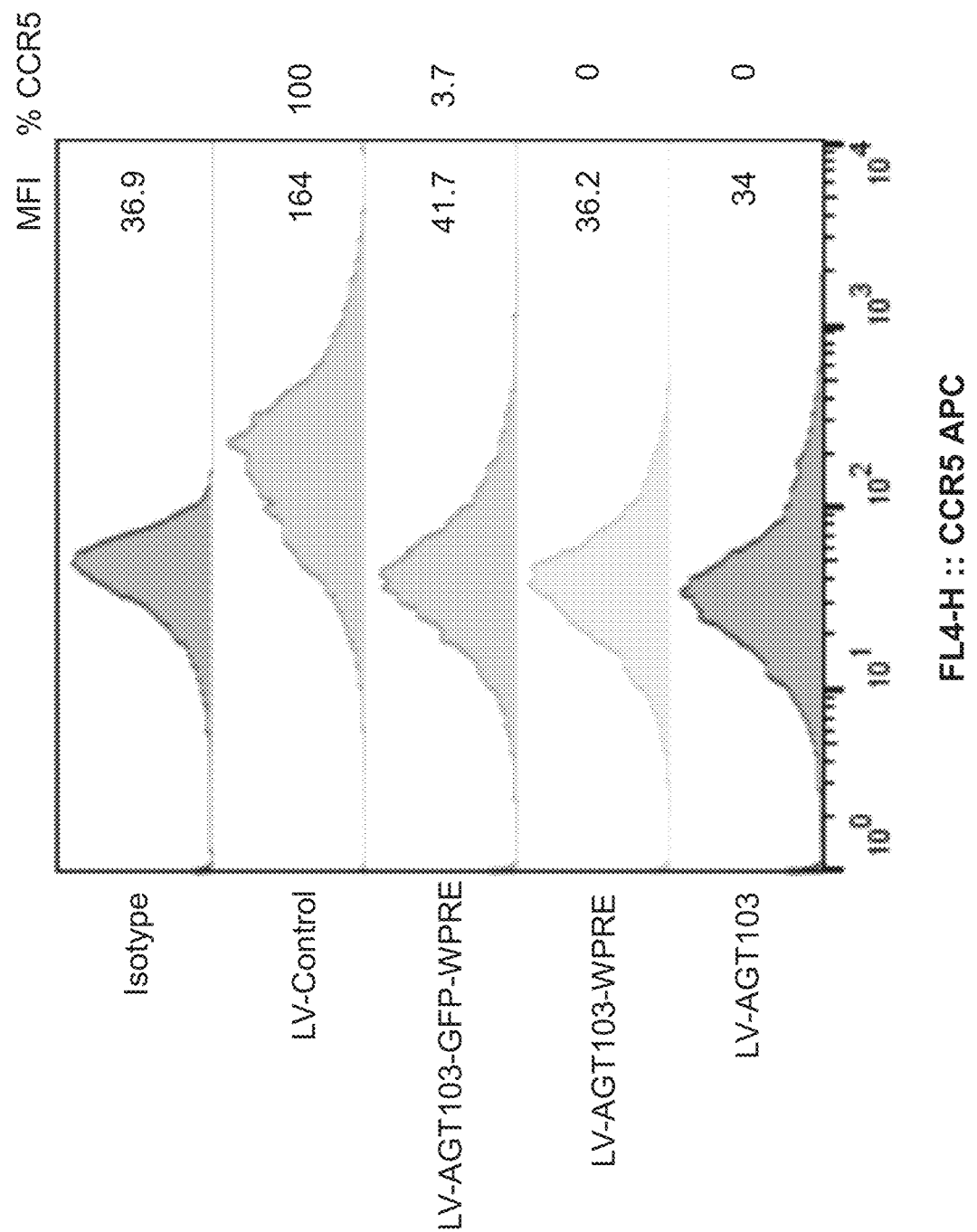
FIG. 15 depicts data demonstrating regulation of CCR5 expression by synthetic microRNA sequences in a lentiviral vector of the present disclosure with or without a WPRE sequence.

CEM-CCR5 cells were transduced with AGT103 with or without GFP and WPRE. After 6 days, CCR5 expression was determined by FACS analysis with an APC-conjugated CCR5 antibody and quantified as mean fluorescence intensity (MFI). CCR5 levels were expressed as % CCR5 with LV-Control set at 100%. The reduction in CCR5 levels was similar for AGT103 with (0% of total CCR5) or without (0% of total CCR5) the WPRE sequence. This data is demonstrated in FIG. 15.

Example 12: Regulation of CCR5 Expression by a CD4 Promoter Regulating Synthetic microRNA Sequences in a Lentiviral Vector Vector Construction. A modified version of AGT103 was constructed to test the effect of substituting alternate promoters for expressing the microRNA cluster that suppresses CCR5, Vif and Tat gene expression. In place of the normal EF-1 promoter we substituted the T cell-specific promoter for CD4 glycoprotein expression using the sequence:

(SEQ ID NO: 30)
```
(5'TGTTGGGGTTCAAATTTGAGCCCAGCTGTTAGCCCTCTGCAAAGA

AAAAAAAAAAAAAAAAGAACAAAGGGCCTAGATTTCCCTTCTGAGCCC

CACCCTAAGATGAAGCCTCTTCTTTCAAGGGAGTGGGGTTGGGGTGGAG

GCGGATCCTGTCAGCTTTGCTCTCTCTGTGGCTGGCAGTTTCTCCAAAG

GGTAACAGGTGTCAGCTGGCTGAGCCTAGGCTGAACCCTGAGACATGCT

ACCTCTGTCTTCTCATGGCTGGAGGCAGCCTTTGTAAGTCACAGAAAGT

AGCTGAGGGGCTCTGGAAAAAAGACAGCCAGGGTGGAGGTAGATTGGTC

TTTGACTCCTGATTTAAGCCTGATTCTGCTTAACTTTTTCCCTTGACTT
```

-continued

```
TGGCATTTTCACTTTGACATGTTCCCTGAGAGCCTGGGGGTGGGGAAC

CCAGCTCCAGCTGGTGACGTTTGGGGCCGGCCCAGGCCTAGGGTGTGGA

GGAGCCTTGCCATCGGGCTTCCTGTCTCTCTTCATTTAAGCACGACTCT

GCAGA-3').
```

Functional assay comparing EF-1 and CD4 gene promoters in terms of potency for reducing cell surface ('C'R5 protein expression. AGT103 modified by substituting the CD4 gene promoter for the normal EF-1 promoter was used for transducing CEM-CCR5 T cells. Six days after transduction cells were collected and stained with a monoclonal antibody capable of recognizing cell surface CCR5 protein. The monoclonal antibody was conjugated to a fluorescent marker and staining intensity is directly proportional to the level of cell surface CCR5 protein. A control lentivirus transduction resulted in a population of CEM-CCR5 T cells that were stained with a CCR5-specific monoclonal antibody and produced a mean fluorescence intensity of 81.7 units. The modified AGT103 using a CD4 gene promoter in place of the EF-1 promoter for expressing microRNA showed a broad distribution of staining with a mean fluorescence intensity roughly equal to 17.3 units. Based on this result, the EF-1 promoter is at least similar and likely superior to the CD4 gene promoter for microRNA expression. Depending on the desired target cell population, the EF-1 promoter is universally active in all cell types and the CD4 promoter is only active in T-lymphocytes.

Figure 16:
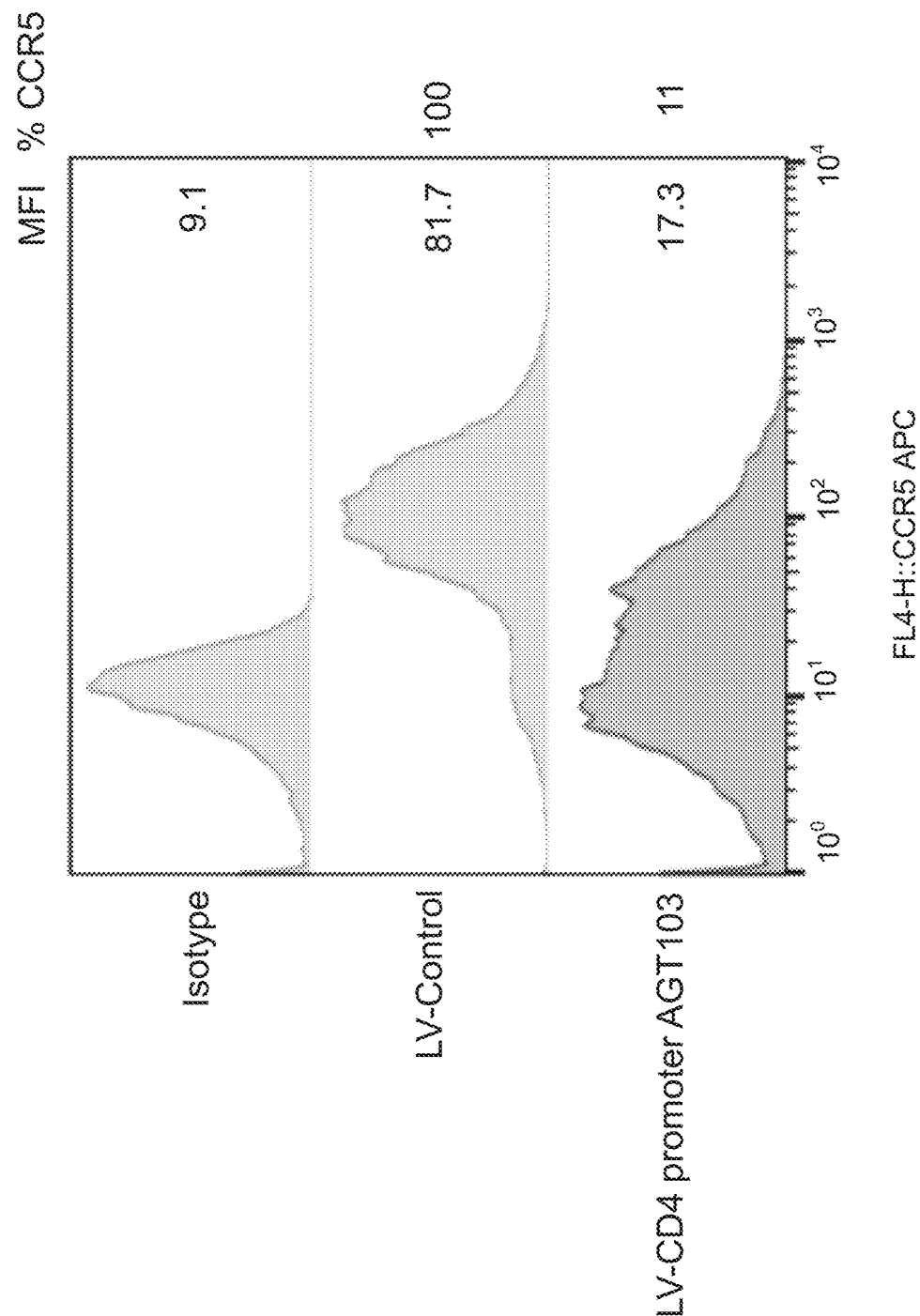
FIG. 16 depicts data demonstrating regulation of CCR5 expression by a CD4 promoter regulating synthetic microRNA sequences in a lentiviral vector of the present disclosure.

CEM-CCR5 cells were transduced with a lentiviral vector containing a CD4 promoter regulating a synthetic microRNA sequence for CCR5, Vif, and Tat (AGT103). After 6 days, CCR5 expression was determined by FACS analysis with an APC-conjugated CCR5 antibody and quantified as mean fluorescence intensity (MFI). CCR5 levels were expressed as % CCR5 with LV-Control set at 100%. In cells transduced with LV-CD4-AGT103, CCR5 levels were 11% of total CCR5. This is comparable to that observed for LV-AGT103 which contains the EF1 promoter. This data is demonstrated in FIG. 16.

Example 13: Detecting HIV Gag-Specific CD4 T Cells

Cells and reagents. Viable frozen peripheral blood mononuclear cells (PBMC) were obtained from a vaccine company. Data were obtained with a representative specimen from an HIV+ individual who was enrolled into an early stage clinical trial (TRIAL REGISTRATION: clinicaltrials.gov NCT01378156) testing a candidate HIV therapeutic vaccine. Two specimens were obtained for the "Before vaccination" and "After vaccination" studies. Cell culture products, supplements and cytokines were from commercial suppliers. Cells were tested for responses to recombinant Modified Vaccinia Ankara 62B from Geovax Corporation as described in Thompson, M., S. L. Heath, B. Sweeton, K. Williams, P. Cunningham, B. F. Keele, B. Sen, B. E. Palmer, N. Chomont, Y. Xu, R. Basu, M. S. Hellerstein, S. Kwa and H. L. Robinson (2016). "DNA/MVA Vaccination of HIV-1 Infected Participants with Viral Suppression on Antiretroviral Therapy, followed by Treatment Interruption: Elicitation of Immune Responses without Control of Re-Emergent Virus." PLOS One 11 (10): e0163164. Synthetic peptides representing the entire HIV-1 Gag polyprotein were obtained from GeoVax the HIV (GAG) Ultra peptide sets were obtained from JPT Peptide Technologies GmbH (www.jpt.com), Berlin, Germany. HIV (GAG) Ultra contains 150 peptides each being 15 amino acids in length and overlapping by 11 amino acids. They were chemically synthesized then purified and analyzed by liquid chromatography-mass spectrometry. Collectively these peptides represent major immunogenic regions of the HIV Gag polyprotein and are designed for average coverage of 57.8% among known HIV strains. Peptide sequences are based on the HIV sequence database from the Los Alamos National Laboratory (www.biy lanl gov/content/sequence/NEWALIGN/align.html). Peptides are provided as dried trifluoroacetate salts, 25 micrograms per peptide, and are dissolved in approximately 40 microliters of DMSO then diluted with PBS to final concentration. Monoclonal antibodies for detecting CD4 and cytoplasmic IFN-gamma were obtained from commercial sources and intracellular staining was done with the BD Pharmingen Intracellular Staining Kit for interferon-gamma. Peptides were resuspended in DMSO and we include a DMSO only control condition.

Functional assay for detecting HIV-specific CD4. T cells. Frozen PBMC were thawed, washed and resuspended in RPMI medium containing 10% fetal bovine serum, supplements and cytokines. Cultured PBMC collected before or after vaccination were treated with DMSO control, MVA GeoVax (multiplicity of infection equal to 1 plaque forming unit per cell), Peptides Geo Vax (1 microgram/ml) or HIV (GAG) Ultra peptide mixture (1 microgram/ml) for 20 hours in the presence of Golgi Stop reagent. Cells were collected, washed, fixed, permeabilized and stained with monoclonal antibodies specific for cell surface CD4 or intracellular interferon-gamma. Stained cells were analyzed with a FACSCalibur analytical flow cytometer and data were gated on the CD4+ T cell subset. Cells highlighted within boxed regions are double-positive and designated HIV-specific CD4 T cells on the basis of interferon-gamma expression after MVA or peptide stimulation. Numbers within the boxed regions show the percentage of total CD4 that were identified as HIV-specific. We did not detect strong responses to DMSO or MVA. Peptides from GeoVax elicited fewer responding cells compared to HIV (GAG) Ultra peptide mixture from JPT but differences were small and not significant.

Figure 17:
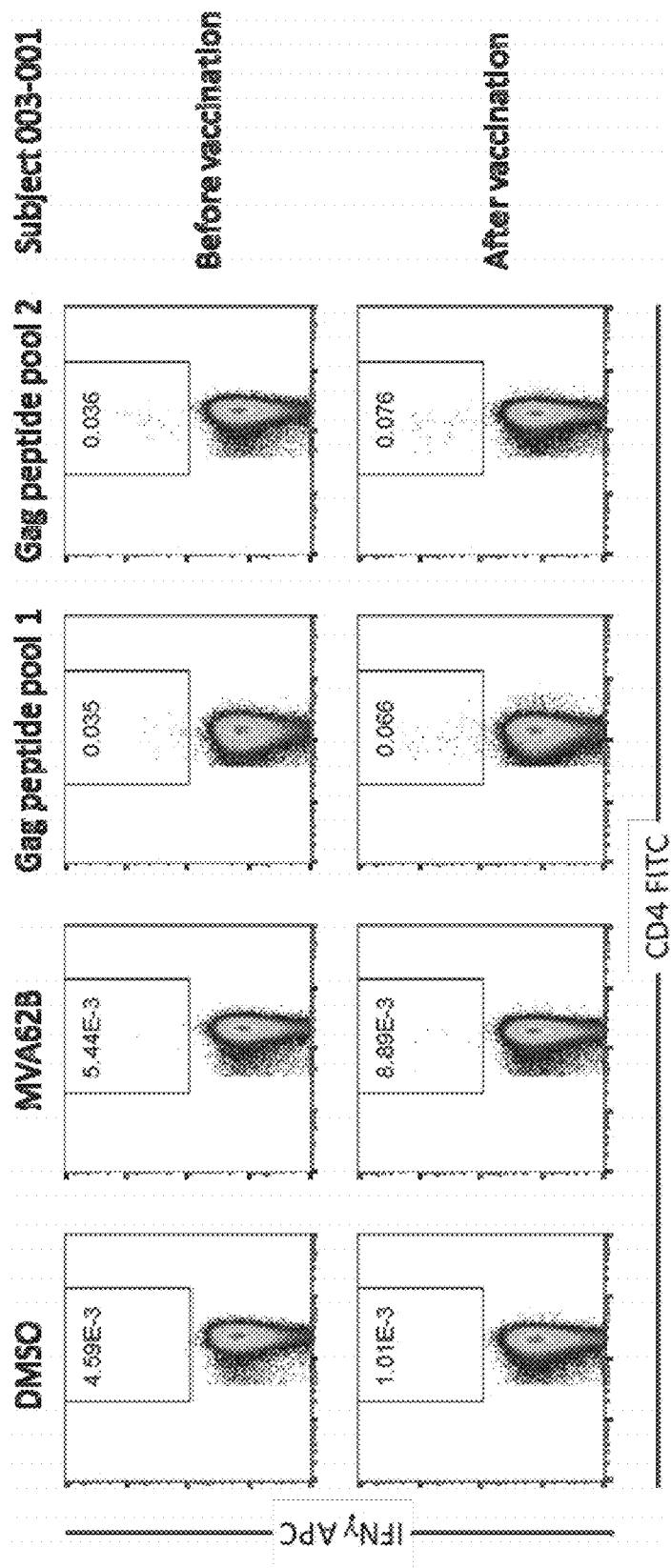
FIG. 17 depicts data demonstrating detection of HIV Gag-specific CD4 T cells.

As shown in FIG. 17, PBMCs from a HIV-positive patient before or after vaccination were stimulated with DMSO (control), recombinant MVA expressing HIV Gag from GeoVax (MVA Geo Vax), Gag peptide from GeoVax (Pep Geo Vax, also referred to herein as Gag peptide pool 1) or Gag peptides from JPT (HIV (GAG) Ultra, also referred to herein as Gag peptide pool 2) for 20 hours. IFNg production was detected by intracellular staining and flow cytometry using standard protocols. Flow cytometry data were gated on CD4 T cells. Numbers captured in boxes are the percentage of total CD4 T cells designated "HIV-specific" on the basis of cytokine response to antigen-specific stimulation.

Example 14: HIV-Specific CD4 T Cell Expansion and Lentivirus Transduction

Designing and testing methods for enriching PBMC to increase the proportion of HIV-specific CD4 T cells and transducing these cells with AGT103 to produce the cellular product AGT103T.

The protocol was designed for ex vivo culture of PBMC (peripheral blood mononuclear cells) from HIV-positive patients who had received a therapeutic HIV vaccine. In this example, the therapeutic vaccine consisted of three doses of plasmid DNA expressing HIV Gag, Pol and Env genes followed by two doses of MVA 62-B (modified vaccinia Ankara number 62-B) expressing the same HIV Gag, Pol, and Env genes. The protocol is not specific for a vaccine product and only requires a sufficient level of HIV-specific CD4+ T cells after immunization. Venous blood was collected and PBMC were purified by Ficoll-Paque density gradient centrifugation. Alternately, PBMC or defined cellular tractions can be prepared by positive or negative selection methods using antibody cocktails and fluorescence activated or magnetic bead sorting. The purified PBMC are washed and cultured in standard medium containing supplements, antibiotics and fetal bovine serum. To these cultures, a pool of synthetic peptides was added representing possible T cell epitopes within the HIV Gag polyprotein. Cultures are supplemented by adding cytokines interleukin-2 and interleukin-12 that were selected after testing combinations of interleukin-2 and interleukin-12, interleukin 2 and interleukin-7, interleukin 2 and interleukin-15. Peptide stimulation is followed by a culture interval of approximately 12 days. During the 12 days culture, fresh medium and fresh cytokine supplements were added approximately once every four days.

The peptide stimulation interval is designed to increase the frequency of HIV-specific CD4 T cells in the PBMC culture. These HIV-specific CD4 T cells were activated by prior therapeutic immunization and can be re-stimulated and caused to proliferate by synthetic peptide exposure. Our goal is to achieve greater than or equal to 1% of total CD4 T cells being HIV-specific by end of the peptide stimulation culture period.

On approximately day 12 of culture cells are washed to remove residual materials then stimulated with synthetic beads decorated with antibodies against CD4 T cell surface proteins CD3 and CD28. This well-established method for polyclonal stimulation of T cells will reactivate the cells and make them more susceptible for AGT103 lentivirus transduction. The lentivirus transduction is performed on approximately day 13 of culture and uses a multiplicity of infection between 1 and 5. After transduction cells are washed to remove residual lentivirus vector and cultured in media containing interleukin-2 and interleukin-12 with fresh medium and cytokines added approximately once every four days until approximately day 24 of culture.

Throughout the culture interval the antiretroviral drug Saquinavir is added at a concentration of approximately 100 nM to suppress any possible outgrowth of HIV.

On approximately day 24 of culture cells are harvested, washed, a sample is set aside for potency and release assay, then the remaining cells are suspended in cryopreservation medium before freezing in single aliquots of approximately $1\times10^{10}$ cells per dose that will contain approximately $1\times10^{8}$ HIV-specific CD4 T cells that are transduced with AGT103.

Potency of the cell product (AGT103T) is tested in one of two alternate potency assays. Potency assay 1 tests for the average number of genome copies (integrated AGT103 vector sequences) per CD4 T cell. The minimum potency is approximately 0.5 genome copies per CD4 T cell in order to release the product. The assay is performed by positive selection of CD3 positive/CD4 positive T cells using magnetic bead labeled monoclonal antibodies, extracting total cellular DNA and using a quantitative PCR reaction to detect sequences unique to the AGT103 vector. Potency assay 2 tests for the average number of genome copies of integrated AGT103 within the subpopulation of HIV-specific CD4 T cells. This essay is accomplished by first stimulating the PBMC with the pool of synthetic peptides representing HIV Gag protein. Cells are then stained with a specific antibody reagent capable of binding to the CD4 T cell and also capturing secreted interferon-gamma cytokine. The CD4 positive/interferon-gamma positive cells are captured by magnetic bead selection, total cellular DNA is prepared, and the number of genome copies of AGT103 per cell is determined with a quantitative PCR reaction. Release criterion based on potency using Assay 2 require that greater than or equal to 0.5 genome copies per HIV-specific CD4 T-cell are present in the AGT103 cell product.

Functional test for enriching and transducing HIV-specific CD4 T cells from PBMC of HIV-positive patients that received a therapeutic HIV vaccine. The impact of therapeutic vaccination on the frequency of HIV-specific CD4 T cells was tested by a peptide stimulation assay (FIG. 14 panel B). Before vaccination the frequency of HIV-specific CD4 T cells was 0.036% in this representative individual. After vaccination, the frequency of HIV-specific CD4 T cells was increased approximately 2-fold to the value of 0.076%. Responding cells (HIV-specific) identified by accumulation of cytoplasmic interferon-gamma, were only detected after specific peptide stimulation.

We also tested whether peptide stimulation to enrich for HIV-specific CD4 T cells followed by AGT103 transduction would reach our goal of generating approximately 1% of total CD4 T cells in culture that were both HIV-specific and transduced by AGT103. In this case, we used an experimental version of AGT103 that expresses green fluorescence protein (see GFP). In FIG. 14, panel C the post-vaccination culture after peptide stimulation (HIV (GAG) Ultra) and AGT103 transduction demonstrated that 1.11% of total CD4 T cells were both HIV-specific (based on expressing interferon-gamma in response to peptide stimulation) and AGT103 transduced (based on expression of GFP).

Several patients from a therapeutic HIV vaccine study were tested to assess the range of responses to peptide stimulation and to begin defining eligibility criteria for entering a gene therapy arm in a future human clinical trial. FIG. 18D shows the frequency of HIV-specific CD4 T cells in 4 vaccine trial participants comparing their pre- and post-vaccination specimens. In three cases the post-vaccination specimens show a value of HIV-specific CD4 T cells that was greater than or equal to 0.076% of total CD4 T cells. The ability to reach this value was not predicted by the pre-vaccination specimens as patient 001-004 and patient 001-006 both started with pre-vaccination values of 0.02% HIV-specific CD4 T cells but one reached an eventual post-vaccination value of 0.12% HIV-specific CD4 T cells while the other individual fail to increase this value after vaccination. The same three patients that responded well to vaccine, in terms of increasing the frequency of HIV-specific CD4 T cells, also showed substantial enrichment of HIV-specific CD4 T cells after peptide stimulation and culture. In the three cases shown in FIG. 18E, peptide stimulation and subsequent culture generated samples where 2.07%, 0.72% or 1.54% respectively of total CD4 T cells were HIV-specific. These values indicate that a majority of individuals responding to a therapeutic HIV vaccine will have a sufficiently large ex vivo response to peptide stimulation in order to enable our goal of achieving approximately 1% of total CD4 T cells that are HIV-specific and transduced with AGT103 in the final cell product.

Figure 18A:
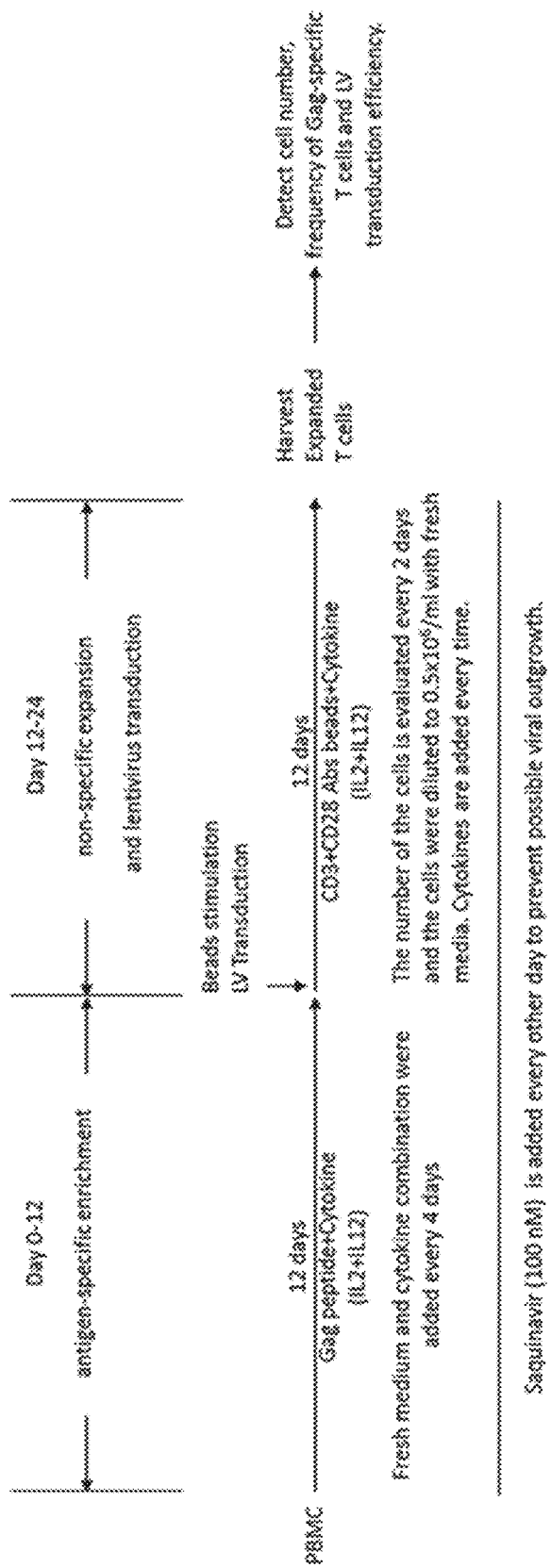
FIGS. 18A-18E depict data demonstrating HIV-specific CD4 T cell expansion and lentivirus transduction.
Figure 18B:
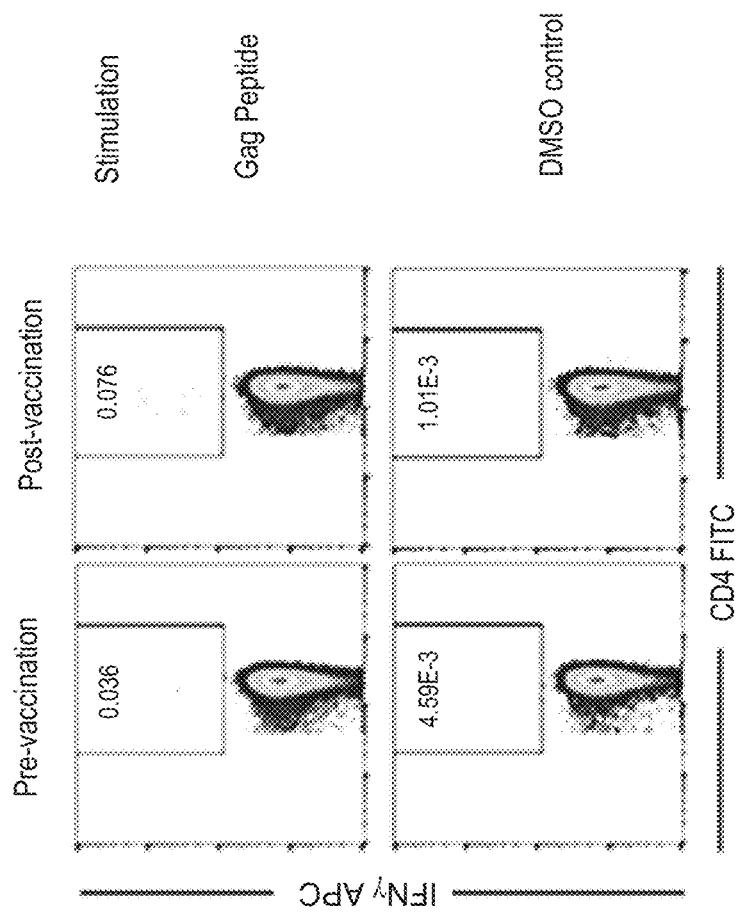
Figure 18C:
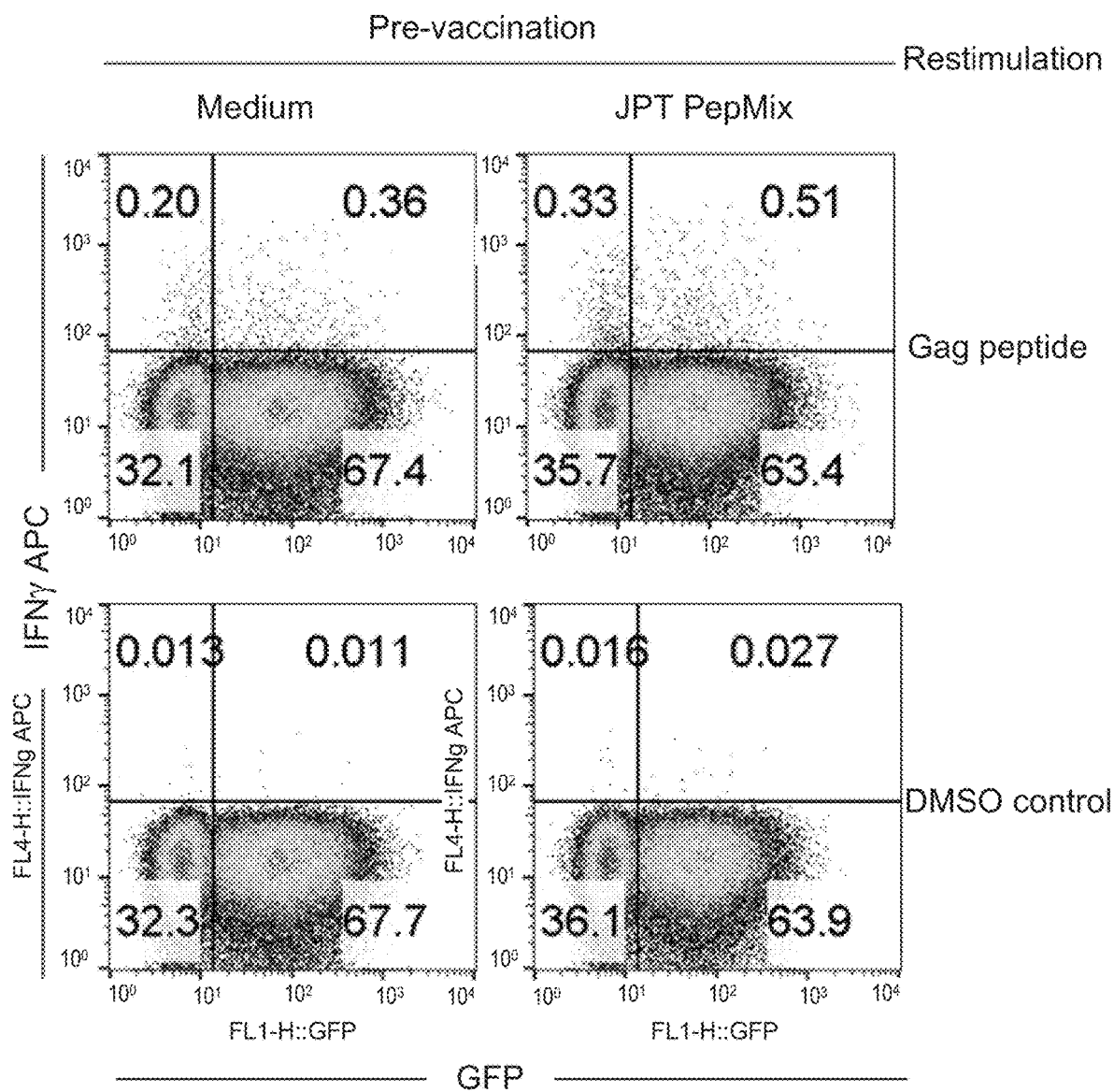
Figure 18C:
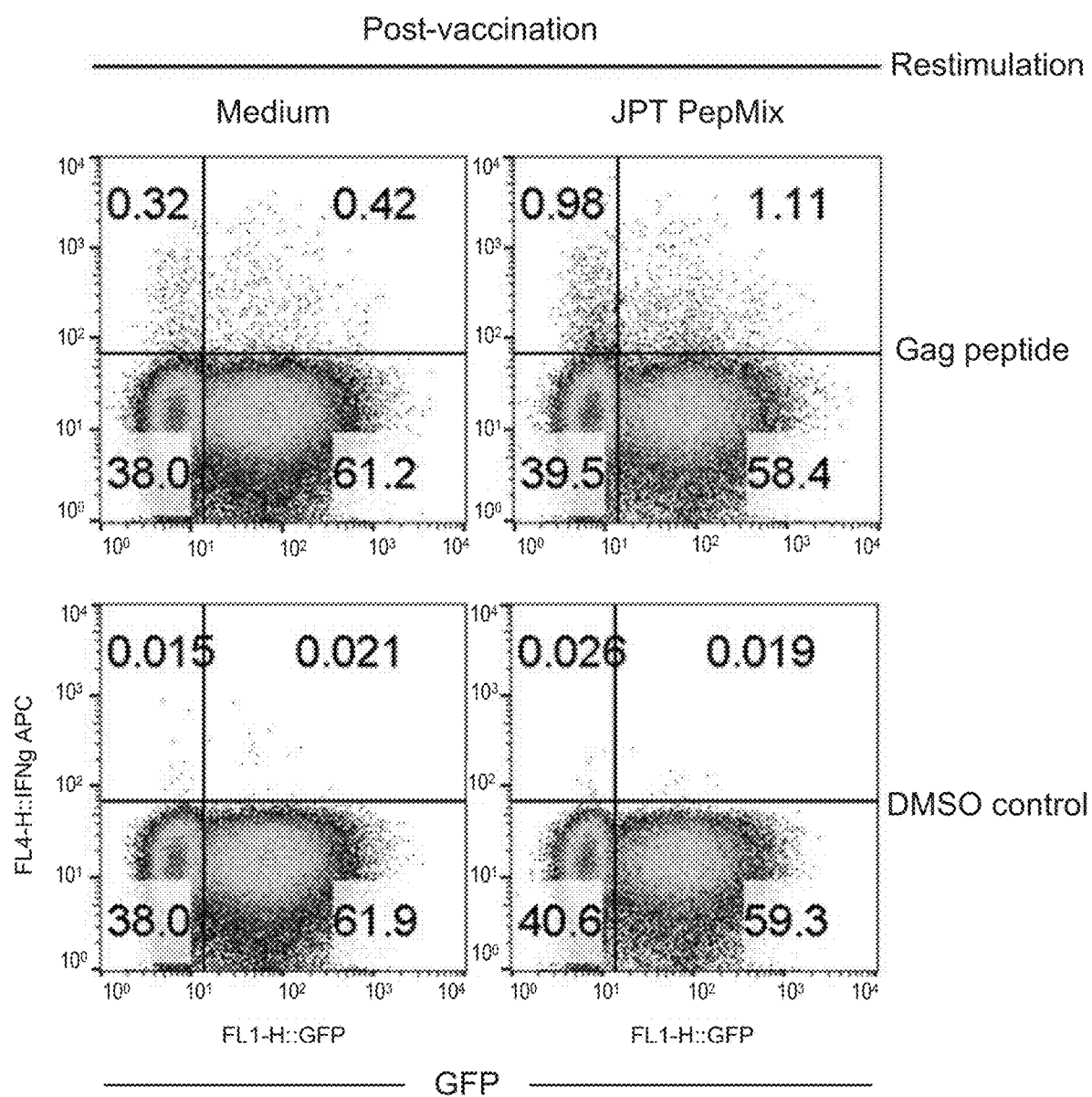
Figure 18D:
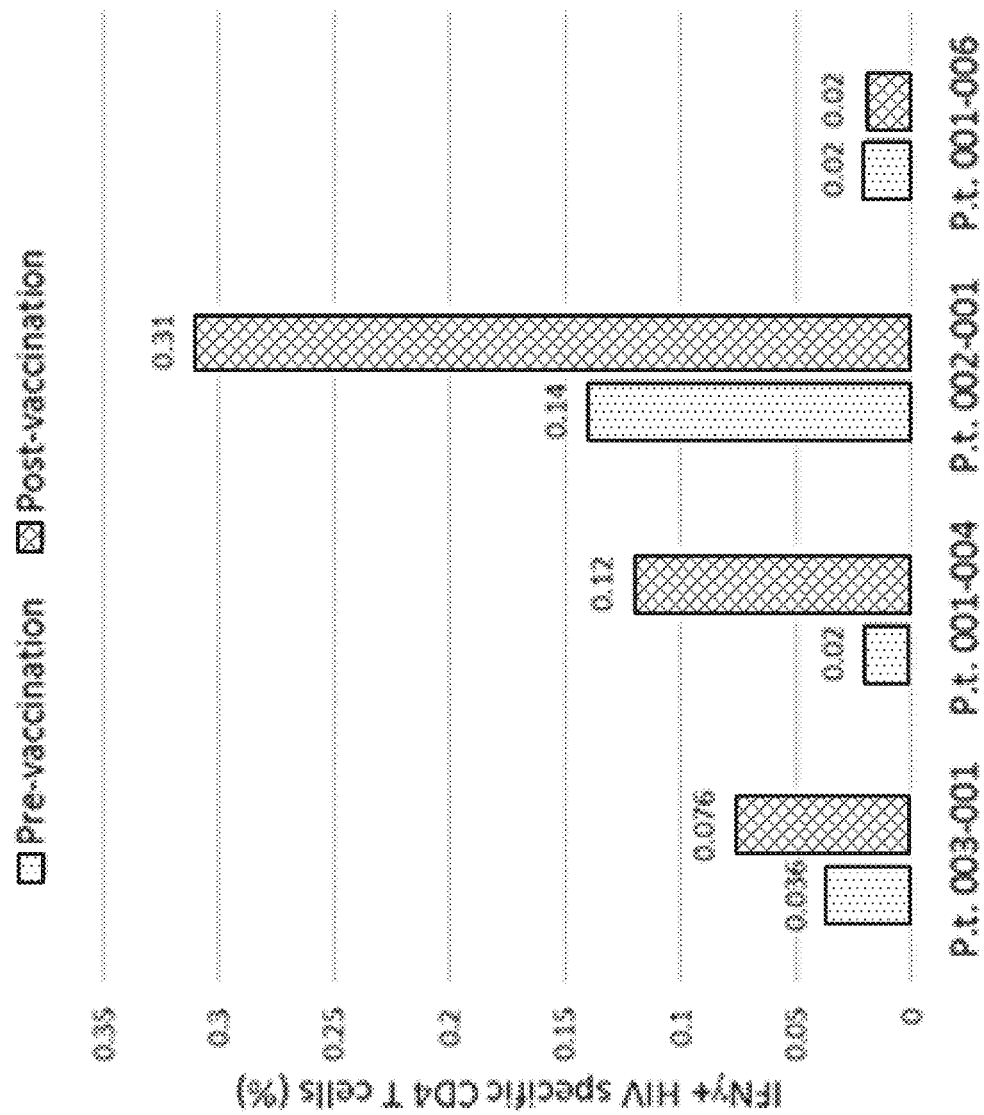
Figure 18E:
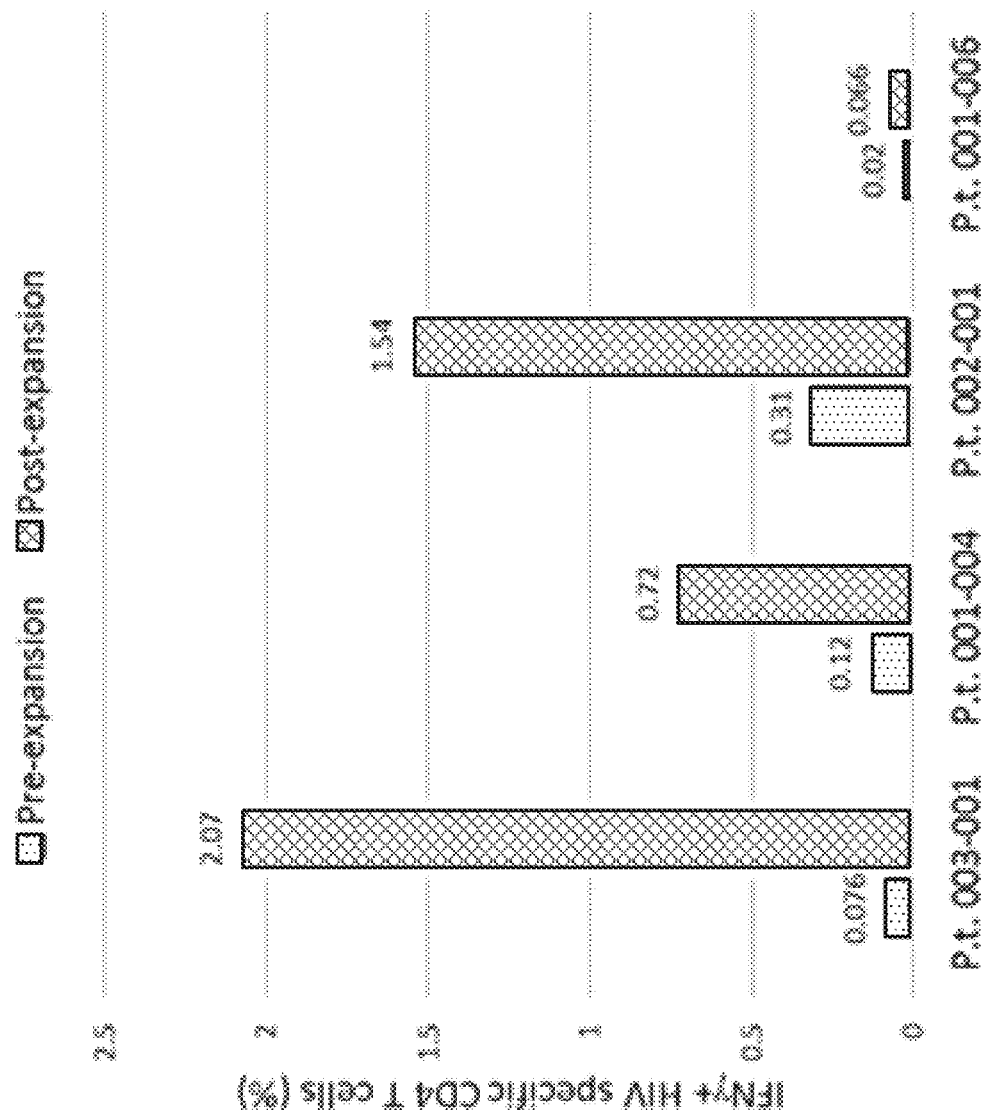

FIG. 18A describes the schedule of treatment. FIG. 18B demonstrates that PBMCs were stimulated with Gag peptide or DMSO control for 20 hours. IFN gamma production was detected by intracellular staining by FACS. CD4$^+$ T cells were gated for analysis. FIG. 18C demonstrates CD4 T cells were expanded and transduced with AGT103-GFP using the method as shown in FIG. 18A. Expanded CD4 T cells were rested in fresh medium without any cytokine for 2 days and re-stimulated with Gag peptide or DMSO control for 20 hours. IFN gamma production and GFP expression was detected by FACS. CD4 T cells were gated for analysis. FIG. 18D demonstrates frequency of HIV-specific CD4 T cells (IFN gamma positive, pre- and post-vaccination) were detected from 4 patients. Panel E demonstrates Post-vaccination PBMCs from 4 patients were expanded and HIV-specific CD4 T cells were examined.

Example 15: Dose Response

Vector Construction. A modified version of AGT103 was constructed to test the dose response for increasing AGT103 and its effects on cell surface CCR5 levels. The AGT103 was modified to include a green fluorescent protein (GFP) expression cassette under control of the CMV promoter. Transduced cells expression the miR30CCR5 miR21 Vif miR 185Tat micro RNA cluster and emit green light due to expressing GFP.

Functional assay for dose response of increasing AGT103-GFP and inhibition of CCR5 expression. CEM-CCR5 T cells were transduced with AGT103-GFP using multiplicity of infection per cell from 0 to 5. Transduced cells were stained with a fluorescently conjugated (APC) monoclonal antibody specific for cell surface CCR5. The intensity of staining is proportional to the number of CCR5 molecules per cell surface. The intensity of green fluorescence is proportional to the number of integrated AGT103-GFP copies per cell.

Figure 19A:
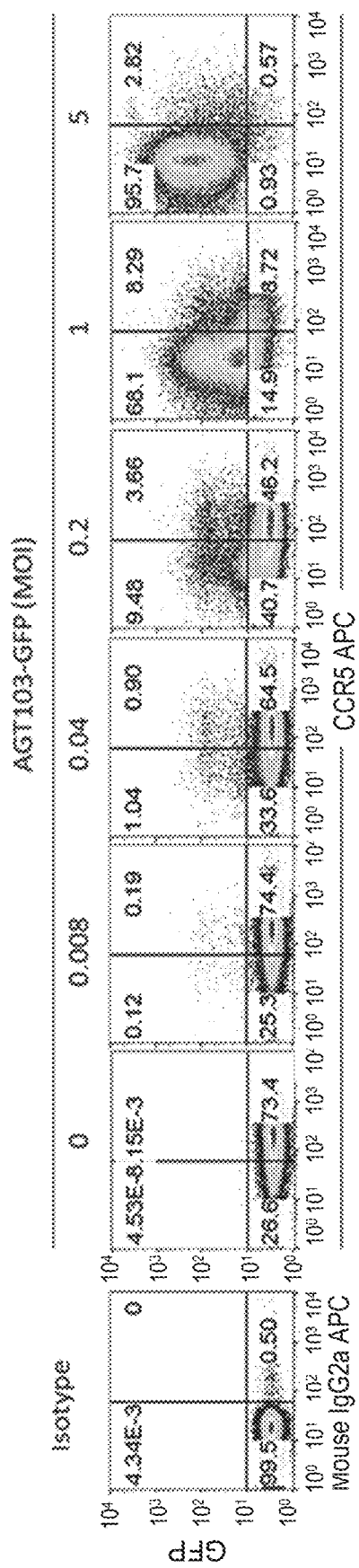
FIGS. 19A-19C depict data demonstrating a functional assay for a dose response of increasing AGT103-GFP and inhibition of CCR5 expression.
Figure 19B:
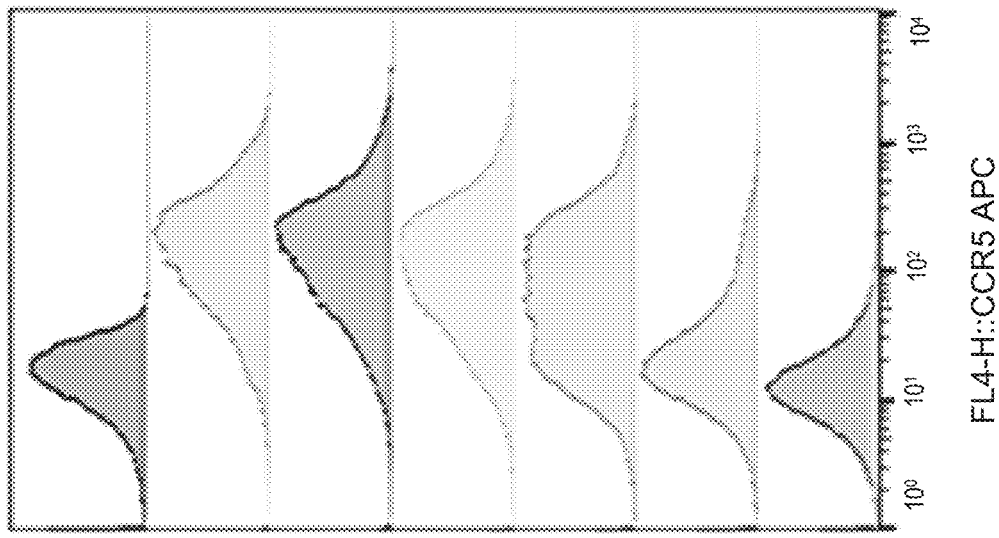
Figure 19C:
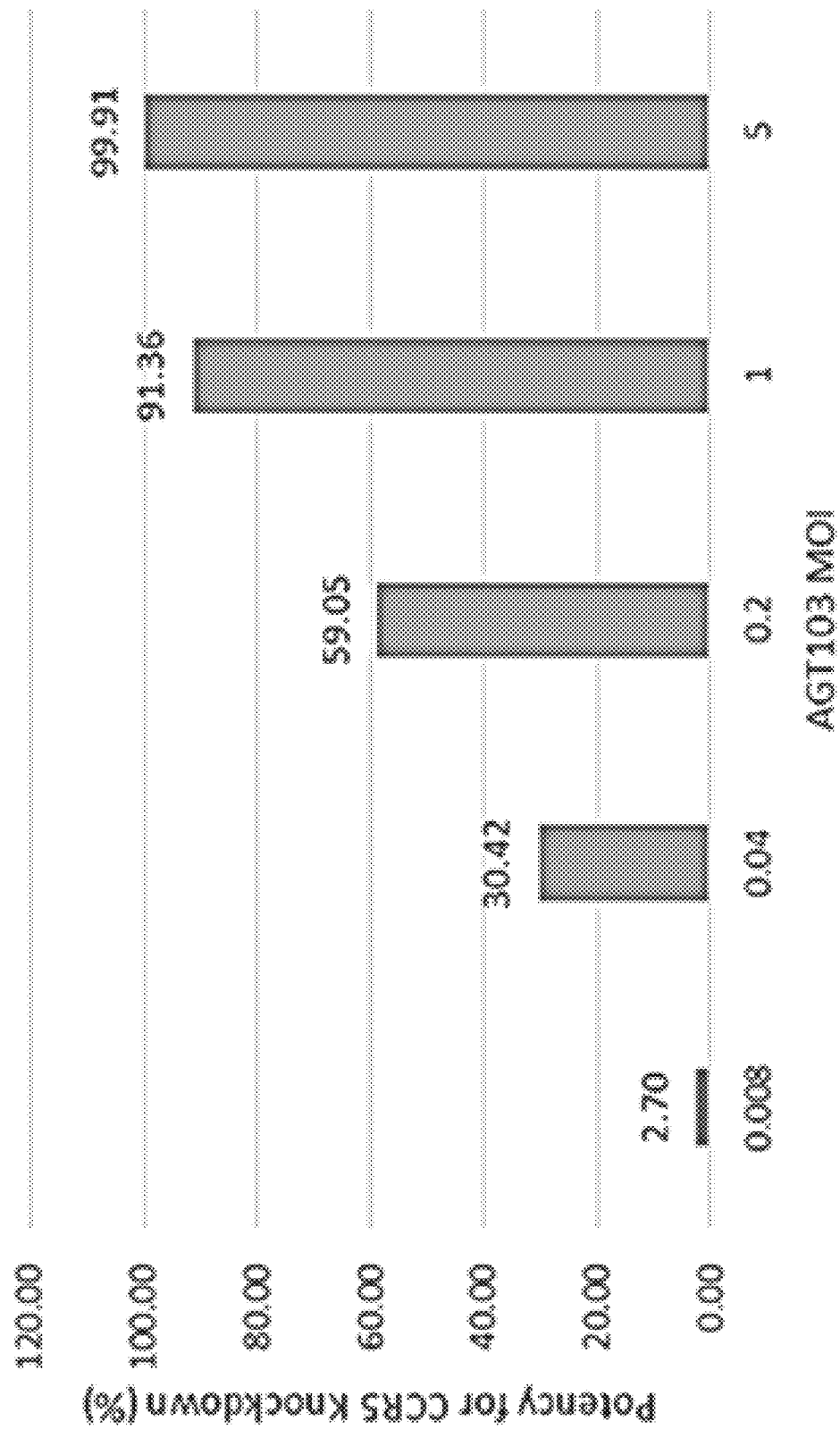

FIG. 19A demonstrates the dose response for increasing AGT103-GFP and its effects on cell surface CCR5 expression. At multiplicity of infection equal to 0.4 only 1.04% of cells are both green (indicating transduction) and showing significantly reduced CCR5 expression. At multiplicity of infection equal to 1 the number of CCR5low, GFP+ cells increases to 68.1%/At multiplicity of infection equal to 5 the number of CCR5low, GFP+ cells increased to 95.7%. These data are presented in histogram form in FIG. 19B that shows a normally distribution population in terms of CCR5 staining, moving toward lower mean fluorescence intensity with increasing doses of AGT103-GFP. The potency of AGT103-GFP is presented in graphical form in FIG. 19C showing the percentage inhibition of CCR5 expression with increasing doses of AGT103-GFP. At multiplicity of infection equal to 5, there was greater than 99% reduction in CCR5 expression levels.

Example 16: AGT103 Efficiently Transduces Primary Human CD4+ T Cells

Transducing primary CD4 T cells with AGT103 lentivirus vector. A modified AGT103 vector containing the green fluorescence protein marker (GFP) was used at multiplicities of infection between 0.2 and 5 for transducing purified, primary human CD4 T cells.

Figure 20A:
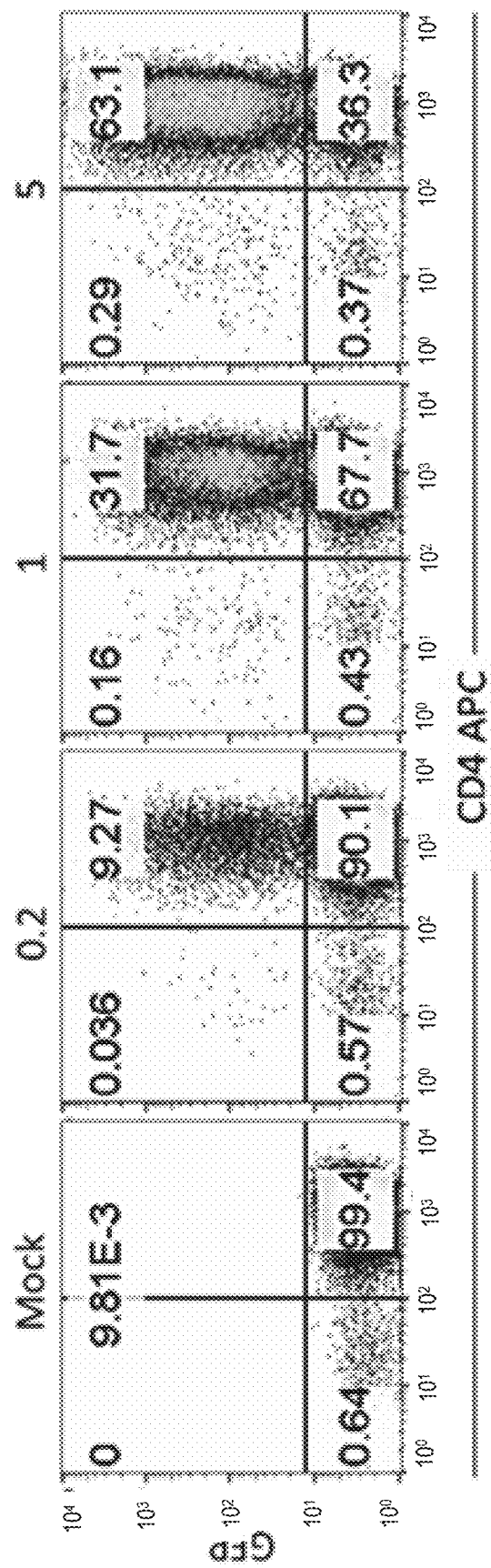
FIGS. 20A-20B depict data demonstrating AGT103 transduction efficiency for primary human CD4+ T cells.
Figure 20B:
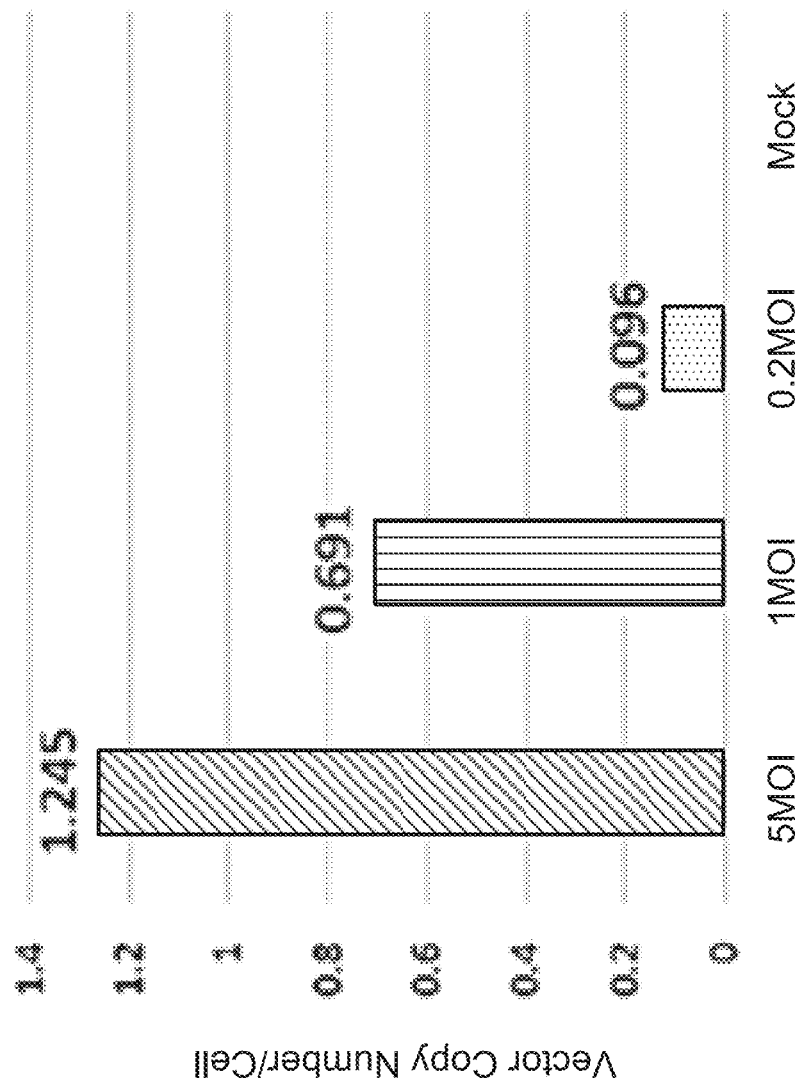

Functional assay for transduction efficiency of AGT103 in primary human CD4 T cells. CD4 T cells were isolated from human PBMC (HIV-negative donor) using magnetic bead labeled antibodies and standard procedures. The purified CD4 T cells were stimulated ex vivo with CD3/CD28 beads and cultured in media containing interleukin-2 for 1 day before AGT103 transduction. The relationship between lentivirus vector dose (the multiplicity of infection) and transduction efficiency is demonstrated in FIG. 20A showing that multiplicity of infection equal to 0.2 resulted in 9.27% of CD4 positive T cells being transduced by AGT103 and that value was increased to 63.1% of CD4 positive T cells being transduced by AGT103 with a multiplicity of infection equal to 5. In addition to achieving efficient transduction of primary CD4 positive T cells it is also necessary to quantify the number of genome copies per cell. In FIG. 20B total cellular DNA from primary human CD4 T cells transduced at several multiplicities of infection were tested by quantitative PCR to determine the number of genome copies per cell. In a multiplicity of infection equal to 0.2 we measured 0.096 genome copies per cell that was in good agreement with 9.27% GFP positive CD4 T cells in FIG. 20A. Multiplicity of infection equal to 1 generated 0.691 genome copies per cell and multiplicity of infection equal to 5 generated 1.245 genome copies per cell.

As shown in FIGS. 20A-20B, CD4 T cells isolated from PBMC were stimulated with CD3/CD28 beads plus IL-2 for 1 day and transduced with AGT103 at various concentrations. After 2 days, beads were removed and CD4 T cells were collected. As shown in FIG. 20A, frequency of transduced cells (GFP positive) were detected by FACS. As shown in FIG. 20B, the number of vector copies per cell was determined by qPCR. At a multiplicity of infection (MOI) of 5, 63% of CD4 T cells were transduced with an average of 1 vector copy per cell.

Example 17: AGT103 Inhibits HIV Replication in Primary CD4+ T Cells

Protecting primary human CD4 positive T cells from HIV infection by transducing cells with AGT103. Therapeutic lentivirus AGT103 was used for transducing primary human CD4 positive T cells at multiplicities of infection between 0.2 and 5 per cell. The transduced cells were then challenged with a CXCR4-tropic HIV strain NL4.3 that does not require cell surface CCR5 for penetration. This assay tests the potency of microRNA against Vif and Tat genes of HIV in terms of preventing productive infection in primary CD4 positive T cells, but uses an indirect method to detect the amount of HIV released from infected, primary human CD4 T cells.

Functional assay for AGT103 protection against CXCR4-tropic HIV infection of primary human ('D4 positive T cells. CD4 T cells were isolated from human PBMC (HIV-negative donor) using magnetic bead labeled antibodies and standard procedures. The purified CD4 T cells were stimulated ex vivo with CD3/CD28 beads and cultured in media containing interleukin-2 for 1 day before AGT103 transduction using multiplicities of infection between 0.2 and 5. Two days after transduction the CD4 positive T cell cultures were challenged with HIV strain NL4.3 that was engineered to express the green fluorescent protein (GFP). The transduced and HIV-exposed primary CD4 T cell cultures were maintained for 7 days before collecting cell-free culture fluids containing HIV. The cell-free culture fluids were used to infect a highly permissive T cell line C8166 for 2 days. The proportion of HIV-infected C8166 cells was determined by flow cytometry detecting GFP fluorescence. With a mock lentivirus infection, the dose of 0.1 multiplicity of infection for NL4.3 HIV resulted in an amount of HIV being released into culture fluids that was capable of establishing productive infection in 15.4% of C8166 T cells. With the dose 0.2 multiplicity of infection for AGT103, this value for HIV infection of C8166 cells is reduced to 5.3% and multiplicity of infection equal to 1 for AGT103 resulted in only 3.19% of C8166 T cells being infected by HIV. C8166 infection was reduced further to 0.62% after AGT103 transduction using a multiplicity of infection equal to 5. There is a clear dose response relationship between the amount of AGT103 used for transduction and the amount of HIV released into the culture medium.

Figure 21:
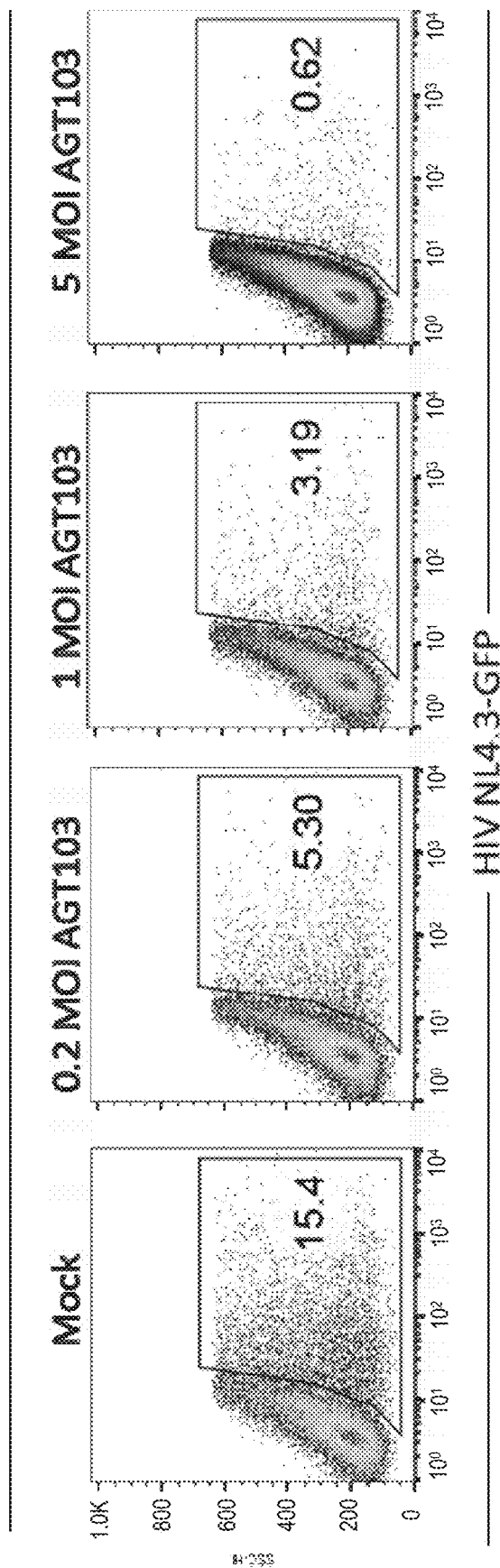
FIG. 21 depicts data demonstrating AGT103 inhibition of HIV replication in primary CD4+ T cells, as described herein.

As shown in FIG. 21, CD4 T cells isolated from PBMC were stimulated with CD3/CD28 beads plus IL-2 for 1 day and transduced with AGT103 at various concentrations (MOI). After 2 days, beads were removed and CD4 T cells were infected with 0.1 MOI of HIV NL4.3-GFP. 24 hours later, cells were washed 3 times with PBS and cultured with IL-2 (30U/ml) for 7 days. At the end of the culture, supernatant was collected to infect the HIV permissive cell line C8166 for 2 days. HIV-infected C8166 cells (GFP positive) were detected by FACS. There was a reduction in viable HIV with an increase in the multiplicity of infection of AGT103 as observed by less infection of C8166 cells MOI 0.2-65.6%, MOI 1=79.3%, and MOI 5=96%).

Example 18: AGT103 Protects Primary Human CD4$^+$ T Cells from HIV-Induced Depletion AGT103 Transduction of Primary Human CD4 T Cells to Protect Against HIV-Mediated cytopathology and cell depletion. PBMC were obtained from healthy, HIV-negative donors and stimulated with CD3/CD28 beads then cultured for 1 day in medium containing interleukin-2 before AGT103 transduction using multiplicities of infection between 0.2 and 5.

Functional assay for AGT103 protection of primary human CD4 T cells against HIV-mediated cytopathology. AGT103-transduced primary human CD4 T cells were infected with HIV NL 4.3 strain (CXCR4-tropic) that does not require CCR5 for cellular entry. When using the CXCR4-tropic NL 4.3, only the effect of Vif and Tat microRNA on HIV replication is being tested. The dose of HIV NL 4.3 was 0.1 multiplicity of infection. One day after HIV infection, cells were washed to remove residual virus and cultured in medium plus interleukin-2. Cells were collected every three days during a 14-day culture then stained with a monoclonal antibody that was specific for CD4 and directly conjugated to a fluorescent marker to allow measurement of the proportion of CD4 positive T cells in PBMC. Untreated CD4 T cells or CD4 T cells transduced with the control lentivirus vector were highly susceptible to HIV challenge and the proportion of CD4 positive T cells in PBMC fell below 10% by day 14 culture. In contrast, there was a dose-dependent effect of AGT103 on preventing cell depletion by HIV challenge. With a AGT103 dose of 0.2 multiplicity of infection more than 20% of PBMC were CD4 T cells by day 14 of culture and this value increased to more than 50% of PBMC being CD4 positive T cells by day 14 of culture with a AGT103 dose of multiplicity of infection equal to 5. Again, there is a clear dose response effect of AGT103 on HIV cytopathogenicity in human PBMC.

Figure 22:
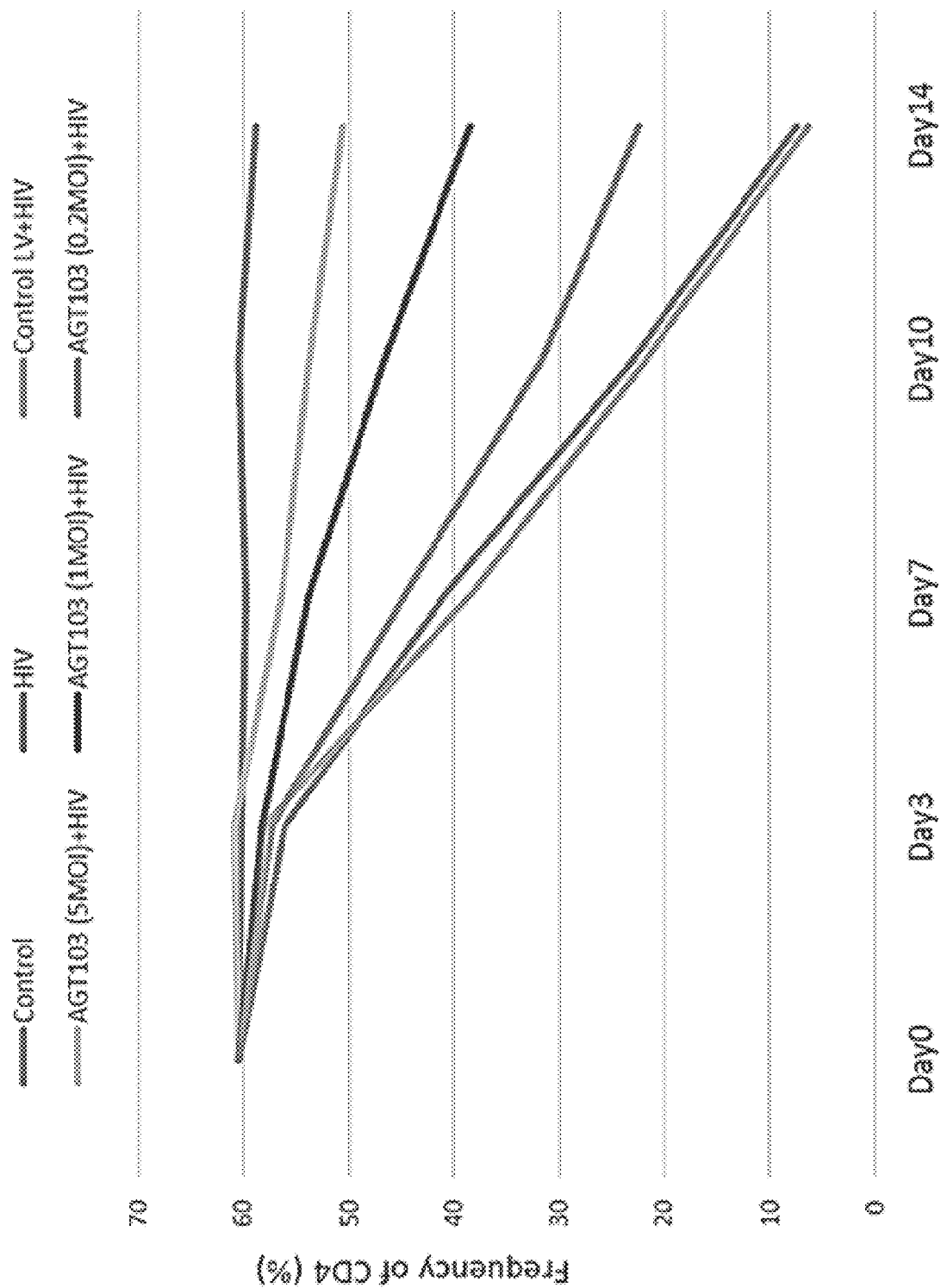
FIG. 22 depicts data demonstrating AGT103 protection of primary human CD4 T cells from HIV-induced depletion.

As shown in FIG. 22, PBMCs were stimulated with CD3/CD28 beads plus IL-2 for 1 day and transduced with AGT103 at various concentrations (MOI). After 2 days, beads were removed and cells were infected with 0.1 MOI of HIV NL4.3. 24 hours later, cells were washed 3 times with PBS and cultured with IL-2 (30U/ml). Cells were collected every 3 days and the frequency of CD4 T cells were analyzed by FACS. After 14 days of exposure to HIV, there was an 87% reduction in CD4 T cells transduced with LV-Control, a 60% reduction with AGT103 MOI 0.2, a 37% reduction with AGT103 MOI 1, and a 17% reduction with AGT103 MOI 5.

Figure 23A:
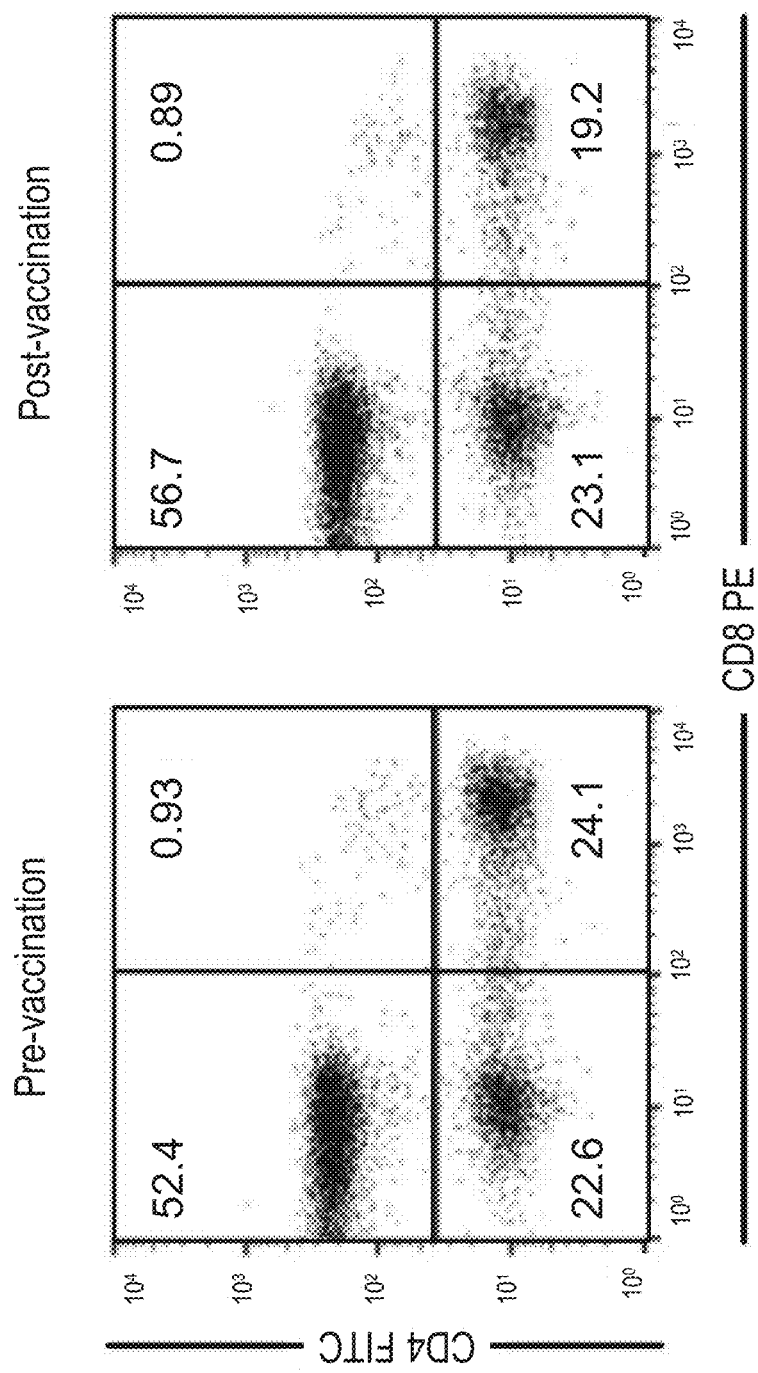
FIGS. 23A-D depict data demonstrating generation of a CD4+ T cell population that is highly enriched for HIV-specific, AGT103-transduced CD4 T cells.

Example 19: Generating a Population of CD4+ T Cells Enriched for HIV-Specificity and Transduced with AGT103/CMV-GFP Therapeutic vaccination against HIV had minimal effect on the distribution of CD4+, CD8+ and CD4+/CD8+ T cells. As shown in FIG. 23A, the CD4 T cell population is shown in the upper left quadrant of the analytical flow cytometry dot plots, and changes from 52% to 57% of total T cells after the vaccination series. These are representative data.

Figure 23B:
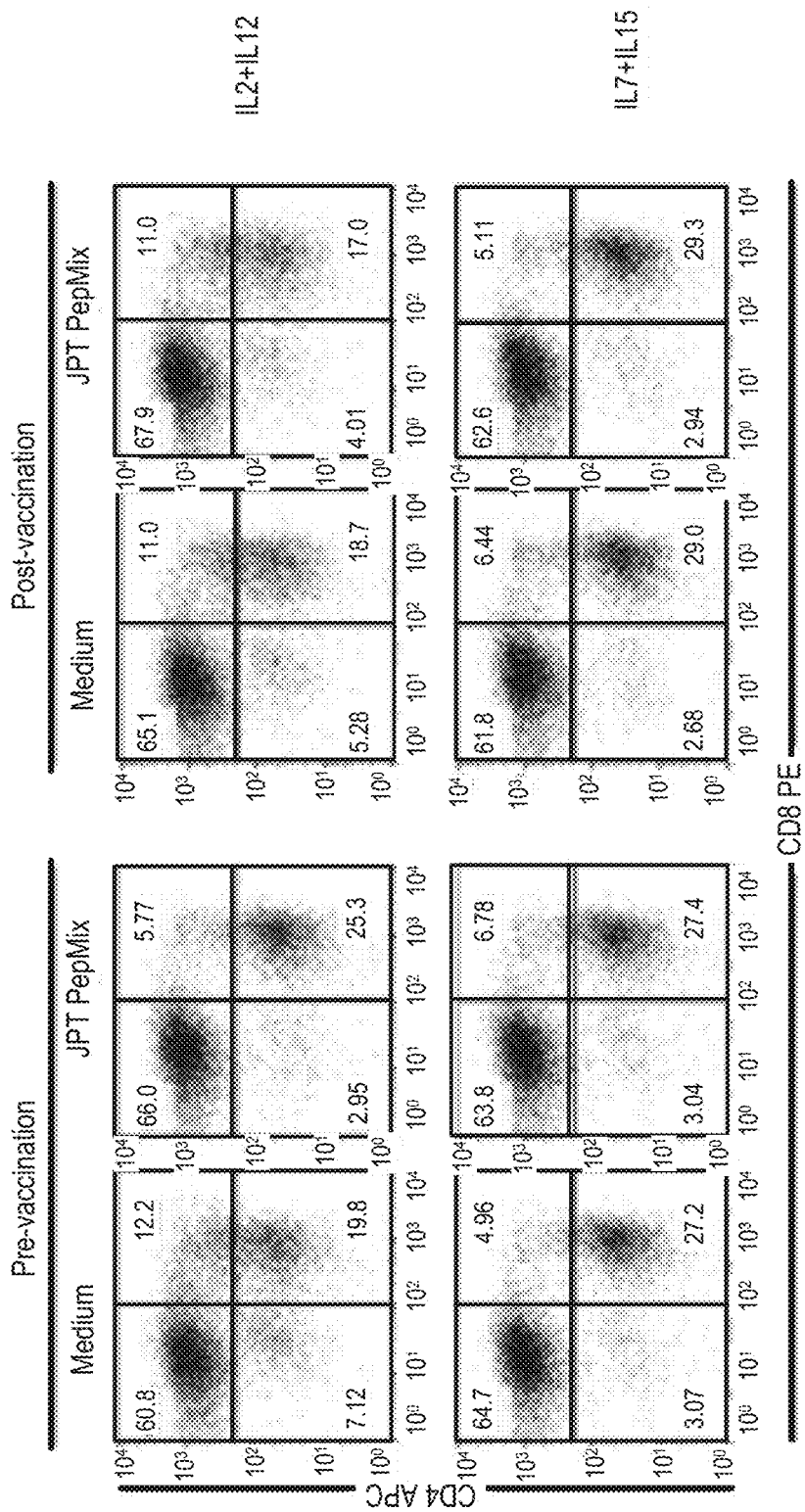

Peripheral blood mononuclear cells from a participant in an HIV therapeutic vaccine trial were cultured for 12 days in medium +/−interleukin-2/interleukin-12 or +/−interleukin-7/interleukin-15. Some cultures were stimulated with overlapping peptides representing the entire p55 Gag protein of HIV-1 (HIV (GAG) Ultra peptide mixture) as a source of epitope peptides for T cell stimulation. These peptides are 10-20 amino acids in length and overlap by 20-50% of their length to represent the entire Gag precursor protein (p55) from HIV-1 BaL strain. The composition and sequence of individual peptides can be adjusted to compensate for regional variations in the predominant circulating HIV sequences or when detailed sequence information is available for an individual patient receiving this therapy. At culture end, cells were recovered and stained with anti-CD4 or anti-CD8 monoclonal antibodies and the CD3+ population was gated and displayed here. The HIV (GAG) Ultra peptide mixture stimulation for either pre- or post-vaccination samples was similar to the medium control indicating that HIV (GAG) Ultra peptide mixture was not toxic to cells and was not acting as a polyclonal mitogen. The results of this analysis can be found in FIG. 23B.

HIV (GAG) Ultra peptide mixture and interleukin-2/interleukin-12 provided for optimal expansion of antigen-specific CD4 T cells. As shown in the upper panels of FIG. 23C, there was an increase in cytokine (interferon-gamma) secreting cells in post-vaccination specimens exposed to HIV (GAG) Ultra peptide mixture. In the pre-vaccination sample, cytokine secreting cells increased from 0.43 to 0.69% as a result of exposure to antigenic peptides. In contrast, the post-vaccination samples showed an increase of cytokine secreting cells from 0.62 to 1.76% of total CD4 T cells as a result of peptide stimulation. These data demonstrate the strong impact of vaccination on the CD4 T cell responses to HIV antigen.

Figure 23C:
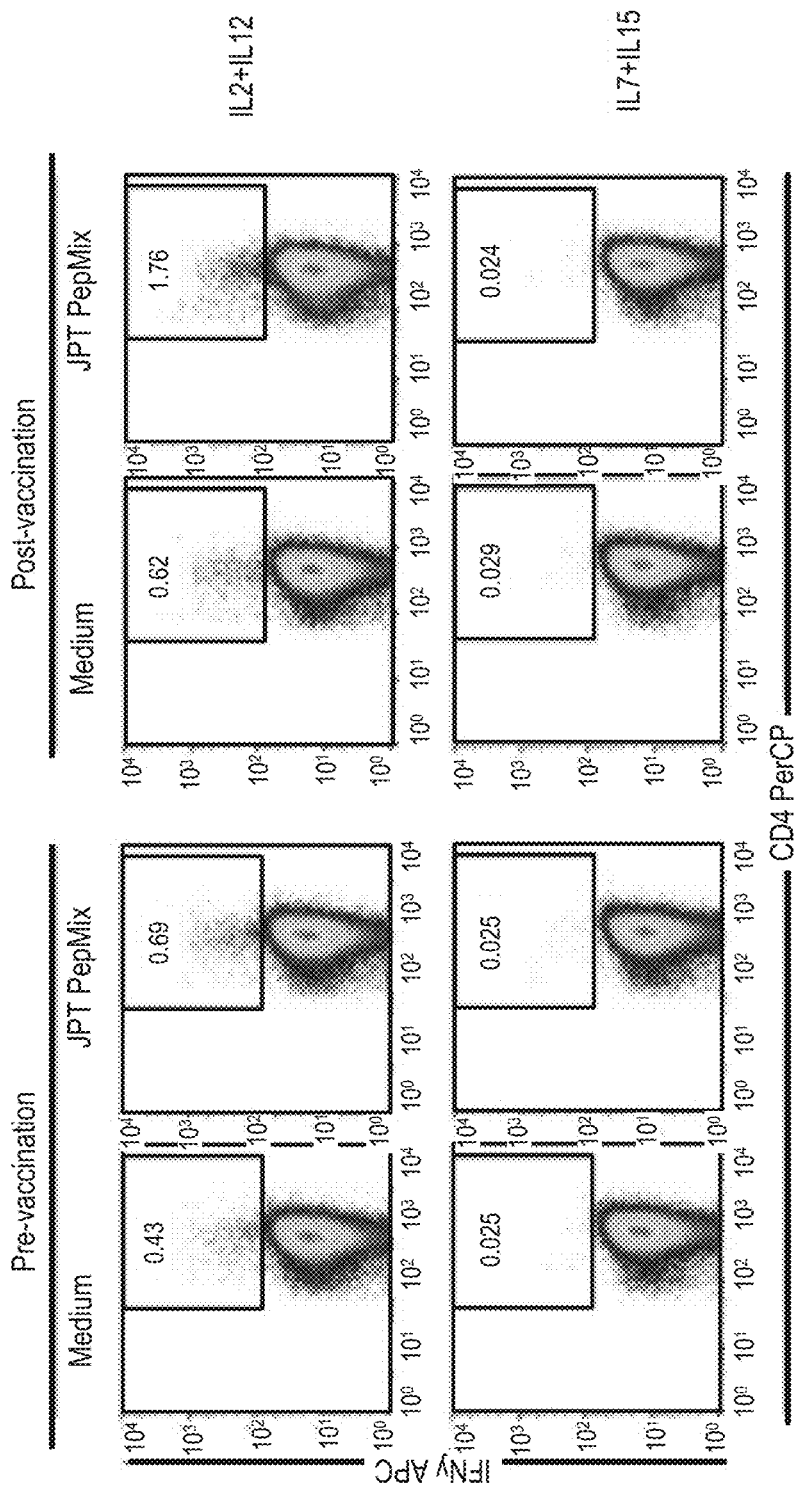
Figure 23D:
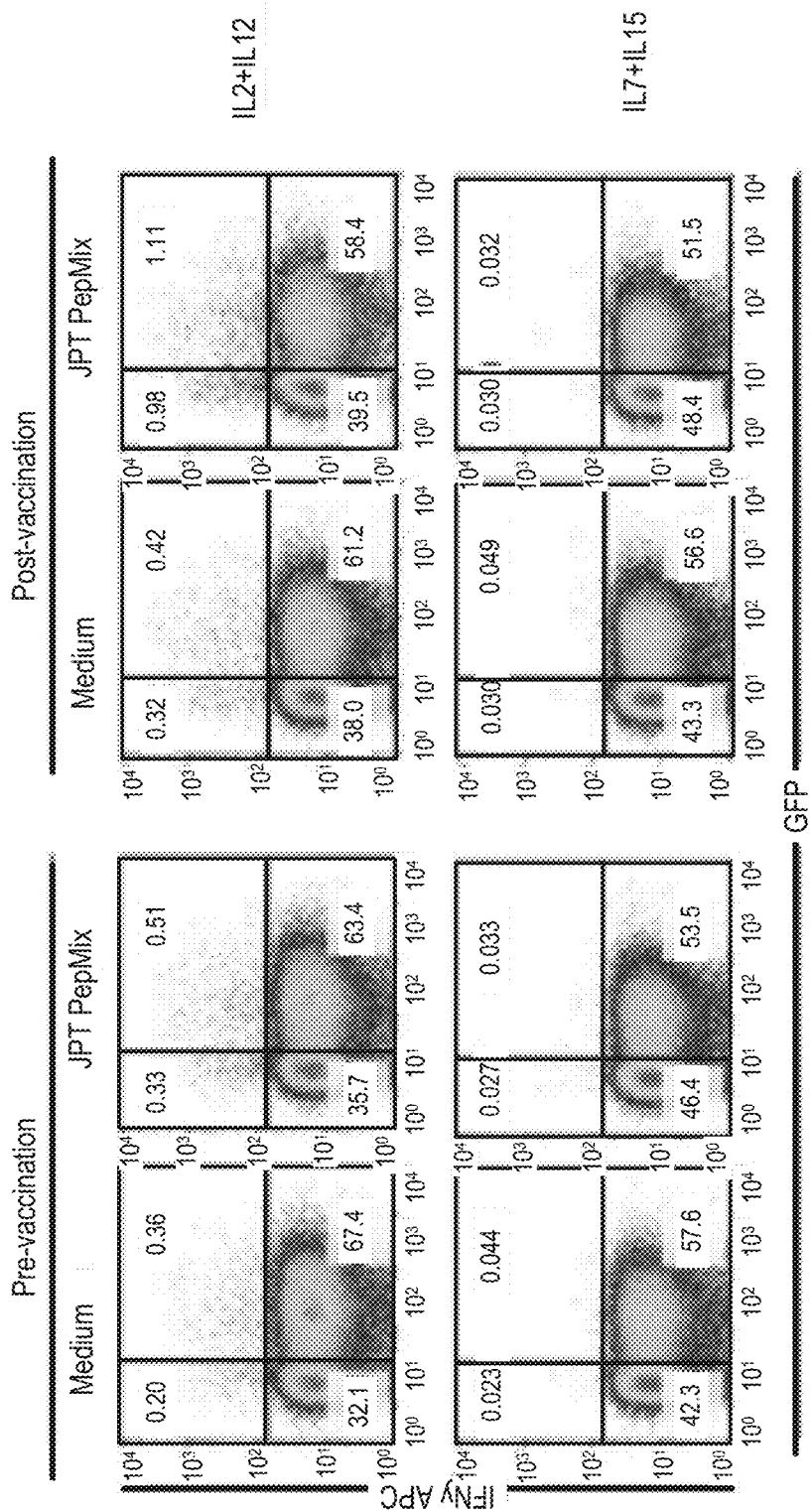

Finally, AGT103/CMV-GFP transduction of antigen-expanded CD4 T cells produced HIV-specific and HIV-resistant helper CD4 T cells that are needed for infusion into patients as part of a functional cure for HIV (in accordance with other various aspects and embodiments, AGT103 alone is used; for example, clinical embodiments may not include the CMV-GFP segment). The upper panels of FIG. 23C show the results of analyzing the CD4+ T cell population in culture. The x axis of FIG. 23C shows Green Fluorescent Protein (GFP) emission indicating that individual cells were transduced with the AGT103/CMV-GFP. In the post-vaccination samples 1.11% of total CD4 T cells that were both cytokine secreting was recovered, indicating that the cells are responding specifically to HIV antigen, and transduced with AGT103/CMV-GFP. This is the target cell population and the clinical product intended for infusion and functional cure of HIV. With the efficiency of cell expansion during the antigen stimulation and subsequent polyclonal expansion phases of ex vivo culture, 4×10$^8$ antigen-specific, lentivirus transduced CD4 T cells can be produced. This exceeds the target for cell production by 4-fold and will allow achievement of a count of antigen-specific and HIV-resistant CD4

T cells of approximately 40 cells/microliter of blood or around 5.7% of total circulating CD4 T cells.

Table 4 below shows the results of the ex vivo production of HIV-specific and HIV-resistant CD4 T cells using the disclosed vectors and methods.

TABLE 4

| Material/manipulation | Total CD4 T cells | Percentage HIV-specific | Percentage HIV-specific and HIV-resistant |
|---|---|---|---|
| Leukapheresis pack from HIV+ patient | ~7 × 10$^8$ | ~0.12 | N/A |
| Peptide expansion ex vivo | ~8 × 10$^8$ | ~2.4 | N/A |
| Mitogen expansion | ~1.5 × 10$^{10}$ | ~2.4 | N/A |
| Lentivirus transduction | ~1.5 × 10$^{10}$ | ~2.4 | ~1.6 |

Example 20: Clinical Study for Treatment of HIV

AGT103T is a genetically modified autologous PBMC containing >5×10$^7$ HIV-specific CD4 T cells that are also transduced with AGT103 lentivirus vector.

A Phase I clinical trial will test the safety and feasibility of infusing ex vivo modified autologous CD4 T cells (AGT103T) in adult research participants with confirmed HIV infection, CD4+ T-cell counts >600 cells per mm$^3$ of blood and stable virus suppression below 200 copies per ml of plasma while on cART. All study participants will continue receiving their standard antiretroviral medications through the Phase I clinical trial. Up to 40 study participants receive two doses by intramuscular injection 8 weeks apart, of recombinant modified vaccinia Ankara (rMVA) expressing HIV Gag, Pol and Env proteins. Seven to 10 days after the second immunization a blood sample is collected for in vitro testing to measure the frequency of CD4+ T-cells that respond to stimulation with a pool of overlapping, synthetic peptides representing the HIV-1 Gag polyprotein. Subjects in the upper half of vaccine responders, based on measuring the frequency of Gag-specific CD4 T cells are enrolled in the gene therapy arm and subjects in the lower half of responders do not continue in the study. We anticipate that the cut-off for higher responders is a HIV-specific CD4+ T cell frequency≥0.065% of total CD4 T cells. Subjects enrolled into the gene therapy arm of our trial undergo leukapheresis followed by purification of PBMC (using Ficoll density gradient centrifugation or negative selection with antibodies) that are cultured ex vivo and stimulated with HIV Gag peptides plus interleukin-2 and interleukin-12 for 12 days, then stimulated again with beads decorated with CD3/CD28 bispecific antibody. The antiretroviral drug Saquinavir is included at 100 nM to prevent emergence of autologous HIV during ex vivo culture. One day after CD3/CD28 stimulation cells are transduced with AGT103 at multiplicity of infection between 1 and 10. The transduced cells are cultured for an additional 7-14 days during which time they expand by polyclonal proliferation. The culture period is ended by harvesting and washing cells, setting aside aliquots for potency and safety release assays, and resuspending the remaining cells in cryopreservation medium. A single dose is ≤1×10$^{10}$ autologous PBMC. The potency assay measures the frequency of CD4 T cells that respond to peptide stimulation by expressing interferon-gamma. Other release criteria include the product must include≥0.5×10$^7$ HIV-specific CD4 T cells that are also transduced with AGT103. Another release criterion is that the number of AGT103 genome copies per cell must not exceed 3. Five days before infusion with AGT103T subjects receive one dose of busulfuram (or Cytoxan) conditioning regimen followed by infusion of ≤1 ×10$^{10}$ PBMC containing genetically modified CD4 T cells.

A Phase II study will evaluate efficacy of AGT103T cell therapy. Phase II study participants include individuals enrolled previously in our Phase I study who were judged to have successful and stable engraftment of genetically modified, autologous, HIV-specific CD4 T cells and clinical responses defined as positive changes in parameters monitored as described in efficacy assessments (1.3.). Study participants will be asked to add Maraviroc to their existing regimen of antiretroviral medication. Maraviroc is a CCR5 antagonist that will enhance the effectiveness of genetic therapy directed at reducing CCR5 levels. Once the Maraviroc regimen is in place subjects will be asked to discontinue the previous antiretroviral drug regimen and only maintain Maraviroc monotherapy for 28 days or until plasma viral RNA levels exceed 10,000 per ml on 2 sequential weekly blood draws. Persistently high viremia requires participants to return to their original antiretroviral drug regimen with or without Maraviroc according to recommendations of their HIV care physician.

If participants remain HIV suppressed (below 2,000 vRNA copies per ml of plasma) for >28 days on Maraviroc monotherapy, they will be asked to gradually reduce Maraviroc dosing over a period of 4 weeks followed by intensive monitoring for an additional 28 days. Subjects who maintained HIV suppression with Maraviroc monotherapy are considered to have a functional cure. Subjects who maintain HIV suppression even after Maraviroc withdrawal also have a functional cure. Monthly monitoring for 6 months followed by less intensive monitoring will establish the durability of functional cure.

Patient Selection
Inclusion Criteria:
  Aged between 18 and 60 years.
  Documented HIV infection prior to study entry.
  Must be willing to comply with study-mandated evaluations; including not changing their antiretroviral regimen (unless medically indicated) during the study period.
  CD4+ T-cell count >600 cell per millimeter cubed (cells/mm3)
  CD4+ T-cell nadir of >400 cells/mm3
  HIV viral load <1,000 copies per milliliter (mL)
Exclusion Criteria:
  Any viral hepatitis
  Acute HIV infection
  HIV viral load >1,000 copies/mL
  Active or recent (prior 6 months) AIDS defining complication.
  Any change in HIV medications within 12 weeks of entering the study
  Cancer or malignancy that has not been in remission for at least 5 years with the exception of successfully treated basal cell carcinoma of the skin
  Current diagnosis of NYHA grade 3 or 4 congestive heart failure or uncontrolled angina or arrhythmias
  History of bleeding problems
  Use of chronic steroids in past 30 days
  Pregnant or breast feeding
  Active drug or alcohol abuse
  Serious illness in past 30 days
  Currently participating in another clinical trial or any prior gene therapy Safety Assessments
  Acute infusion reaction
  Post-infusion safety follow-up
Efficacy Assessments—Phase I
  Number and frequency of modified CD4 T cells.
  Durability of modified CD4 T cells.
  In vitro response to Gag peptide restimulation (ICS assay) as a measure of memory T cell function.
  Polyfunctional anti-HIV CD8 T cell responses compare to pre- and post-vaccination time points.
  Frequency of CD4 T cells making doubly spliced HIV mRNA after in vitro stimulation.
Efficacy Assessments—Phase II
  Number and frequency of genetically modified CD4 T cells.
  Maintenance of viral suppression (<2,000 vRNA copies per ml but 2 consecutive weekly draws not exceeding 5×104 vRNA copies per ml are permitted) with Maraviroc monotherapy.
  Continued virus suppression during and after Maraviroc withdrawal.
  Stable CD4 T cell count.

AGT103T consists of up to $1 \times 10^{10}$ genetically modified, autologous CD4+ T cells containing $\geq 5 \times 10^7$ HIV-specific CD4 T cells that are also transduced with AGT103 lentivirus vector. A Phase I clinical trial will test the safety and feasibility of infusing ex vivo modified autologous CD4 T cells (AGT103T) in adult research participants with confirmed HIV infection, CD4+ T-cell counts >600 cells per $mm^3$ of blood and stable virus suppression below 200 copies per ml of plasma while on cART. Up to 40 study participants receive two doses by intramuscular injection 8 weeks apart, of recombinant modified vaccinia Ankara (rMVA) expressing HIV Gag, Pol and Env proteins. Seven to 10 days after the second immunization a blood sample is collected for in vitro testing to measure the frequency of CD4+ T-cells that respond to stimulation with a pool of overlapping, synthetic peptides representing the HIV-1 Gag polyprotein. Subjects in the upper half of vaccine responders, based on measuring the frequency of Gag-specific CD4 T cells are enrolled in the gene therapy arm and subjects in the lower half of responders do not continue in the study. We anticipate that the cut-off for higher responders is a HIV-specific CD4+ T cell frequency ≥0.065% of total CD4 T cells. Subjects enrolled into the gene therapy arm of our trial undergo leukapheresis and the CD4+ T cells are enriched by negative selection. The enriched CD4 subset is admixed with 10% the number of cells from the CD4-negative subset to provide a source and antigen-presenting cells. The enriched CD4 T cells are stimulated with HIV Gag peptides plus interleukin-2 and interleukin-12 for 12 days, then stimulated again with beads decorated with CD3/CD28 bispecific antibody. The antiretroviral drug Saquinavir is included at 100 nM to prevent emergence of autologous HIV during ex vivo culture. One day after CD3/CD28 stimulation cells are transduced with AGT103 at multiplicity of infection between 1 and 10. The transduced cells are cultured for an additional 7-14 days during which time they expand by polyclonal proliferation. The culture period is ended by harvesting and washing cells, setting aside aliquots for potency and safety release assays, and resuspending the remaining cells in cryopreservation medium. A single dose is $\leq 1 \times 10^{10}$ autologous cells enriched for the CD4+ T cell subset. The potency assay measures the frequency of CD4 T cells that respond to peptide stimulation by expressing interferon-gamma. Other release criteria include that the product must include $\geq 0.5 \times 10^7$ HIV-specific CD4 T cells that are also transduced with AGT103. Another release criterion is that the number of AGT103 genome copies per cell must not exceed 3. Five days before infusion with AGT103T subjects receive one dose of busulfuram (or Cytoxan) conditioning regimen followed by infusion of $\leq 1 \times 10^{10}$ enriched and genetically modified CD4 T cell.

A Phase II study will evaluate efficacy of AGT103T cell therapy. Phase II study participants include individuals enrolled previously in our Phase I study who were judged to have successful and stable engraftment of genetically modified, autologous, HIV-specific CD4 T cells and clinical responses defined as positive changes in parameters monitored as described in efficacy assessments (1.3.). Study participants will be asked to add Maraviroc to their existing regimen of antiretroviral medication. Maraviroc is a CCR5 antagonist that will enhance the effectiveness of genetic therapy directed at reducing CCR5 levels. Once the Maraviroc regimen is in place subjects will be asked to discontinue the previous antiretroviral drug regimen and only maintain Maraviroc monotherapy for 28 days or until plasma viral RNA levels exceed 10,000 per ml on 2 sequential weekly blood draws. Persistently high viremia requires participants to return to their original antiretroviral drug regimen with or without Maraviroc according to recommendations of their HIV care physician.

If participants remain HIV suppressed (below 2,000 vRNA copies per ml of plasma) for >28 days on Maraviroc monotherapy, they will be asked to gradually reduce Maraviroc dosing over a period of 4 weeks followed by intensive monitoring for an additional 28 days. Subjects who maintained HIV suppression with Maraviroc monotherapy are considered to have a functional cure. Subjects who maintain HIV suppression even after Maraviroc withdrawal also have a functional cure. Monthly monitoring for 6 months followed by less intensive monitoring will establish the durability of functional cure.

Sequences
  The following sequences are referred to herein:

| SEQ ID NO: | Description | Sequence |
| --- | --- | --- |
| 1 | miR30 CCR5 | AGGTATATTGCTGTTGACAGTGAGCGACTGTAAAC TGAGCTTGCTCTACTGTGAAGCCACAGATGGGTAG AGCAAGCACAGTTTACCGCTGCCTACTGCCTCGGA CTTCAAGGGGCTT |
| 2 | miR21 Vif | CATCTCCATGGCTGTACCACCTTGTCGGGGGATGT GTACTTCTGAACTTGTGTTGAATCTCATGGAGTTCA GAAGAACACATCCGCACTGACATTTTGGTATCTTT CATCTGACCA |
| 3 | miR185 Tat | GGGCCTGGCTCGAGCAGGGGGCGAGGGATTCCGCT TCTTCCTGCCATAGCGTGG |

-continued

| SEQ ID NO: | Description | Sequence |
|---|---|---|
| | | TCCCCTCCCCTATGGCAGGCAGAAGCGGCACCTTC CCTCCCAATGACCGCGTCTTCGTCG |
| 4 | Elongation Factor-1 alpha (EF1-alpha) promoter | CCGGTGCCTAGAGAAGGTGGCGCGGGGTAAACTG GGAAAGTGATGTCGTGTACTGGCTCCGCCTTTTCC CGAGGGTGGGGGAGAACCGTATATAAGTGCAGTA GTCGCCGTGAACGTTCTTTTTCGCAACGGGTTTGCC GCCAGAACACAGGTAAGTGCCGTGTGTGGTTCCCG CGGGCCTGGCCTCTTTACGGGTTATGGCCCTTGCGT GCCTTGAATTACTTCCACGCCCCTGGCTGCAGTAC GTGATTCTTGATCCCGAGCTTCGGGTTGGAAGTGG GTGGGAGAGTTCGAGGCCTTGCGCTTAAGGAGCCC CTTCGCCTCGTGCTTGAGTTGAGGCCTGGCCTGGG CGCTGGGGCCGCCGCGTGCGAATCTGGTGGCACCT TCGCGCCTGTCTCGCTGCTTTCGATAAGTCTCTAGC CATTTAAAATTTTTGATGACCTGCTGCGACGCTTTT TTTCTGGCAAGATAGTCTTGTAAATGCGGGCCAAG ATCTGCACACTGGTATTTCGGTTTTTGGGGCCGCGG GCGGCGACGGGCCCGTGCGTCCCAGCGCACATGT TCGGCGAGGCGGGGCCTGCGAGCGCGGCCACCGA GAATCGGACGGGGGTAGTCTCAAGCTGGCCGGCCT GCTCTGGTGCCTGGCCTCGCGCCGCCGTGTATCGC CCCGCCCTGGGCGGCAAGGCTGGCCCGGTCGGCAC CAGTTGCGTGAGCGGAAAGATGGCCGCTTCCCGGC CCTGCTGCAGGGAGCTCAAAATGGAGGACGCGGC GCTCGGGAGAGCGGGCGGGTGAGTCACCCACACA AAGGAAAAGGGCCTTTCCGTCCTCAGCCGTCGCTT CATGTGACTCCACGGAGTACCGGGCGCCGTCCAGG CACCTCGATTAGTTCTCGAGCTTTTGGAGTACGTCG TCTTTAGGTTGGGGGGAGGGGTTTTATGCGATGGA GTTTCCCCACACTGAGTGGGTGGAGACTGAAGTTA GGCCAGCTTGGCACTTGATGTAATTCTCCTTGGAAT TTGCCCTTTTTGAGTTTGGATCTTGGTTCATTCTCA AGCCTCAGACAGTGGTTCAAAGTTTTTTTCTTCCAT TTCAGGTGTCGTGA |
| 5 | CCR5 miRNA target sequence | GAGCAAGCTCAGTTTACA |
| 6 | Vif miRNA target sequence | GGGATGTGTACTTCTGAACTT |
| 7 | Tat miRNA target sequence | TCCGCTTCTTCCTGCCATAG |
| 8 | TAR decoy sequence | CTTGCAATGATGTCGTAATTTGCGTCTTACCTCGTT CTCGACAGCGACCAGATCTGAGCCTGGGAGCTCTC TGGCTGTCAGTAAGCTGGTACAGAAGGTTGACGAA AATTCTTACTGAGCAAGAAA |
| 9 | Rev/Tat shRNA target sequence | GCGGAGACAGCGACGAAGAGC |
| 10 | Rev/Tat shRNA sequence | GCGGAGACAGCGACGAAGAGCTTCAAGAGAGCTC TTCGTCGCTGTCTCCGCTTTTT |
| 11 | Gag shRNA target sequence | GAAGAAATGATGACAGCAT |
| 12 | Gag shRNA sequence | GAAGAAATGATGACAGCATTTCAAGAGAATGCTGT CATCATTTCTTCTTTTT |
| 13 | Pol shRNA target sequence | CAGGAGCAGATGATACAG |
| 14 | Pol shRNA sequence | CAGGAGATGATACAGTTCAAGAGACTGTATCATCT GCTCCTGTTTTT |
| 15 | CCR5 shRNA target sequence #1 | GTGTCAAGTCCAATCTATG |
| 16 | CCR5 shRNA sequence #1 | GTGTCAAGTCCAATCTATGTTCAAGAGACATAGAT TGGACTTGACACTTTTT |

-continued

| SEQ ID NO: | Description | Sequence |
|---|---|---|
| 17 | CCR5 shRNA target sequence #2 | GAGCATGACTGACATCTAC |
| 18 | CCR5 shRNA sequence #2 | GAGCATGACTGACATCTACTTCAAGAGAGTAGATG TCAGTCATGCTCTTTTT |
| 19 | CCR5 shRNA target sequence #3 | GTAGCTCTAACAGGTTGGA |
| 20 | CCR5 shRNA sequence #3 | GTAGCTCTAACAGGTTGGATTCAAGAGATCCAACC TGTTAGAGCTACTTTTT |
| 21 | CCR5 shRNA target sequence #4 | GTTCAGAAACTACCTCTTA |
| 22 | CCR5 shRNA sequence #4 | GTTCAGAAACTACCTCTTATTCAAGAGATAAGAGG TAGTTTCTGAACTTTTT |
| 23 | CCR5 shRNA target sequence #5 | GAGCAAGCTCAGTTTACACC |
| 24 | CCR5 shRNA sequence #5 | GAGCAAGCTCAGTTTACACCTTCAAGAGAGGTGTA AACTGAGCTTGCTCTTTTT |
| 25 | *Homo sapiens* CCR5 gene, sequence 1 | ATGGATTATCAAGTGTCAAGTCCAATCTATGACAT CAATTATTATACATCGGAGCCCTGCCAAAAAATCA ATGTGAAGCAAATCGCAGCCCGCCTCCTGCCTCCG CTCTACTCACTGGTGTTCATCTTTGGTTTTGTGGGC |
| 26 | *Homo sapiens* CCR5 gene, sequence 2 | AACATGCTGGTCATCCTCATCCTGATAAACTGCAA AAGGCTGAAGAGCATGACTGACATCTACCTGCTCA ACCTGGCCATCTCTGACCTGTTTTTCCTTCTTACTG TCCCCTTCTGGGCTCACTATGCTGCCGCCCAGTGGG ACTTTGGAAATACAATGTGTCAACTCTTGACAGGG CTCTATTTTATAGGCTTCTTCTCTGGAATCTTCTTCA TCATCCTCCTGACAATCGATAGGTACCTGGCTGTC GTCCATGCTGTGTTTGCTTTAAAAGCCAGGACGGT CACCTTTGGGGTGGTGACAAGTGTGATCACTTGGG TGGTGGCTGTGTTTGCGTCTCTCCCAGGAATCATCT TTACCAGATCTCAAAAAGAAGGTCTTCATTACACC TGCAGCTCTCATTTTCCATACAGTCAGTATCAATTC TGGAAGAATTTCCAGACATTAAAGATAGTCATCTT GGGGCTGGTCCTGCCGCTGCTTGTCATGGTCATCTG CTACTCGGGAATCCTAAAAACTCTGCTTCGGTGTC GAAATGAGAAGAAGAGGCACAGGGCTGTGAGGCT TATCTTCACCATCATGATTGTTTATTTTCTCTTCTGG GCTCCCTACAACATTGTCCTTCTCCTGAAC |
| 27 | *Homo sapiens* CCR5 gene, sequence 3 | ACCTTCCAGGAATTCTTTGGCCTGAATAATTGCAGT AGCTCTAACAGGTTGGACCAAGCTATGCAGGTGA |
| 28 | *Homo sapiens* CCR5 gene, sequence 4 | CAGAGACTCTTGGGATGACGCACTGCTGCATCAAC CCCATCATCTATGCCTTTGTCGGGGAGAAGTTCAG AAACTACCTCTTAGTCTTCTTCCAAAAGCACATTGC CAAACGCTTCTGCAAATGCTGTTCTATTTTCCAG |
| 29 | *Homo sapiens* CCR5 gene, sequence 5 | CAAGAGGCTCCCGAGCGAGCAAGCTCAGTTTACAC CCGATCCACTGGGGAGCAGGAAATATCTGTGGGCT TGTGA |
| 30 | CD4 promoter sequence | TGTTGGGGTTCAAATTTGAGCCCCAGCTGTTAGCC CTCTGCAAAGAAAAAAAAAAAAAAAAAGAACAA AGGGCCTAGATTTCCCTTCTGAGCCCCACCCTAAG ATGAAGCCTCTTCTTTCAAGGGAGTGGGGTTGGGG TGGAGGCGGATCCTGTCAGCTTTGCTCTCTCTGTGG CTGGCAGTTTCTCCAAAGGGTAACAGGTGTCAGCT GGCTGAGCCTAGGCTGAACCCTGAGACATGCTACC TCTGTCTTCTCATGGCTGGAGGCAGCCTTTGTAAGT CACAGAAAGTAGCTGAGGGGCTCTGGAAAAAGA CAGCCAGGGTGGAGGTAGATTGGTCTTTGACTCCT |

| SEQ ID NO: | Description | Sequence |
|---|---|---|
| | | GATTTAAGCCTGATTCTGCTTAACTTTTTCCCTTGA<br>CTTTGGCATTTTCACTTTGACATGTTCCCTGAGAGC<br>CTGGGGGGTGGGGAACCCAGCTCCAGCTGGTGACG<br>TTTGGGGCCGGCCCAGGCCTAGGGTGTGGAGGAGC<br>CTTGCCATCGGGCTTCCTGTCTCTCTTCATTTAAGC<br>ACGACTCTGCAGA |
| 31 | miR30-<br>CCR5/miR21-<br>Vif/miR185 Tat<br>microRNA<br>cluster sequence | AGGTATATTGCTGTTGACAGTGAGCGACTGTAAAC<br>TGAGCTTGCTCTACTGTGAAGCCACAGATGGGTAG<br>AGCAAGCACAGTTTACCGCTGCCTACTGCCTCGGA<br>CTTCAAGGGGCTTCCCGGGCATCTCCATGGCTGTA<br>CCACCTTGTCGGGGATGTGTACTTCTGAACTTGTG<br>TTGAATCTCATGGAGTTCAGAAGAACACATCCGCA<br>CTGACATTTTGGTATCTTTCATCTGACCAGCTAGCG<br>GGCCTGGCTCGAGCAGGGGGCGAGGGATTCCGCTT<br>CTTCCTGCCATAGCGTGGTCCCCTCCCCTATGGCAG<br>GCAGAAGCGGCACCTTCCCTCCCAATGACCGCGTC<br>TTCGTC |
| 32 | Long WPRE<br>sequence | AATCAACCTCTGATTACAAAATTTGTGAAAGATTG<br>ACTGGTATTCTTAACTATGTTGCTCCTTTTACGCTA<br>TGTGGATACGCTGCTTTAATGCCTTTGTATCATGCT<br>ATTGCTTCCCGTATGGCTTTCATTTTCTCCTCCTTGT<br>ATAAATCCTGGTTGCTGTCTCTTTATGAGGAGTTGT<br>GGCCCGTTGTCAGGCAACGTGGCGTGGTGTGCACT<br>GTGTTTGCTGACGCAACCCCCACTGGTTGGGGCAT<br>TGCCACCACCTGTCAGCTCCTTTCCGGGACTTTCGC<br>TTTCCCCCTCCCTATTGCCACGGCGGAACTCATCGC<br>CGCCTGCCTTGCCCGCTGCTGGACAGGGGCTCGGC<br>TGTTGGGCACTGACAATTCCGTGGTGTTGTCGGGG<br>AAATCATCGTCCTTTCCTTGGCTGCTCGCCTGTGTT<br>GCCACCTGGATTCTGCGCGGGACGTCCTTCTGCTA<br>CGTCCCTTCGGCCCTCAATCCAGCGGACCTTCCTTC<br>CCGCGGCCTGCTGCCGGCTCTGCGGCCTCTTCCGC<br>GTCTTCGCCTTCGCCCTCAGACGAGTCGGATCTCCC<br>TTTGGGCCGCCTCCCCGCCT |
| 33 | Elongation<br>Factor-1 alpha<br>(EF1-alpha)<br>promoter;<br>miR30CCR5;<br>miR21Vif;<br>miR185 Tat | CCGGTGCCTAGAGAAGGTGGCGCGGGGTAAACTG<br>GGAAAGTGATGTCGTGTACTGGCTCCGCCTTTTTCC<br>CGAGGGTGGGGGAGAACCGTATATAAGTGCAGTA<br>GTCGCCGTGAACGTTCTTTTTCGCAACGGGTTTGCC<br>GCCAGAACACAGGTAAGTGCCGTGTGTGGTTCCCG<br>CGGGCCTGGCCTCTTTACGGGTTATGGCCCTTGCGT<br>GCCTTGAATTACTTCCACGCCCCTGGCTGCAGTAC<br>GTGATTCTTGATCCCGAGCTTCGGGTTGGAAGTGG<br>GTGGGAGAGTTCGAGGCCTTGCGCTTAAGGAGCCC<br>CTTCGCCTCGTGCTTGAGTTGAGGCCTGGCCTGGG<br>CGCTGGGGCCGCCGCGTGCGAATCTGGTGGCACCT<br>TCGCGCCTGTCTCGCTGCTTTCGATAAGTCTCTAGC<br>CATTTAAAATTTTTGATGACCTGCTGCGACGCTTTT<br>TTTCTGGCAAGATAGTCTTGTAAATGCGGGCCAAG<br>ATCTGCACACTGGTATTTCGGTTTTTGGGGCCGCGG<br>GCGGCGACGGGGCCCGTGCGTCCCAGCGCACATGT<br>TCGGCGAGGCGGGGCCTGCGAGCGCGGCCACCGA<br>GAATCGGACGGGGGTAGTCTCAAGCTGGCCGGCCT<br>GCTCTGGTGCCTGGCCTCGCGCCGCCGTGTATCGC<br>CCCGCCCTGGGCGGCAAGGCTGGCCCGGTCGGCAC<br>CAGTTGCGTGAGCGGAAAGATGGCCGCTTCCCGGC<br>CCTGCTGCAGGGAGCTCAAAATGGAGGACGCGGC<br>GCTCGGGAGAGCGGGCGGGTGAGTCACCCACACA<br>AAGGAAAAGGGCCTTTCCGTCCTCAGCCGTCGCTT<br>CATGTGACTCCACGGAGTACCGGGCGCCGTCCAGG<br>CACCTCGATTAGTTCTCGAGCTTTTGGAGTACGTCG<br>TCTTTAGGTTGGGGGGAGGGGTTTTATGCGATGGA<br>GTTTCCCCACACTGAGTGGGTGGAGACTGAAGTTA<br>GGCCAGCTTGGCACTTGATGTAATTCTCCTTGGAAT<br>TTGCCCTTTTTGAGTTTGGATCTTGGTTCATTCTCA<br>AGCCTCAGACAGTGGTTCAAAGTTTTTTTCTTCCAT<br>TTCAGGTGTCGTGATGTACAAGGTATATTGCTGTTG<br>ACAGTGAGCGACTGTAAACTGAGCTTGCTCTACTG<br>TGAAGCCACAGATGGGTAGAGCAAGCACAGTTTAC<br>CGCTGCCTACTGCCTCGGACTTCAAGGGGCTTCCC<br>GGGCATCTCCATGGCTGTACCACCTTGTCGGGGGA<br>TGTGTACTTCTGAACTTGTGTTGAATCTCATGGAGT<br>TCAGAAGAACACATCCGCACTGACATTTTGGTATC<br>TTTCATCTGACCAGCTAGCGGGCCTGGCTCGAGCA |

-continued

| SEQ ID NO: | Description | Sequence |
|---|---|---|
|  |  | GGGGGCGAGGGATTCCGCTTCTTCCTGCCATAGCG TGGTCCCCTCCCCTATGGCAGGCAGAAGCGGCACC TTCCCTCCCAATGACCGCGTCTTCGTC |
| 34 | Rous Sarcoma virus (RSV) promoter | GTAGTCTTATGCAATACTCTTGTAGTCTTGCAACAT GGTAACGATGAGTTAGCAACATGCCTTACAAGGAG AGAAAAAGCACCGTGCATGCCGATTGGTGGAAGT AAGGTGGTACGATCGTGCCTTATTAGGAAGGCAAC AGACGGGTCTGACATGGATTGGACGAACCACTGAA TTGCCGCATTGCAGAGATATTGTATTTAAGTGCCTA GCTCGATACAATAAACG |
| 35 | 5' Long terminal repeat (LTR) | GGTCTCTCTGGTTAGACCAGATCTGAGCCTGGGAG CTCTCTGGCTAACTAGGGAACCCACTGCTTAAGCC TCAATAAAGCTTGCCTTGAGTGCTTCAAGTAGTGT GTGCCCGTCTGTTGTGTGACTCTGGTAACTAGAGA TCCCTCAGACCCTTTTAGTCAGTGTGGAAAATCTCT AGCA |
| 36 | Psi Packaging signal | TACGCCAAAAATTTTGACTAGCGGAGGCTAGAAGG AGAGAG |
| 37 | Rev response element (RRE) | AGGAGCTTTGTTCCTTGGGTTCTTGGGAGCAGCAG GAAGCACTATGGGCGCAGCCTCAATGACGCTGACG GTACAGGCCAGACAATTATTGTCTGGTATAGTGCA GCAGCAGAACAATTTGCTGAGGGCTATTGAGGCGC AACAGCATCTGTTGCAACTCACAGTCTGGGGCATC AAGCAGCTCCAGGCAAGAATCCTGGCTGTGGAAA GATACCTAAAGGATCAACAGCTCC |
| 38 | Central polypurine tract (cPPT) | TTTTAAAAGAAAAGGGGGGATTGGGGGGTACAGT GCAGGGGAAAGAATAGTAGACATAATAGCAACAG ACATACAAACTAAAGAATTACAAAAACAAATTAC AAAATTCAAAATTTTA |
| 39 | 3' delta LTR | TGGAAGGGCTAATTCACTCCCAACGAAGATAAGAT CTGCTTTTTGCTTGTACTGGGTCTCTCTGGTTAGAC CAGATCTGAGCCTGGGAGCTCTCTGGCTAACTAGG GAACCCACTGCTTAAGCCTCAATAAAGCTTGCCTT GAGTGCTTCAAGTAGTGTGTGCCCGTCTGTTGTGTG ACTCTGGTAACTAGAGATCCCTCAGACCCTTTTAGT CAGTGTGGAAAATCTCTAGCAGTAGTAGTTCATGT CA |
| 40 | Helper/Rev; CMV early (CAG) enhancer; Enhance Transcription | TAGTTATTAATAGTAATCAATTACGGGGTCATTAG TTCATAGCCCATATATGGAGTTCCGCGTTACATAA CTTACGGTAAATGGCCCGCCTGGCTGACCGCCCAA CGACCCCCGCCCATTGACGTCAATAATGACGTATG TTCCCATAGTAACGCCAATAGGGACTTTCCATTGA CGTCAATGGGTGGACTATTTACGGTAAACTGCCCA CTTGGCAGTACATCAAGTGTATCATATGCCAAGTA CGCCCCCTATTGACGTCAATGACGGTAAATGGCCC GCCTGGCATTATGCCCAGTACATGACCTTATGGGA CTTTCCTACTTGGCAGTACATCTACGTATTAGTCAT C |
| 41 | Helper/Rev; Chicken beta actin (CAG) promoter; Transcription | GCTATTACCATGGGTCGAGGTGAGCCCCACGTTCT GCTTCACTCTCCCCATCTCCCCCCCCTCCCCACCCC CAATTTTGTATTTATTTATTTTTTAATTATTTTGTGC AGCGATGGGGGCGGGGGGGGGGGGGCGCGCGCC AGGCGGGGCGGGCGGGCGGGGCGGGGCGGGCGGG GCGAGGCGGAGAGGTGCGGCGGCAGCCAATCAGA GCGGCGCGCTCCGAAAGTTTCCTTTTATGGCGAGG CGGCGGCGGCGGCGGCCCTATAAAAAGCGAAGCG CGCGGCGGGCG |
| 42 | Helper/Rev; Chicken beta actin intron; Enhance gene expression | GGAGTCGCTGCGTTGCCTTCGCCCCGTGCCCCGCTC CGCGCCGCCTCGCGCCGCCCGCCCCGGCTCTGACT GACCGCGTTACTCCCACAGGTGAGCGGGCGGGACG GCCCTTCTCCTCCGGGCTGTAATTAGCGCTTGGTTT AATGACGGCTCGTTTCTTTTCTGTGGCTGCGTGAAA GCCTTAAAGGGCTCCGGGAGGGCCCTTTGTGCGGG GGGAGCGGCTCGGGGGGTGCGTGCGTGTGTGTGT GCGTGGGAGCGCCGCGTGCGGCCCGCGCTGCCCG GCGGCTGTGAGCGCTGCGGGCGCGGCGCGGGGCTT TGTGCGCTCCGCGTGTGCGCGAGGGGAGCGCGGCC |

-continued

| SEQ ID NO: | Description | Sequence |
|---|---|---|
|  |  | GGGGGCGGTGCCCCGCGGTGCGGGGGGCTGCGA GGGGAACAAAGGCTGCGTGCGGGGTGTGTGCGTG GGGGGGTGAGCAGGGGGTGTGGGCGCGGCGGTCG GGCTGTAACCCCCCCTGCACCCCCCTCCCCGAGT TGCTGAGCACGGCCCGGCTTCGGGTGCGGGCTCC GTGCGGGCGTGGCGCGGGGCTCGCCGTGCCGGGC GGGGGGTGGCGGCAGGTGGGGGTGCCGGGCGGGG CGGGGCCGCCTCGGGCCGGGGAGGGCTCGGGGGA GGGGCGCGGCGGCCCCGGAGCGCCGGCGGCTGTC GAGGCGCGGCGAGCCGCAGCCATTGCCTTTTATGG TAATCGTGCGAGAGGGCGCAGGGACTTCCTTTGTC CCAAATCTGGCGGAGCCGAAATCTGGGAGGCGCC GCCGCACCCCCTCTAGCGGGCGCGGGCGAAGCGGT GCGGCGCCGGCAGGAAGGAAATGGGCGGGGAGGG CCTTCGTGCGTCGCCGCGCCGCCGTCCCCTTCTCCA TCTCCAGCCTCGGGGCTGCCGCAGGGGGACGGCTG CCTTCGGGGGGGACGGGGCAGGGCGGGGTTCGGC TTCTGGCGTGTGACCGGCGG |
| 43 | Helper/Rev; HIV Gag; Viral capsid | ATGGGTGCGAGAGCGTCAGTATTAAGCGGGGGAG AATTAGATCGATGGGAAAAAATTCGGTTAAGGCCA GGGGGAAAGAAAAAATATAAATTAAAACATATAG TATGGGCAAGCAGGGAGCTAGAACGATTCGCAGTT AATCCTGGCCTGTTAGAAACATCAGAAGGCTGTAG ACAAATACTGGGACAGCTACAACCATCCCTTCAGA CAGGATCAGAAGAACTTAGATCATTATATAATACA GTAGCAACCCTCTATTGTGTGCATCAAAGGATAGA GATAAAAGACACCAAGGAAGCTTTAGACAAGATA GAGGAAGAGCAAAACAAAAGTAAGAAAAAAGCAC AGCAAGCAGCAGCTGACACAGGACACAGCAATCA GGTCAGCCAAAATTACCCTATAGTGCAGAACATCC AGGGGCAAATGGTACATCAGGCCATATCACCTAGA ACTTTAAATGCATGGGTAAAAGTAGTAGAAGAGA AGGCTTTCAGCCCAGAAGTGATACCCATGTTTTCA GCATTATCAGAAGGAGCCACCCCACAAGATTTAAA CACCATGCTAAACACAGTGGGGGGACATCAAGCA GCCATGCAAATGTTAAAAGAGACCATCAATGAGG AAGCTGCAGAATGGGATAGAGTGCATCCAGTGCAT GCAGGGCCTATTGCACCAGGCCAGATGAGAGAAC CAAGGGGAAGTGACATAGCAGGAACTACTAGTAC CCTTCAGGAACAAATAGGATGGATGACACATAATC CACCTATCCCAGTAGGAGAAATCTATAAAAGATGG ATAATCCTGGGATTAAATAAAATAGTAAGAATGTA TAGCCCTACCAGCATTCTGGACATAAGACAAGGAC CAAAGGAACCCTTTAGAGACTATGTAGACCGATTC TATAAAACTCTAAGAGCCGAGCAAGCTTCACAAGA GGTAAAAAATTGGATGACAGAAACCTTGTTGGTCC AAAATGCGAACCCAGATTGTAAGACTATTTTAAAA GCATTGGGACCAGGAGCGACACTAGAAGAAATGA TGACAGCATGTCAGGGAGTGGGGGGACCCGGCCA TAAAGCAAGAGTTTTGGCTGAAGCAATGAGCCAAG TAACAAATCCAGCTACCATAATGATACAGAAAGGC AATTTTAGGAACCAAAGAAAGACTGTTAAGTGTTT CAATTGTGGCAAAGAAGGGCACATAGCCAAAAAT TGCAGGGCCCCTAGGAAAAAGGGCTGTTGGAAAT GTGGAAAGGAAGGACACCAAATGAAAGATTGTAC TGAGAGACAGGCTAATTTTTTAGGGAAGATCTGGC CTTCCCACAAGGGAAGGCCAGGGAATTTTCTTCAG AGCAGACCAGAGCCAACAGCCCCACCAGAAGAGA GCTTCAGGTTTGGGGAAGAGACAACAACTCCCTCT CAGAAGCAGGAGCCGATAGACAAGGAACTGTATC CTTTAGCTTCCCTCAGATCACTCTTTGGCAGCGACC CCTCGTCACAATAA |
| 44 | Helper/Rev; HIV Pol; Protease and reverse transcriptase | ATGAATTTGCCAGGAAGATGGAAACCAAAAATGA TAGGGGGAATTGGAGGTTTTATCAAAGTAGGACAG TATGATCAGATACTCATAGAAATCTGCGGACATAA AGCTATAGGTACAGTATTAGTAGGACCTACACCTG TCAACATAATTGGAAGAAATCTGTTGACTCAGATT GGCTGCACTTTAAATTTTCCCATTAGTCCTATTGAG ACTGTACCAGTAAAATTAAAGCCAGGAATGGATGG CCCAAAAGTTAAACAATGGCCATTGACAGAAGAA AAAATAAAAGCATTAGTAGAAATTTGTACAGAAAT GGAAAAGGAAGGAAAAATTTCAAAAATTGGGCCT GAAAATCCATACAATACTCCAGTATTTGCCATAAA GAAAAAAGACAGTACTAAATGGAGAAAATTAGTA |

| SEQ ID NO: | Description | Sequence |
|---|---|---|
| | | GATTTCAGAGAACTTAATAAGAGAACTCAAGATTT<br>CTGGGAAGTTCAATTAGGAATACCACATCCTGCAG<br>GGTTAAAACAGAAAAAATCAGTAACAGTACTGGA<br>TGTGGGCGATGCATATTTTCAGTTCCCTTAGATAA<br>AGACTTCAGGAAGTATACTGCATTTACCATACCTA<br>GTATAAACAATGAGACACCAGGGATTAGATATCAG<br>TACAATGTGCTTCCACAGGGATGGAAAGGATCACC<br>AGCAATATTCCAGTGTAGCATGACAAAAATCTTAG<br>AGCCTTTTAGAAAACAAAATCCAGACATAGTCATC<br>TATCAATACATGGATGATTTGTATGTAGGATCTGA<br>CTTAGAAATAGGGCAGCATAGAACAAAAATAGAG<br>GAACTGAGACAACATCTGTTGAGGTGGGGATTTAC<br>CACACCAGACAAAAAACATCAGAAAGAACCTCCA<br>TTCCTTTGGATGGGTTATGAACTCCATCCTGATAAA<br>TGGACAGTACAGCCTATAGTGCTGCCAGAAAAGGA<br>CAGCTGGACTGTCAATGACATACAGAAATTAGTGG<br>GAAAATTGAATTGGGCAAGTCAGATTTATGCAGGG<br>ATTAAAGTAAGGCAATTATGTAAACTTCTTAGGGG<br>AACCAAAGCACTAACAGAAGTAGTACCACTAACA<br>GAAGAAGCAGAGCTAGAACTGGCAGAAAACAGGG<br>AGATTCTAAAAGAACCGGTACATGGAGTGTATTAT<br>GACCCATCAAAAGACTTAATAGCAGAAATACAGA<br>AGCAGGGGCAAGGCCAATGGACATATCAAATTTAT<br>CAAGAGCCATTTAAAAATCTGAAAACAGGAAAAT<br>ATGCAAGAATGAAGGGTGCCCACACTAATGATGTG<br>AAACAATTAACAGAGGCAGTACAAAAAATAGCCA<br>CAGAAAGCATAGTAATATGGGGAAAGACTCCTAA<br>ATTTAAATTACCCATACAAAAGGAAACATGGGAAG<br>CATGGTGGACAGAGTATTGGCAAGCCACCTGGATT<br>CCTGAGTGGGAGTTTGTCAATACCCCTCCCTTAGTG<br>AAGTTATGGTACCAGTTAGAGAAAGAACCCATAAT<br>AGGAGCAGAAACTTTCTATGTAGATGGGGCAGCCA<br>ATAGGGAAACTAAATTAGGAAAAGCAGGATATGT<br>AACTGACAGAGGAAGACAAAAAGTTGTCCCCCTA<br>ACGGACACAACAAATCAGAAGACTGAGTTACAAG<br>CAATTCATCTAGCTTTGCAGGATTCGGGATTAGAA<br>GTAAACATAGTGACAGACTCACAATATGCATTGGG<br>AATCATTCAAGCACAACCAGATAAGAGTGAATCAG<br>AGTTAGTCAGTCAAATAATAGAGCAGTTAATAAAA<br>AAGGAAAAAGTCTACCTGGCATGGGTACCAGCAC<br>ACAAAGGAATTGGAGGAAATGAACAAGTAGATGG<br>GTTGGTCAGTGCTGGAATCAGGAAAGTACTA |
| 45 | Helper Rev; HIV Integrase; Integration of viral RNA | TTTTTAGATGGAATAGATAAGGCCCAAGAAGAACA<br>TGAGAAATATCACAGTAATTGGAGAGCAATGGCTA<br>GTGATTTTAACCTACCACCTGTAGTAGCAAAAGAA<br>ATAGTAGCCAGCTGTGATAAATGTCAGCTAAAAGG<br>GGAAGCCATGCATGGACAAGTAGACTGTAGCCCA<br>GGAATATGGCAGCTAGATTGTACACATTTAGAAGG<br>AAAAGTTATCTTGGTAGCAGTTCATGTAGCCAGTG<br>GATATATAGAAGCAGAAGTAATTCCAGCAGAGAC<br>AGGGCAAGAAACAGCATACTTCCTCTTAAAATTAG<br>CAGGAAGATGGCCAGTAAAAACAGTACATACAGA<br>CAATGGCAGCAATTTCACCAGTACTACAGTTAAGG<br>CCGCCTGTTGGTGGGCGGGATCAAGCAGGAATTT<br>GGCATTCCCTACAATCCCCAAAGTCAAGGAGTAAT<br>AGAATCTATGAATAAAGAATTAAAGAAAATTATAG<br>GACAGGTAAGAGATCAGGCTGAACATCTTAAGAC<br>AGCAGTACAAATGGCAGTATTCATCCACAATTTTA<br>AAAGAAAAGGGGGGATTGGGGGGTACAGTGCAGG<br>GGAAAGAATAGTAGACATAATAGCAACAGACATA<br>CAAACTAAAGAATTACAAAAACAAATTACAAAAA<br>TTCAAAATTTTCGGGTTTATTACAGGGACAGCAGA<br>GATCCAGTTTGGAAAGGACCAGCAAAGCTCCTCTG<br>GAAAGGTGAAGGGGCAGTAGTAATACAAGATAAT<br>AGTGACATAAAAGTAGTGCCAAGAAGAAAAGCAA<br>AGATCATCAGGGATTATGGAAAACAGATGGCAGG<br>TGATGATTGTGTGGCAAGTAGACAGGATGAGGATT<br>AA |
| 46 | Helper/Rev; HIV RRE; Binds Rev element | AGGAGCTTTGTTCCTTGGGTTCTTGGGAGCAGCAG<br>GAAGCACTATGGGCGCAGCGTCAATGACGCTGACG<br>GTACAGGCCAGACAATTATTGTCTGGTATAGTGCA<br>GCAGCAGAACAATTTGCTGAGGGCTATTGAGGCGC<br>AACAGCATCTGTTGCAACTCACAGTCTGGGGCATC |

-continued

| SEQ ID NO: | Description | Sequence |
|---|---|---|
| | | AAGCAGCTCCAGGCAAGAATCCTGGCTGTGGAAA GATACCTAAAGGATCAACAGCTCCT |
| 47 | Helper/Rev; HIV Rev; Nuclear export and stabilize viral mRNA | ATGGCAGGAAGAAGCGGAGACAGCGACGAAGAAC TCCTCAAGGCAGTCAGACTCATCAAGTTTCTCTATC AAAGCAACCCACCTCCCAATCCCGAGGGGACCCG ACAGGCCCGAAGGAATAGAAGAAGAAGGTGGAGA GAGAGACAGAGACAGATCCATTCGATTAGTGAAC GGATCCTTAGCACTTATCTGGGACGATCTGCGGAG CCTGTGCCTCTTCAGCTACCACCGCTTGAGAGACTT ACTCTTGATTGTAACGAGGATTGTGGAACTTCTGG GACGCAGGGGGTGGGAAGCCCTCAAATATTGGTG GAATCTCCTACAATATTGGAGTCAGGAGCTAAAGA ATAG |
| 48 | Helper/Rev; Rabbit beta globin poly A; RNA stability | AGATCTTTTTCCCTCTGCCAAAAATTATGGGGACAT CATGAAGCCCCTTGAGCATCTGACTTCTGGCTAAT AAAGGAAATTTATTTTCATTGCAATAGTGTGTTGG AATTTTTTGTGTCTCTCACTCGGAAGGACATATGG AGGGCAAATCATTTAAAACATCAGAATGAGTATTT GGTTTAGAGTTTGGCAACATATGCCATATGCTGGC TGCCATGAACAAAGGTGGCTATAAAGAGGTCATCA GTATATGAAACAGCCCCCTGCTGTCCATTCCTTATT CCATAGAAAAGCCTTGACTTGAGGTTAGATTTTTTT TATATTTTGTTTTGTGTTATTTTTTCTTTAACATCC CTAAAATTTTCCTTACATGTTTTACTAGCCAGATTT TTCCTCCTCTCCTGACTACTCCCAGTCATAGCTGTC CCTCTTCTCTTATGAAGATC |
| 49 | Helper; CMV early (CAG) enhancer; Enhance transcription | TAGTTATTAATAGTAATCAATTACGGGGTCATTAG TTCATAGCCCATATATGGAGTTCCGCGTTACATAA CTTACGGTAAATGGCCCGCCTGGCTGACCGCCCAA CGACCCCCGCCCATTGACGTCAATAATGACGTATG TTCCCATAGTAACGCCAATAGGGACTTTCCATTGA CGTCAATGGGTGGACTATTTACGGTAAACTGCCCA CTTGGCAGTACATCAAGTGTATCATATGCCAAGTA CGCCCCCTATTGACGTCAATGACGGTAAATGGCCC GCCTGGCATTATGCCCAGTACATGACCTTATGGGA CTTTCCTACTTGGCAGTACATCTACGTATTAGTCAT C |
| 50 | Helper; Chicken beta actin (CAG) promoter; Transcription | GCTATTACCATGGGTCGAGGTGAGCCCCACGTTCT GCTTCACTCTCCCCATCTCCCCCCCCTCCCCACCCC CAATTTTGTATTTATTTATTTTTTAATTATTTTGTGC AGCGATGGGGGCGGGGGGGGGGGGGCGCGCGCC AGGCGGGGCGGGCGGGCGAGGGGCGGGGCGGG GCGAGGCGGAGAGGTGCGGCGGCAGCCAATCAGA GCGGCGCGCTCCGAAAGTTTCCTTTTATGGCGAGG CGGCGGCGGCGGCGGCCCTATAAAAAGCGAAGCG CGCGGCGGGCG |
| 51 | Helper; Chicken beta actin intron; Enhance gene expression | GGAGTCGCTGCGTTGCCTTCGCCCCGTGCCCCGCTC CGCGCCGCCTCGCGCCGCCCGCCCCGGCTCTGACT GACCGCGTTACTCCCACAGGTGAGCGGGCGGGACG GCCCTTCTCCTCCGGGCTGTAATTAGCGCTTGGTTT AATGACGGCTCGTTTCTTTTCTGTGGCTGCGTGAAA GCCTTAAAGGGCTCCGGGAGGGCCCTTTGTGCGGG GGGGAGCGGCTCGGGGGGTGCGTGCGTGTGTGT GCGTGGGGAGCGCCGCGTGCGGCCCGCGCTGCCCG GCGGCTGTGAGCGCTGCGGGCGCGGCGCGGGGCTT TGTGCGCTCCGCGTGTGCGCGAGGGGAGCGCGGCC GGGGCGGTGCCCCGCGGTGCGGGGGGCTGCGA GGGGAACAAAGGCTGCGTGCGGGGTGTGTGCGTG GGGGGGTGAGCAGGGGGTGTGGGCGCGGCGGTCG GGCTGTAACCCCCCCCTGCACCCCCCTCCCCGAGT TGCTGAGCACGGCCCGGCTTCGGGTGCGGGGCTCC GTGCGGGGCGTGGCGCGGGGCTCGCCGTGCCGGGC GGGGGGTGGCGGCAGGTGGGGGTGCCGGGCGGGG CGGGGCCGCCTCGGGCCGGGGAGGGCTCGGGGA GGGGCGCGGCGGCCCCGGAGCGCCGGCGGCTGTC GAGGCGCGGCGAGCCGCAGCCATTGCCTTTTATGG TAATCGTGCGAGAGGGCGCAGGGACTTCCTTTGTC CCAAATCTGGCGGAGCCGAAATCTGGGAGGCGCC GCCGCACCCCCTCTAGCGGGCGCGGGCGAAGCGGT GCGGCGCCGGCAGGAAGGAAATGGGCGGGGAGGG CCTTCGTGCGTCGCCGCGCCGCCGTCCCCTTCTCCA |

-continued

| SEQ ID NO: | Description | Sequence |
|---|---|---|
| | | TCTCCAGCCTCGGGGCTGCCGCAGGGGACGGCTG CCTTCGGGGGGACGGGGCAGGGCGGGGTTCGGC TTCTGGCGTGTGACCGGCGG |
| 52 | Helper; HIV Gag; Viral capsid | ATGGGTGCGAGAGCGTCAGTATTAAGCGGGGAG AATTAGATCGATGGGAAAAAATTCGGTTAAGGCCA GGGGGAAAGAAAAAATATAAATTAAAACATATAG TATGGGCAAGCAGGGAGCTAGAACGATTCGCAGTT AATCCTGGCCTGTTAGAAACATCAGAAGGCTGTAG ACAAATACTGGGACAGCTACAACCATCCCTTCAGA CAGGATCAGAAGAACTTAGATCATTATATAATACA GTAGCAACCCTCTATTGTGTGCATCAAAGGATAGA GATAAAAGACACCAAGGAAGCTTTAGACAAGATA GAGGAAGAGCAAAACAAAAGTAAGAAAAAAGCAC AGCAAGCAGCAGCTGACACAGGACACAGCAATCA GGTCAGCCAAAATTACCCTATAGTGCAGAACATCC AGGGGCAAATGGTACATCAGGCCATATCACCTAGA ACTTTAAATGCATGGGTAAAAGTAGTAGAAGAGA AGGCTTTCAGCCCAGAAGTGATACCCATGTTTTCA GCATTATCAGAAGGAGCCACCCCACAAGATTTAAA CACCATGCTAAACACAGTGGGGGGACATCAAGCA GCCATGCAAATGTTAAAAGAGACCATCAATGAGG AAGCTGCAGAATGGGATAGAGTGCATCCAGTGCAT GCAGGGCCTATTGCACCAGGCCAGATGAGAGAAC CAAGGGGAAGTGACATAGCAGGAACTACTAGTAC CCTTCAGGAACAAATAGGATGGATGACACATAATC CACCTATCCCAGTAGGAGAAATCTATAAAAGATGG ATAATCCTGGGATTAAATAAAATAGTAAGAATGTA TAGCCCTACCAGCATTCTGGACATAAGACAAGGAC CAAAGGAACCCTTTAGAGACTATGTAGACCGATTC TATAAAACTCTAAGAGCCGAGCAAGCTTCACAAGA GGTAAAAAATTGGATGACAGAAACCTTGTTGGTCC AAAATGCGAACCCAGATTGTAAGACTATTTTAAAA GCATTGGGACCAGGAGCGACACTAGAAGAAATGA TGACAGCATGTCAGGGAGTGGGGGGACCCGGCCA TAAAGCAAGAGTTTTGGCTGAAGCAATGAGCCAAG TAACAAATCCAGCTACCATAATGATACAGAAAGGC AATTTTAGGAACCAAAGAAAGACTGTTAAGTGTTT CAATTGTGGCAAAGAAGGGCACATAGCCAAAAAT TGCAGGGCCCCTAGGAAAAAGGGCTGTTGGAAAT GTGGAAAGGAAGGACACCAAATGAAAGATTGTAC TGAGAGACAGGCTAATTTTTTAGGGAAGATCTGGC CTTCCCACAAGGGAAGGCCAGGGAATTTTCTTCAG AGCAGACCAGAGCCAACAGCCCCACCAGAAGAGA GCTTCAGGTTTGGGGAAGAGACAACAACTCCCTCT CAGAAGCAGGAGCCGATAGACAAGGAACTGTATC CTTTAGCTTCCCTCAGATCACTCTTTGGCAGCGACC CCTCGTCACAATAA |
| 53 | Helper; HIV Pol; Protease and reverse transcriptase | ATGAATTTGCCAGGAAGATGGAAACCAAAAATGA TAGGGGGAATTGGAGGTTTTATCAAAGTAGGACAG TATGATCAGATACTCATAGAAATCTGCGGACATAA AGCTATAGGTACAGTATTAGTAGGACCTACACCTG TCAACATAATTGGAAGAAATCTGTTGACTCAGATT GGCTGCACTTTAAATTTTCCCATTAGTCCTATTGAG ACTGTACCAGTAAAATTAAAGCCAGGAATGGATGG CCCAAAAGTTAAACAATGGCCATTGACAGAAGAA AAAATAAAAGCATTAGTAGAAATTTGTACAGAAAT GGAAAAGGAAGGAAAAATTTCAAAAATTGGGCCT GAAAATCCATACAATACTCCAGTATTTGCCATAAA GAAAAAAGACAGTACTAAATGGAGAAAATTAGTA GATTTCAGAGAACTTAATAAGAGAACTCAAGATTT CTGGGAAGTTCAATTAGGAATACCACATCCTGCAG GGTTAAAACAGAAAAAATCAGTAACAGTACTGGA TGTGGGCGATGCATATTTTTCAGTTCCCTTAGATAA AGACTTCAGGAAGTATACTGCATTTACCATACCTA GTATAAACAATGAGACACCAGGGATTAGATATCAG TACAATGTGCTTCCACAGGGATGGAAAGGATCACC AGCAATATTCCAGTGTAGCATGACAAAAATCTTAG AGCCTTTTAGAAAACAAAATCCAGACATAGTCATC TATCAATACATGGATGATTTGTATGTAGGATCTGA CTTAGAAATAGGGCAGCATAGAACAAAAATAGAG GAACTGAGACAACATCTGTTGAGGTGGGGATTTAC CACACCAGACAAAAAACATCAGAAAGAACCTCCA TTCCTTTGGATGGGTTATGAACTCCATCCTGATAAA TGGACAGTACAGCCTATAGTGCTGCCAGAAAAGGA |

-continued

| SEQ ID NO: | Description | Sequence |
|---|---|---|
| | | CAGCTGGACTGTCAATGACATACAGAAATTAGTGG<br>GAAAATTGAATTGGGCAAGTCAGATTTATGCAGGG<br>ATTAAAGTAAGGCAATTATGTAAACTTCTTAGGGG<br>AACCAAAGCACTAACAGAAGTAGTACCACTAACA<br>GAAGAAGCAGAGCTAGAACTGGCAGAAAACAGGG<br>AGATTCTAAAAGAACCGGTACATGGAGTGTATTAT<br>GACCCATCAAAAGACTTAATAGCAGAAATACAGA<br>AGCAGGGGCAAGGCCAATGGACATATCAAATTTAT<br>CAAGAGCCATTTAAAAATCTGAAAACAGGAAAAT<br>ATGCAAGAATGAAGGGTGCCCACACTAATGATGTG<br>AAACAATTAACAGAGGCAGTACAAAAAATAGCCA<br>CAGAAAGCATAGTAATATGGGGAAAGACTCCTAA<br>ATTTAAATTACCCATACAAAAGGAAACATGGGAAG<br>CATGGTGGACAGAGTATTGGCAAGCCACCTGGATT<br>CCTGAGTGGGAGTTTGTCAATACCCCTCCCTTAGTG<br>AAGTTATGGTACCAGTTAGAGAAAGAACCCATAAT<br>AGGAGCAGAAACTTTCTATGTAGATGGGGCAGCCA<br>ATAGGGAAACTAAATTAGGAAAAGCAGGATATGT<br>AACTGACAGAGGAAGACAAAAAGTTGTCCCCCTA<br>ACGGACACAACAAATCAGAAGACTGAGTTACAAG<br>CAATTCATCTAGCTTTGCAGGATTCGGGATTAGAA<br>GTAAACATAGTGACAGACTCACAATATGCATTGGG<br>AATCATTCAAGCACAACCAGATAAGAGTGAATCAG<br>AGTTAGTCAGTCAAATAATAGAGCAGTTAATAAAA<br>AAGGAAAAAGTCTACCTGGCATGGGTACCAGCAC<br>ACAAAGGAATTGGAGGAAATGAACAAGTAGATGG<br>GTTGGTCAGTGCTGGAATCAGGAAAGTACTA |
| 54 | Helper; HIV Integrase; Integration of viral RNA | TTTTTAGATGGAATAGATAAGGCCCAAGAAGAACA<br>TGAGAAATATCACAGTAATTGGAGAGCAATGGCTA<br>GTGATTTTAACCTACCACCTGTAGTAGCAAAAGAA<br>ATAGTAGCCAGCTGTGATAAATGTCAGCTAAAAGG<br>GGAAGCCATGCATGGACAAGTAGACTGTAGCCCA<br>GGAATATGGCAGCTAGATTGTACACATTTAGAAGG<br>AAAAGTTATCTTGGTAGCAGTTCATGTAGCCAGTG<br>GATATATAGAAGCAGAAGTAATTCCAGCAGAGAC<br>AGGGCAAGAAACAGCATACTTCCTCTTAAAATTAG<br>CAGGAAGATGGCCAGTAAAAACAGTACATACAGA<br>CAATGGCAGCAATTTCACCAGTACTACAGTTAAGG<br>CCGCCTGTTGGTGGGCGGGGATCAAGCAGGAATTT<br>GGCATTCCCTACAATCCCCAAAGTCAAGGAGTAAT<br>AGAATCTATGAATAAAGAATTAAAGAAAATTATAG<br>GACAGGTAAGAGATCAGGCTGAACATCTTAAGAC<br>AGCAGTACAAATGGCAGTATTCATCCACAATTTTA<br>AAAGAAAAGGGGGGATTGGGGGGTACAGTGCAGG<br>GGAAAGAATAGTAGACATAATAGCAACAGACATA<br>CAAACTAAAGAATTACAAAAACAAATTACAAAAA<br>TTCAAAATTTTCGGGTTTATTACAGGGACAGCAGA<br>GATCCAGTTTGGAAAGGACCAGCAAAGCTCCTCTG<br>GAAAGGTGAAGGGGCAGTAGTAATACAAGATAAT<br>AGTGACATAAAAGTAGTGCCAAGAAGAAAAGCAA<br>AGATCATCAGGGATTATGGAAAACAGATGGCAGG<br>TGATGATTGTGTGGCAAGTAGACAGGATGAGGATT<br>AA |
| 55 | Helper; HIV RRE; Binds Rev element | AGGAGCTTTGTTCCTTGGGTTCTTGGGAGCAGCAG<br>GAAGCACTATGGGCGCAGCGTCAATGACGCTGACG<br>GTACAGGCCAGACAATTATTGTCTGGTATAGTGCA<br>GCAGCAGAACAATTTGCTGAGGGCTATTGAGGCGC<br>AACAGCATCTGTTGCAACTCACAGTCTGGGGCATC<br>AAGCAGCTCCAGGCAAGAATCCTGGCTGTGGAAA<br>GATACCTAAAGGATCAACAGCTCCT |
| 56 | Helper; Rabbit beta globin poly A; RNA stability | AGATCTTTTTCCCTCTGCCAAAAATTATGGGGACAT<br>CATGAAGCCCCTTGAGCATCTGACTTCTGGCTAAT<br>AAAGGAAATTTATTTTCATTGCAATAGTGTGTTGG<br>AATTTTTTGTGTCTCTCACTCGGAAGGACATATGGG<br>AGGGCAAATCATTTAAAACATCAGAATGAGTATTT<br>GGTTTAGAGTTTGGCAACATATGCCCATATGCTGGC<br>TGCCATGAACAAAGGTGGCTATAAAGAGGTCATCA<br>GTATATGAAACAGCCCCCTGCTGTCCATTCCTTATT<br>CCATAGAAAAGCCTTGACTTGAGGTTAGATTTTTTT<br>TATATTTTGTTTTGTGTTATTTTTTCTTTAACATCC<br>CTAAAATTTTCCTTACATGTTTTACTAGCCAGATTT<br>TTCCTCCTCTCCTGACTACTCCCAGTCATAGCTGTC<br>CCTCTTCTCTTATGAAGATC |

-continued

| SEQ ID NO: | Description | Sequence |
|---|---|---|
| 57 | Rev; RSV promoter; Transcription | ATGGCAGGAAGAAGCGGAGACAGCGACGAAGAAC<br>TCCTCAAGGCAGTCAGACTCATCAAGTTTCTCTATC<br>AAAGCAACCCACCTCCCAATCCCGAGGGGACCCG<br>ACAGGCCCGAAGGAATAGAAGAAGAAGGTGGAGA<br>GAGAGACAGAGACAGATCCATTCGATTAGTGAAC<br>GGATCCTTAGCACTTATCTGGGACGATCTGCGGAG<br>CCTGTGCCTCTTCAGCTACCACCGCTTGAGAGACTT<br>ACTCTTGATTGTAACGAGGATTGTGGAACTTCTGG<br>GACGCAGGGGGTGGGAAGCCCTCAAATATTGGTG<br>GAATCTCCTACAATATTGGAGTCAGGAGCTAAAGA<br>ATAG |
| 58 | Rev; HIV Rev; Nuclear export and stabilize viral mRNA | ATGGCAGGAAGAAGCGGAGACAGCGACGAAGAAC<br>TCCTCAAGGCAGTCAGACTCATCAAGTTTCTCTATC<br>AAAGCAACCCACCTCCCAATCCCGAGGGGACCCG<br>ACAGGCCCGAAGGAATAGAAGAAGAAGGTGGAGA<br>GAGAGACAGAGACAGATCCATTCGATTAGTGAAC<br>GGATCCTTAGCACTTATCTGGGACGATCTGCGGAG<br>CCTGTGCCTCTTCAGCTACCACCGCTTGAGAGACTT<br>ACTCTTGATTGTAACGAGGATTGTGGAACTTCTGG<br>GACGCAGGGGGTGGGAAGCCCTCAAATATTGGTG<br>GAATCTCCTACAATATTGGAGTCAGGAGCTAAAGA<br>ATAG |
| 59 | Rev; Rabbit beta globin poly A; RNA stability | AGATCTTTTTCCCTCTGCCAAAAATTATGGGGACAT<br>CATGAAGCCCCTTGAGCATCTGACTTCTGGCTAAT<br>AAAGGAAATTTATTTTCATTGCAATAGTGTGTTGG<br>AATTTTTTGTGTCTCTCACTCGGAAGGACATATGGG<br>AGGGCAAATCATTTAAAACATCAGAATGAGTATTT<br>GGTTTAGAGTTTGGCAACATATGCCCATATGCTGG<br>CTGCCATGAACAAAGGTTGGCTATAAAGAGGTCAT<br>CAGTATATGAAACAGCCCCCTGCTGTCCATTCCTTA<br>TTCCATAGAAAAGCCTTGACTTGAGGTTAGATTTTT<br>TTTATATTTTGTTTTGTGTTATTTTTTTCTTTAACAT<br>CCCTAAAATTTTCCTTACATGTTTTACTAGCCAGAT<br>TTTTCCTCCTCTCCTGACTACTCCCAGTCATAGCTG<br>TCCCTCTTCTCTTATGGAGATC |
| 60 | Envelope; CMV promoter; Transcription | ACATTGATTATTGACTAGTTATTAATAGTAATCAAT<br>TACGGGGTCATTAGTTCATAGCCCATATATGGAGT<br>TCCGCGTTACATAACTTACGGTAAATGGCCCGCCT<br>GGCTGACCGCCCAACGACCCCCGCCCATTGACGTC<br>AATAATGACGTATGTTCCCATAGTAACGCCAATAG<br>GGACTTTCCATTGACGTCAATGGGTGGAGTATTTA<br>CGGTAAACTGCCCACTTGGCAGTACATCAAGTGTA<br>TCATATGCCAAGTACGCCCCCTATTGACGTCAATG<br>ACGGTAAATGGCCCGCCTGGCATTATGCCCAGTAC<br>ATGACCTTATGGGACTTTCCTACTTGGCAGTACATC<br>TACGTATTAGTCATCGCTATTACCATGGTGATGCG<br>GTTTTGGCAGTACATCAATGGGCGTGGATAGCGGT<br>TTGACTCACGGGGATTTCCAAGTCTCCACCCCATTG<br>ACGTCAATGGGAGTTTGTTTTGGCACCAAAATCAA<br>CGGGACTTTCCAAAATGTCGTAACAACTCCGCCCC<br>ATTGACGCAAATGGGCGGTAGGCGTGTACGGTGGG<br>AGGTCTATATAAGC |
| 61 | Envelope; Beta globin intron; Enhance gene expression | GTGAGTTTGGGGACCCTTGATTGTTCTTTCTTTTTC<br>GCTATTGTAAAATTCATGTTATATGGAGGGGCAA<br>AGTTTTCAGGGTGTTGTTTAGAATGGGAAGATGTC<br>CCTTGTATCACCATGGACCCTCATGATAATTTTGTT<br>TCTTTCACTTTCTACTCTGTTGACAACCATTGTCTC<br>CTCTTATTTTCTTTTCATTTTCTGTAACTTTTTCGTT<br>AAACTTTAGCTTGCATTTGTAACGAATTTTTAAATT<br>CACTTTTGTTTATTTGTCAGATTGTAAGTACTTTCT<br>CTAATCACTTTTTTTTCAAGGCAATCAGGGTATATT<br>ATATTGTACTTCAGCACAGTTTTAGAGAACAATTG<br>TTATAATTAAATGATAAGGTAGAATATTTCTGCAT<br>ATAAATTCTGGCTGGCGTGGAAATATTCTTATTGGT<br>AGAAACAACTACACCCTGGTCATCATCCTGCCTTT<br>CTCTTTATGGTTACAATGATATACACTGTTTGAGAT<br>GAGGATAAAATACTCTGAGTCCAAACCGGGCCCCT<br>CTGCTAACCATGTTCATGCCTTCTTCTCTTTCCTAC<br>AG |

-continued

| SEQ ID NO: | Description | Sequence |
|---|---|---|
| 62 | Envelope; VSV-G; Glycoprotein envelope-cell entry | ATGAAGTGCCTTTTGTACTTAGCCTTTTTATTCATT<br>GGGGTGAATTGCAAGTTCACCATAGTTTTTCCACA<br>CAACCAAAAAGGAAACTGGAAAAATGTTCCTTCTA<br>ATTACCATTATTGCCCGTCAAGCTCAGATTTAAATT<br>GGCATAATGACTTAATAGGCACAGCCTTACAAGTC<br>AAAATGCCCAAGAGTCACAAGGCTATTCAAGCAG<br>ACGGTTGGATGTGTCATGCTTCCAAATGGGTCACT<br>ACTTGTGATTTCCGCTGGTATGGACCGAAGTATAT<br>AACACATTCCATCCGATCCTTCACTCCATCTGTAGA<br>ACAATGCAAGGAAAGCATTGAACAAACGAAACAA<br>GGAACTTGGCTGAATCCAGGCTTCCCTCCTCAAAG<br>TTGTGGATATGCAACTGTGACGGATGCCGAAGCAG<br>TGATTGTCCAGGTGACTCCTCACCATGTGCTGGTTG<br>ATGAATACACAGGAGAATGGGTTGATTCACAGTTC<br>ATCAACGGAAAATGCAGCAATTACATATGCCCCAC<br>TGTCCATAACTCTACAACCTGGCATTCTGACTATAA<br>GGTCAAAGGGCTATGTGATTCTAACCTCATTTCCAT<br>GGACATCACCTTCTTCTCAGAGGACGGAGAGCTAT<br>CATCCCTGGGAAAGGAGGGCACAGGGTTCAGAAG<br>TAACTACTTTGCTTATGAAACTGGAGGCAAGGCCT<br>GCAAAATGCAATACTGCAAGCATTGGGGAGTCAG<br>ACTCCCATCAGGTGTCTGGTTCGAGATGGCTGATA<br>AGGATCTCTTTGCTGCAGCCAGATTCCCTGAATGC<br>CCAGAAGGGTCAAGTATCTCTGCTCCATCTCAGAC<br>CTCAGTGGATGTAAGTCTAATTCAGGACGTTGAGA<br>GGATCTTGGATTATTCCCTCTGCCAAGAAACCTGG<br>AGCAAAATCAGAGCGGGTCTTCCAATCTCTCCAGT<br>GGATCTCAGCTATCTTGCTCCTAAAAACCCAGGAA<br>CCGGTCCTGCTTTCACCATAATCAATGGTACCCTAA<br>AATACTTTGAGACCAGATACATCAGAGTCGATATT<br>GCTGCTCCAATCCTCTCAAGAATGGTCGGAATGAT<br>CAGTGGAACTACCACAGAAAGGGAACTGTGGGAT<br>GACTGGGCACCATATGAAGACGTGGAAATTGGACC<br>CAATGGAGTTCTGAGGACCAGTTCAGGATATAAGT<br>TTCCTTTATACATGATTGGACATGGTATGTTGGACT<br>CCGATCTTCATCTTAGCTCAAAGGCTCAGGTGTTCG<br>AACATCCTCACATTCAAGACGCTGCTTCGCAACTT<br>CCTGATGATGAGAGTTTATTTTTTGGTGATACTGGG<br>CTATCCAAAAATCCAATCGAGCTTGTAGAAGGTTG<br>GTTCAGTAGTTGGAAAAGCTCTATTGCCTCTTTTTT<br>CTTTATCATAGGGTTAATCATTGGACTATTCTTGGT<br>TCTCCGAGTTGGTATCCATCTTTGCATTAAATTAAA<br>GCACACCAAGAAAAGACAGATTTATACAGACATA<br>GAGATGA |
| 63 | Envelope; Rabbit beta globin poly A; RNA stability | AGATCTTTTTCCCTCTGCCAAAAATTATGGGGACAT<br>CATGAAGCCCCTTGAGCATCTGACTTCTGGCTAAT<br>AAAGGAAATTTATTTTCATTGCAATAGTGTGTTGG<br>AATTTTTTGTGTCTCTCACTCGGAAGGACATATGGG<br>AGGGCAAATCATTTAAAACATCAGAATGAGTATTT<br>GGTTTAGAGTTTGGCAACATATGCCCATATGCTGG<br>CTGCCATGAACAAAGGTTGGCTATAAAGAGGTCAT<br>CAGTATATGAAACAGCCCCTGCTGTCCATTCCTTA<br>TTCCATAGAAAAGCCTTGACTTGAGGTTAGATTTTT<br>TTTATATTTTGTTTTGTGTTATTTTTTTCTTTAACAT<br>CCCTAAAATTTTCCTTACATGTTTTACTAGCCAGAT<br>TTTTCCTCCTCCTGACTACTCCCAGTCATAGCTG<br>TCCCTCTTCTCTTATGGAGATC |
| 64 | Promoter; EF-1 | CCGGTGCCTAGAGAAGGTGGCGCGGGGTAAACTG<br>GGAAAGTGATGTCGTGTACTGGCTCCGCCTTTTTCC<br>CGAGGGTGGGGGAGAACCGTATATAAGTGCAGTA<br>GTCGCCGTGAACGTTCTTTTTCGCAACGGGTTTGCC<br>GCCAGAACACAGGTAAGTGCCGTGTGTGGTTCCCG<br>CGGGCCTGGCCTCTTTACGGGTTATGGCCCTTGCGT<br>GCCTTGAATTACTTCCACGCCCCTGGCTGCAGTAC<br>GTGATTCTTGATCCCGAGCTTCGGGTTGGAAGTGG<br>GTGGGAGAGTTCGAGGCCTTGCGCTTAAGGAGCCC<br>CTTCGCCTCGTGCTTGAGTTGAGGCCTGGCCTGGG<br>CGCTGGGGCCGCCGCGTGCGAATCTGGTGGCACCT<br>TCGCGCCTGTCTCGCTGCTTTCGATAAGTCTCTAGC<br>CATTTAAAATTTTTGATGACCTGCTGCGACGCTTTT<br>TTTCTGGCAAGATAGTCTTGTAAATGCGGGCCAAG<br>ATCTGCACACTGGTATTTCGGTTTTTGGGGCCGCGG<br>GCGGCGACGGGGCCCGTGCGTCCCAGCGCACATGT |

| SEQ ID NO: | Description | Sequence |
|---|---|---|
| | | TCGGCGAGGCGGGGCCTGCGAGCGCGGCCACCGA<br>GAATCGGACGGGGGTAGTCTCAAGCTGGCCGGCCT<br>GCTCTGGTGCCTGGCCTCGCGCCGCCGTGTATCGC<br>CCCGCCCTGGGCGGCAAGGCTGGCCCGGTCGGCAC<br>CAGTTGCGTGAGCGGAAAGATGGCCGCTTCCCGGC<br>CCTGCTGCAGGGAGCTCAAAATGGAGGACGCGGC<br>GCTCGGGAGAGCGGGCGGGTGAGTCACCCACACA<br>AAGGAAAAGGGCCTTTCCGTCCTCAGCCGTCGCTT<br>CATGTGACTCCACGGAGTACCGGGCGCCGTCCAGG<br>CACCTCGATTAGTTCTCGAGCTTTTGGAGTACGTCG<br>TCTTTAGGTTGGGGGGAGGGGTTTTATGCGATGGA<br>GTTTCCCCACACTGAGTGGGTGGAGACTGAAGTTA<br>GGCCAGCTTGGCACTTGATGTAATTCTCCTTGGAAT<br>TTGCCCTTTTTGAGTTTGGATCTTGGTTCATTCTCA<br>AGCCTCAGACAGTGGTTCAAAGTTTTTTTCTTCCAT<br>TTCAGGTGTCGTGA |
| 65 | Promoter; PGK | GGGGTTGGGGTTGCGCCTTTTCCAAGGCAGCCCTG<br>GGTTTGCGCAGGGACGCGGCTGCTCTGGGCGTGGT<br>TCCGGGAAACGCAGCGGCGCCGACCCTGGGTCTCG<br>CACATTCTTCACGTCCGTTCGCAGCGTCACCCGGAT<br>CTTCGCCGCTACCCTTGTGGGCCCCCCGGCGACGC<br>TTCCTGCTCCGCCCCTAAGTCGGGAAGGTTCCTTGC<br>GGTTCGCGGCGTGCCGGACGTGACAAACGGAAGC<br>CGCACGTCTCACTAGTACCCTCGCAGACGGACAGC<br>GCCAGGGAGCAATGGCAGCGCGCCGACCGCGATG<br>GGCTGTGGCCAATAGCGGCTGCTCAGCAGGGCGCG<br>CCGAGAGCAGCGGCCGGGAAGGGGCGGTGCGGGA<br>GGCGGGGTGTGGGGCGGTAGTGTGGGCCCTGTTCC<br>TGCCCGCGCGGTGTTCCGCATTCTGCAAGCCTCCG<br>GAGCGCACGTCGGCAGTCGGCTCCCTCGTTGACCG<br>AATCACCGACCTCTCTCCCCAG |
| 66 | Promoter; UbC | GCGCCGGGTTTTGGCGCCTCCCGCGGGCGCCCCCC<br>TCCTCACGGCGAGCGCTGCCACGTCAGACGAAGGG<br>CGCAGGAGCGTTCCTGATCCTTCCGCCCGGACGCT<br>CAGGACAGCGGCCCGCTGCTCATAAGACTCGGCCT<br>TAGAACCCCAGTATCAGCAGAAGGACATTTTAGGA<br>CGGGACTTGGGTGACTCTAGGGCACTGGTTTTCTTT<br>CCAGAGAGCGGAACAGGCGAGGAAAAGTAGTCCC<br>TTCTCGGCGATTCTGCGGAGGGATCTCCGTGGGGC<br>GGTGAACGCCGATGATTATATAAGGACGCGCCGGG<br>TGTGGCACAGCTAGTTCCGTCGCAGCCGGGATTTG<br>GGTCGCGGTTCTTGTTTGTGGATCGCTGTGATCGTC<br>ACTTGGTGAGTTGCGGGCTGCTGGGCTGGCCGGGG<br>CTTTCGTGGCCGCCGGGCCGCTCGGTGGGACGGAA<br>GCGTGTGGAGAGACCGCCAAGGGCTGTAGTCTGGG<br>TCCGCGAGCAAGGTTGCCCTGAACTGGGGGTTGGG<br>GGGAGCGCACAAAATGGCGGCTGTTCCCGAGTCTT<br>GAATGGAAGACGCTTGTAAGGCGGGCTGTGAGGTC<br>GTTGAAACAAGGTGGGGGGCATGGTGGGCGGCAA<br>GAACCCAAGGTCTTGAGGCCTTCGCTAATGCGGGA<br>AAGCTCTTATTCGGGTGAGATGGGCTGGGGCACCA<br>TCTGGGGACCCTGACGTGAAGTTTGTCACTGACTG<br>GAGAACTCGGGTTTGTCGTCTGGTTGCGGGGGCGG<br>CAGTTATGCGGTGCCGTTGGGCAGTGCACCCGTAC<br>CTTTGGGAGCGCGCGCCTCGTCGTGTCGTGACGTC<br>ACCCGTTCTGTTGGCTTATAATGCAGGGTGGGGCC<br>ACCTGCCGGTAGGTGTGCGGTAGGCTTTTCTCCGTC<br>GCAGGACGCAGGGTTCGGGCCTAGGGTAGGCTCTC<br>CTGAATCGACAGGCGCCGGACCTCTGGTGAGGGGA<br>GGGATAAGTGAGGCGTCAGTTTCTTTGGTCGGTTTT<br>ATGTACCTATCTTCTTAAGTAGCTGAAGCTCCGGTT<br>TTGAACTATGCGCTCGGGGTTGGCGAGTGTGTTTT<br>GTGAAGTTTTTTAGGCACCTTTTGAAATGTAATCAT<br>TTGGGTCAATATGTAATTTTCAGTGTTAGACTAGTA<br>AA |
| 67 | Poly A; SV40 | GTTTATTGCAGCTTATAATGGTTACAAATAAAGCA<br>ATAGCATCACAAATTTCACAAATAAAGCATTTTTTT<br>CACTGCATTCTAGTTGTGGTTTGTCCAAACTCATCA<br>ATGTATCTTATCA |
| 68 | Poly A; bGH | GACTGTGCCTTCTAGTTGCCAGCCATCTGTTGTTTG<br>CCCCTCCCCCGTGCCTTCCTTGACCCTGGAAGGTGC<br>CACTCCCACTGTCCTTTCCTAATAAAATGAGGAAA |

| SEQ ID NO: | Description | Sequence |
|---|---|---|
|  |  | TTGCATCGCATTGTCTGAGTAGGTGTCATTCTATTC<br>TGGGGGGTGGGTGGGCAGGACAGCAAGGGGGA<br>GGATTGGGAAGACAATAGCAGGCATGCTGGGGAT<br>GCGGTGGGCTCTATGG |
| 69 | HIV Gag; Bal | ATGGGTGCGAGAGCGTCAGTATTAAGCGGGGGAG<br>AATTAGATAGGTGGGAAAAAATTCGGTTAAGGCCA<br>GGGGGAAAGAAAAAATATAGATTAAAACATATAG<br>TATGGGCAAGCAGGGAACTAGAAAGATTCGCAGT<br>CAATCCTGGCCTGTTAGAAACATCAGAAGGCTGCA<br>GACAAATACTGGGACAGCTACAACCATCCCTTCAG<br>ACAGGATCAGAAGAACTTAGATCATTATATAATAC<br>AGTAGCAACCCTCTATTGTGTACATCAAAAGATAG<br>AGGTAAAAGACACCAAGGAAGCTTTAGACAAAAT<br>AGAGGAAGAGCAAAACAAATGTAAGAAAAAGGCA<br>CAGCAAGCAGCAGCTGACACAGGAAACAGCGGTC<br>AGGTCAGCCAAAATTTCCCTATAGTGCAGAACCTC<br>CAGGGGCAAATGGTACATCAGGCCATATCACCTAG<br>AACTTTAAATGCATGGGTAAAAGTAATAGAAGAG<br>AAAGCTTTCAGCCCAGAAGTAATACCCATGTTTTC<br>AGCATTATCAGAAGGAGCCACCCCACAAGATTTAA<br>ACACCATGCTAAACACAGTGGGGGACATCAAGC<br>AGCCATGCAAATGTTAAAAGAACCCATCAATGAGG<br>AAGCTGCAAGATGGGATAGATTGCATCCCGTGCAG<br>GCAGGGCCTGTTGCACCAGGCCAGATAAGAGATCC<br>AAGGGGAAGTGACATAGCAGGAACTACCAGTACC<br>CTTCAGGAACAAATAGGATGGATGACAAGTAATCC<br>ACCTATCCCAGTAGGAGAAATCTATAAAAGATGGA<br>TAATCCTGGGATTAAATAAAATAGTAAGGATGTAT<br>AGCCCTACCAGCATTTTGGACATAAGACAAGGACC<br>AAAGGAACCCTTTAGAGACTATGTAGACCGGTTCT<br>ATAAAACTCTAAGAGCCGAGCAAGCTTCACAGGA<br>GGTAAAAAATTGGATGACAGAAACCTTGTTGGTCC<br>AAAATGCGAACCCAGATTGTAAGACTATTTTAAAA<br>GCATTGGGACCAGCAGCTACACTAGAAGAAATGAT<br>GACAGCATGTCAGGGAGTGGGAGGACCCAGCCAT<br>AAAGCAAGAATTTTGGCAGAAGCAATGAGCCAAG<br>TAACAAATTCAGCTACCATAATGATGCAGAAAGGC<br>AATTTTAGGAACCAAAGAAAGATTGTTAAATGTTT<br>CAATTGTGGCAAAGAAGGGCACATAGCCAGAAAC<br>TGCAGGGCCCCTAGGAAAAGGGGCTGTTGGAAAT<br>GTGGAAAGGAAGGACACCAAATGAAAGACTGTAC<br>TGAGAGACAGGCTAATTTTTTAGGGAAAATCTGGC<br>CTTCCCACAAAGGAAGGCCAGGGAATTTCCTTCAG<br>AGCAGACCAGAGCCAACAGCCCCACCAGCCCCAC<br>CAGAAGAGAGCTTCAGGTTTGGGGAAGAGACAAC<br>AACTCCCTCTCAGAAGCAGGAGCTGATAGACAAGG<br>AACTGTATCCTTTAGCTTCCCTCAGATCACTCTTTG<br>GCAACGACCCCTCGTCACAATAA |
| 70 | HIV Pol; Bal | ATGAATTTGCCAGGAAGATGGAAACCAAAAATGA<br>TAGGGGGAATTGGAGGTTTTATCAAAGTAAGACAG<br>TATGATCAGATACTCATAGAAATCTGTGGACATAA<br>AGCTATAGGTACAGTATTAATAGGACCTACACCTG<br>TCAACATAATTGGAAGAAATCTGTTGACTCAGATT<br>GGTTGCACTTTAAATTTTCCCATTAGTCCTATTGAA<br>ACTGTACCAGTAAAATTAAAACCAGGAATGGATGG<br>CCCAAAAGTTAAACAATGGCCACTGACAGAAGAA<br>AAAATAAAAGCATTAATGGAAATCTGTACAGAAAT<br>GGAAAAGGAAGGGAAAATTTCAAAAATTGGGCCT<br>GAAAATCCATACAATACTCCAGTATTTGCCATAAA<br>GAAAAAAGACAGTACTAAATGGAGAAAATTAGTA<br>GATTTCAGAGAACTTAATAAGAAAACTCAAGACTT<br>CTGGGAAGTACAATTAGGAATACACATCCCGCAGG<br>GGTTAAAAAAGAAAAAATCAGTAACAGTACTGGA<br>TGTGGGTGATGCATATTTTTCAGTTCCCTTAGATAA<br>AGAATTCAGGAAGTATACTGCATTTACCATACCTA<br>GTATAAACAATGAAACACCAGGGATCAGATATCA<br>GTACAATGTACTTCCACAGGGATGGAAAGGATCAC<br>CAGCAATATTTCAAAGTAGCATGACAAGAATCTTA<br>GAGCCTTTTAGAAAACAAAATCCAGAAATAGTGAT<br>CTATCAATACATGGATGATTTGTATGTAGGATCTG<br>ACTTAGAAATAGGGCAGCATAGAACAAAAATAGA<br>GGAACTGAGACAACATCTGTTGAGGTGGGGATTTA<br>CCACACCAGACAAAAAACATCAGAAAGAACCTCC<br>ATTCCTTTGGATGGGTTATGAACTCCATCCTGATAA |

| SEQ ID NO: | Description | Sequence |
|---|---|---|
| | | ATGGACAGTACAGCCTATAGTGCTGCCAGAAAAG<br>ACAGCTGGACTGTCAATGACATACAGAAGTTAGTG<br>GGAAAATTGAATTGGGCAAGTCAGATTTACCCAGG<br>AATTAAAGTAAAGCAATTATGTAGGCTCCTTAGGG<br>GAACCAAGGCATTAACAGAAGTAATACCACTAAC<br>AAAAGAAACAGAGCTAGAACTGGCAGAGAACAGG<br>GAAATTCTAAAAGAACCAGTACATGGGGTGTATTA<br>TGACCCATCAAAAGACTTAATAGCAGAAATACAGA<br>AGCAGGGGCAAGGCCAATGGACATATCAAATTTAT<br>CAAGAGCCATTTAAAAATCTGAAAACAGGAAAAT<br>ATGCAAGAATGAGGGGTGCCCACACTAATGATGTA<br>AAACAATTAACAGAGGCAGTGCAAAAAATAACCA<br>CAGAAAGCATAGTAATATGGGGAAAGACTCCTAA<br>ATTTAAACTACCCATACAAAAAGAAACATGGGAA<br>ACATGGTGGACAGAGTATTGGCAAGCCACCTGGAT<br>TCCTGAGTGGGAGTTTGTCAATACCCCTCCCTTAGT<br>GAAATTATGGTACCAGTTAGAGAAAGAACCCATAA<br>TAGGAGCAGAAACATTCTATGTAGATGGAGCAGCT<br>AACCGGGAGACTAAATTAGGAAAAGCAGGATATG<br>TTACTAACAGAGGAAGACAAAAAGTTGTCTCCCTA<br>ACTGACACAACAAATCAGAAGACTGAGTTACAAG<br>CAATTCATCTAGCTTTACAAGATTCAGGATTAGAA<br>GTAAACATAGTAACAGACTCACAATATGCATTAGG<br>AATCATTCAAGCACAACCAGATAAAAGTGAATCAG<br>AGTTAGTCAGTCAAATAATAGAACAGTTAATAAAA<br>AAGGAAAAGGTCTACCTGGCATGGGTACCAGCGC<br>ACAAAGGAATTGGAGGAAATGAACAAGTAGATAA<br>ATTAGTCAGTACTGGAATCAGGAAAGTACTA |
| 71 | HIV Integrase; Bal | TTTTTAGATGGAATAGATATAGCCCAAGAAGAACA<br>TGAGAAATATCACAGTAATTGGAGAGCAATGGCTA<br>GTGATTTTAACCTGCCACCTGTGGTAGCAAAAGAA<br>ATAGTAGCCAGCTGTGATAAATGTCAGCTAAAAGG<br>AGAAGCCATGCATGGACAAGTAGACTGTAGTCCAG<br>GAATATGGCAACTAGATTGTACACATTTAGAAGGA<br>AAAATTATCCTGGTAGCAGTTCATGTAGCCAGTGG<br>ATATATAGAAGCAGAAGTTATTCCAGCAGAGACAG<br>GGCAGGAAACAGCATACTTTCTCTTAAAATTAGCA<br>GGAAGATGGCCAGTAAAAACAATACATACAGACA<br>ATGGCAGCAATTTCACTAGTACTACAGTCAAGGCC<br>GCCTGTTGGTGGGCGGGATCAAGCAGGAATTTGG<br>CATTCCCTACAATCCCCAAAGTCAGGGAGTAGTAG<br>AATCTATAAATAAAGAATTAAAGAAAATTATAGGA<br>CAGGTAAGAGATCAGGCTGAACATCTTAAAACAGC<br>AGTACAAATGGCAGTATTCATCCACAATTTTAAAA<br>GAAAAGGGGGGATTGGGGGGTATAGTGCAGGGGA<br>AAGAATAGTAGACATAATAGCAACAGACATACAA<br>ACTAAAGAATTACAAAAACAAATTACAAAAATTCA<br>AAATTTTCGGGTTTATTACAGGGACAGCAGAGATC<br>CACTTTGGAAAGGACCAGCAAAGCTTCTCTGGAAA<br>GGTGAAGGGGCAGTAGTAATACAAGATAATAGTG<br>ACATAAAAGTAGTACCAAGAAGAAAAGCAAAGAT<br>CATTAGGGATTATGGAAAACAGATGGCAGGTGATG<br>ATTGTGTGGCAAGTAGACAGGATGAGGATTAG |
| 72 | Envelope; RD114 | ATGAAACTCCCAACAGGAATGGTCATTTTATGTAG<br>CCTAATAATAGTTCGGGCAGGGTTTGACGACCCCC<br>GCAAGGCTATCGCATTAGTACAAAAACAACATGGT<br>AAACCATGCAATGCAGCGGAGGGCAGGTATCCG<br>AGGCCCCACCGAACTCCATCCAACAGGTAACTTGC<br>CCAGGCAAGACGGCCTACTTAATGACCAACCAAAA<br>ATGGAAATGCAGAGTCACTCCAAAAAATCTCACCC<br>CTAGCGGGGAGAACTCCAGAACTGCCCCTGTAAC<br>ACTTTCCAGGACTCGATGCACAGTTCTTGTTATACT<br>GAATACCGGCAATGCAGGGCGAATAATAAGACAT<br>ACTACACGCCACCTTGCTTAAAATACGGTCTGGG<br>AGCCTCAACGAGGTACAGATATTACAAAACCCCAA<br>TCAGCTCCTACAGTCCCCTTGTAGGGGCTCTATAA<br>ATCAGCCCGTTTGCTGGAGTGCCACAGCCCCCATC<br>CATATCTCCGATGGTGGAGGACCCCTCGATACTAA<br>GAGAGTGTGGACAGTCCAAAAAAGGCTAGAACAA<br>ATTCATAAGGCTATGCATCCTGAACTTCAATACCA<br>CCCCTTAGCCCTGCCCAAAGTCAGAGATGACCTTA<br>GCTTGATGCACGGACTTTTGATATCCTGAATACC<br>ACTTTTAGGTTACTCCAGATGTCCAATTTTAGCCTT<br>GCCCAAGATTGTTGGCTCTGTTTAAAACTAGGTAC |

-continued

| SEQ ID NO: | Description | Sequence |
|---|---|---|
| | | CCCTACCCCTCTTGCGATACCCACTCCCTCTTTAAC CTACTCCCTAGCAGACTCCCTAGCGAATGCCTCCT GTCAGATTATACCTCCCCTCTTGGTTCAACCGATGC AGTTCTCCAACTCGTCCTGTTTATCTTCCCCTTTCAT TAACGATACGGAACAAATAGACTTAGGTGCAGTCA CCTTTACTAACTGCACCTCTGTAGCCAATGTCAGTA GTCCTTTATGTGCCCTAAACGGGTCAGTCTTCCTCT GTGGAAATAACATGGCATACACCTATTTACCCCAA AACTGGACAGGACTTTGCGTCCAAGCCTCCCTCCT CCCCGACATTGACATCATCCCGGGGGATGAGCCAG TCCCCATTCCTGCCATTGATCATTATATACATAGAC CTAAACGAGCTGTACAGTTCATCCCTTTACTAGCTG GACTGGGAATCACCGCAGCATTCACCACCGGAGCT ACAGGCCTAGGTGTCTCCGTCACCCAGTATACAAA ATTATCCCATCAGTTAATATCTGATGTCCAAGTCTT ATCCGGTACCATACAAGATTTACAAGACCAGGTAG ACTCGTTAGCTGAAGTAGTTCTCCAAAATAGGAGG GGACTGGACCTACTAACGGCAGAACAAGGAGGAA TTTGTTTAGCCTTACAAGAAAAATGCTGTTTTTATG CTAACAAGTCAGGAATTGTGAGAAACAAAATAAG AACCCTACAAGAAGAATTACAAAAACGCAGGGAA AGCCTGGCATCCAACCCTCTCTGGACCGGGCTGCA GGGCTTTCTTCCGTACCTCCTACCTCTCCTGGGACC CCTACTCACCCTCCTACTCATACTAACCATTGGGCC ATGCGTTTTCAATCGATTGGTCCAATTTGTTAAAGA CAGGATCTCAGTGGTCCAGGCTCTGGTTTTGACTC AGCAATATCACCAGCTAAAACCCATAGAGTACGAG CCATGA |
| 73 | Envelope; GALV | ATGCTTCTCACCTCAAGCCCGCACCACCTTCGGCA CCAGATGAGTCCTGGGAGCTGGAAAAGACTGATCA TCCTCTTAAGCTGCGTATTCGGAGACGGCAAAACG AGTCTGCAGAATAAGAACCCCCACCAGCCTGTGAC CCTCACCTGGCAGGTACTGTCCCAAACTGGGGACG TTGTCTGGGACAAAAAGGCAGTCCAGCCCCTTTGG ACTTGGTGGCCCTCTCTTACACCTGATGTATGTGCC CTGGCGGCCGGTCTTGAGTCCTGGGATATCCCGGG ATCCGATGTATCGTCCTCTAAAAGAGTTAGACCTC CTGATTCAGACTATACTGCCGCTTATAAGCAAATC ACCTGGGGAGCCATAGGGTGCAGCTACCCTCGGGC TAGGACCAGGATGGCAAATTCCCCCTTCTACGTGT GTCCCCGAGCTGGCCGAACCCATTCAGAAGCTAGG AGGTGTGGGGGGCTAGAATCCCTATACTGTAAAGA ATGGAGTTGTGAGACCACGGGTACCGTTTATTGGC AACCCAAGTCCTCATGGGACCTCATAACTGTAAAA TGGGACCAAAATGTGAATGGGAGCAAAAATTTC AAAAGTGTGAACAAACCGGCTGGTGTAACCCCCTC AAGATAGACTTCACAGAAAAAGGAAAACTCTCCA GAGATTGGATAACGGAAAAAAACCTGGGAATTAAG GTTCTATGTATATGGACACCCAGGCATACAGTTGA CTATCCGCTTAGAGGTCACTAACATGCCGGTTGTG GCAGTGGGCCCAGACCCTGTCCTTGCGGAACAGGG ACCTCCTAGCAAGCCCCTCACTCTCCCTCTCTCCCC ACGGAAAGCGCCGCCCACCCCTCTACCCCCGGCGG CTAGTGAGCAAACCCCTGCGGTGCATGGAGAAACT GTTACCCTAAACTCTCCGCCTCCCACCAGTGGCGA CCGACTCTTTTGGCCTTGTGCAGGGGGCCTTCCTAAC CTTGAATGCTACCAACCCAGGGGCCACTAAGTCTT GCTGGCTCTGTTTGGGCATGAGCCCCCCTTATTATG AAGGGATAGCCTCTTCAGGAGAGGTCGCTTATACC TCCAACCATACCCGATGCCACTGGGGGCCCAAGG AAAGCTTACCCTCACTGAGGTCTCCGGACTCGGGT CATGCATAGGGAAGGTGCCTCTTACCCATCAACAT CTTTGCAACCAGACCTTACCCATCAATTCCTCTAAA AACCATCAGTATCTGCTCCCCTCAAACCATAGCTG GTGGGCCTGCAGCACTGGCCTCACCCCCTGCCTCT CCACCTCAGTTTTTAATCAGTCTAAAGACTTCTGTG TCCAGGTCCAGCTGATCCCCGCATCTATTACCATT CTGAAGAAACCTTGTTACAAGCCTATGACAAATCA CCCCCCAGGTTTAAAAGAGGCTGCCTCACTTAC CCTAGCTGTCTTCCTGGGGTTAGGGATTGCGGCAG GTATAGGTACTGGCTCAACCGCCCTAATTAAAGGG CCCATAGACCTCCAGCAAGGCCTAACCAGCCTCCA AATCGCCATTGACGCTGACCTCCGGGCCCTTCAGG ACTCAATCAGCAAGCTAGAGGACTCACTGACTTCC CTATCTGAGGTAGTACTCCAAAATAGGAGAGGCCT |

-continued

| SEQ ID NO: | Description | Sequence |
|---|---|---|
| | | TGACTTACTATTCCTTAAAGAAGGAGGCCTCTGCG CGGCCCTAAAAGAAGAGTGCTGTTTTTATGTAGAC CACTCAGGTGCAGTACGAGACTCCATGAAAAAACT TAAAGAAAGACTAGATAAAAGACAGTTAGAGCGC CAGAAAAACCAAAACTGGTATGAAGGGTGGTTCA ATAACTCCCCTTGGTTTACTACCCTACTATCAACCA TCGCTGGGCCCCTATTGCTCCTCCTTTTGTTACTCA CTCTTGGGCCCTGCATCATCAATAAATTAATCCAAT TCATCAATGATAGGATAAGTGCAGTCAAAATTTTA GTCCTTAGACAGAAATATCAGACCCTAGATAACGA GGAAAACCTTTAA |
| 74 | Envelope; FUG | ATGGTTCCGCAGGTTCTTTTGTTTGTACTCCTTCTG GGTTTTTCGTTGTGTTTCGGGAAGTTCCCCATTTAC ACGATACCAGACGAACTTGGTCCCTGGAGCCCTAT TGACATACACCATCTCAGCTGTCCAAATAACCTGG TTGTGGAGGATGAAGGATGTACCAACCTGTCCGAG TTCTCCTACATGGAACTCAAAGTGGGATACATCTC AGCCATCAAAGTGAACGGGTTCACTTGCACAGGTG TTGTGACAGAGGCAGAGACCTACACCAACTTTGTT GGTTATGTCACAACCACATTCAAGAGAAAGCATTT CCGCCCCACCCCAGACGCATGTAGAGCCGCGTATA ACTGGAAGATGGCCGGTGACCCCAGATATGAAGA GTCCCTACACAATCCATACCCCGACTACCACTGGC TTCGAACTGTAAGAACCACCAAAGAGTCCCTCATT ATCATATCCCCAAGTGTGACAGATTTGGACCCATA TGACAAATCCCTTCACTCAAGGGTCTTCCCTGGCG GAAAGTGCTCAGGAATAACGGTGTCCTCTACCTAC TGCTCAACTAACCATGATTACACCATTTGGATGCC CGAGAATCCGAGACCAAGGACACCTTGTGACATTT TTACCAATAGCAGAGGGAAGAGAGCATCCAACGG GAACAAGACTTGCGGCTTTGTGGATGAAAGAGGCC TGTATAAGTCTCTAAAAGGAGCATGCAGGCTCAAG TTATGTGGAGTTCTTGGACTTAGACTTATGGATGG AACATGGGTCGCGATGCAAACATCAGATGAGACC AAATGGTGCCCTCCAGATCAGTTGGTGAATTTGCA CGACTTTCGCTCAGACGAGATCGAGCATCTCGTTG TGGAGGAGTTAGTTAAGAAAAGAGAGGAATGTCT GGATGCATTAGAGTCCATCATGACCACCAAGTCAG TAAGTTTCAGACGTCTCAGTCACCTGAGAAAACTT GTCCCAGGGTTTGGAAAAGCATATACCATATTCAA CAAAACCTTGATGGAGGCTGATGCTCACTACAAGT CAGTCCGGACCTGGAATGAGATCATCCCCTCAAAA GGGTGTTTGAAAGTTGGAGGAAGGTGCCATCCTCA TGTGAACGGGGTGTTTTTCAATGGTATAATATTAG GGCCTGACGACCATGTCCTAATCCCAGAGATGCAA TCATCCCTCCTCCAGCAACATATGGAGTTGTTGGA ATCTTCAGTTATCCCCCTGATGCACCCCCTGGCAGA CCCTTCTACAGTTTTCAAAGAAGGTGATGAGGCTG AGGATTTTGTTGAAGTTCACCTCCCCGATGTGTACA AACAGATCTCAGGGGTTGACCTGGGTCTCCCGAAC TGGGGAAAGTATGTATTGATGACTGCAGGGGCCAT GATTGGCCTGGTGTTGATATTTTCCCTAATGACATG GTGCAGAGTTGGTATCCATCTTTGCATTAAATTAA AGCACACCAAGAAAAGACAGATTTATACAGACAT AGAGATGAACCGACTTGGAAAGTAA |
| 75 | Envelope; LCMV | ATGGGTCAGATTGTGACAATGTTTGAGGCTCTGCC TCACATCATCGATGAGGTGATCAACATTGTCATTA TTGTGCTTATCGTGATCACGGGTATCAAGGCTGTCT ACAATTTTGCCACCTGTGGGATATTCGCATTGATCA GTTTCCTACTTCTGGCTGGCAGGTCCTGTGGCATGT ACGGTCTTAAGGGACCCGACATTTACAAAGGAGTT TACCAATTTAAGTCAGTGGAGTTTGATATGTCACA TCTGAACCTGACCATGCCCAACGCATGTTCAGCCA ACAACTCCCACCATTACATCAGTATGGGGACTTCT GGACTAGAATTGACCTTCACCAATGATTCCATCAT CAGTCACAACTTTTGCAATCTGACCTCTGCCTTCAA CAAAAAGACCTTTGACCACACACTCATGAGTATAG TTTCGAGCCTACACCTCAGTATCAGAGGGAACTCC AACTATAAGGCAGTATCCTGCGACTTCAACAATGG CATAACCATCCAATACAACTTGACATTCTCAGATC GACAAAGTGCTCAGAGCCAGTGTAGAACCTTCAGA GGTAGAGTCCTAGATATGTTTAGAACTGCCTTCGG GGGGAAATACATGAGGAGTGGCTGGGGCTGGACA GGCTCAGATGGCAAGACCACCTGGTGTAGCCAGAC |

| SEQ ID NO: | Description | Sequence |
|---|---|---|
| | | GAGTTACCAATACCTGATTATACAAAATAGAACCT
GGGAAAACCACTGCACATATGCAGGTCCTTTTGGG
ATGTCCAGGATTCTCCTTTCCCAAGAGAAGACTAA
GTTCTTCACTAGGAGACTAGCGGGCACATTCACCT
GGACTTTGTCAGACTCTTCAGGGGTGGAGAATCCA
GGTGGTTATTGCCTGACCAAATGGATGATTCTTGCT
GCAGAGCTTAAGTGTTTCGGGAACACAGCAGTTGC
GAAATGCAATGTAAATCATGATGCCGAATTCTGTG
ACATGCTGCGACTAATTGACTACAACAAGGCTGCT
TTGAGTAAGTTCAAAGAGGACGTAGAATCTGCCTT
GCACTTATTCAAAACAACAGTGAATTCTTTGATTTC
AGATCAACTACTGATGAGGAACCACTTGAGAGATC
TGATGGGGGTGCCATATTGCAATTACTCAAAGTTT
TGGTACCTAGAACATGCAAAGACCGGCGAAACTA
GTGTCCCCAAGTGCTGGCTTGTCACCAATGGTTCTT
ACTTAAATGAGACCCACTTCAGTGATCAAATCGAA
CAGGAAGCCGATAACATGATTACAGAGATGTTGAG
GAAGGATTACATAAAGAGGCAGGGGAGTACCCCC
CTAGCATTGATGGACCTTCTGATGTTTTCCACATCT
GCATATCTAGTCAGCATCTTCCTGCACCTTGTCAAA
ATACCAACACACAGGCACATAAAAGGTGGCTCATG
TCCAAAGCCACACCGATTAACCAACAAAGGAATTT
GTAGTTGTGGTGCATTTAAGGTGCCTGGTGTAAAA
ACCGTCTGGAAAAGACGCTGA |
| 76 | Envelope; FPV | ATGAACACTCAAATCCTGGTTTTCGCCCTTGTGGCA
GTCATCCCCACAAATGCAGACAAAATTTGTCTTGG
ACATCATGCTGTATCAAATGGCACCAAAGTAAACA
CACTCACTGAGAGAGGAGTAGAAGTTGTCAATGCA
ACGGAAACAGTGGAGCGGACAAACATCCCCAAAA
TTTGCTCAAAAGGGAAAAGAACCACTGATCTTGGC
CAATGCGGACTGTTAGGGACCATTACCGGACCACC
TCAATGCGACCAATTTCTAGAATTTTCAGCTGATCT
AATAATCGAGAGACGAGAAGGAAATGATGTTTGTT
ACCCGGGGAAGTTTGTTAATGAAGAGGCATTGCGA
CAAATCCTCAGAGGATCAGGTGGGATTGACAAAG
AAACAATGGGATTCACATATAGTGGAATAAGGACC
AACGGAACAACTAGTGCATGTAGAAGATCAGGGT
CTTCATTCTATGCAGAAATGGAGTGGCTCCTGTCA
AATACAGACAATGCTGCTTTCCCACAAATGACAAA
ATCATACAAAAACACAAGGAGAGAATCAGCTCTG
ATAGTCTGGGGAATCCACCATTCAGGATCAACCAC
CGAACAGACCAAACTATATGGGAGTGGAAATAAA
CTGATAACAGTCGGGAGTTCCAAATATCATCAATC
TTTTTGTGCCGAGTCCAGGAACACGACCGCAGATAA
ATGGCCAGTCCGGACGGATTGATTTTCATTGGTTG
ATCTTGGATCCCAATGATACAGTTACTTTTAGTTTC
AATGGGGCTTTCATAGCTCCAAATCGTGCCAGCTT
CTTGAGGGGAAAGTCCATGGGGATCCAGAGCGAT
GTGCAGGTTGATGCCAATTGCGAAGGGGAATGCTA
CCACAGTGGAGGGACTATAACAAGCAGATTGCCTT
TTCAAAACATCAATAGCAGAGCAGTTGGCAAATGC
CCAAGATATGTAAAACAGGAAGTTTATTATTGGC
AACTGGGATGAAGAACGTTCCCGAACCTTCCAAAA
AAAGGAAAAAAGAGGCCTGTTTGGCGCTATAGC
AGGGTTTATTGAAAATGGTTGGGAAGGTCTGGTCG
ACGGGTGGTACGGTTTCAGGCATCAGAATGCACAA
GGAGAAGGAACTGCAGCAGACTACAAAAGCACCC
AATCGGCAATTGATCAGATAACCGGAAAGTTAAAT
AGACTCATTGAGAAAACCAACCAGCAATTTGAGCT
AATAGATAATGAATTCACTGAGGTGGAAAAGCAG
ATTGGCAATTTAATTAACTGGACCAAAGACTCCAT
CACAGAAGTATGGTCTTACAATGCTGAACTTCTTG
TGGCAATGGAAAACCAGCACACTATTGATTTGGCT
GATTCAGAGATGAACAAGCTGTATGAGCGAGTGA
GGAAACAATTAAGGGAAATGCTGAAGAGGATGG
CACTGGTTGCTTTGAAATTTTTCATAAATGTGACGA
TGATTGTATGGCTAGTATAAGGAACAATACTTATG
ATCACAGCAAATACAGAGAAGAAGCGATGCAAAA
TAGAATACAAATTGACCCAGTCAAATTGAGTAGTG
GCTACAAAGATGTGATACTTTGGTTTAGCTTCGGG
GCATCATGCTTTTTGCTTCTTGCCATTGCAATGGGC
CTTGTTTTCATATGTGTGAAGAACGGAAACATGCG
GTGCACTATTTGTATATAA |

| SEQ ID NO: | Description | Sequence |
|---|---|---|
| 77 | Envelope; RRV | AGTGTAACAGAGCACTTTAATGTGTATAAGGCTAC TAGACCATACCTAGCACATTGCGCCGATTGCGGGG ACGGGTACTTCTGCTATAGCCCAGTTGCTATCGAG GAGATCCGAGATGAGGCGTCTGATGGCATGCTTAA GATCCAAGTCTCCGCCCAAATAGGTCTGGACAAGG CAGGCACCCACGCCCACACGAAGCTCCGATATATG GCTGGTCATGATGTTCAGGAATCTAAGAGAGATTC CTTGAGGGTGTACACGTCCGCAGCGTGCTCCATAC ATGGGACGATGGGACACTTCATCGTCGCACACTGT CCACCAGGCGACTACCTCAAGGTTTCGTTCGAGGA CGCAGATTCGCACGTGAAGGCATGTAAGGTCCAAT ACAAGCACAATCCATTGCCGGTGGGTAGAGAGAA GTTCGTGGTTAGACCACACTTTGGCGTAGAGCTGC CATGCACCTCATACCAGCTGACAACGGCTCCCACC GACGAGGAGATTGACATGCATACACCGCCAGATAT ACCGGATCGCACCCTGCTATCACAGACGGCGGGCA ACGTCAAAATAACAGCAGGCGGCAGGACTATCAG GTACAACTGTACCTGCGGCCGTGACAACGTAGGCA CTACCAGTACTGACAAGACCATCAACACATGCAAG ATTGACCAATGCCATGCTGCCGTCACCAGCCATGA CAAATGGCAATTTACCTCTCCATTTGTTCCCAGGGC TGATCAGACAGCTAGGAAAGGCAAGGTACACGTTC CGTTCCCTCTGACTAACGTCACCTGCCGAGTGCCGT TGGCTCGAGCGCCGGATGCCACCTATGGTAAGAAG GAGGTGACCCTGAGATTACACCCAGATCATCCGAC GCTCTTCTCCTATAGGAGTTTAGGAGCCGAACCGC ACCCGTACGAGGAATGGGTTGACAAGTTCTCTGAG CGCATCATCCCAGTGACGGAAGAAGGGATTGAGTA CCAGTGGGGCAACAACCCGCCGGTCTGCCTGTGGG CGCAACTGACGACCGAGGGCAAACCCCATGGCTG GCCACATGAAATCATTCAGTACTATTATGGACTAT ACCCCGCCGCCACTATTGCCGCAGTATCCGGGGCG AGTCTGATGGCCCTCCTAACTCTGGCGGCCACATG CTGCATGCTGGCCACCGCGAGGAGAAAGTGCCTAA CACCGTACGCCCTGACGCCAGGAGCGGTGGTACCG TTGACACTGGGGCTGCTTTGCTGCGCACCGAGGGC GAATGCA |
| 78 | Envelope; MLV 10A1 | AGTGTAACAGAGCACTTTAATGTGTATAAGGCTAC TAGACCATACCTAGCACATTGCGCCGATTGCGGGG ACGGGTACTTCTGCTATAGCCCAGTTGCTATCGAG GAGATCCGAGATGAGGCGTCTGATGGCATGCTTAA GATCCAAGTCTCCGCCCAAATAGGTCTGGACAAGG CAGGCACCCACGCCCACACGAAGCTCCGATATATG GCTGGTCATGATGTTCAGGAATCTAAGAGAGATTC CTTGAGGGTGTACACGTCCGCAGCGTGCTCCATAC ATGGGACGATGGGACACTTCATCGTCGCACACTGT CCACCAGGCGACTACCTCAAGGTTTCGTTCGAGGA CGCAGATTCGCACGTGAAGGCATGTAAGGTCCAAT ACAAGCACAATCCATTGCCGGTGGGTAGAGAGAA GTTCGTGGTTAGACCACACTTTGGCGTAGAGCTGC CATGCACCTCATACCAGCTGACAACGGCTCCCACC GACGAGGAGATTGACATGCATACACCGCCAGATAT ACCGGATCGCACCCTGCTATCACAGACGGCGGGCA ACGTCAAAATAACAGCAGGCGGCAGGACTATCAG GTACAACTGTACCTGCGGCCGTGACAACGTAGGCA CTACCAGTACTGACAAGACCATCAACACATGCAAG ATTGACCAATGCCATGCTGCCGTCACCAGCCATGA CAAATGGCAATTTACCTCTCCATTTGTTCCCAGGGC TGATCAGACAGCTAGGAAAGGCAAGGTACACGTTC CGTTCCCTCTGACTAACGTCACCTGCCGAGTGCCGT TGGCTCGAGCGCCGGATGCCACCTATGGTAAGAAG GAGGTGACCCTGAGATTACACCCAGATCATCCGAC GCTCTTCTCCTATAGGAGTTTAGGAGCCGAACCGC ACCCGTACGAGGAATGGGTTGACAAGTTCTCTGAG CGCATCATCCCAGTGACGGAAGAAGGGATTGAGTA CCAGTGGGGCAACAACCCGCCGGTCTGCCTGTGGG CGCAACTGACGACCGAGGGCAAACCCCATGGCTG GCCACATGAAATCATTCAGTACTATTATGGACTAT ACCCCGCCGCCACTATTGCCGCAGTATCCGGGGCG AGTCTGATGGCCCTCCTAACTCTGGCGGCCACATG CTGCATGCTGGCCACCGCGAGGAGAAAGTGCCTAA CACCGTACGCCCTGACGCCAGGAGCGGTGGTACCG TTGACACTGGGGCTGCTTTGCTGCGCACCGAGGGC GAATGCA |

-continued

| SEQ ID NO: | Description | Sequence |
|---|---|---|
| 79 | Envelope; Ebola | ATGGGTGTTACAGGAATATTGCAGTTACCTCGTGA TCGATTCAAGAGGACATCATTCTTTCTTTGGGTAAT TATCCTTTTCCAAAGAACATTTTCCATCCCACTTGG AGTCATCCACAATAGCACATTACAGGTTAGTGATG TCGACAAACTGGTTTGCCGTGACAAACTGTCATCC ACAAATCAATTGAGATCAGTTGGACTGAATCTCGA AGGGAATGGAGTGGCAACTGACGTGCCATCTGCAA CTAAAAGATGGGGCTTCAGGTCCGGTGTCCCACCA AAGGTGGTCAATTATGAAGCTGGTGAATGGGCTGA AAAACTGCTACAATCTTGAAATCAAAAAACCTGACG GGAGTGAGTGTCTACCAGCAGCGCCAGACGGGATT CGGGGCTTCCCCCGGTGCCGGTATGTGCACAAAGT ATCAGGAACGGGACCGTGTGCCGGAGACTTTGCCT TCCACAAAGAGGGTGCTTTCTTCCTGTATGACCGA CTTGCTTCCACAGTTATCTACCGAGGAACGACTTTC GCTGAAGGTGTCGTTGCATTTCTGATACTGCCCCA AGCTAAGAAGGACTTCTTCAGCTCACACCCCTTGA GAGAGCCGGTCAATGCAACGGAGGACCCGTCAGT GGCTACTATTCTACCACAATTAGATATCAAGCTAC CGGTTTTGGAACCAATGAGACAGAGTATTGTTCG AGGTTGACAATTTGACCTACGTCCAACTTGAATCA AGATTCACACCACAGTTTCTGCTCCAGCTGAATGA GACAATATATACAAGTGGGAAAAGGAGCAATACC ACGGGAAAACTAATTTGGAAGGTCAACCCCGAAAT TGATACAACAATCGGGGAGTGGGCCTTCTGGGAAA CTAAAAAAACCTCACTAGAAAAATTCGCAGTGAAG AGTTGTCTTTCACAGCTGTATCAAACAGAGCCAAA AACATCAGTGGTCAGAGTCCGGCGCGAACTTCTTC CGACCCAGGGACCAACACAACAACTGAAGACCAC AAAATCATGGCTTCAGAAAATTCCTCTGCAATGGT TCAAGTGCACAGTCAAGGAAGGGAAGCTGCAGTG TCGCATCTGACAACCCTTGCCACAATCTCCACGAG TCCTCAACCCCCCACAACCAAACCAGGTCCGGACA ACAGCACCCACAATACACCCGTGTATAAACTTGAC ATCTCTGAGGCAACTCAAGTTGAACAACATCACCG CAGAACAGACAACGACAGCACAGCCTCCGACACT CCCCCCGCCACGACCGCAGCCGGACCCCTAAAAGC AGAGAACACCAACACGAGCAAGGGTACCGACCTC CTGGACCCCGCCACCACAACAAGTCCCCAAAACCA CAGCGAGACCGCTGGCAACAACAACACTCATCACC AAGATACCGGAGAAGAGAGTGCCAGCAGCGGGAA GCTAGGCTTAATTACCAATACTATTGCTGGAGTCG CAGGACTGATCACAGGCGGGAGGAGAGCTCGAAG AGAAGCAATTGTCAATGCTCAACCCAAATGCAACC CTAATTTACATTACTGGACTACTCAGGATGAAGGT GCTGCAATCGGACTGGCCTGGATACCATATTTCGG GCCAGCAGCCGAGGGAATTTACATAGAGGGGCTG ATGCACAATCAAGATGGTTTAATCTGTGGGTTGAG ACAGCTGGCCAACGAGACGACTCAAGCTCTTCAAC TGTTCCTGAGAGCCACAACCGAGCTACGCACCTTT TCAATCCTCAACCGTAAGGCAATTGATTTCTTGCTG CAGCGATGGGGCGGCACATGCCACATTTTGGGACC GGACTGCTGTATCGAACCACATGATTGGACCAAGA ACATAACAGACAAAATTGATCAGATTATTCATGAT TTTGTTGATAAAACCCTTCCGGACCAGGGGGACAA TGACAATTGGTGGACAGGATGGAGACAATGGATA CCGGCAGGTATTGGAGTTACAGGCGTTATAATTGC AGTTATCGCTTTATTCTGTATATGCAAATTTGTCTT TTAG |
| 80 | Short WPRE sequence | AATCAACCTCTGGATTACAAAATTTGTGAAAGATT GACTGATATTCTTAACTATGTTGCTCCTTTTACGCT GTGTGGATATGCTGCTTTAATGCCTCTGTATCATGC TATTGCTTCCCGTACGGCTTTCGTTTTCTCCTCCTTG TATAAATCCTGGTTGCTGTCTCTTTATGAGGAGTTG TGGCCCGTTGTCCGTCAACGTGGCGTGGTGTGCTCT GTGTTTGCTGACGCAACCCCCACTGGCTGGGGCAT TGCCACCACCTGTCAACTCCTTTCTGGGACTTTCGC TTTCCCCCTCCCGATCGCCACGGCAGAACTCATCG CCGCCTGCCTTGCCCGCTGCTGGACAGGGGCTAGG TTGCTGGGCACTGATAATTCCGTGGTGTTGTC |
| 81 | Helper Plasmid Forward Primer | TAAGCAGAATTC ATGAATTTGCCAGGAAGAT |

| SEQ ID NO: | Description | Sequence |
|---|---|---|
| 82 | Helper Plasmid Reverse Primer | CCATACAATGAATGGACACTAGGCGGCCGCACGA<br>AT |
| 83 | Gag, Pol, Integrase fragment | GAATTCATGAATTTGCCAGGAAGATGGAAACCAAA<br>AATGATAGGGGGAATTGGAGGTTTTATCAAAGTAA<br>GACAGTATGATCAGATACTCATAGAAATCTGCGGA<br>CATAAAGCTATAGGTACAGTATTAGTAGGACCTAC<br>ACCTGTCAACATAATTGGAAGAAATCTGTTGACTC<br>AGATTGGCTGCACTTTAAATTTTCCCATTAGTCCTA<br>TTGAGACTGTACCAGTAAAATTAAAGCCAGGAATG<br>GATGGCCCAAAAGTTAAACAATGGCCATTGACAGA<br>AGAAAAAATAAAAGCATTAGTAGAAATTTGTACA<br>GAAATGGAAAAGGAAGGAAAAATTTCAAAAATTG<br>GGCCTGAAAATCCATACAATACTCCAGTATTTGCC<br>ATAAAGAAAAAAGACAGTACTAAATGGAGAAAAT<br>TAGTAGATTTCAGAGAACTTAATAAGAGAACTCAA<br>GATTTCTGGGAAGTTCAATTAGGAATACCACATCC<br>TGCAGGGTTAAAACAGAAAAAATCAGTAACAGTA<br>CTGGATGTGGGCGATGCATATTTTTCAGTTCCCTTA<br>GATAAAGACTTCAGGAAGTATACTGCATTTACCAT<br>ACCTAGTATAAACAATGAGACACCAGGGATTAGAT<br>ATCAGTACAATGTGCTTCCACAGGGATGGAAAGGA<br>TCACCAGCAATATTCCAGTGTAGCATGACAAAAAT<br>CTTAGAGCCTTTTAGAAAACAAAATCCAGACATAG<br>TCATCTATCAATACATGGATGATTTGTATGTAGGAT<br>CTGACTTAGAAATAGGGCAGCATAGAACAAAAAT<br>AGAGGAACTGAGACAACATCTGTTGAGGTGGGGA<br>TTTACCACACCAGACAAAAAACATCAGAAAGAAC<br>CTCCATTCCTTTGGATGGGTTATGAACTCCATCCTG<br>ATAAATGGACAGTACAGCCTATAGTGCTGCCAGAA<br>AAGGACAGCTGGACTGTCAATGACATACAGAAATT<br>AGTGGGAAAATTGAATTGGGCAAGTCAGATTTATG<br>CAGGGATTAAAGTAAGGCAATTATGTAAACTTCTT<br>AGGGGAACCAAAGCACTAACAGAAGTAGTACCAC<br>TAACAGAAGAAGCAGAGCTAGAACTGGCAGAAAA<br>CAGGGAGATTCTAAAAGAACCGGTACATGGAGTGT<br>ATTATGACCCATCAAAAGACTTAATAGCAGAAATA<br>CAGAAGCAGGGGCAAGGCCAATGGACATATCAAA<br>TTTATCAAGAGCCATTTAAAAATCTGAAAACAGGA<br>AAGTATGCAAGAATGAAGGGTGCCCACACTAATG<br>ATGTGAAACAATTAACAGAGGCAGTACAAAAAAT<br>AGCCACAGAAAGCATAGTAATATGGGGAAAGACT<br>CCTAAATTTAAATTACCCATACAAAAGGAAACATG<br>GGAAGCATGGTGGACAGAGTATTGGCAAGCCACCT<br>GGATTCCTGAGTGGGAGTTTGTCAATACCCCTCCCT<br>TAGTGAAGTTATGGTACCAGTTAGAGAAAGAACCC<br>ATAATAGGAGCAGAAACTTTCTATGTAGATGGGGC<br>AGCCAATAGGGAAACTAAATTAGGAAAAGCAGGA<br>TATGTAACTGACAGAGGAAGACAAAAAGTTGTCCC<br>CCTAACGGACACAACAAATCAGAAGACTGAGTTAC<br>AAGCAATTCATCTAGCTTTGCAGGATTCGGGATTA<br>GAAGTAAACATAGTGACAGACTCACAATATGCATT<br>GGGAATCATTCAAGCACAACCAGATAAGAGTGAA<br>TCAGAGTTAGTCAGTCAAATAATAGAGCAGTTAAT<br>AAAAAAGGAAAAGTCTACCTGGCATGGGTACCA<br>GCACACAAAGGAATTGGAGGAAATGAACAAGTAG<br>ATAAATTGGTCAGTGCTGGAATCAGGAAAGTACTA<br>TTTTTAGATGGAATAGATAAGGCCCAAGAAGAACA<br>TGAGAAATATCACAGTAATTGGAGAGCAATGGCTA<br>GTGATTTTAACCTACCACCTGTAGTAGCAAAAGAA<br>ATAGTAGCCAGCTGTGATAAATGTCAGCTAAAAGG<br>GGAAGCCATGCATGGACAAGTAGACTGTAGCCCA<br>GGAATATGGCAGCTAGATTGTACACATTTAGAAGG<br>AAAAGTTATCTTGGTAGCAGTTCATGTAGCCAGTG<br>GATATATAGAAGCAGAAGTAATTCCAGCAGAGAC<br>AGGGCAAGAAACAGCATACTTCCTCTTAAAATTAG<br>CAGGAAGATGGCCAGTAAAAACAGTACATACAGA<br>CAATGGCAGCAATTTCACCAGTACTACAGTTAAGG<br>CCGCCTGTTGGTGGCGGGGATCAAGCAGGAATTT<br>GGCATTCCCTACAATCCCCAAAGTCAAGGAGTAAT<br>AGAATCTATGAATAAAGAATTAAAGAAAATTATAG<br>GACAGGTAAGAGATCAGGCTGAACATCTTAAGAC<br>AGCAGTACAAATGGCAGTATTCATCCACAATTTTA<br>AAAGAAAAGGGGGGATTGGGGGGTACAGTGCAGG<br>GGAAAGAATAGTAGACATAATAGCAACAGACATA<br>CAAACTAAAGAATTACAAAAACAAATTACAAAAA |

-continued

| SEQ ID NO: | Description | Sequence |
|---|---|---|
| | | TTCAAAATTTTCGGGTTTATTACAGGGACAGCAGA GATCCAGTTTGGAAAGGACCAGCAAAGCTCCTCTG GAAAGGTGAAGGGGCAGTAGTAATACAAGATAAT AGTGACATAAAAGTAGTGCCAAGAAGAAAAGCAA AGATCATCAGGGATTATGGAAAACAGATGGCAGG TGATGATTGTGTGGCAAGTAGACAGGATGAGGATT AA |
| 84 | DNA Fragment containing Rev, RRE and rabbit beta globin poly A | TCTAGAATGGCAGGAAGAAGCGGAGACAGCGACG AAGAGCTCATCAGAACAGTCAGACTCATCAAGCTT CTCTATCAAAGCAACCCACCTCCCAATCCCGAGGG GACCCGACAGGCCCGAAGGAATAGAAGAAGAAGG TGGAGAGAGAGACAGAGACAGATCCATTCGATTA GTGAACGGATCCTTGGCACTTATCTGGGACGATCT GCGGAGCCTGTGCCTCTTCAGCTACCACCGCTTGA GAGACTTACTCTTGATTGTAACGAGGATTGTGGAA CTTCTGGGACGCAGGGGGTGGGAAGCCCTCAAATA TTGGTGGAATCTCCTACAATATTGGAGTCAGGAGC TAAAGAATAGAGGAGCTTTGTTCCTTGGGTTCTTG GGAGCAGCAGGAAGCACTATGGGCGCAGCGTCAA TGACGCTGACGGTACAGGCCAGACAATTATTGTCT GGTATAGTGCAGCAGCAGAACAATTTGCTGAGGGC TATTGAGGCGCAACAGCATCTGTTGCAACTCACAG TCTGGGGCATCAAGCAGCTCCAGGCAAGAATCCTG GCTGTGGAAAGATACCTAAAGGATCAACAGCTCCT AGATCTTTTTCCCTCTGCCAAAAATTATGGGGACAT CATGAAGCCCCTTGAGCATCTGACTTCTGGCTAAT AAAGGAAATTTATTTTCATTGCAATAGTGTGTTGG AATTTTTTGTGTCTCTCACTCGGAAGGACATATGGG AGGGCAAATCATTTAAAACATCAGAATGAGTATTT GGTTTAGAGTTTGGCAACATATGCCATATGCTGGC TGCCATGAACAAAGGTGGCTATAAAGAGGTCATCA GTATATGAAACAGCCCCCTGCTGTCCATTCCTTATT CCATAGAAAAGCCTTGACTTGAGGTTAGATTTTTTT TATATTTTGTTTTGTGTTATTTTTTTCTTTAACATCC CTAAAATTTTCCTTACATGTTTTACTAGCCAGATTT TTCCTCCTCTCCTGACTACTCCCAGTCATAGCTGTC CCTCTTCTCTTATGAAGATCCCTCGACCTGCAGCCC AAGCTTGGCGTAATCATGGTCATAGCTGTTTCCTGT GTGAAATTGTTATCCGCTCACAATTCCACACAACA TACGAGCCGGAAGCATAAAGTGTAAAGCCTGGGG TGCCTAATGAGTGAGCTAACTCACATTAATTGCGT TGCGCTCACTGCCCGCTTTCCAGTCGGGAAACCTG TCGTGCCAGCGGATCCGCATCTCAATTAGTCAGCA ACCATAGTCCCGCCCCTAACTCCGCCCATCCCGCC CCTAACTCCGCCCAGTTCCGCCCATTCTCCGCCCCA TGGCTGACTAATTTTTTTTATTTATGCAGAGGCCGA GGCCGCCTCGGCCTCTGAGCTATTCCAGAAGTAGT GAGGAGGCTTTTTTGGAGGCCTAGGCTTTTGCAAA AAGCTAACTTGTTTATTGCAGCTTATAATGGTTACA AATAAAGCAATAGCATCACAAATTTCACAAATAAA GCATTTTTTTCACTGCATTCTAGTTGTGGTTTGTCC AAACTCATCAATGTATCTTATCAGCGGCCGCCCCG GG |
| 85 | DNA fragment containing the CAG enhancer/promoter/ intron sequence | ACGCGTTAGTTATTAATAGTAATCAATTACGGGGT CATTAGTTCATAGCCCATATATGGAGTTCCGCGTTA CATAACTTACGGTAAATGGCCCGCCTGGCTGACCG CCCAACGACCCCCGCCCATTGACGTCAATAATGAC GTATGTTCCCATAGTAACGCCAATAGGGACTTTCC ATTGACGTCAATGGGTGGACTATTTACGGTAAACT GCCCACTTGGCAGTACATCAAGTGTATCATATGCC AAGTACGCCCCCTATTGACGTCAATGACGGTAAAT GGCCCGCCTGGCATTATGCCCAGTACATGACCTTA TGGGACTTTCCTACTTGGCAGTACATCTACGTATTA GTCATCGCTATTACCATGGGTCGAGGTGAGCCCCA CGTTCTGCTTCACTCTCCCCATCTCCCCCCCCTCCC CACCCCCAATTTTGTATTTATTTATTTTTTAATTATT TTGTGCAGCGATGGGGGCGGGGGGGGGGGGGCG CGCGCCAGGCGGGGCGGGGCGGGGCGAGGGGCGG GGCGGGGCGAGGCGGAGAGGTGCGGCGGCAGCCA ATCAGAGCGGCGCGCTCCGAAAGTTTCCTTTTATG GCGAGGCGGCGGCGGCGGCGGCCCTATAAAAAGC GAAGCGCGCGGCGGGCGGGAGTCGCTGCGTTGCCT TCGCCCCGTGCCCCGCTCCGCGCCGCCTCGCGCCG CCCGCCCCGGCTCTGACTGACCGCGTTACTCCCAC |

| SEQ ID NO: | Description | Sequence |
|---|---|---|
| | | AGGTGAGCGGGCGGGACGGCCCTTCTCCTCCGGGC<br>TGTAATTAGCGCTTGGTTTAATGACGGCTCGTTTCT<br>TTTCTGTGGCTGCGTGAAAGCCTTAAAGGGCTCCG<br>GGAGGGCCCTTTGTGCGGGGGGGAGCGGCTCGGG<br>GGGTGCGTGCGTGTGTGTGCGTGGGGAGCGCCG<br>CGTGCGGCCCGCGCTGCCCGGCGGCTGTGAGCGCT<br>GCGGGCGCGGCGCGGGGCTTTGTGCGCTCCGCGTG<br>TGCGCGAGGGGAGCGCGGCCGGGGGCGGTGCCCC<br>GCGGTGCGGGGGGGCTGCGAGGGGAACAAAGGCT<br>GCGTGCGGGGTGTGTGCGTGGGGGGGTGAGCAGG<br>GGGTGTGGGCGCGGCGGTCGGGCTGTAACCCCCCC<br>CTGCACCCCCTCCCCGAGTTGCTGAGCACGGCCC<br>GGCTTCGGGTGCGGGGCTCCGTGCGGGGCGTGGCG<br>CGGGGCTCGCCGTGCCGGGCGGGGGGTGGCGGCA<br>GGTGGGGGTGCCGGGCGGGGCGGGGCCGCCTCGG<br>GCCGGGGAGGGCTCGGGGGAGGGGCGCGGCGGCC<br>CCGGAGCGCCGGCGGCTGTCGAGGCGCGGCGAGC<br>CGCAGCCATTGCCTTTTATGGTAATCGTGCGAGAG<br>GGCGCAGGGACTTCCTTTGTCCCAAATCTGGCGGA<br>GCCGAAATCTGGGAGGCGCCGCCGCACCCCCTCTA<br>GCGGGCGCGGGCGAAGCGGTGCGGCGCCGGCAGG<br>AAGGAAATGGGCGGGAGGGCCTTCGTGCGTCGC<br>CGCGCCGCCGTCCCCTTCTCCATCTCCAGCCTCGGG<br>GCTGCCGCAGGGGACGGCTGCCTTCGGGGGGA<br>CGGGGCAGGGCGGGGTTCGGCTTCTGGCGTGTGAC<br>CGGCGGGAATTC |
| 86 | DNA fragment containing VSV-G | GAATTCATGAAGTGCCTTTTGTACTTAGCCTTTTTA<br>TTCATTGGGGTGAATTGCAAGTTCACCATAGTTTTT<br>CCACACAACCAAAAAGGAAACTGGAAAAATGTTC<br>CTTCTAATTACCATTATTGCCCGTCAAGCTCAGATT<br>TAAATTGGCATAATGACTTAATAGGCACAGCCTTA<br>CAAGTCAAAATGCCCAAGAGTCACAAGGCTATTCA<br>AGCAGACGGTTGGATGTGTCATGCTTCCAAATGGG<br>TCACTACTTGTGATTTCCGCTGGTATGGACCGAAGT<br>ATATAACACATTCCATCCGATCCTTCACTCCATCTG<br>TAGAACAATGCAAGGAAAGCATTGAACAAACGAA<br>ACAAGGAACTTGGCTGAATCCAGGCTTCCCTCCTC<br>AAAGTTGTGGATATGCAACTGTGACGGATGCCGAA<br>GCAGTGATTGTCCAGGTGACTCCTCACCATGTGCT<br>GGTTGATGAATACACAGGAGAATGGGTTGATTCAC<br>AGTTCATCAACGGAAAATGCAGCAATTACATATGC<br>CCCACTGTCCATAACTCTACAACCTGGCATTCTGAC<br>TATAAGGTCAAAGGGCTATGTGATTCTAACCTCAT<br>TTCCATGGACATCACCTTCTTCTCAGAGGACGGAG<br>AGCTATCATCCCTGGGAAAGGAGGGCACAGGGTTC<br>AGAAGTAACTACTTTGCTTATGAAACTGGAGGCAA<br>GGCCTGCAAAATGCAATACTGCAAGCATTGGGGAG<br>TCAGACTCCCATCAGGTGTCTGGTTCGAGATGGCT<br>GATAAGGATCTCTTTGCTGCAGCCAGATTCCCTGA<br>ATGCCCAGAAGGGTCAAGTATCTCTGCTCCATCTC<br>AGACCTCAGTGGATGTAAGTCTAATTCAGGACGTT<br>GAGAGGATCTTGGATTATTCCCTCTGCCAAGAAAC<br>CTGGAGCAAAATCAGAGCGGGTCTTCCAATCTCTC<br>CAGTGGATCTCAGCTATCTTGCTCCTAAAAACCCA<br>GGAACCGGTCCTGCTTTCACCATAATCAATGGTAC<br>CCTAAAATACTTTGAGACCAGATACATCAGAGTCG<br>ATATTGCTGCTCCAATCCTCTCAAGAATGGTCGGA<br>ATGATCAGTGGAACTACCACAGAAAGGGAACTGT<br>GGGATGACTGGGCACCATATGAAGACGTGGAAATT<br>GGACCCAATGGAGTTCTGAGGACCAGTTCAGGATA<br>TAAGTTTCCTTTATACATGATTGGACATGGTATGTT<br>GGACTCCGATCTTCATCTTAGCTCAAAGGCTCAGG<br>TGTTCGAACATCCTCACATTCAAGACGCTGCTTCGC<br>AACTTCCTGATGATGAGAGTTTATTTTTTGGTGATA<br>CTGGGCTATCCAAAAATCCAATCGAGCTTGTAGAA<br>GGTTGGTTCAGTAGTTGGAAAAGCTCTATTGCCTCT<br>TTTTTCTTTATCATAGGGTTAATCATTGGACTATTC<br>TTGGTTCTCCGAGTTGGTATCCATCTTTGCATTAAA<br>TTAAAGCACACCAAGAAAAGACAGATTTATACAG<br>ACATAGAGATGAGAATTC |
| 87 | Helper plasmid containing RRE and rabbit beta globin poly A | TCTAGAAGGAGCTTTGTTCCTTGGGTTCTTGGGAGC<br>AGCAGGAAGCACTATGGGCGCAGCGTCAATGACG<br>CTGACGGTACAGGCCAGACAATTATTGTCTGGTAT<br>AGTGCAGCAGCAGAACAATTTGCTGAGGGCTATTG |

-continued

| SEQ ID NO: | Description | Sequence |
|---|---|---|
| | | AGGCGCAACAGCATCTGTTGCAACTCACAGTCTGG GGCATCAAGCAGCTCCAGGCAAGAATCCTGGCTGT GGAAAGATACCTAAAGGATCAACAGCTCCTAGATC TTTTTCCCTCTGCCAAAAATTATGGGGACATCATGA AGCCCCTTGAGCATCTGACTTCTGGCTAATAAAGG AAATTTATTTTCATTGCAATAGTGTGTTGGAATTTT TTGTGTCTCTCACTCGGAAGGACATATGGGAGGGC AAATCATTTAAAACATCAGAATGAGTATTTGGTTT AGAGTTTGGCAACATATGCCATATGCTGGCTGCCA TGAACAAAGGTGGCTATAAAGAGGTCATCAGTATA TGAAACAGCCCCCTGCTGTCCATTCCTTATTCCATA GAAAAGCCTTGACTTGAGGTTAGATTTTTTTTATAT TTTGTTTTGTGTTATTTTTTCTTTAACATCCCTAAA ATTTTCCTTACATGTTTTACTAGCCAGATTTTCCTC CTCTCCTGACTACTCCCAGTCATAGCTGTCCCTCTT CTCTTATGAAGATCCCTCGACCTGCAGCCCAAGCT TGGCGTAATCATGGTCATAGCTGTTTCCTGTGTGAA ATTGTTATCCGCTCACAATTCCACACAACATACGA GCCGGAAGCATAAAGTGTAAAGCCTGGGGTGCCTA ATGAGTGAGCTAACTCACATTAATTGCGTTGCGCT CACTGCCCGCTTTCCAGTCGGGAAACCTGTCGTGC CAGCGGATCCGCATCTCAATTAGTCAGCAACCATA GTCCCGCCCCTAACTCCGCCCATCCCGCCCCTAACT CCGCCCAGTTCCGCCCATTCTCCGCCCCATGGCTG ACTAATTTTTTTTATTTATGCAGAGGCCGAGGCCGC CTCGGCCTCTGAGCTATTCCAGAAGTAGTGAGGAG GCTTTTTTGGAGGCCTAGGCTTTTGCAAAAAGCTA ACTTGTTTATTGCAGCTTATAATGGTTACAAATAAA GCAATAGCATCACAAATTTCACAAATAAAGCATTT TTTTCACTGCATTCTAGTTGTGGTTTGTCCAAACTC ATCAATGTATCTTATCACCCGGG |
| 88 | RSV promoter and HIV Rev | CAATTGCGATGTACGGGCCAGATATACGCGTATCT GAGGGGACTAGGGTGTGTTTAGGCGAAAAGCGGG GCTTCGGTTGTACGCGGTTAGGAGTCCCCTCAGGA TATAGTAGTTTCGCTTTTGCATAGGGAGGGGGAAA TGTAGTCTTATGCAATACACTTGTAGTCTTGCAACA TGGTAACGATGAGTTAGCAACATGCCTTACAAGGA GAGAAAAAGCACCGTGCATGCCGATTGGTGGAAG TAAGGTGGTACGATCGTGCCTTATTAGGAAGGCAA CAGACAGGTCTGACATGGATTGGACGAACCACTGA ATTCCGCATTGCAGAGATAATTGTATTTAAGTGCCT AGCTCGATACAATAAACGCCATTTGACCATTCACC ACATTGGTGTGCACCTCCAAGCTCGAGCTCGTTTA GTGAACCGTCAGATCGCCTGGAGACGCCATCCACG CTGTTTTGACCTCCATAGAAGACACCGGGACCGAT CCAGCCTCCCCTCGAAGCTAGCGATTAGGCATCTC CTATGGCAGGAAGAAGCGGAGACAGCGACGAAGA ACTCCTCAAGGCAGTCAGACTCATCAAGTTTCTCT ATCAAAGCAACCCACCTCCCAATCCCGAGGGGACC CGACAGGCCCGAAGGAATAGAAGAAGAAGGTGGA GAGAGAGACAGAGACAGATCCATTCGATTAGTGA ACGGATCCTTAGCACTTATCTGGGACGATCTGCGG AGCCTGTGCCTCTTCAGCTACCACCGCTTGAGAGA CTTACTCTTGATTGTAACGAGGATTGTGGAACTTCT GGGACGCAGGGGGTGGGAAGCCCTCAAATATTGG TGGAATCTCCTACAATATTGGAGTCAGGAGCTAAA GAATAGTCTAGA |
| 89 | Rev/Tat shRNA Target sequence | ATGGCAGGAAGAAGCGGAG |
| 90 | Rev/Tat shRNA sequence | ATGGCAGGAAGAAGCGGAGTTCAAGAGACTCCGC TTCTTCCTGCCATTTTTT |
| 91 | H1 promoter and shRT sequence | GAACGCTGACGTCATCAACCCGCTCCAAGGAATCG CGGGCCCAGTGTCACTAGGCGGGAACACCCAGCGC GCGTGCGCCCTGGCAGGAAGATGGCTGTGAGGGA CAGGGGAGTGGCGCCCTGCAATATTTGCATGTCGC TATGTGTTCTGGGAAATCACCATAAACGTGAAATG TCTTTGGATTTGGGAATCTTATAAGTTCTGTATGAG ACCACTTGGATCCGCGGAGACAGCGACGAAGAGC TTCAAGAGAGCTCTTCGTCGCTGTCTCCGCTTTTT |
| 92 | H1 CCR5 sequence | GAACGCTGACGTCATCAACCCGCTCCAAGGAATCG CGGGCCCAGTGTCACTAGGCGGGAACACCCAGCGC |

-continued

| SEQ ID NO: | Description | Sequence |
|---|---|---|
| | | GCGTGCGCCCTGGCAGGAAGATGGCTGTGAGGGA CAGGGGAGTGGCGCCCTGCAATATTTGCATGTCGC TATGTGTTCTGGGAAATCACCATAAACGTGAAATG TCTTTGGATTTGGGAATCTTATAAGTTCTGTATGAG ACCACTTGGATCCGTGTCAAGTCCAATCTATGTTCA AGAGACATAGATTGGACTTGACACTTTTT |
| 93 | Primer | AGGAATTGATGGCGAGAAGG |
| 94 | Primer | CCCCAAAGAAGGTCAAGGTAATCA |
| 95 | Beta Actin Forward Primer | AGCGCGGCTACAGCTTCA |
| 96 | Beta Actin Reverse Primer | GGCGACGTAGCACAGCTTCP |
| 97 | AGT103 CCR5 miR30 | TGTAAACTGAGCTTGCTCTA |
| 98 | AGT103-R5-1 [CCR5 miRNA target sequence] | TGTAAACTGAGCTTGCTCGC |
| 99 | AGT103-R5-2 [CCR5 miRNA target sequence] | CATAGATTGGACTTGACAC |
| 100 | CAG promoter | TAGTTATTAATAGTAATCAATTACGGGGTCATTAG TTCATAGCCCATATATGGAGTTCCGCGTTACATAA CTTACGGTAAATGGCCCGCCTGGCTGACCGCCCAA CGACCCCCGCCCATTGACGTCAATAATGACGTATG TTCCCATAGTAACGCCAATAGGGACTTTCCATTGA CGTCAATGGGTGGACTATTTACGGTAAACTGCCCA CTTGGCAGTACATCAAGTGTATCATATGCCAAGTA CGCCCCCTATTGACGTCAATGACGGTAAATGGCCC GCCTGGCATTATGCCCAGTACATGACCTTATGGGA CTTTCCTACTTGGCAGTACATCTACGTATTAGTCAT CGCTATTACCATGGGTCGAGGTGAGCCCCACGTTC TGCTTCACTCTCCCCATCTCCCCCCCCTCCCCACCC CCAATTTTGTATTTATTTATTTTTTAATTATTTTGTG CAGCGATGGGGGCGGGGGGGGGGGGGCGCGCGC CAGGCGGGGCGGGGCGGGGCGAGGGGCGGGGCGG GGCGAGGCGGAGAGGTGCGGCGGCAGCCAATCAG AGCGGCGCGCTCCGAAAGTTTCCTTTTATGGCGAG GCGGCGGCGGCGGCGGCCCTATAAAAAGCGAAGC GCGCGGCGGGCG |
| 101 | H1 element | GAACGCTGACGTCATCAACCCGCTCCAAGGAATCG CGGGCCCAGTGTCACTAGGCGGGAACACCCAGCGC GCGTGCGCCCTGGCAGGAAGATGGCTGTGAGGGA CAGGGGAGTGGCGCCCTGCAATATTTGCATGTCGC TATGTGTTCTGGGAAATCACCATAAACGTGAAATG TCTTTGGATTTGGGAATCTTATAAGTTCTGTATGAG ACCACTT |
| 102 | 3' LTR | TGGAAGGGCTAATTCACTCCCAACGAAGATAAGAT CTGCTTTTTGCTTGTACTGGGTCTCTCTGGTTAGAC CAGATCTGAGCCTGGGAGCTCTCTGGCTAACTAGG GAACCCACTGCTTAAGCCTCAATAAAGCTTGCCTT GAGTGCTTCAAGTAGTGTGTGCCCGTCTGTTGTGTG ACTCTGGTAACTAGAGATCCCTCAGACCCTTTTAGT CAGTGTGGAAAATCTCTAGCAGTAGTAGTTCATGT CA |
| 103 | 7SK promoter | CTGCAGTATTTAGCATGCCCCACCCATCTGCAAGG CATTCTGGATAGTGTCAAAACAGCCGGAAATCAAG TCCGTTTATCTCAAACTTTAGCATTTGGGAATAAA TGATATTTGCTATGCTGGTTAAATTAGATTTTAGTT AAATTTCCTGCTGAAGCTCTAGTACGATAAGCAAC TTGACCTAAGTGTAAAGTTGAGATTTCCTTCAGGTT TATATAGCTTGTGCGCCGCCTGGCTACCTC |

| SEQ ID NO: | Description | Sequence |
|---|---|---|
| 104 | miR155 Tat | CTGGAGGCTTGCTGAAGGCTGTATGCTGTCCGCTT CTTCCTGCCATAGGGTTTTGGCCACTGACTGACCCT ATGGGGAAGAAGCGGACAGGACACAAGGCCTGTT ACTAGCACTCACATGGAACAAATGGCC |
| 105 | Elongation Factor-1 alpha (EF1-alpha) promoter with 3' restriction recognition site | CCGGTGCCTAGAGAAGGTGGCGCGGGGTAAACTG GGAAAGTGATGTCGTGTACTGGCTCCGCCTTTTTCC CGAGGGTGGGGGAGAACCGTATATAAGTGCAGTA GTCGCCGTGAACGTTCTTTTTCGCAACGGGTTTGCC GCCAGAACACAGGTAAGTGCCGTGTGTGGTTCCCG CGGGCCTGGCCTCTTTACGGGTTATGGCCCTTGCGT GCCTTGAATTACTTCCACGCCCTGGCTGCAGTAC GTGATTCTTGATCCCGAGCTTCGGGTTGGAAGTGG GTGGGAGAGTTCGAGGCCTTGCGCTTAAGGAGCCC CTTCGCCTCGTGCTTGAGTTGAGGCCTGGCCTGGG CGCTGGGGCCGCCGCGTGCGAATCTGGTGGCACCT TCGCGCCTGTCTCGCTGCTTTCGATAAGTCTCTAGC CATTTAAAATTTTTGATGACCTGCTGCGACGCTTTT TTTCTGGCAAGATAGTCTTGTAAATGCGGGCCAAG ATCTGCACACTGGTATTTCGGTTTTTGGGGCCGCGG GCGGCGACGGGGCCCGTGCGTCCCAGCGCACATGT TCGGCGAGGCGGGGCCTGCGAGCGCGGCCACCGA GAATCGGACGGGGGTAGTCTCAAGCTGGCCGGCCT GCTCTGGTGCCTGGCCTCGCGCCGCCGTGTATCGC CCCGCCCTGGGCGGCAAGGCTGGCCCGGTCGGCAC CAGTTGCGTGAGCGGAAAGATGGCCGCTTCCCGGC CCTGCTGCAGGGAGCTCAAAATGGAGGACGCGGC GCTCGGGAGAGCGGGCGGGTGAGTCACCCACACA AAGGAAAAGGGCCTTTCCGTCCTCAGCCGTCGCTT CATGTGACTCCACGGAGTACCGGGCGCCGTCCAGG CACCTCGATTAGTTCTCGAGCTTTTGGAGTACGTCG TCTTTAGGTTGGGGGGAGGGGTTTTATGCGATGGA GTTTCCCCACACTGAGTGGGTGGAGACTGAAGTTA GGCCAGCTTGGCACTTGATGTAATTCTCCTTGGAAT TTGCCCTTTTTGAGTTTGGATCTTGGTTCATTCTCA AGCCTCAGACAGTGGTTCAAAGTTTTTTTCTTCCAT TTCAGGTGTCGTGATGTACA |
| 106 | miR21 Vif coding sequence with 5' restriction recognition site | CCCGGGCATCTCCATGGCTGTACCACCTTGTCGGG GGATGTGTACTTCTGAACTTGTGTTGAATCTCATGG AGTTCAGAAGAACACATCCGCACTGACATTTTGGT ATCTTTCATCTGACCA |
| 107 | miR185 Tat coding sequence with 5' restriction recognition site | GCTAGCGGGCCTGGCTCGAGCAGGGGCGAGGGA TTCCGCTTCTTCCTGCCATAGCGTGGTCCCCTCCCC TATGGCAGGCAGAAGCGGCACCTTCCCTCCCAATG ACCGCGTCTTCGTC |
| 108 | miR185 Tat coding sequence | GGGCCTGGCTCGAGCAGGGGCGAGGGATTCCGCT TCTTCCTGCCATAGCGTGGTCCCCTCCCCTATGGCA GGCAGAAGCGGCACCTTCCCTCCCAATGACCGCGT CTTCGTC |

While certain of the preferred embodiments of the present invention have been described and specifically exemplified above, it is not intended that the invention be limited to such embodiments. Various modifications may be made thereto without departing from the scope and spirit of the present invention.

---

What is claimed is:

1. A method for treating HIV infection in a subject in need thereof comprising:
   (a) ex vivo contacting peripheral blood mononuclear cells (PBMC) isolated from a subject with a stimulatory agent;
   (b) transducing the PBMC ex vivo with a viral delivery system encoding at least one genetic element; and
   (c) culturing the transduced PBMC for at least 1 day, wherein the at least one genetic element comprises (i) a sequence having at least 90% sequence identity with SEQ ID NO: 6, (ii) a sequence having at least 90% sequence identity with SEQ ID NO: 7, and (iii) a sequence having at least 90% sequence identity with SEQ ID NO: 97, wherein the at least one genetic element does not comprise any small RNA targeting HIV sequences other than Vif and Tat.

2. The method of claim 1, further comprising administering a stimulatory agent to the subject prior to isolation of PBMC.

3. The method of claim 1, further comprising infusing transduced CD4+ T cells into a subject.

4. The method of claim 1, wherein the stimulatory agent comprises a peptide.

5. The method of claim 4, wherein the peptide comprises a gag peptide.

6. The method of claim 1, wherein the stimulatory agent comprises a vaccine.

7. The method of claim 1, wherein the stimulatory agent comprises a HIV vaccine.

8. The method of claim 7, wherein the HIV vaccine comprises a MVA/HIV62B vaccine or a variant thereof.

9. The method of claim 1, wherein the viral delivery system comprises a lentiviral particle.

10. The method of claim 1, wherein the at least one genetic element comprises SEQ ID NO: 6, SEQ ID NO: 7, and SEQ ID NO: 97.

* * * * *